United States Patent
Tsuruta et al.

(10) Patent No.: US 9,958,775 B2
(45) Date of Patent: May 1, 2018

(54) ACTINIC RAY-SENSITIVE OR RADIATION-SENSITIVE RESIN COMPOSITION, ACTINIC RAY-SENSITIVE OR RADIATION-SENSITIVE FILM, MASK BLANKS INCLUDING ACTINIC RAY-SENSITIVE OR RADIATION-SENSITIVE FILM, PATTERN FORMING METHOD AND PHOTOMASK

(71) Applicant: FUJIFILM Corporation, Minato-ku, Tokyo (JP)

(72) Inventors: Takuya Tsuruta, Haibara-gun (JP); Tomotaka Tsuchimura, Haibara-gun (JP); Tadeteru Yatsuo, Haibara-gun (JP)

(73) Assignee: FUJIFILM Corporation, Tokyo (JP)

(*) Notice: Subject to any disclaimer, the term of this patent is extended or adjusted under 35 U.S.C. 154(b) by 0 days. days.

(21) Appl. No.: 14/560,650

(22) Filed: Dec. 4, 2014

(65) Prior Publication Data
US 2015/0086911 A1    Mar. 26, 2015

Related U.S. Application Data

(63) Continuation of application No. PCT/JP2013/067157, filed on Jun. 17, 2013.

(30) Foreign Application Priority Data

Jul. 9, 2012 (JP) ................ 2012-154118

(51) Int. Cl.
| | |
|---|---|
| *G03F 7/004* | (2006.01) |
| *G03F 7/039* | (2006.01) |
| *G03F 7/038* | (2006.01) |
| *G03F 7/20* | (2006.01) |
| *G03F 7/32* | (2006.01) |
| *C07D 333/46* | (2006.01) |
| *C07D 327/08* | (2006.01) |
| *C07C 309/65* | (2006.01) |
| *C07C 381/12* | (2006.01) |

(52) U.S. Cl.
CPC .......... *G03F 7/0045* (2013.01); *C07C 309/65* (2013.01); *C07C 381/12* (2013.01); *C07D 327/08* (2013.01); *C07D 333/46* (2013.01); *G03F 7/0046* (2013.01); *G03F 7/038* (2013.01); *G03F 7/0382* (2013.01); *G03F 7/0397* (2013.01); *G03F 7/2037* (2013.01); *G03F 7/325* (2013.01); *C07C 2601/14* (2017.05)

(58) Field of Classification Search
None
See application file for complete search history.

(56) References Cited

U.S. PATENT DOCUMENTS

| | | | |
|---|---|---|---|
| 2005/0123859 A1 | 6/2005 | Wada et al. | |
| 2006/0172228 A1 | 8/2006 | Wada et al. | |
| 2006/0194982 A1* | 8/2006 | Harada | C07C 309/17 560/150 |
| 2007/0100096 A1* | 5/2007 | Harada | C07C 309/17 526/135 |
| 2007/0141512 A1 | 6/2007 | Wada et al. | |
| 2007/0248897 A1* | 10/2007 | Yoshikawa et al. | 430/5 |
| 2009/0258315 A1* | 10/2009 | Ober | C07D 309/10 430/270.1 |
| 2010/0081066 A1* | 4/2010 | Nozawa | G03F 1/32 430/5 |
| 2010/0143830 A1 | 6/2010 | Ohashi et al. | |
| 2011/0076615 A1 | 3/2011 | Kawabata et al. | |
| 2011/0200936 A1 | 8/2011 | Ichikawa et al. | |
| 2011/0250543 A1* | 10/2011 | Tsubaki | 430/325 |
| 2011/0287234 A1* | 11/2011 | Tsuchihashi et al. | 428/195.1 |
| 2012/0322007 A1 | 12/2012 | Kato et al. | |

FOREIGN PATENT DOCUMENTS

| | | |
|---|---|---|
| JP | 2000-199953 A | 7/2000 |
| JP | 2001-019799 A | 1/2001 |
| JP | 2005-148291 A | 6/2005 |

(Continued)

OTHER PUBLICATIONS

JPO English translation of JP 2012-73401 (2012).*

(Continued)

*Primary Examiner* — Sin J Lee
(74) *Attorney, Agent, or Firm* — Sughrue Mion, PLLC

(57) ABSTRACT

An actinic ray-sensitive or radiation-sensitive resin composition includes; a compound (A) which generates an acid by irradiation with actinic rays or radiation, wherein the acid is linked with a group represented by the following general formula (M) through covalent bonding. In the formula, $Y_1$ and $Y_2$ each independently represent a hydrogen atom, an alkyl group, a cycloalkyl group, an alkenyl group, an alkynyl group, an aryl group, or an acyl group. Z represents a hydrogen atom or a substituent. * represents a linking site with a residue of the compound (A)

[Chem. 1]

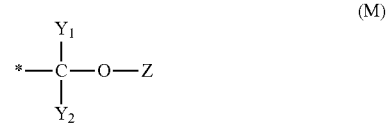

20 Claims, No Drawings

(56) References Cited

FOREIGN PATENT DOCUMENTS

| | | | |
|---|---|---|---|
| JP | 2005-173549 A | | 6/2005 |
| JP | 2006-208781 A | | 8/2006 |
| JP | 2007-199692 A | | 8/2007 |
| JP | 2010-155824 A | | 7/2010 |
| JP | 2011-095700 A | | 5/2011 |
| JP | 2011-191753 A | | 9/2011 |
| JP | 2011-246439 A | | 12/2011 |
| JP | 2012-006911 A1 | | 1/2012 |
| JP | 2012-73401 | * | 4/2012 |
| KR | 10-2006-0092125 A | | 8/2006 |
| KR | 10-2007-0104289 A | | 10/2007 |
| KR | 10-2010-0064343 A | | 6/2010 |
| TW | 200632551 A | | 9/2006 |
| TW | 200804969 A | | 1/2008 |

OTHER PUBLICATIONS

Machine-assisted English translation for JP 2012-73401, as provided by JPO (2012).*

International Search Report of PCT/JP2013/067157 dated Sep. 3, 2013 [PCT/ISA/210], 4pages.

Written Opinion of PCT/JP2013/067157 dated Sep. 3, 2013 [PCT/ISA/237], 6 pages.

Notice of Reasons for Rejection, dated Jul. 14, 2015, issued in corresponding JP Application No. 2012-154118, 29 pages in English and Japanese.

Office Action dated Jun. 9, 2016, issued by the Korean Intellectual Property Office in corresponding Korean Application No. 10-2014-7034031.

Office Action dated Sep. 22, 2016, from the Intellectual Property Office of Taiwan in counterpart Taiwanese Application No. 102122754.

Office Action dated Dec. 1, 2016, issued by the Korean Intellectual Property Office in corresponding Korean Application No. 10-2014-7034031.

Office Action dated Mar. 7, 2017 from the Korean Intellectual Property Office in counterpart Korean Application No. 10-2014-7034031.

* cited by examiner

ACTINIC RAY-SENSITIVE OR RADIATION-SENSITIVE RESIN COMPOSITION, ACTINIC RAY-SENSITIVE OR RADIATION-SENSITIVE FILM, MASK BLANKS INCLUDING ACTINIC RAY-SENSITIVE OR RADIATION-SENSITIVE FILM, PATTERN FORMING METHOD AND PHOTOMASK

CROSS-REFERENCE TO RELATED APPLICATIONS

This application is a Continuation of PCT International Application No. PCT/JP2013/067157 filed on Jun. 17, 2013, which claims priority under 35 U.S.C. § 119(a) to Japanese Patent Application No. 2012-154118 filed on Jul. 9, 2012. Each of the above application(s) is hereby expressly incorporated by reference, in its entirety, into the present application.

BACKGROUND OF THE INVENTION

1. Field of the Invention

The present invention relates to an actinic ray-sensitive or radiation-sensitive resin composition which is suitable for use in an ultramicrolithography process applicable to a process for manufacturing such as a manufacture of a super-LSI or a high-capacity microchip, a process for fabricating a nanoimprint mold, a process for producing a high-density information recording medium, and the like, and other photofabrication processes, and is able to form a high definition negative-tone pattern using an electron beam or extreme ultraviolet rays, an actinic ray-sensitive or radiation-sensitive film using the same, mask blanks including an actinic ray-sensitive or radiation-sensitive film, a pattern forming method, and a photomask. Particularly, the present invention relates to an actinic ray-sensitive or radiation-sensitive resin composition which is suitable for use in a photofabrication processes using a substrate having a specific underlying film, an actinic ray-sensitive or radiation-sensitive film using the same, mask blanks including an actinic ray-sensitive or radiation-sensitive film, a pattern forming method, and a photomask.

2. Description of the Related Art

In the production process for semiconductor devices such as ICs and LSIs, it is a practice in the related art to perform microfabrication by lithography using a photoresist composition. Recently, the formation of an ultrafine pattern in the submicron region or quarter-micron region has been demanded in accordance with the realization of high integration for integrated circuits. In accompaniment with this, a trend of wavelength shortening in the exposure wavelength from g-rays to i-rays, further to an excimer laser light can be seen, and in recent years, developments in lithography using an electron beam, X-rays has been progressed.

In particular, electron beam and extreme ultraviolet ray lithography are positioned as pattern forming technology of the next generation or a more advanced generation and are also widely used for manufacturing a photomask which is used for a semiconductor exposure because of high resolution. For example, in a process for manufacturing the photomask by electron beam lithography, after a resist layer is formed on a shielding substrate provided with a shielding layer consisting mainly of chrome or the like, and further an electronic beam exposure is selectively conducted, an alkali development is performed to form a resist pattern on a transparent substrate. Next, by setting this resist pattern as a mask and etching the shielding layer to form a pattern on the shielding layer, it is possible to obtain a photomask including the shielding layer having a predetermined pattern on the transparent substrate.

However, since it is difficult for an electron beam to collectively expose unlike ultraviolet rays, a resist with high sensitivity is required for reducing the treatment time and as a resist which is suitable for electron beam lithography, a so-called positive-tone resist composition which is a combination of an acid-decomposable polymer compound with a photo-acid generator, and a so-called negative-tone resist composition which is a combination of a cross-linking polymer compound with a cross-linking agent have been effectively used. However, in such a resist composition, when trying to make higher sensitivity, the decrease in resolution, the deterioration of a pattern shape and the occurrence of a scum tend to occur. Furthermore, the deterioration of line edge roughness (a phenomenon in which the edge becomes uneven because a resist pattern and the edge of a substrate interface irregularly changes in the vertical direction to a line, and the accuracy of dimension is decreased by the unevenness being transcribed by an etching process) tends to occur. The improvement of line edge roughness is particularly very important subject in an ultrastructural region in which the line width is 0.25 μm or less.

As a method which solves some of these problems, a photo-acid generator including a cross-linking group in a molecule is disclosed. For example, a compound having a photo-acid generator group and a vinyl ether group which is cross-linked by the generated acid in the same molecule is disclosed in JP2001-19799A. In addition, a compound having a photo-acid generator group and a cross-linking group including a ring structure such as an oxetane ring in the same molecule is disclosed in JP2011-246439A. However, it was difficult to satisfy high sensitivity, high resolution (for example, high resolving power, an excellent pattern shape and small line edge roughness (LER)) and excellent dry etching resistance at the same time depending on the resist compositions using these compounds. In addition, it is speculated that particularly, a compound disclosed in JP2001-19799A has a cross-linking group at a cation part that may be one of the causes, however, the temporal stability is poor, therefore, a non-exposed portion is reacted and this becomes one of the causes of deterioration of a scum.

SUMMARY OF THE INVENTION

An object of the present invention is to provide an actinic ray-sensitive or radiation-sensitive resin composition that can form a pattern which satisfies high sensitivity, high resolution (for example, high resolving power, an excellent pattern shape and small line edge roughness (LER)) and excellent dry etching resistance at the same time as well as has excellent scum characteristics and the excellent temporal stability.

Another object of the present invention is to provide an actinic ray-sensitive or radiation-sensitive film which is formed from the actinic ray-sensitive or radiation-sensitive resin composition, mask blanks including an actinic ray-sensitive or radiation-sensitive film, a pattern forming method, and a photomask.

The inventors have discovered that the object described above can be achieved by a compound which generates a acid including at least one methylol group (a group represented by the general formula (M)) as a cross-linking group through covalent bonding by irradiation with actinic rays or radiation as a result of extensive studies. The present invention has been conducted based on these findings.

In other words, the present invention is as follows in one embodiment.

[1] An actinic ray-sensitive or radiation-sensitive resin composition (A) including; a compound which generates an acid by irradiation with actinic rays or radiation, wherein the acid is linked with a group represented by the following general formula (M) through covalent bonding.

[Chem. 1]

$$*-\underset{Y_2}{\overset{Y_1}{\underset{|}{C}}}-O-Z \quad (M)$$

In the formula, $Y_1$ and $Y_2$ each independently represent a hydrogen atom, an alkyl group, a cycloalkyl group, an alkenyl group, an alkynyl group, an aryl group, or an acyl group;

Z represents a hydrogen atom or a substituent; and

* represents a linking site with a residue of the compound (A).

[2] The actinic ray-sensitive or radiation-sensitive resin composition according to [1], wherein the compound (A) has two or more groups represented by the general formula (M).

[3] The actinic ray-sensitive or radiation-sensitive resin composition according to [1] or [2], wherein the group represented by the general formula (M) is a hydroxymethyl group or an alkoxymethyl group.

[4] The actinic ray-sensitive or radiation-sensitive resin composition according to any one of [1] to [3] which is used for the formation of a negative-tone pattern further including; (B1) a compound having a phenolic hydroxyl group.

[5] The actinic ray-sensitive or radiation-sensitive resin composition according to [4], wherein the compound (B1) having the phenolic hydroxyl group is a polymer compound having a repeating unit represented by the following general formula (1).

[Chem. 2]

$$\begin{array}{c} R_{11} \\ | \\ \wedge \\ | \\ B_1 \\ | \\ Ar \\ | \\ (OH)_{m1} \end{array} \quad (1)$$

In the formula, $R_{11}$ represents a hydrogen atom, a methyl group which may have a substituent, or a halogen atom;

$B_1$ represents a single bond or a divalent linking group;

Ar represents an aromatic ring; and m1 represents an integer of 1 or more.

[6] The actinic ray-sensitive or radiation-sensitive resin composition according to any one of [1] to [5], further including; (C) a cross-linking agent.

[7] The actinic ray-sensitive or radiation-sensitive resin composition according to any one of [1] to [6], further including; (D) a compound that generates an acid which dose not include a cross-linking group in a molecule by irradiation with actinic rays or radiation.

[8] The actinic ray-sensitive or radiation-sensitive resin composition according to [6] or [7], including; a compound having two or more groups represented by the general formula (M) in a molecule as the cross-linking agent (C).

[9] The actinic ray-sensitive or radiation-sensitive resin composition according to [6] or [7], including; a compound having two or more alkoxymethyl groups in a molecule as the cross-linking agent (C).

[10] The actinic ray-sensitive or radiation-sensitive resin composition according to any one of [1] to [3], further including; (B2) a compound having a group which is capable of decomposing by the action of an acid.

[11] A negative-tone pattern forming method including; forming a film using the actinic ray-sensitive or radiation-sensitive resin composition according to [10], exposing the film and developing the exposed film with a developer containing an organic solvent.

[12] An actinic ray-sensitive or radiation-sensitive film which is formed from the actinic ray-sensitive or radiation-sensitive resin composition according to any one of [1] to [10].

[13] Mask blanks including; the actinic ray-sensitive or radiation-sensitive film according to [12].

[14] A pattern forming method including; exposing the actinic ray-sensitive or radiation-sensitive film according to [12], and developing the exposed film.

[15] A pattern forming method including; exposing the actinic ray-sensitive or radiation-sensitive film of the mask blanks according to [13], and developing the exposed actinic ray-sensitive or radiation-sensitive film.

[16] The pattern forming method according to [14] or [15], wherein the exposing is performed using an electron beam or extreme ultraviolet rays.

[17] A photomask which is manufactured by a method including; exposing the actinic ray-sensitive or radiation-sensitive film of the mask blanks according to [13], developing the exposed actinic ray-sensitive or radiation-sensitive film to form a pattern and etching mask blanks using the pattern.

[18] A compound represented by the following general formula (I):

[Chem. 3]

$$M^+ \; {}^-O-\underset{O}{\overset{O}{\underset{\|}{S}}}-\left(\underset{F}{\overset{F}{\underset{|}{C}}}\right)_n-\underset{O}{\overset{O}{\underset{\|}{S}}}-O-\underset{(X)_p}{\overset{(O-Z)_o}{\bigcirc}} \quad (I)$$

(In the formula, M+ represents a sulfonium cation. X represents an alkyl group, a cycloalkyl group, an aryl group, a halogen atom, a hydroxyl group, an alkoxy group, or an acyl group. Z represents a hydrogen atom, an alkyl group, a cycloalkyl group, an aryl group or an acyl group. n represents an integer of 1 to 3. o represents an integer of 1 to 5, p represents an integer of 0 to 4, and o+p≤5 is satisfied.)

According to the present invention, an actinic ray-sensitive or radiation-sensitive resin composition that can form a pattern which satisfies high sensitivity, high resolution (for example, high resolving power, an excellent pattern shape and small line edge roughness (LER)) and excellent dry etching resistance at the same time having excellent scum characteristics and excellent temporal stability, can be provided.

According to the present invention, an actinic ray-sensitive or radiation-sensitive film which is formed from the actinic ray-sensitive or radiation-sensitive resin composition, mask blanks including an actinic ray-sensitive or radiation-sensitive film, a pattern forming method, and a photomask can be further provided.

DESCRIPTION OF THE PREFERRED EMBODIMENTS

In denotation of a group (atomic group) in the specification, in a case where substituted or unsubstituted is not specified, both a group (atomic group) which do not have a substituent and a group (atomic group) which have a substituent are included. For example, "an alkyl group" includes not only an alkyl group which has no substituent (unsubstituted alkyl group) but also an alkyl group which has a substituent (substituted alkyl group).

In the present invention, "actinic rays" or "radiation" refers to, for example, a bright line spectrum of a mercury lamp, far ultraviolet rays typified by an excimer laser, extreme ultraviolet rays (EUV light), an X-ray, an electron beam, and the like. In addition, "light" in the present invention refers to the actinic rays or the radiation. Unless otherwise specified, "exposure" in the specification includes not only the exposure performed using a mercury lamp, far ultraviolet rays which are typified by an excimer laser, an X-ray, an EUV light, or the like, but also drawing performed using a particle beam such as an electron beam or an ion beam.

The actinic ray-sensitive or radiation-sensitive resin composition in the present invention (hereinafter, also referred to as a "composition of the present invention") includes (A) a compound which generates a acid having one or more methylol groups represented by the general formula (M) described later as a cross-linking group in a molecule through covalent bonding by irradiation with actinic rays or radiation. In other words, the composition of the present invention includes a compound which generates an acid by irradiation with actinic rays or radiation, the acid has one or more methylol groups represented by the general formula (M) described later in a molecule through covalent bonding, and the methylol group functions as a cross-linking group.

In one embodiment, the composition according to the present invention is used for the formation of a negative-tone pattern and in another embodiment, is used for the formation of a positive-tone pattern.

In one embodiment, the composition according to the present invention, includes (B1) a compound having a phenolic hydroxyl group, and in another embodiment, includes (B2) a compound having a group which is capable of decomposing by the action of an acid.

In one embodiment, the composition according the present invention may include one of or both of (C) a cross-linking agent and (D) a compound that generates an acid which dose not include a cross-linking group in a molecule by irradiation with actinic rays or radiation.

In addition, the composition of the present invention can further include a basic compound described later, a fluorine-based and/or a silicon-based surfactant described later, an organic solvent described later, and/or another additive agent described later. Then, the composition of the present invention, for example, can be used for a pattern formation by a method described in the section of a pattern forming method described later.

Hereinafter, each component of an actinic ray-sensitive or radiation-sensitive composition according to the present invention will be described in sequence.

[1] Compound (A)

The composition of the present invention includes a compound (hereinafter, also referred to as a "compound (A)", a "cross-linking-type acid generator (A)", or the like) which generates an acid having one or more methylol groups represented by the general formula (M) described later as a cross-linking group in a molecule through covalent bonding by irradiation with actinic rays or radiation.

Since the compound (A) has a structure in which a methylol group is linked through covalent bonding in a molecule of an acid (hereinafter, also referred to as a "generated acid") which generates by irradiation with actinic rays or radiation, the diffusion of the generated acid can be suppressed and it is possible to realize high resolving power, an excellent pattern shape and small line edge roughness (LER). Furthermore, by including this compound (A), it is possible to satisfy the high temporal stability and excellent dry etching resistance at the same time as well as to form a pattern in which scum occurs less. In addition, in a case where the composition of the present invention includes a compound (B1) having a phenolic hydroxyl group described later and is used for the formation of a negative-tone pattern, the hardenability of a pattern is also improved.

Here, "a cross-linking group" means a group which can generate a new bonding by reacting an addition reaction and a substitution reaction with respect to an atom with low electron density (mainly carbon) from a nucleophilic group having high reactivity such as a hydroxyl group and a phenolic part under the existence of an acid. In addition, "a methylol group" contained in the compound (A) means a group represented by the general formula (M) described later, without mentioning in particular.

The compound (A) may have a structure which further has the other cross-linking group other than a methylol group in a molecule of the generated acid, as a cross-linking group other than a methylol group, specifically, a vinyl ether group or a group having a ring structure, and the like are included, and examples of the group having a ring structure include an oxirane group, an oxetane group, a tioxirane group, a tioxetane group, and the like.

In one embodiment of the present invention, the compound (A) preferably has two or more methylol groups as a cross-linking group. For example, in a case where the composition of the present invention includes a compound (B1) having a phenolic hydroxyl group described later and a cross-linking agent (C), and is used for the formation of a negative-tone pattern, dry etching resistance, sensitivity and solving power are further improved, since a plurality of methylol groups contained in the compound (A) also contributes to the cross-linking reaction along with the cross-linking reaction of the compound (B1) and a cross-linking agent (C).

A methylol group is a group represented by the following general formula (M), and in one embodiment of the present invention, is preferably a hydroxymethyl group which may have a substituent, an alkoxymethyl group which may have a substituent, and an acyloxymethyl group which may have a substituent (for example, an acetoxymethyl group).

[Chem. 4]

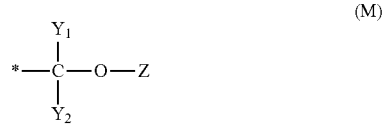

In the formula, $Y_1$ and $Y_2$ each independently represent a hydrogen atom, an alkyl group, a cycloalkyl group, an alkenyl group, an alkynyl group, an aryl group, or an acyl group;

Z represents a hydrogen atom or a substituent; and

* represents a linking site with a residue of a compound (A).

Here, specific examples of each group described above as a substituent represented by $Y_1$ and $Y_2$ include the same as specific examples of each group as a substituent represented by $Y_1$ and $Y_2$ in the general formula (9) described later.

In one embodiment of the present invention, $Y_1$ and $Y_2$ are preferably a hydrogen atom, an alkyl group and a cycloalkyl group.

Examples of the substituent represented by Z include an alkyl group, an alkenyl group, an alkynyl group, a cycloalkyl group, an aryl group, a haloalkyl group, an alkoxy group, an aryloxy group, an acyl group, an alkoxycarbonyl group, an aryloxycarbonyl group, an alkylsulfonyloxy group, an arylsulfonyloxy group, an alkylsulfonyl group, an arylsulfonyl group, a cyano group, an alkylthio group, an arylthio group and a heterocyclic group. These groups may further have a substituent.

Here, specific examples of each group described above as a substituent represented by Z include the same as specific examples of each group as a substituent represented by Z in the general formula (9) described later.

In one embodiment of the present invention, Z is preferably a hydrogen atom, an alkyl group, a cycloalkyl group, an aryl group or an acyl group and more preferably a hydrogen atom, an alkyl group or an acyl group.

In one embodiment, the compound (A) preferably have a structure in which a methylol group or a group including a methylol group is linked to a ring structure. For example, the compound (A) preferably have a structure which is selected from a hydroxymethyl group, an alkoxymethyl group and an acyloxymethyl group (for example, an acetoxymethyl group, or the like) and is substituted with at least one methylol group in a ring structure, and more preferably have a structure which is substituted with at least two methylol groups.

Here, "a ring structure" may be an aromatic ring (including a heterocyclic group) and may be a non-aromatic ring (including a heterocyclic group). In addition, "a ring structure" may be monocyclic and may be polycyclic. A "polycyclic structure" may be a condensed ring, may be a bridged ring and may be a Spiro ring. In addition, "a polycyclic structure" may be a form in which two or more monocyclic structures are linked by a single bond. Specifically, in the general formula (9) described later, description of a cyclic structure represented by B can be referred.

In addition, in a case where the compound (A) further includes a cross-linking group other than a methylol group and in a case where the cross-linking group, for example, has a ring structure such as a epoxy group, as a ring structure linked to a cross-linking group, a ring-containing cross-linking group such as a epoxy group may condense with a ring (monocyclic and polycyclic) structure or may be linked by a spiro bond or a single bond to form a polycyclic structure.

In addition, "a ring structure" may further have a substituent, and as the substituent, a group represented by X in the general formula (I) described above is included.

As a ring structure linked to a methylol group which the compound (A) may have, for example, a structure represented by the following general formula (0) is preferable.

[Chem. 5]

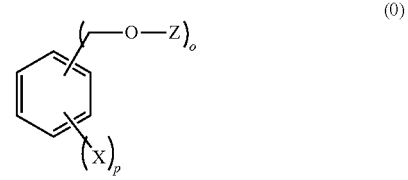

In the formula, Z represents a hydrogen atom or a substituent. The substituent is the same as a substituent represented by Z in the general formula (M) described above. Z is preferably a hydrogen atom, an alkyl group, an alkenyl group, an alkynyl group, a cycloalkyl group, or an acyl group.

X represents a hydrogen atom or a substituent. Examples of the substituent represented by X include the same as a group which a cyclic structure can have as B in the general formula (9) described later.

o represents an integer of 1 to 5, p represents an integer of 0 to 4 and o+p≤5 is satisfied.

o is preferably 2 or 3. In a case where o is two or more, a plurality of Z's may be the same as or different from each other. p is preferably 1.

In one embodiment of the present invention, the compound (A) particularly preferably has a structure which is substituted with a hydroxyl group of a benzene ring linked to a methylol group from the viewpoint of resolving power and LER. For example, as a ring structure linked to a methylol group, the compound (A) preferably has a partial structure represented by the following formula. In the following formula, Z is the same as Z in the general formula (O) described above.

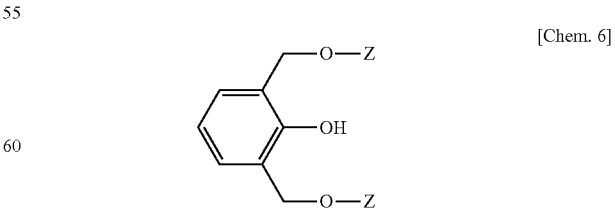

[Chem. 6]

Examples of the ring structure linked to a methylol group or a group including a methylol group include the following structures.

[Chem. 7]
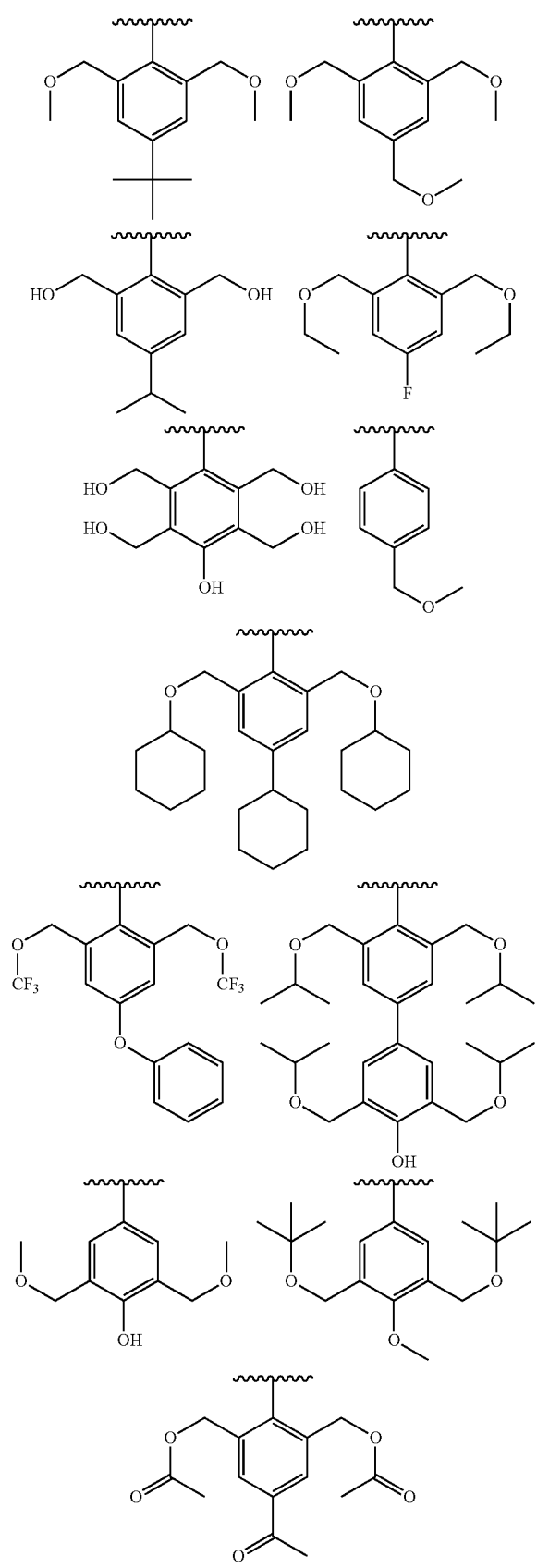
-continued
[Chem. 8]
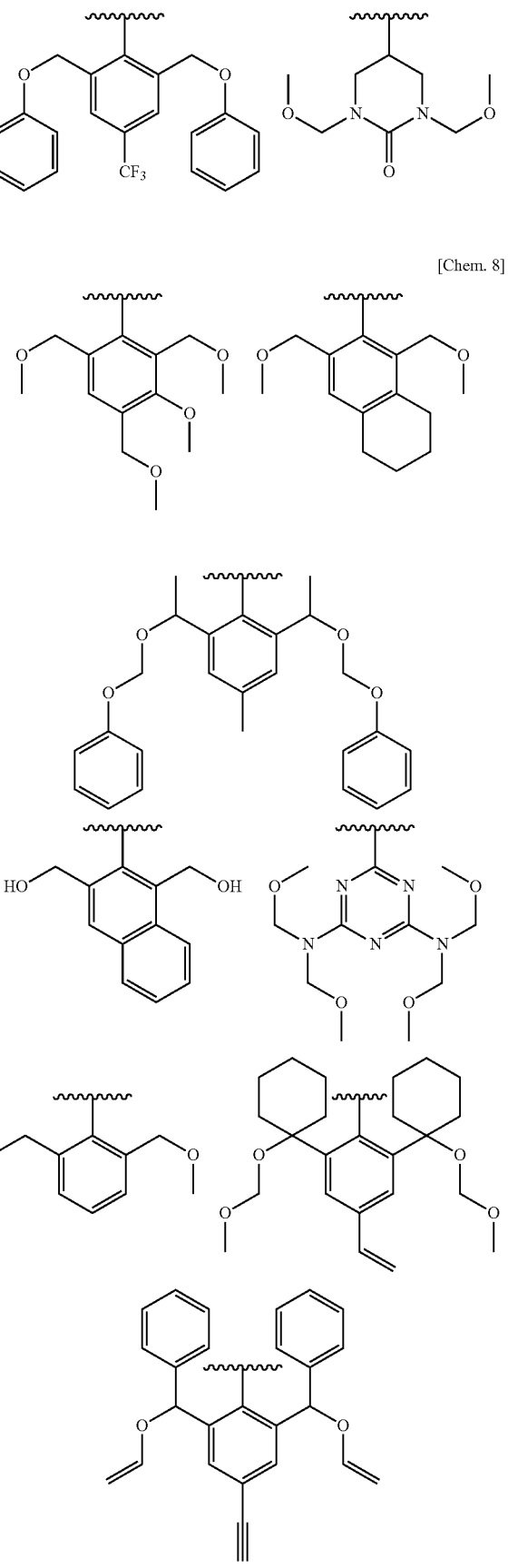

-continued

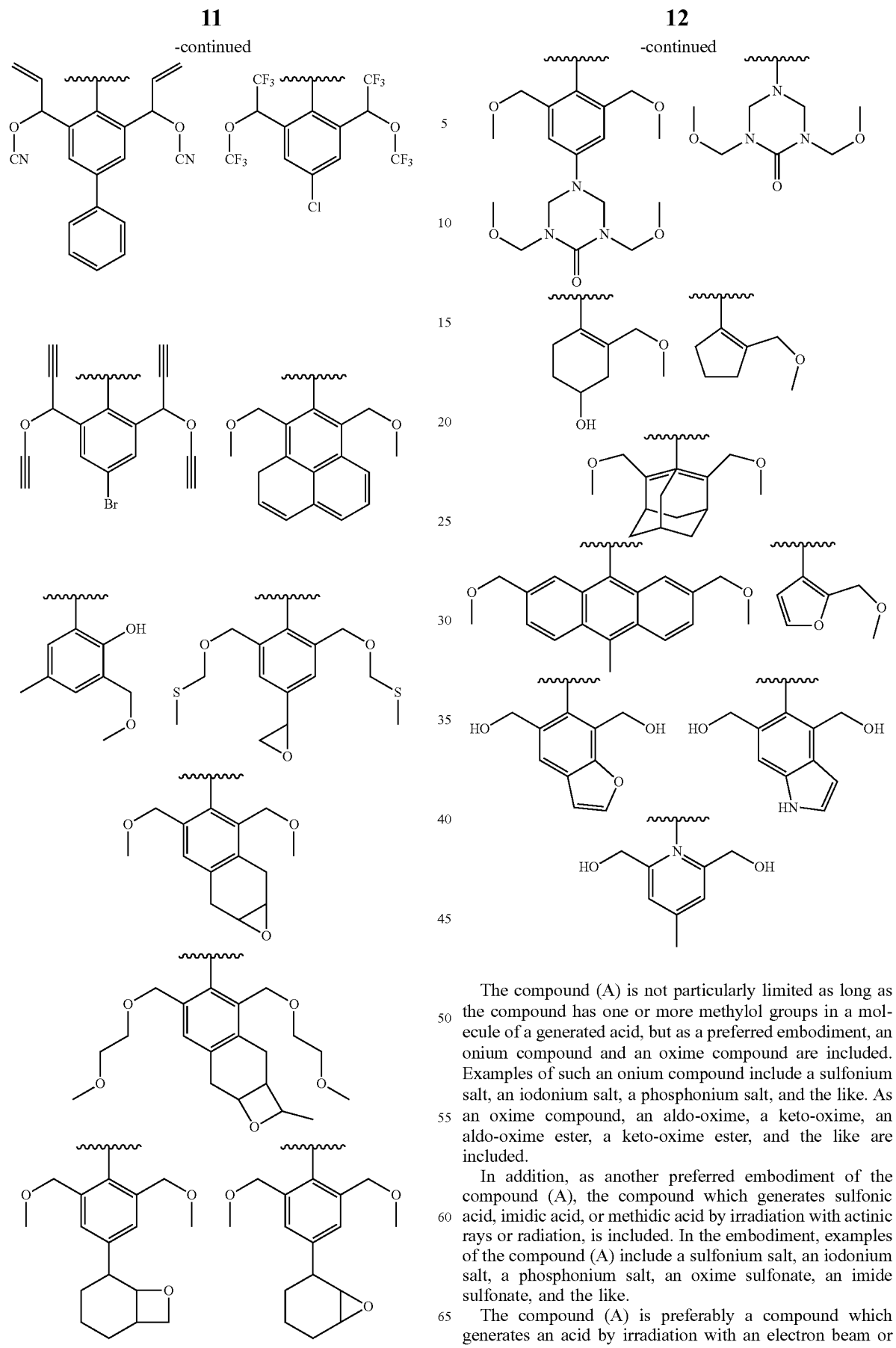

The compound (A) is not particularly limited as long as the compound has one or more methylol groups in a molecule of a generated acid, but as a preferred embodiment, an onium compound and an oxime compound are included. Examples of such an onium compound include a sulfonium salt, an iodonium salt, a phosphonium salt, and the like. As an oxime compound, an aldo-oxime, a keto-oxime, an aldo-oxime ester, a keto-oxime ester, and the like are included.

In addition, as another preferred embodiment of the compound (A), the compound which generates sulfonic acid, imidic acid, or methidic acid by irradiation with actinic rays or radiation, is included. In the embodiment, examples of the compound (A) include a sulfonium salt, an iodonium salt, a phosphonium salt, an oxime sulfonate, an imide sulfonate, and the like.

The compound (A) is preferably a compound which generates an acid by irradiation with an electron beam or extreme ultraviolet rays.

In the present invention, as a preferred onium compound, a sulfonium compound represented by the following general formula (4) or an iodonium compound represented by the general formula (5).

[Chem. 9]

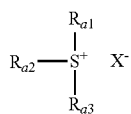

(4)

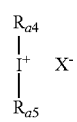

(5)

In the general formulae (4) and (5),

Ra$_1$, Ra$_2$, Ra$_3$, Ra$_4$, and Ra$_5$ each independently represent an organic group; and X$^-$ represents an organic anion.

Hereinafter, the sulfonium compound represented by the general formula (4) and the iodonium compound represented by the general formula (5) will be described in more detail.

Ra$_1$ to Ra$_3$ in the general formula (4) described above and Ra$_4$ and Ra$_5$ in the general formula (5) described above each independently represent an organic group, however, it is preferable that at least one of Ra$_1$ to Ra$_3$ and at least one of Ra$_4$ and Ra$_5$ be respectively an aryl group. As the aryl group, a phenyl group and a naphthyl group are preferable and a phenyl group is more preferable.

In addition, a plurality of organic groups of Ra$_1$ to Ra$_3$, and Ra$_4$ and Ra$_5$ described above may be linked to each other to form a ring. In this case, a plurality of these organic groups may be linked through a single bond, an alkylene group, an ether group, a thioether group, and the like.

Examples of the cation structure of an onium salt represented by the general formula (4) and the general formula (5) include the following structures.

[Chem. 10]

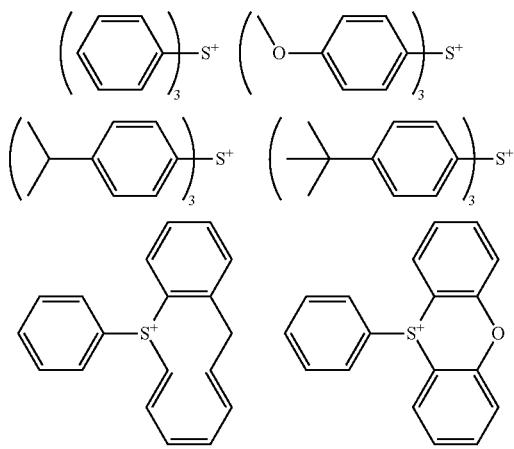

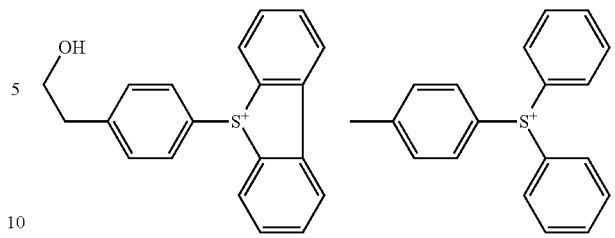

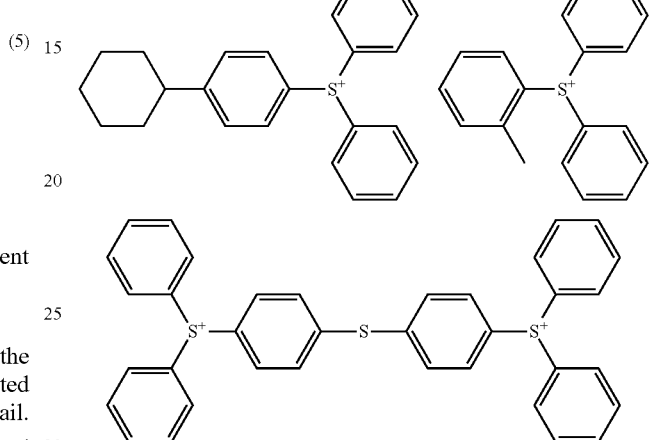

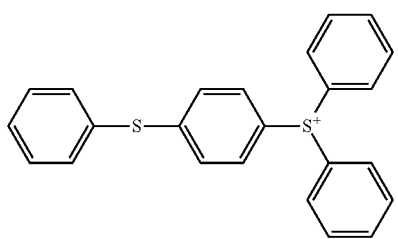

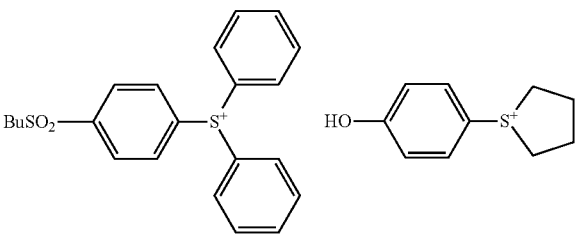

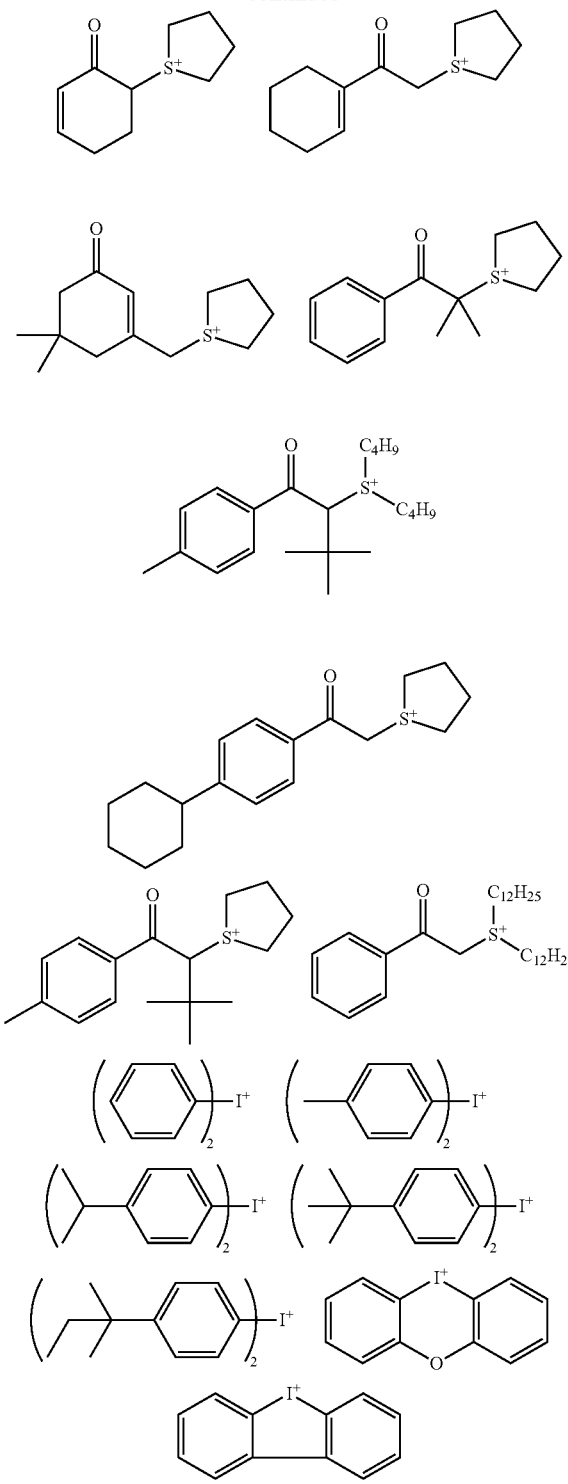

Examples of the organic anion represented by X⁻ in the general formulae (4) and (5) described above include a sulfonate anion, a carboxylate anion, a bis(alkylsulfonyl)amide anion, a tris(alkylsulfonyl)methide anion, and the like, the organic anions represented by the general formulae (6), (7) or (8) described below are preferable and a sulfonate anion represented by the general formula (6) described below is more preferable.

[Chem. 11]

$$Rc_1-SO_3^- \quad (6)$$

$$\begin{array}{c} R_{c2}SO_2 \\ \phantom{R_{c2}SO_2}\diagdown \\ \phantom{R_{c2}SO_2}N^- \\ \phantom{R_{c2}SO_2}\diagup \\ R_{c3}SO_2 \end{array} \quad (7)$$

$$\begin{array}{c} R_{c2}SO_2 \\ R_{c3}SO_2-C^- \\ R_{c4}SO_2 \end{array} \quad (8)$$

In the general formulae (6), (7) and (8) described above, $Rc_1$, $Rc_2$, $Rc_3$ and $Rc_4$ are respectively an organic group.

In addition, $Rc_2$ and $Rc_3$ in the general formula (7) described above may be linked to each other to form a ring, a plurality of the organic groups of $Rc_2$ to $Rc_4$ in the general formula (8) are linked to each other to form a ring and as a group which is linked to a plurality of these organic groups, a alkylene group substituted with a fluorine atom or a fluoroalkyl group is preferable. By containing a fluorine atom or a fluoroalkyl group, the acidity of an acid generated by irradiation with light is increased and sensitivity is improved.

An organic anion of X⁻ describe above corresponds to sulfonic acid, imidic acid, methidic acid, or the like which is an acid generated by irradiation with actinic rays or radiation and containing one or more methylol groups as a cross-linking group.

In one embodiment, a sulfonate anion represented by the general formula (6) described above is preferably represented by the general formula (9) below.

[Chem. 12]

$$^-O_3S-A-\underset{B}{\bigcirc}\left(\underset{}{\overset{Y_2\ Y_1}{\diagdown\diagup}}-O-Z\right)_o \quad (9)$$

In the general formula (9) described above, A represents a divalent linking group or a single bond. B represents a cyclic structure. $Y_1$ and $Y_2$ are each independently represent a hydrogen atom or a substituent. Z represents a hydrogen atom or a substituent. o represents an integer of 1 to 5 and is preferably 2 or 3. In a case where o is an integer of 2 or more, a plurality of $Y_1$'s may be the same as or different from each other, a plurality of $Y_2$'s may be the same as or different from each other, and a plurality of Z's may be the same as or different from each other.

In the general formula (9) described above, A represents a divalent linking group or a single bond. This divalent linking group includes —COO—, —OCO—, —CO—, —O—, —S—, —SO—, —SO2-, —NH—, —C(=S)—, —NRCO— (R is a hydrogen atom, an alkyl group having 1 to 10 carbon atoms and a cycloalkyl group having 5 to 20 carbon atoms), an alkylene group (preferably 1 to 10 carbon atoms), a cycloalkylene group (preferably 3 to 10 carbon atoms), an alkenylene group, an alkynylene group, and an arylene group (preferably 6 to 15 carbon atoms), and may be a combination of a plurality of these groups.

As the alkylene group represented by A, a group having 1 to 10 carbon atoms is preferable and, for example, a methylene group, an ethylene group, a propylene group, a butylene group, a pentylene group, a hexylene group, a heptylene group, an octylene group, a nonalene group and decalene group are included. As a preferred example, a methylene group, an ethylene group, a propylene group, a butylene group, a pentylene group and a hexylene group are included, and as a more preferred example, a methylene group, an ethylene group and a propylene group are included.

As the cycloalkylene group represented by A, a group having 3 to 10 carbon atoms is preferable, for example, a cyclopropylene group, a cyclobutylene group, a cyclopentylene group or a cyclohexylene group is included, and a cyclopentylene group or a cyclohexylene group is preferably included.

As the alkenylene group represented by A, an alkenylene group having 2 to 10 carbon atoms is preferable, for example, an ethenylene group, 1-propenylene group, 2-propenylene group, and the like are included.

As the alkynylene group represented by A, an alkynylene group having 2 to 10 carbon atoms is preferable, for example, an ethynylene group, a propargylene group, and the like are included.

As the arylene group represented by A, a group having 6 to 15 carbon atoms is preferable, for example, a phenylene group, a tolylene group, a naphthylene group, an anthracene group and a fluorirene group are included. As a preferred example, a phenylene group is included.

The alkylene group, the cycloalkylene group, the alkenylene group, the alkynylene group, and the arylene group described above may further have a substituent and examples of the substituent include an alkyl group, an alkenyl group, an alkynyl group, a cycloalkyl group, an aryl group, a halogen group, a haloalkyl group, an alkoxy group, an aryloxy group, an acyl group, an alkoxycarbonyl group, an aryloxycarbonyl group, an alkylsulfonyloxy group, an arylsulfonyloxy group, an alkylsulfonyl group, an arylsulfonyl group, a cyano group, an alkylthio group, an arylthio group and a heterocyclic group. As a preferred example, an alkyl group, a cycloalkyl group, a halogen group and a haloalkyl group are included.

As the alkyl group, an alkyl group having 1 to 30 carbon atoms is preferable, and, for example, a methyl group, an ethyl group, a propyl group, a butyl group, a hexyl group, a octyl group, a decyl group, a dodecyl group, a octadecyl group, a isopropyl group, an isobutyl group, a sec-butyl group, a t-butyl group, a 1-ethylpentyl group, a trifluoromethyl group, a 2-ethylhexyl group, a phenacyl group, a 1-naphthoylmethyl group, a 2-naphthoylmethyl group, a 4-methylsulfanylphenacyl group, a 4-phenylsulfanylphenacyl group, a 4-dimethylaminophenacyl group, a 4-cyanophenacyl group, a 4-methylphenacyl group, a 2-methylphenacyl group, a 3-fluorophenacyl group, a 3-trifluoromethylphenacyl group, and a 3-nitrophenacyl group are included.

As a particular preferred group, a methyl group, an ethyl group, an isopropyl group and a t-butyl group are included.

As the alkenyl group, an alkenyl group having 2 to 10 carbon atoms is preferable, for example, a vinyl group, an allyl group, a styryl group, and the like are included.

As the alkynyl group, an alkynyl group having 2 to 10 carbon atoms is preferable, for example, an ethynyl group, a propynyl group, a propargyl group, and the like are included.

The cycloalkyl group may have a monocyclic structure or may have a polycyclic structure. As the cycloalkyl group having a monocyclic structure, a cyclopentyl group, a cyclohexyl group, a cyclooctyl group, and the like are preferable. As the cycloalkyl group having a polycyclic structure, a norbornyl group, a tricyclodecanyl group, a tetracyclodecanyl group, a tetracyclododecanyl group, an adamantyl group, and the like are preferable. The cycloalkyl group having 3 to 8 carbon atoms is preferable and, for example, a cyclopentyl group and a cyclohexyl group are more preferable.

As the aryl group, an aryl group having 6 to 30 carbon atoms is preferable, and for example, a phenyl group, a biphenyl group, a 1-naphthyl group, a 2-naphthyl group, a 9-anthryl group, a 9-phenanthryl group, a 1-pyrenyl group, a 5-naphthacenyl group, a 1-indenyl group, a 2-azulenyl group, a 9-fluorenyl group, a terphenyl group, a quarterphenyl group, an o-, m-, and p-tolyl group, a xylyl group, an o-, m-, and p-cumenyl group, a mesityl group, a pentalenyl group, a binaphthalenyl group, a ternaphthalenyl group, a quarternaphthalenyl group, a heptalenyl group, a biphenylenyl group, an indacenyl group, a fluoranthenyl group, an acenaphthylenyl group, an aceanthrylenyl group, a phenalenyl group, a fluorenyl group, an anthryl group, a bianthracenyl group, a teranthracenyl group, a quarteranthracenyl group, an anthraquinolyl group, a phenanthryl group, a triphenylenyl group, a pyrenyl group, a chrysenyl group, a naphthacenyl group, a pleiadenyl group, a picenyl group, a perylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group and an ovalenyl group are included.

The halogen atom includes a fluorine atom, a chlorine atom, a bromine atom and an iodine atom.

As the haloalkyl group, an alkyl group and a cycloalkyl group having 1 to 30 carbon atoms, in which at least one or more hydrogens are substituted with a fluorine atom, a chlorine atom, a bromine atom and an iodine atom, are included. As a specific example, a fluoromethyl group, a trifluoromethyl group, a pentafluoroethyl group, a heptafluoropropyl group, and an undecafluorocyclohexyl group are included.

As the alkoxy group, an alkoxy group having 1 to 30 carbon atoms is included and, for example, a methoxy group, an ethoxy group, a propoxy group, n-butoxy group, a trifluoromethoxy group, a hexyloxy group, a t-butoxy group, a 2-ethylhexyloxy group, a cyclohexyloxy group, a decyloxy group and a dodecyloxy group are included.

As the aryloxy group, an aryloxy group having 6 to 30 carbon atoms is included and, for example, a phenyloxy group, a 1-naphthyloxy group, a 2-naphthyloxy group, a tolyloxy group, a methoxyphenyloxy group, a naphthyloxy group, a chlorophenyloxy group, a trifluoromethylphenyloxy group, a cyanophenyloxy group and a nitrophenyloxy group are included.

As the acyl group, an acyl group having 2 to 20 carbon atoms is included and, for example, an acetyl group, a propanoyl group, a butanoyl group, a trifluoromethylcarbonyl group, a pentanoyl group, a benzoyl group, a 1-naphthoyl group, a 2-naphthoyl group, a 4-methylsulfanylbenzoyl group, a 4-phenylsulfanylbenzoyl group, a 4-dimethylaminobenzoyl group, a 4-diethylaminobenzoyl group, a 2-chlorobenzoyl group, a 2-methylbenzoyl group, a 2-methoxybenzoyl group, a 2-butoxybenzoyl group, a 3-chlorobenzoyl group, a 3-trifluoromethylbenzoyl group, a 3-cyanobenzoyl group, a 3-nitrobenzoyl group, a 4-fluorobenzoyl group, a 4-cyanobenzoyl group, and a 4-methoxybenzoyl group are included.

As the alkoxycarbonyl group, an alkoxycarbonyl group having 2 to 20 carbon atoms is included and, for example, a methoxycarbonyl group, an ethoxycarbonyl group, a propoxycarbonyl group, a butoxycarbonyl group, a hexyloxycarbonyl group, an octyloxycarbonyl group, a decyloxycarbonyl group, an octadecyloxycarbonyl group, and a trifluoromethyloxycarbonyl group are included.

As the aryloxycarbonyl group, an aryloxycarbonyl group having 7 to 30 carbon atoms is included and, for example, a phenoxycarbonyl group, a 1-naphthyloxycarbonyl group, a 2-naphthyloxycarbonyl group, a 4-methylsulfanylphenyloxycarbonyl group, a 4-phenylsulfanylphenyloxycarbonyl group, a 4-dimethylaminophenyloxycarbonyl group, a 4-diethylaminophenyloxycarbonyl group, a 2-chlorophenyloxycarbonyl group, a 2-methylphenyloxycarbonyl group, a 2-methoxyphenyloxycarbonyl group, a 2-butoxyphenyloxycarbonyl group, a 3-chlorophenyloxycarbonyl group, a 3-trifluoromethylphenyloxycarbonyl group, a 3-cyanophenyloxycarbonyl group, a 3-nitrophenyloxycarbonyl group, a 4-fluorophenyloxycarbonyl group, a 4-cyanophenyloxycarbonyl group, and a 4-methoxyphenyloxycarbonyl group are included.

As the alkylsulfonyloxy group, an alkylsulfonyloxy group having 1 to 20 carbon atoms is included and, for example, a methylsulfonyloxy group, an ethylsulfonyloxy group, a propylsulfonyloxy group, an isopropylsulfonyloxy group, a butylsulfonyloxy group, a hexylsulfonyloxy group, a cyclohexylsulfonyloxy group, an octylsulfonyloxy group, a 2-ethylhexylsulfonyloxy group, a decanoylsulfonyloxy group, a dodecanoylsulfonyloxy group, an octadecanoylsulfonyloxy group, a cyanomethylsulfonyloxy group, a methoxymethylsulfonyloxy group, and a perfluoroalkylsulfonyloxy group are included.

As the arylsulfonyloxy group, an arylsulfonyloxy group having 6 to 30 carbon atoms is included and, for example, a phenylsulfonyloxy group, a 1-naphthylsulfonyloxy group, a 2-naphthylsulfonyloxy group, a 2-chlorophenylsulfonyloxy group, a 2-methylphenylsulfonyloxy group, a 2-methoxyphenylsulfonyloxy group, a 2-butoxyphenylsulfonyloxy group, a 3-chlorophenylsulfonyloxy group, a 3-trifluoromethylphenylsulfonyloxy group, a 3-cyanophenylsulfonyloxy group, a 3-nitrophenylsulfonyloxy group, a 4-fluorophenylsulfonyloxy group, a 4-cyanophenylsulfonyloxy group, a 4-methoxyphenylsulfonyloxy group, a 4-methylsulfanylphenylsulfonyloxy group, a 4-phenylsulfanylphenylsulfonyloxy group, and a 4-dimethylaminophenylsulfonyloxy group are included.

As the alkylsulfonyl group, an alkylsulfonyl group having 1 to 20 carbon atoms is included and, for example, a methylsulfonyl group, an ethylsulfonyl group, a propylsulfonyl group, an isopropylsulfonyl group, a butylsulfonyl group, a hexylsulfonyl group, a cyclohexylsulfonyl group, an octylsulfonyl group, a 2-ethylhexylsulfonyl group, a decanoylsulfonyl group, a dodecanoylsulfonyl group, an octadecanoylsulfonyl group, a cyanomethylsulfonyl group, a methoxymethylsulfonyl group, and a perfluoroalkylsulfonyl group are included.

As the arylsulfonyl group, an arylsulfonyl group having 6 to 30 carbon atoms is included and, for example, phenylsulfonyl group, a 1-naphthylsulfonyl group, a 2-naphthylsulfonyl group, a 2-chlorophenylsulfonyl group, a 2-methylphenylsulfonyl group, a 2-methoxyphenylsulfonyl group, a 2-butoxyphenylsulfonyl group, a 3-chlorophenylsulfonyl group, a 3-trifluoromethylphenylsulfonyl group, a 3-cyano-phenylsulfonyl group, a 3-nitrophenylsulfonyl group, a 4-fluorophenylsulfonyl group, a 4-cyanophenylsulfonyl group, a 4-methoxyphenylsulfonyl group, a 4-methylsulfanylphenylsulfonyl group, a 4-phenylsulfanylphenylsulfonyl group, and a 4-dimethylaminophenylsulfonyl group are included.

As the alkylthio group, an alkylthio group having 1 to 30 carbon atoms is included and, for example, a methylthio group, an ethylthio group, a propylthio group, a n-butylthio group, a trifluoromethylthio group, a hexylthio group, a t-butylthio group, a 2-ethylhexylthio group, a cyclohexylthio group, a decylthio group, and an dodecylthio group are included.

As the arylthio group, an arylthio group having 6 to 30 carbon atoms is included and, for example, a phenylthio group, a 1-naphthylthio group, a 2-naphthylthio group, a tolylthio group, a methoxyphenylthio group, a naphthylthio group, a chlorophenylthio group, a trifluoromethylphenylthio group, a cyanophenylthio group, and a nitrophenylthio group are included.

As the heterocyclic group, an aromatic or an aliphatic heterocyclic group containing a nitrogen atom, an oxygen atom, a sulfur atom, or a phosphorus atom, is preferably included. Examples of the heterocyclic group include a thienyl group, a benzo[b]thienyl group, a naphtho[2,3-b]thienyl group, a thianthrenyl group, a furyl group, a pyranyl group, an isobenzofuranyl group, a chromenyl group, a xanthenyl group, a phenoxathiinyl group, a 2H-pyrrolyl group, a pyrrolyl group, an imidazolyl group, a pyrazolyl group, a pyridyl group, a pyrazinyl group, a pyrimidinyl group, a pyridazinyl group, an indolizinyl group, an isoindolyl group, a 3H-indolyl group, an indolyl group, a 1H-indazolyl group, a purinyl group, a 4H-quinolizinyl group, an isoquinolyl group, a quinolyl group, a phthalazinyl group, a naphthyridinyl group, a quinoxalinyl group, a quinazolinyl group, a cinnolinyl group, a pteridinyl group, a 4aH-carbazolyl group, a carbazolyl group, a β-carbolinyl group, a phenanthridinyl group, an acridinyl group, a perimidinyl group, a phenanthrolinyl group, a phenazinyl group, a phenarsazinyl group, an isothiazolyl group, a phenothiazinyl group, an isoxazolyl group, a furazanyl group, a phenoxazinyl group, an isochromanyl group, a chromanyl group, a pyrrolidinyl group, a pyrrolinyl group, an imidazolidinyl group, an imidazolinyl group, a pyrazolidinyl group, a pyrazolinyl group, a piperidyl group, a piperazinyl group, an indolinyl group, an isoindolinyl group, a quinuclidinyl group, a tetrahydropyrimidinyl group, a tetrahydro-2-pyrimidinonyl group, a triazinyl group, a morpholinyl group, and a thioxanthonyl group.

In the general formula (9) described above, B represents a cyclic structure as described above. Examples of the cyclic structure include a cyclic aliphatic group, an aryl group, a group having a heterocyclic structure, and the like.

The cyclic aliphatic group as B may have a monocyclic structure or may have a polycyclic structure. As the cyclic aliphatic group having the monocyclic structure, a cycloalkyl group having a monocyclic structure such as a cyclopentyl group, a cyclohexyl group, and a cyclooctyl group, is preferable. As the cyclic aliphatic group having the polycyclic structure, a cycloalkyl group having a polycyclic structure such as a norbornyl group, a tricyclodecanyl group, a tetracyclodecanyl group, a tetracyclododecanyl group, and an adamantyl group is preferable. Particularly, in a case where a cyclic aliphatic group having a bulky structure which is a six or more-membered ring is employed as B, the diffusion in a film is suppressed in PEB (Post Exposure Bake) process and it is possible to further improve resolving power and EL (exposure latitude).

The aryl group as B, for example is a benzene ring, a naphthalene ring, a phenanthrene ring and an anthracene ring.

A group having the heterocyclic structure as B may have an aromatic property or may not have an aromatic property. As a heteroatom included in this group, a nitrogen atom or an oxygen atom is preferable. Specific examples of the heterocyclic structure include a furan ring, a thiophene ring, a benzofuran ring, a benzothiophene ring, a dibenzofuran ring, a dibenzothiophene ring, an indole ring, a pyridine ring, a piperidine ring, a morpholine ring, and the like. Among these, a furan ring, a thiophene ring, a pyridine ring, a piperidine ring and a morpholine ring are preferable.

B may have a substituent. Examples of the substituent include an alkyl group (may be either linear or branched and preferably 1 to 12 carbon atoms), an alkenyl group (preferably 2 to 12 carbon atoms), an alkynyl group (preferably 2 to 12 carbon atoms), a cycloalkyl group (preferably 3 to 8 carbon atoms), an aryl group (preferably 6 to 14 carbon atoms), a hydroxy group, an alkoxy group, an aryloxy group, an acyl group, a halogen atom and a haloalkyl group. These groups may further have a substituent. Preferred examples of the substituent which B can have include an alkyl group, a cycloalkyl group, an aryl group, a halogen atom, a hydroxy group, an alkoxy group and an acyl group and more preferred examples include an alkyl group, an aryl group, a halogen atom and a hydroxy group.

Specific examples of each substituent described above as the substituent which B can have, include the same as those described above for the above substituent of A.

In the general formula (9) described above, $Y_1$ and $Y_2$ each independently represent a hydrogen atom or a substituent. As this substituent, an alkyl group, an alkenyl group, an alkynyl group, a cycloalkyl group, an aryl group, a halogen group, a haloalkyl group, an alkoxy group, an aryloxy group, an acyl group, an alkoxycarbonyl group, an aryloxycarbonyl group, an alkylsulfonyloxy group, an arylsulfonyloxy group, an alkylsulfonyl group, an arylsulfonyl group, a cyano group, an alkylthio group, an arylthio group and a heterocyclic group are included.

Specific examples of each substituent described above as the substituent of $Y_1$ and $Y_2$, include the same as those described above for the above substituent of A.

In one embodiment in the present invention, $Y_1$ and $Y_2$ are preferably a hydrogen atom, an alkyl group, an alkenyl group, an alkynyl group, a cycloalkyl group, and an acyl group.

In the general formula (9) described above, Z represents a hydrogen atom or a substituent. As this substituent, an alkyl group, an alkenyl group, an alkynyl group, a cycloalkyl group, an aryl group, a haloalkyl group, an alkoxy group, an aryloxy group, an acyl group, an alkoxycarbonyl group, an aryloxycarbonyl group, an alkylsulfonyloxy group, an arylsulfonyloxy group, an alkylsulfonyl group, an arylsulfonyl group, a cyano group, an alkylthio group, an arylthio group and a heterocyclic group are included. These groups may further have a substituent.

Specific examples of each substituent described above as the substituent of Z, include the same as those described above for the above substituent of A.

In one embodiment in the present invention, Z is preferably a hydrogen atom, an alkyl group, a cycloalkyl group, an aryl group and an acyl group and more preferably a hydrogen atom, an alkyl group and an acyl group.

In addition, in one embodiment in the present invention, a sulfonate anion represented by the general formula (9) is preferably represented by the general formula (10).

[Chem. 13]

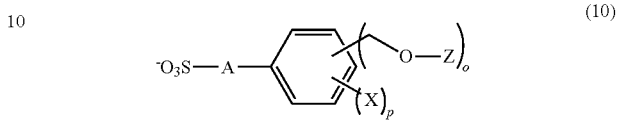

(10)

In the general formula (10), A represents a divalent linking group or a single bond. Z represents a hydrogen atom or a substituent. X represents a substituent. o represents an integer of 1 to 5 and is preferably 2 or 3. p represents an integer of 0 to 4 and is preferably 1. o+p≤5 is also satisfied.

A and Z in the general formula (10) is the same as A and Z in the general formula (9) described above.

In the general formula (10) described above, X includes the same as those described above for the substituent which B in the general formula (9) may have and also the same as the preferred range.

In addition, in one embodiment in the present invention, a sulfonate anion represented by the general formula (9) is more preferably represented by the general formula (11).

[Chem. 14]

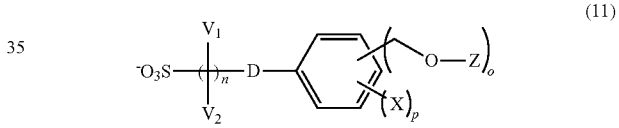

(11)

In the general formula (11) described above, D represents a divalent linking group or a single bond. In addition, Z represents a hydrogen atom or a substituent. X represents a substituent. $V_1$ and $V_2$ represent each independently a hydrogen atom, a fluorine atom and a perfluoroalkyl group. n represents an integer of 1 to 5 and is preferably 1 to 3. o represents an integer of 1 to 5 and is preferably 2 or 3. p represents an integer of 0 to 4 and is preferably 1. o+p≤5 is also satisfied.

In the general formula (11) described above, the divalent linking group represented by D includes —COO—, —OCO—, —CO—, —O—, —S—, —NH—, —SO—, —SO2-, a thiocarbonyl group, —NRCO— (R represents a hydrogen atom, an alkyl group having 1 to 10 carbon atoms or a cycloalkyl group having 6 to 20 carbon atoms), a linear or branched alkylene group (preferably 1 to 10 carbon atoms), a cycloalkylene group (preferably 3 to 10 carbon atoms), and an arylene group (may have a substituent having preferably 6 to 15 carbon atoms and is monocyclic or polycyclic), and may be a combination of a plurality of these groups described above.

Specific examples of the alkylene group, the cycloalkylene group and the arylene group represented by D include the same as specific examples for the each group represented by A in the general formula (9) described above. In addition, these groups may further have a substituent and specific examples of the substituent include the same as specific examples for the substituent which the alkylene group, the cycloalkylene group and the arylene group represented by A in the general formula (9) can have.

In the general formula (11), Z is the same as Z in the general formula (9) described above.

In the general formula (11) described above, X includes the same as those described above for the substituent which B in the general formula (9) may have and also the same as the preferred range.

In one embodiment in the present invention, a sulfonate anion represented by the general formula (9) is most preferably represented by the general formula (12).

[Chem. 15]

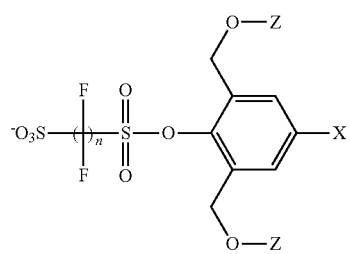

(12)

In the general formula (12) described above, Z represents a hydrogen atom or a substituent. X represents a substituent. n represents an integer of 1 to 5 and is preferably 1 to 3.

In the general formula (12) described above, Z is the same as Z in the general formula (9) described above.

In the general formula (12) described above, X includes the same as those described above for the substituent which B in the general formula (9) may have and also the same as the preferred range.

Specific examples of the organic anions represented by the general formulae (6), (7) and (8) include structures described below.

[Chem. 16]

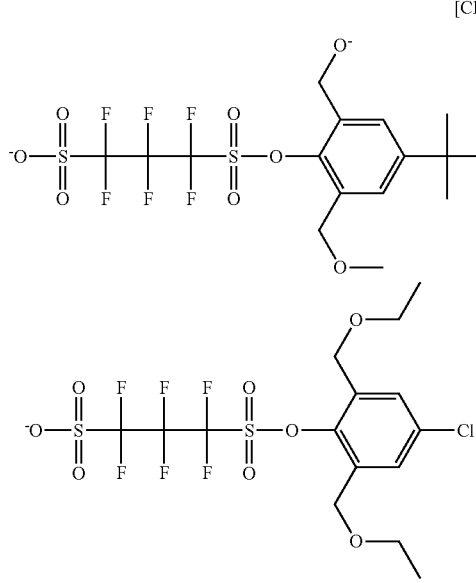

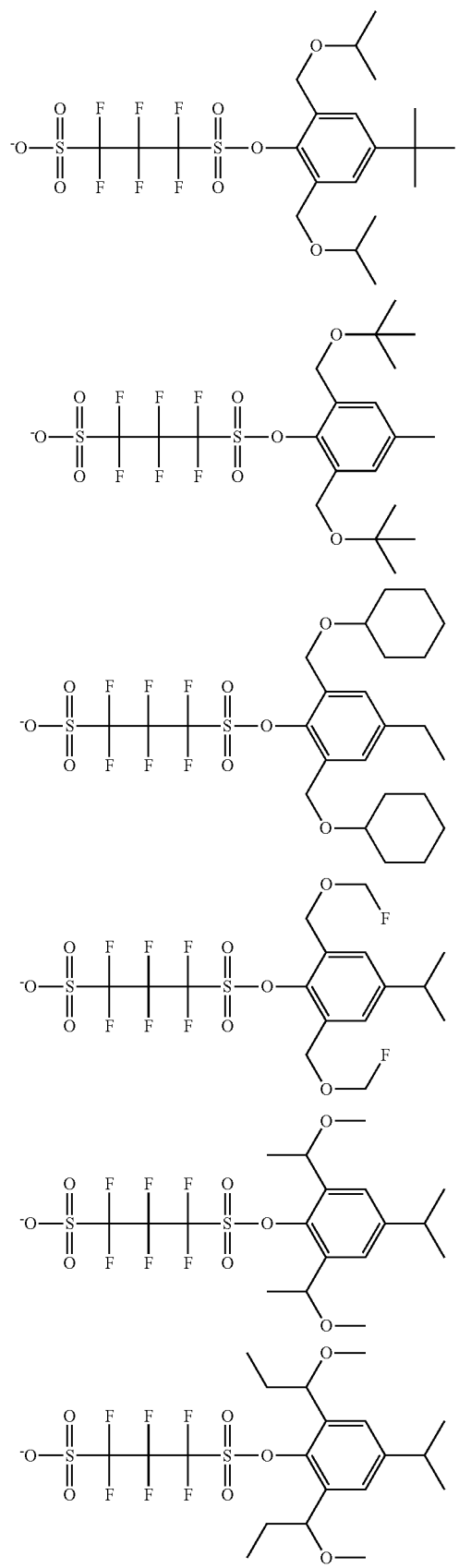

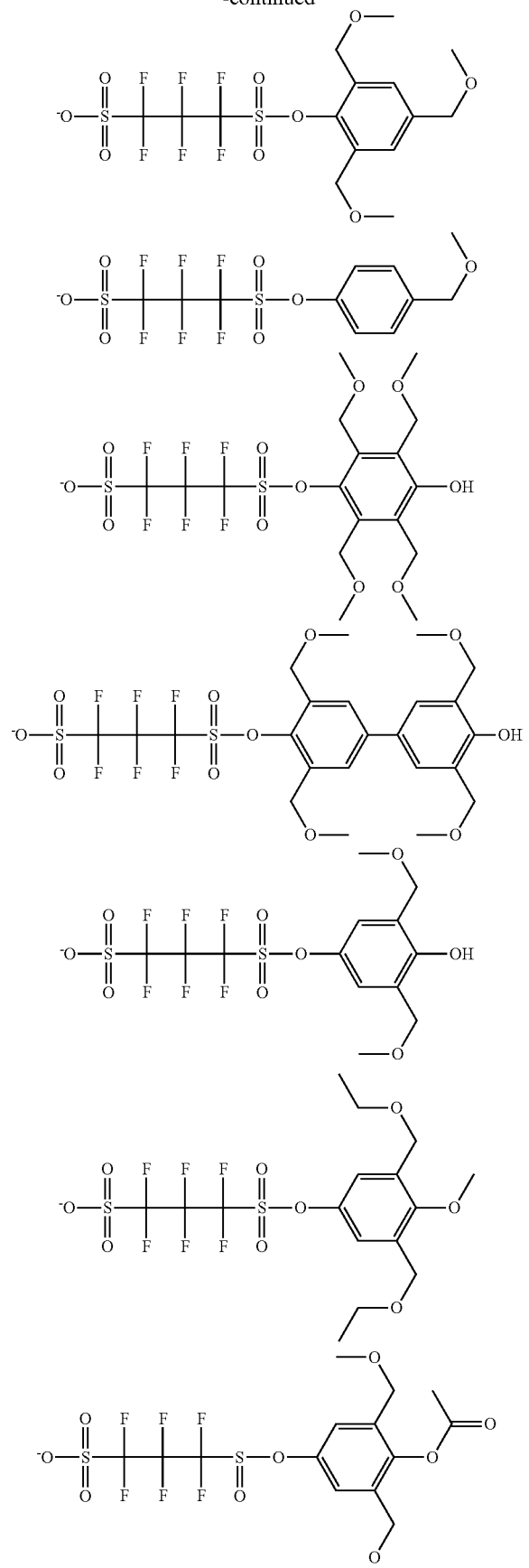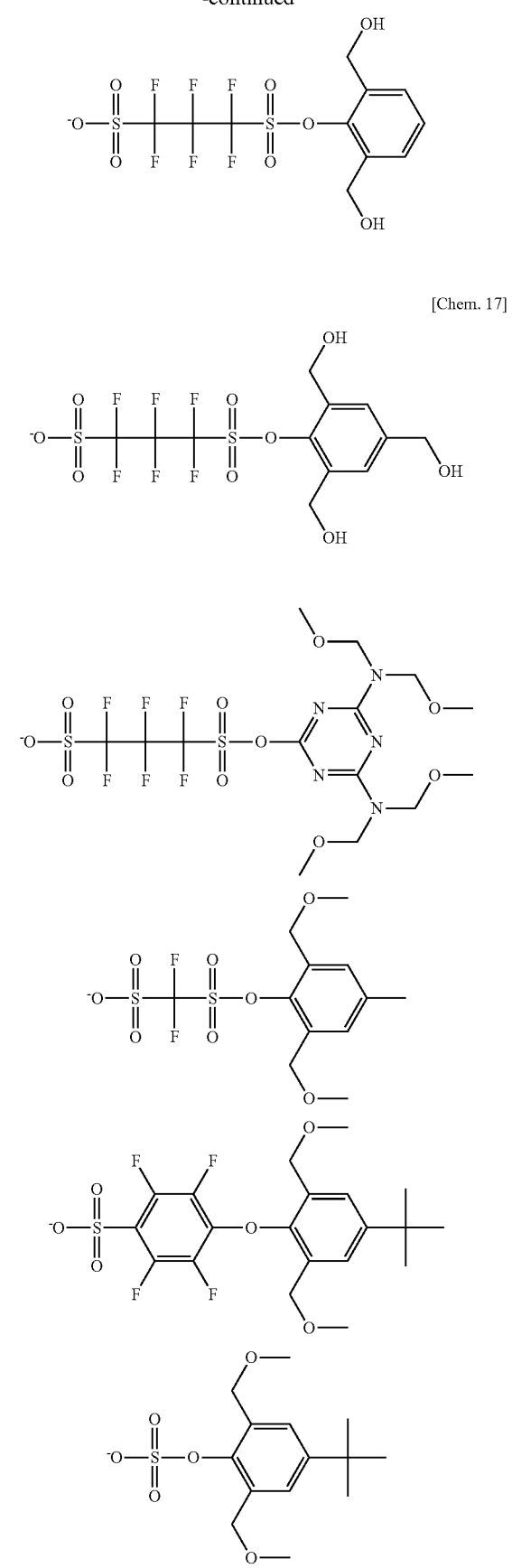

27
-continued
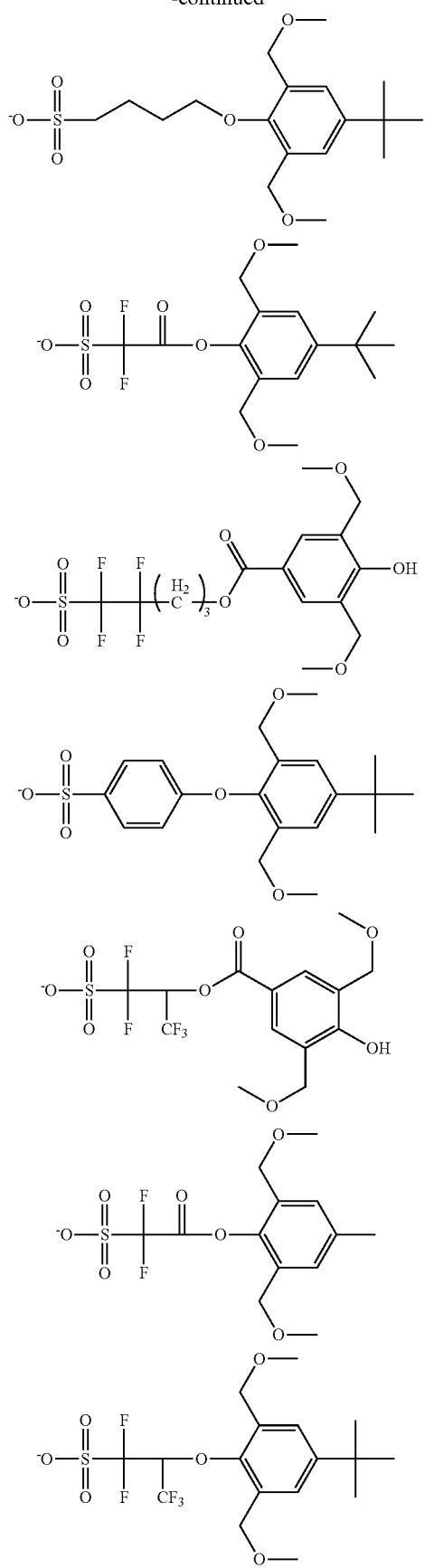
28
-continued
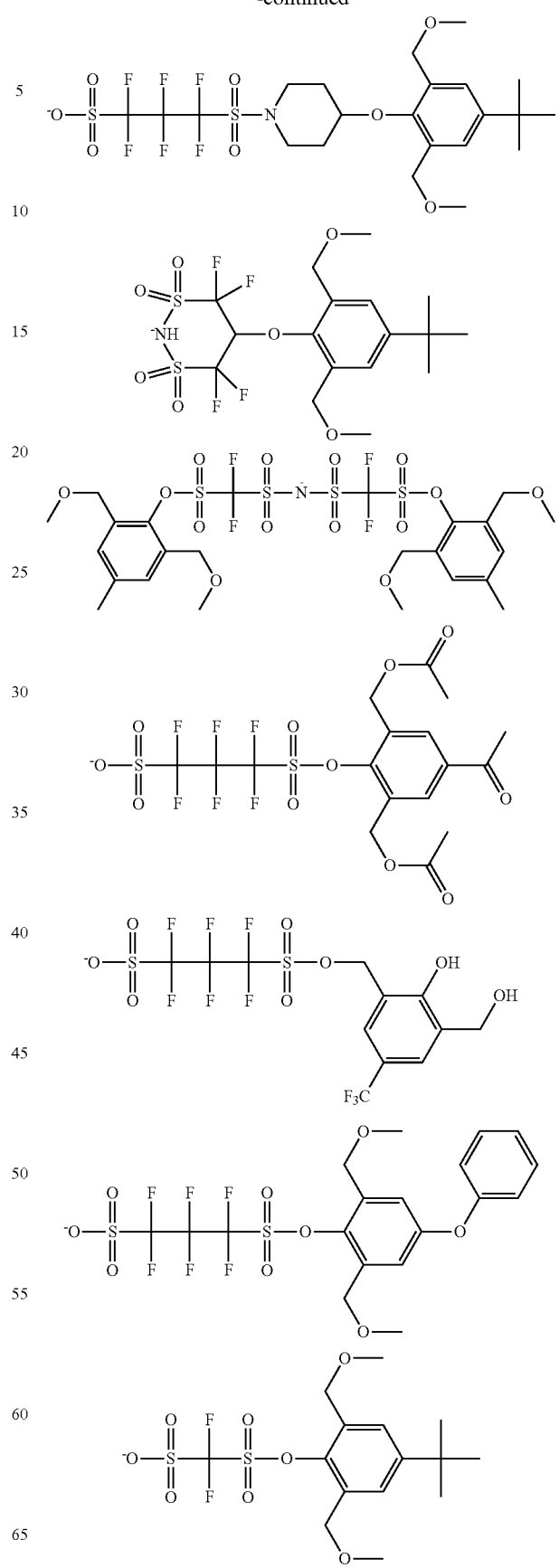

-continued

[Chem. 18]

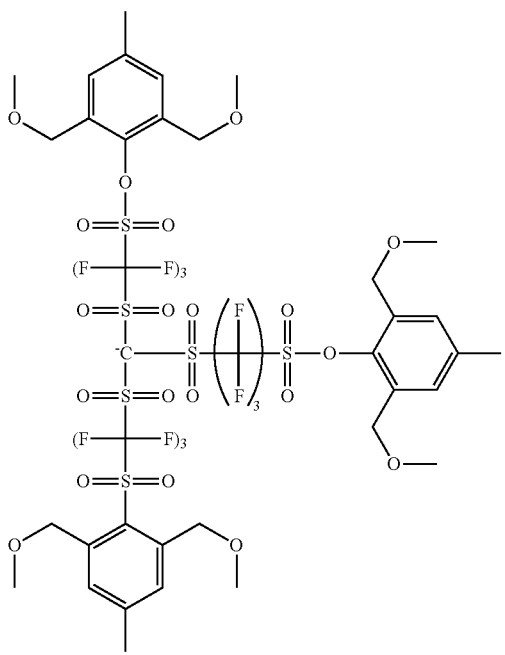

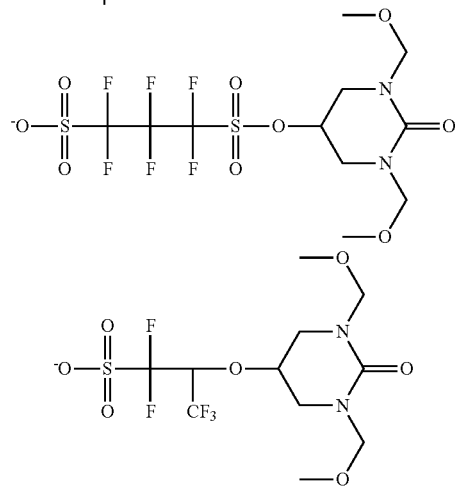

The compound (A), for example, is preferably a sulfonium compound represented by the following general formula (I)

[Chem. 19]

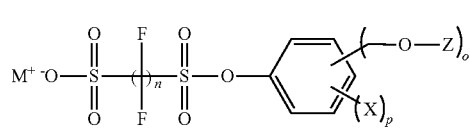

In the formula, M⁺ represents a sulfonium cation.

X represents an alkyl group, a cycloalkyl group, an aryl group, a halogen atom, a hydroxy group, an alkoxy group, an aryloxy group, or an acyl group. These groups may further have a substituent.

Z represents a hydrogen atom, an alkyl group, a cycloalkyl group, an aryl group, or an acyl group. These groups may further have a substituent.

n represents an integer of 1 to 3. o represents an integer of 1 to 5, p represents an integer of 0 to 4 and o+p≤5 is satisfied.

Examples of the sulfonium cation represented by M⁺ include the sulfonium cation represented by the general formula (4) described above.

Specific Examples of the alkyl group, the cycloalkyl group, the aryl group, the halogen atom, the alkoxy group, the aryloxy group, and the acyl group represented by X include the same as the specific examples of each group described above for the substituent which B in the general formula (9) described before may have.

X is preferably an alkyl group, an aryl group, a halogen atom, a hydroxy group or an alkoxy group.

Specific examples of the alkyl group, the cycloalkyl group, the aryl group, and the acyl group represented by Z include the same as the specific examples of each group represented by Z in the general formula (9) described before may have. Z is preferably a hydrogen atom, an alkyl group and an acyl group.

o is preferably 2 or 3 and p is preferably 1.

Next, a preferred oxime compound will be described.

In the present invention, the preferred oxime compound includes a compound represented by the general formula (13).

[Chem. 20]

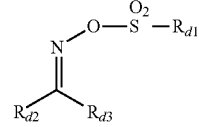

In the general formula (13) described above, $R_{d2}$ and $R_{d3}$ each independently represent an alkyl group, a cycloalkyl group or an aryl group. $R_{d2}$ and $R_{d3}$ may be bonded to each other to form a ring.

$R_{d1}$ represents an organic group. The organic group of $R_{d1}$ is represented by a residue in which sulfonic acid group is removed from the sulfonate anion represented by the general formula (9) described before and is also the same as the preferred range.

Specific examples of the alkyl group, the cycloalkyl group, and the aryl group as $R_{d2}$ and $R_{d3}$ include the same as those of the alkyl group, the cycloalkyl group, and the aryl group described above for A in the general formula (9) and are also the same as the preferred range.

Specific examples of the oxime compound represented by the general formula (13) include, for example, structures described below.

[Chem. 21]

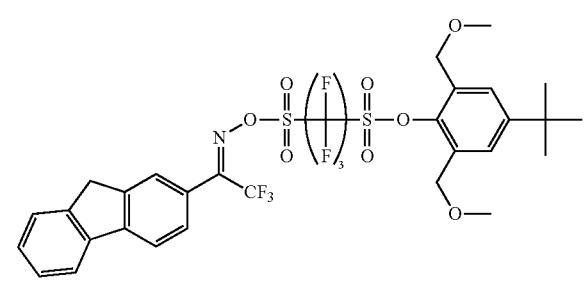

-continued

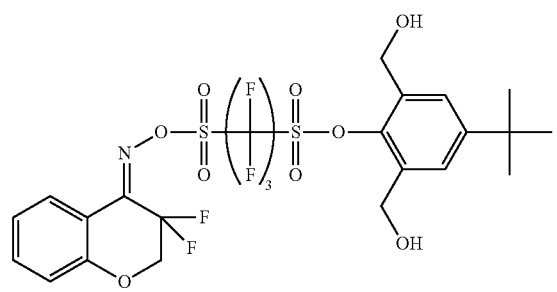
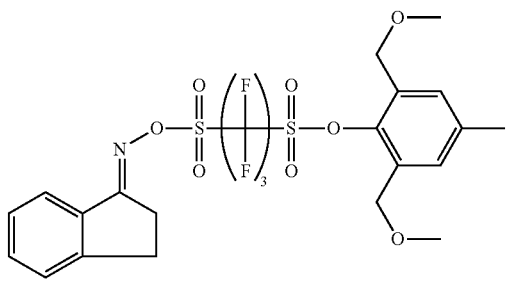
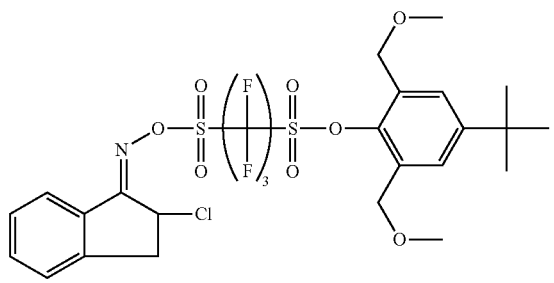
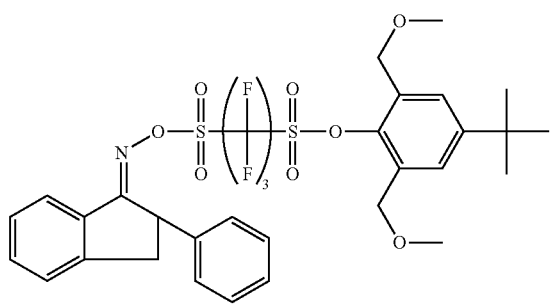
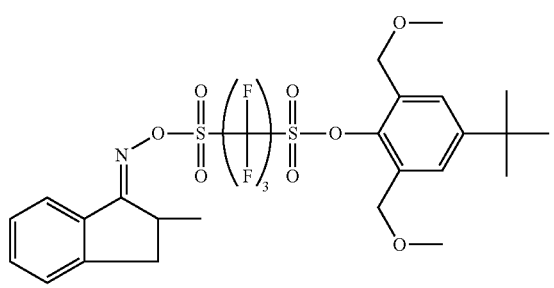
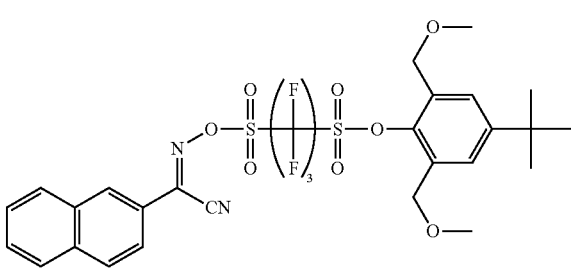

-continued

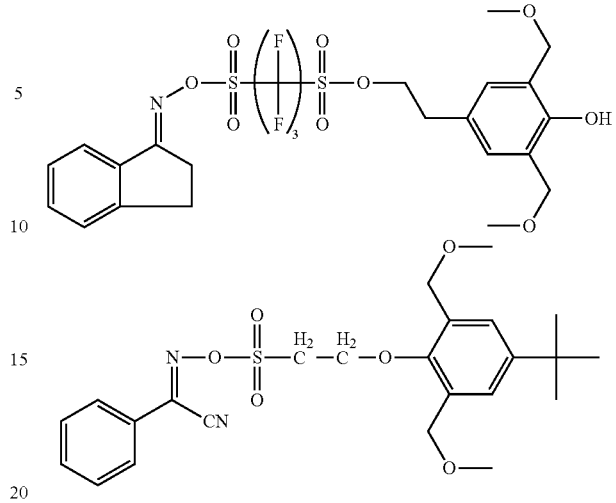

The content of the compound (A) in the composition is preferably 0.1 to 25% by mass, more preferably 0.5 to 20% by mass, and even more preferably 1 to 18% by mass, based on the total solid contents of the composition.

The compound (A) may be used alone or in combination of two or more kinds thereof. In addition, the compound (A) may be used with a compound (D) which is an acid generator described later.

[2] Compound Having a Phenolic Hydroxyl Group

In one embodiment, the composition of the present invention, preferably includes a compound (B1) having a phenolic hydroxyl group (hereinafter also referred to as a compound (B1)).

A phenolic hydroxyl group in the present invention is a group in which a hydrogen atom in an aromatic ring group is substituted with a hydroxy group. An aromatic ring of the aromatic ring group is monocyclic or polycyclic aromatic ring and includes a benzene ring, a naphthalene ring, or the like.

According to the composition having the compound (B1) in the present invention, the cross-linking reaction of the compound having a phenolic hydroxyl group (B1) and an acid cross-linking agent (C) described later proceeds by the action of an acid generated from the compound (A) by irradiation with actinic rays or radiation at exposed portion to form a negative-tone pattern. Particularly, in a case where the compound (A) has a structure in which the generated acid includes two or more methylol groups in a molecule, since a plurality of methylol groups contained in the compound (A) also contributes to the cross-linking reaction along with the cross-linking reaction of the compound (B1) and the cross-linking agent (C), dry etching resistance, sensitivity and solving power are further improved.

The compound (B1) having a phenolic hydroxyl group is not particularly limited as long as the compound has a phenolic hydroxyl group, may be relatively low molecular weight compound such as a molecular resist and may be a polymer compound. Here, as the molecular resist, for example, a low molecular weight cyclic polyphenol compound and the like described in JP2009-173623A and JP2009-173625A can be used.

The compound having a phenolic hydroxyl group (B1) is preferably a polymer compound from the viewpoint of the reactivity and sensitivity.

In a case where the compound having a phenolic hydroxyl group (B1) in the present invention is a polymer compound, the polymer compound preferably includes at least one kind of repeating unit having a phenolic hydroxyl group. The repeating unit having a phenolic hydroxyl group is not particularly limited, however, a repeating unit represented by the following general formula (1) is preferable.

[Chem. 22]

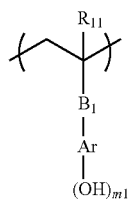

(1)

In the general formula (1), $R_{11}$ represents a hydrogen atom, a methyl group which may have a substituent, or a halogen atom;

$B_1$ represents a single bond or a divalent linking group;

Ar represents an aromatic ring; and m1 represents an integer of 1 or more.

As a methyl group which may have a substituent in $R_{11}$, a trifluoromethyl group, a hydroxymethyl group, and the like are included.

$R_{11}$ is preferably a hydrogen atom or a methyl group and a hydrogen atom is preferable for the reason of developability.

As the divalent linking group of $B_1$, a carbonyl group, an alkylene group (preferably 1 to 10 carbon atoms and more preferably 1 to 5), a sulfonyl group (—S(=O)$_2$—), —O—, —NH— or a divalent linking group in combination thereof is preferable.

$B_1$ preferably represents a single bond, a carbonyloxy group (—C(=O)—O—), or —C(=O)—NH—, more preferably represents a single bond, a carbonyloxy group (—C(=O)—O—), and is particularly preferably a single bond from the viewpint of the improvement of dry etching resistance.

An aromatic ring of Ar is monocyclic or polycyclic aromatic ring, and includes an aromatic hydrocarbon ring having 6 to 18 carbon atoms such as a benzene ring, a naphthalene ring, an anthracene ring, a fluorene ring or a phenanthrene ring, which may have a substituent or, for example, an aromatic ring heterocycle having a heterocycle such as a thiophene ring, a furan ring, a pyrrole ring, a benzothiophene ring, a benzofuran ring, a benzopyrrole ring, a triazine ring, a imidazole ring, a benzoimidazole ring, a triazole ring, a thiadiazole ring or a thiazole ring. Among these, a benzene ring and a naphthalene ring are preferable from the viewpoint of resolution and a benzene ring is most preferable from the viewpoint of sensitivity.

m1 is preferably an integer of 1 to 5, and most preferably 1. When m1 is 1 and Ar is a benzene ring, the position of substitution of —OH may be the para-position, the meta-position, or the ortho-position with respect to the bonding position of a benzene ring to $B_1$ (a polymer main chain when $B_1$ is a single bond), however from the viewpoint of cross-linking reactivity, the para-position and the meta-position are preferred, and the para-position is more preferred.

The aromatic ring of Ar may also have a substituent other than a group represented by —OH described above, and examples of the substituent include an alkyl group, a cycloalkyl group, a halogen atom, a hydroxyl group, an alkoxy group, a carboxyl group, an alkoxycarbonyl group, an alkylcarbonyl group, an alkylcarbonyloxy group, an alkylsulfonyloxy group, and an arylcarbonyl group.

The repeating unit having a phenolic hydroxyl group is more preferably a repeating unit represented by the following general formula (2) for the reasons of cross-linking reactivity, developability and dry etching resistance.

[Chem. 23]

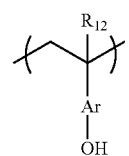

(2)

In the general formula (2), $R_{12}$ represents a hydrogen atom or a methyl group;

Ar represents an aromatic ring; and $R_{12}$ represents a hydrogen atom or a methyl group and is preferably a hydrogen atom for the reason of developability.

Ar in the general formula (2) is the same as Ar in the general formula (1) and the same as the preferred range. The repeating unit represented by the general formula (2) is preferably a repeating unit which is induced from hydroxystyrene (that is, in the general formula (2), a repeating unit wherein $R_{12}$ is a hydrogen atom and Ar is a benzene ring) from the viewpoint of sensitivity.

The compound (B1) as a polymer compound may be configured from only a repeating unit having a phenolic hydroxyl group as described above. The compound (B1) as a polymer compound may have a repeating unit as described later other than a repeating unit having a phenolic hydroxyl group as described above. In this case, the content of the repeating unit having a phenolic hydroxyl group is preferably from 10 to 98% by mol, more preferably from 30 to 97% by mol, and even more preferably from 40 to 95% by mass, with respect to the total repeating units of the compound (B1) as a polymer compound. Thereby, particularly in a case where the resist film is a thin film (for example, in a case where the thickness of the resist film is from 10 to 150 nm), the dissolution rate of the exposed portion in the resist film of the present invention formed by using the compound (B1) with respect to an alkali developer can be more reliably decreased (that is the dissolution rate of the resist film using the compound (B1) can be more reliably controlled to be optimal). As a result, sensitivity can be more reliably increased.

Hereinafter, examples of the repeating unit having a phenolic hydroxyl group will be described, but the present invention is not limited thereto.

[Chem. 24]

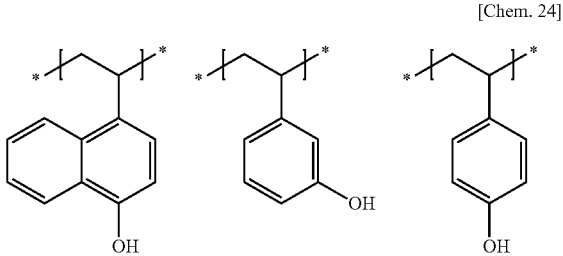

35
-continued
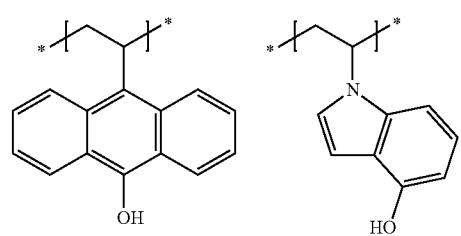
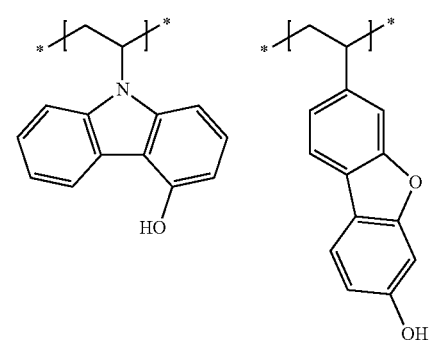
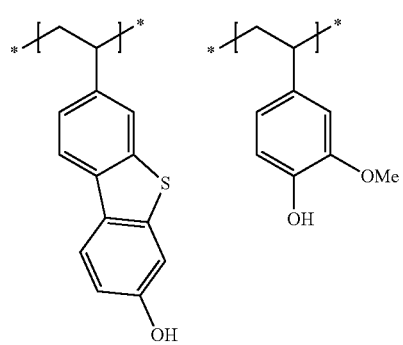
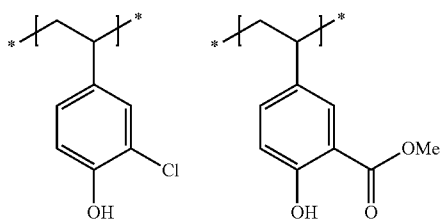
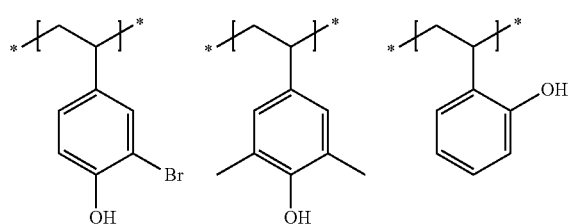
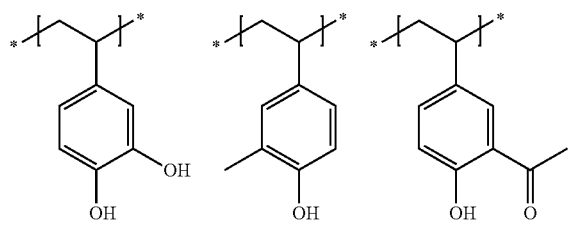
36
-continued
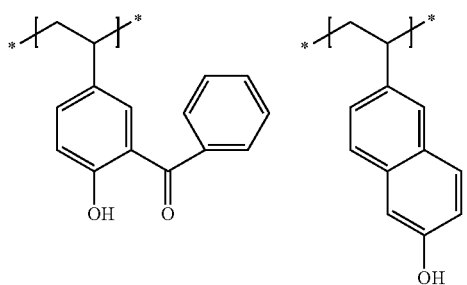
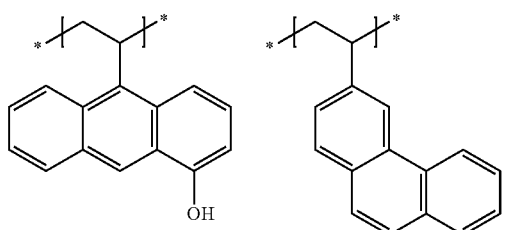
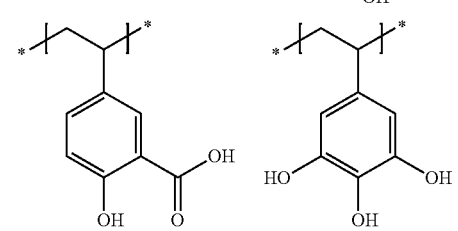
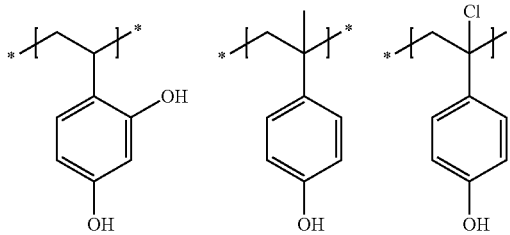
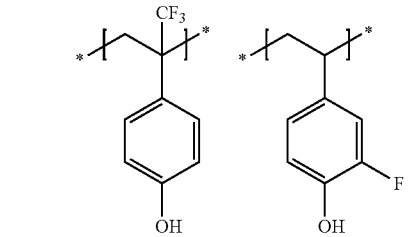
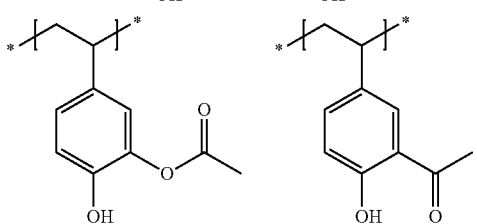
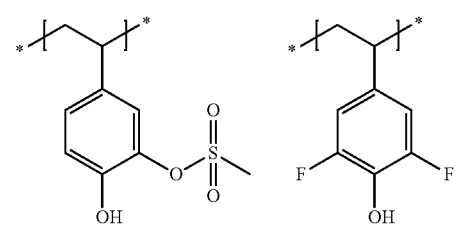

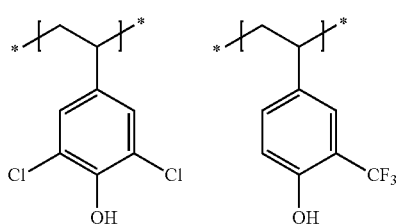
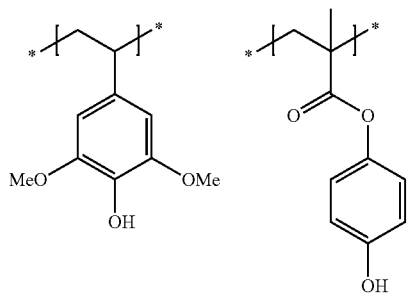
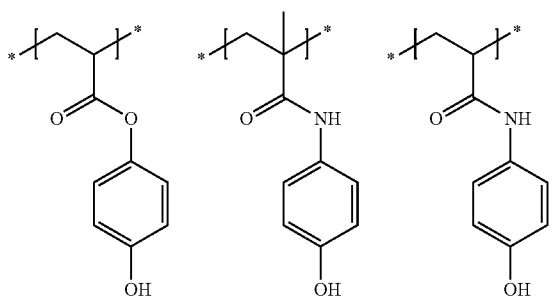
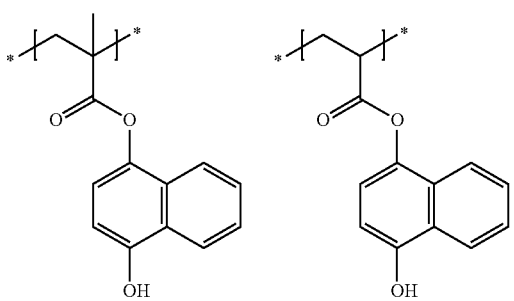
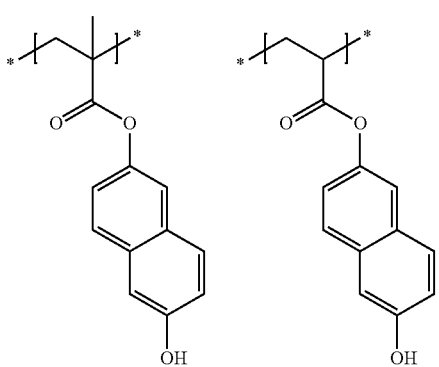
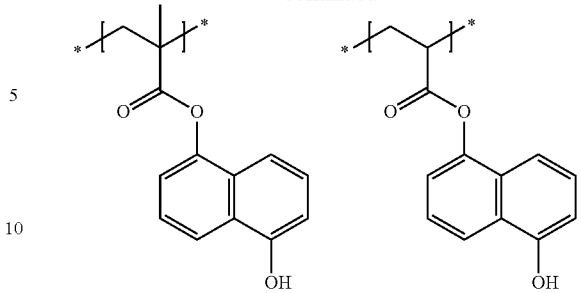

The compound (B1) preferably have a structure in which a hydrogen atom of a phenolic hydroxyl group is substituted with a group having an acid-non-decomposable polycyclic aliphatic hydrocarbon structure due to obtaining the high glassy-transition temperature (Tg) and becoming excellent dry etching resistance.

By the compound (B1) having the specific structure described before, the glassy-transition temperature (Tg) of the compound (B1) becomes higher, and it is possible to form a very hard resist film and to control the diffusion of an acid and dry etching resistance. Therefore, since the diffusion of an acid is highly controlled at the exposed portion of actinic rays or radiation such as an electron beam or extreme ultraviolet rays, resolving power, a pattern shape and LER in a fine pattern are further improved. In addition, since the compound (B1) has an acid-non-decomposable polycyclic aliphatic hydrocarbon structure, it is considered that this contributes to further improve dry etching resistance. Also, although the details are not clearly understood, it is speculated that since the polycyclic aliphatic hydrocarbon structure has a high hydrogen radical donating property and serves as a hydrogen source at the time of the decomposition of the compound (A) which is a photo-acid generator or (D) a compound which generates an acid by irradiation with actinic rays or radiation described later, the decomposition efficiency of the photo-acid generator is further improved and the acid generation efficiency is further increased, and it is considered that this contributes to further excellent sensitivity.

In the specific structure described before in which the compound (B1) according to the present invention may have, an aromatic ring such as a benzene ring and a group having an acid-non-decomposable polycyclic aliphatic hydrocarbon structure are linked through an oxygen atom derived from a phenolic hydroxyl group. As described before, the structure not only contributes high dry etching resistance but also can increase the glassy-transition temperature (Tg) of the compound (B1), and it is speculated that higher resolving power is provided due to the effect of this combination.

In the present invention, acid-non-decomposable means the property in which the decomposition reaction dose not occur by an acid generated by the compound (A) and (D) a compound which generates an acid by irradiation with actinic rays or radiation described later.

More specifically, a group having an acid-non-decomposable polycyclic aliphatic hydrocarbon structure is preferably a group which is stable with respect to an acid and an alkali. A group which is stable with respect to an acid and an alkali means a group which does not show acid-decomposable and alkali-decomposable. Here, acid-decomposable means the property in which the decomposition reaction occurs by the action of an acid generated by the compound (A) and (D) a compound which generates an acid by irradiation with actinic rays or radiation described later and as a group showing acid-decomposable, an acid-decomposable group described in "a repeating unit having an acid-decomposable group" described later is included.

In addition, alkali-decomposable means the property in which the decomposition reaction occurs by the action of an alkali developer, and as a group showing alkali-decomposable, a group which is included in a resin suitably used in a positive-tone chemically amplified-type resist composition and is capable of decomposing by the action of a well-known alkali developer in the related art to increase the dissolution rate into an alkali developer (for example, a group having a lactone structure, and the like) is included.

The group having a polycyclic aliphatic hydrocarbon structure is not particularly limited as long as the group is a monovalent group having a polycyclic aliphatic hydrocarbon structure, but 5 to 40 carbon atoms in total are preferred and 7 to 30 are more preferred. The polycyclic aliphatic hydrocarbon structure may have an unsaturated bond in a ring.

The polycyclic aliphatic hydrocarbon structure in the group having the polycyclic aliphatic hydrocarbon structure means a structure having a plurality of monocyclic-type aliphatic hydrocarbon group or a polycyclic-type aliphatic hydrocarbon structure, and may be a bridged-type. As the monocyclic-type aliphatic hydrocarbon group, a cycloalkyl group having 3 to 8 carbon atoms is preferable, for example, a cyclopropyl group, a cyclopentyl group, a cyclohexyl group, a cyclobutyl group, a cyclooctyl group, and the like are included and the structure having a plurality of monocyclic-type aliphatic hydrocarbon group has a plurality of these groups. The structure having a plurality of monocyclic-type aliphatic hydrocarbon group preferably has 2 to 4 monocyclic-type aliphatic hydrocarbon groups and particularly preferably has 2.

As the polycyclic-type aliphatic hydrocarbon structure, a bicyclo structure, a tricyclo structure, a tetracyclo structure, and the like having 5 or more carbon atoms are included, a polycyclic cyclo structure having 6 to 30 carbon atoms is preferable and, for example, an adamantane structure, a decaline structure, a norbornane structure, a norbornane structure, a cedrol structure, a isobornane structure, a bornane structure, a dicyclopentane structure, an α-pinene structure, a tricyclodecane structure, a tetracyclododecane structure, or an androstane structure is included. Here, the part of carbon atoms in a monocyclic or polycyclic cycloalkyl group may be substituted with a heteroatom such as an oxygen atom.

Preferred examples of the polycyclic aliphatic hydrocarbon structure described above include an adamantane structure, a decaline structure, a norbornane structure, a norbornane structure, a cedrol structure, a structure having a plurality of cyclohexyl groups, a structure having a plurality of cycloheptyl groups, a structure having a plurality of cyclooctyl groups, a structure having a plurality of cyclodecanyl groups, a structure having a plurality of cyclododecanyl groups and a tricyclodecane structure, and an adamantane structure is most preferable from the viewpoint of dry etching resistance (that is, the group having an acid-non-decomposable polycyclic aliphatic hydrocarbon structure described above is most preferably a group having an acid-non-decomposable adamantane structure).

The chemical formulae of these polycyclic aliphatic hydrocarbon structures (as for structures having a plurality of monocyclic-type aliphatic hydrocarbon groups, monocyclic-type aliphatic hydrocarbon structures corresponding to the monocyclic-type aliphatic hydrocarbon groups (specifically, the structures of the following formulae (47) to (50))) are shown below.

[Chem. 25]

(1)

(2)

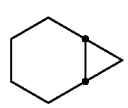
(3)

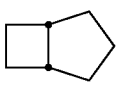
(4)

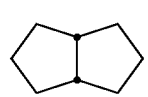
(5)

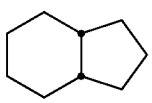
(6)

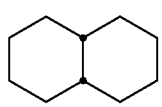
(7)

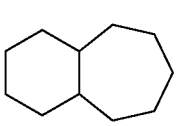
(8)

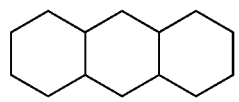
(9)

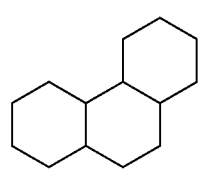
(10)

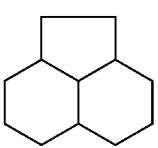
(11)

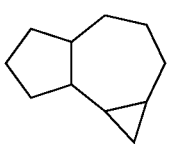
(12)

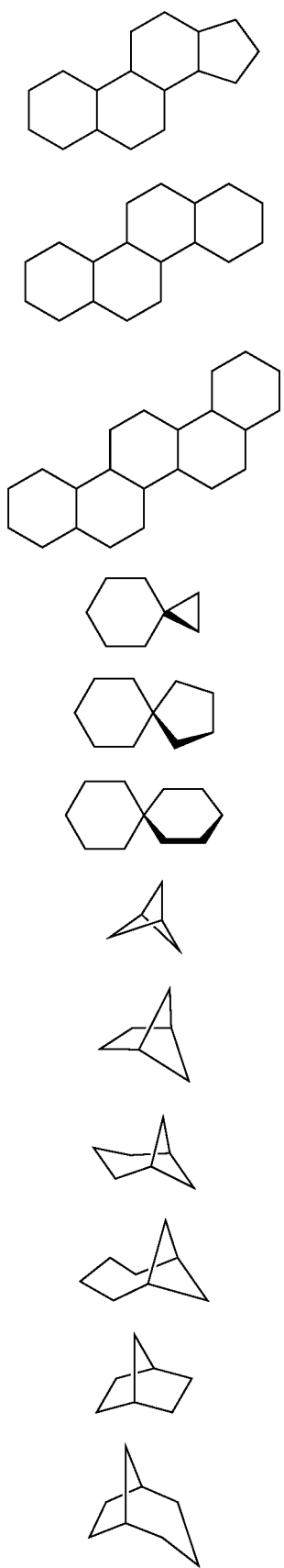
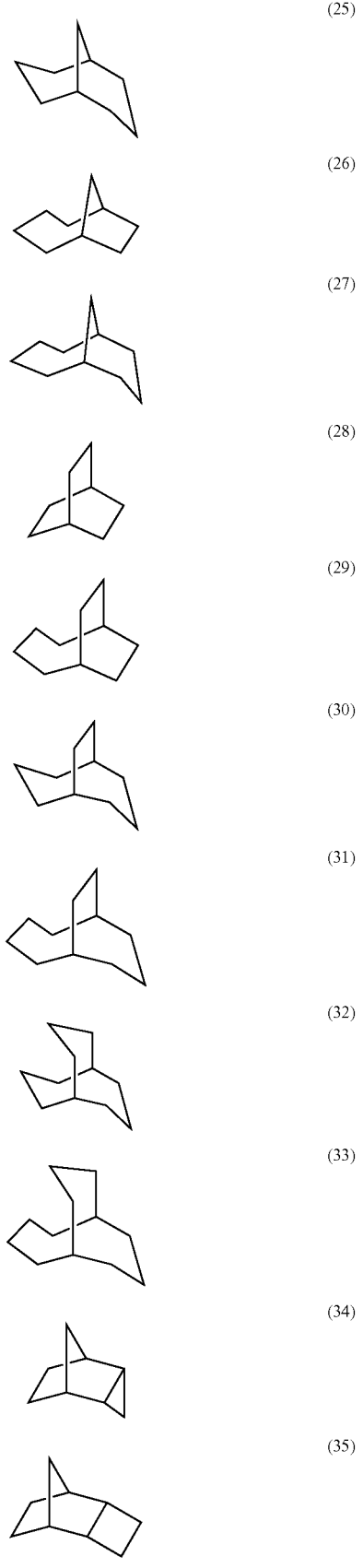

(36) 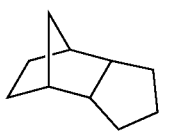

(37) 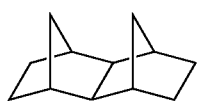

(38) 

(39) 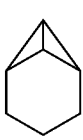

(40) 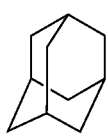

(41) 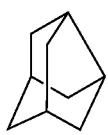

(42) 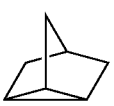

(43) 

(44) 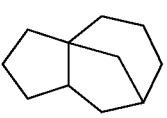

(45) 

(46) 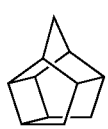

(47) 

(48) 

(49) 

(50) 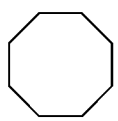

(51) 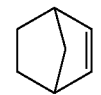

Furthermore, the polycyclic aliphatic hydrocarbon structure may have a substituent, examples of the substituent include an alkyl group (preferably 1 to 6 carbon atoms), a cycloalkyl group (preferably 3 to 10 carbon atoms), an aryl group (preferably 6 to 15 carbon atoms), a halogen atom, a hydroxyl group, an alkoxy group (preferably 1 to 6 carbon atoms), a carboxyl group, a carbonyl group, a thiocarbonyl group, an alkoxycarbonyl group (preferably 2 to 7 carbon atoms) and a group formed by a combination of these groups (preferably 1 to 30 carbon atoms in total and more preferably 1 to 15 carbon atoms in total).

The polycyclic aliphatic hydrocarbon structure is preferably a structure represented by any of the formulae (7), (23), (40), (41), and (51) and a structure having two monovalent groups in which arbitrary one hydrogen atom is set as a combined hand in a structure in the formula (48), is more preferably a structure represented by any of the formulae (23), (40), and (51) and a structure having two monovalent groups in which arbitrary one hydrogen atom is set as a combined hand in a structure in the formula (48), and most preferably a structure represented by the formula (40).

The group having the polycyclic aliphatic hydrocarbon structure is preferably a monovalent group in which arbitrary one hydrogen atom is set as a combined hand in the polycyclic aliphatic hydrocarbon structure.

The structure in which a hydrogen atom of a phenolic hydroxyl group is substituted with a group having an acid-non-decomposable polycyclic aliphatic hydrocarbon structure described before is preferably included in the compound (B1) as a polymer compound, as a repeating unit having the structure in which a hydrogen atom of a phenolic hydroxyl group is substituted with a group having an acid-non-decomposable polycyclic aliphatic hydrocarbon structure described before and more preferably included in the compound (B1) as a repeating unit represented by the following general formula (3).

[Chem. 26]

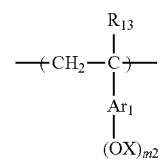

(3)

In the formula (3),
$R_{13}$ represents a hydrogen atom or a methyl group;
X represents a group having an acid-non-decomposable polycyclic aliphatic hydrocarbon structure;

Ar₁ represents an aromatic ring; and m2 is an integer of 1 or more.

In the formula (3), $R_{13}$ represents a hydrogen atom or a methyl group, but a hydrogen atom is particularly preferred.

Examples of the aromatic ring of Ar₁ in the general formula (3) include an aromatic hydrocarbon ring having 6 to 18 carbon atoms such as a benzene ring, a naphthalene ring, an anthracene ring, a fluorene ring or a phenanthrene ring, which may have a substituent or, for example, an aromatic ring heterocycle having a heterocycle such as a thiophene ring, a furan ring, a pyrrole ring, a benzothiophene ring, a benzofuran ring, a benzopyrrole ring, a triazine ring, a imidazole ring, a benzoimidazole ring, a triazole group, a thiadiazole ring, or a thiazole ring. Among these, a benzene ring and a naphthalene ring are preferred from the viewpoint of resolution and a benzene ring is most preferred.

The aromatic ring of Ar₁ may also have a substituent other than a group represented by —OX described above, and examples of the substituent include an alkyl group (preferably 1 to 6 carbon atoms), a cycloalkyl group (preferably 3 to 10 carbon atoms), an aryl group (preferably 6 to 15 carbon atoms), a halogen atom, a hydroxyl group, an alkoxy group (preferably 1 to 6 carbon atoms), a carboxyl group and an alkoxycarbonyl group (preferably 2 to 7 carbon atoms), an alkyl group, an alkoxy group and an alkoxycarbonyl group are preferred and an alkoxy group is more preferred.

X represents a group having an acid-non-decomposable polycyclic aliphatic hydrocarbon structure. Specific examples and the preferred range of the group having the acid-non-decomposable polycyclic aliphatic hydrocarbon structure represented by X are the same as those described above. X is more preferably a group represented by —Y—X₂ in the general formula (4) described later.

m2 is preferably an integer of 1 to 5, and most preferably 1. When m2 is 1 and Ar₁ is a benzene ring, the position of substitution of —OX may be the para-position, the meta-position, or the ortho-position with respect to the bonding position of a benzene ring to a polymer main chain, however, the para-position or the meta-position is preferred, and the para-position is more preferred.

In the present invention, the repeating unit represented by the general formula (3) described above is preferably a repeating unit represented by the following general formula (4).

By using the polymer compound (B1) having the repeating unit represented by the general formula (4), since Tg of the polymer compound (B1) becomes higher and a very hard resist film is formed, it is possible to more reliably control the diffusion of an acid and dry etching resistance.

[Chem. 27]

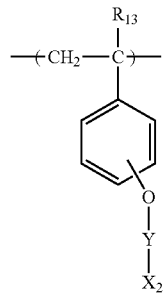

(4)

In the formula (4), $R_{13}$ represents a hydrogen atom or a methyl group;

Y represents a single bond or a divalent connecting group; and

X₂ represents an acid-non-decomposable polycyclic aliphatic hydrocarbon group.

As for the repeating unit represented by the general formula (4), preferred examples used in the present invention will be described below.

In the formula (4), $R_{13}$ represents a hydrogen atom or a methyl group, but a hydrogen atom is particularly preferred.

In the formula (4), Y is preferably a divalent linking group. Preferred groups as a divalent linking group of Y are a carbonyl group, a thiocarbonyl group, an alkylene group (preferably 1 to 10 carbon atoms and more preferably 1 to 5 carbon atoms), a sulfonyl group, —COCH₂—, —NH— or a divalent linking group formed by a combination of these groups (preferably 1 to 20 carbon atoms in total and more preferably 1 to 10 carbon atoms in total), a carbonyl group, —COCH₂—, a sulfonyl group, —CONN— and CSNH are more preferable, a carbonyl group and —COCH₂— are even more preferable, and a carbonyl group is particularly preferable.

X₂ represents a polycyclic aliphatic hydrocarbon group and acid-non-decomposable. Total carbon atoms in the polycyclic aliphatic hydrocarbon group are preferably 5 to 40 and are more preferably 7 to 30. The polycyclic aliphatic hydrocarbon group may have an unsaturated bond in a ring.

Such a polycyclic aliphatic hydrocarbon group is a group having a plurality of monocyclic-type aliphatic hydrocarbon group or a polycyclic-type aliphatic hydrocarbon group, and may be a bridged-type. As the monocyclic-type aliphatic hydrocarbon group, a cycloalkyl group having 3 to 8 carbon atoms is preferable, for example, a cyclopropyl group, a cyclopentyl group, a cyclohexyl group, a cyclobutyl group, a cyclooctyl group, and the like are included and a plurality of these groups are included. The group having a plurality of monocyclic-type aliphatic hydrocarbon group preferably has 2 to 4 monocyclic-type aliphatic hydrocarbon groups and particularly preferably has 2.

As the polycyclic-type aliphatic hydrocarbon group, a group having a bicyclo structure, a tricyclo structure, a tetracyclo structure, and the like having 5 or more carbon atoms are included, a group having a polycyclic cyclo structure having 6 to 30 carbon atoms is preferable and, for example, an adamantyl group, a norbornyl group, a norbornenyl group, an isobornyl group, a camphanyl group, a dicyclopentyl group, an α-pinel group, a tricyclodecanyl group, a tetracyclododecyl group, or an androstanyl group is included. Here, the part of carbon atoms in a monocyclic or polycyclic cycloalkyl group may be substituted with a heteroatom such as an oxygen atom.

The polycyclic-type aliphatic hydrocarbon group of X₂ is preferably an adamantyl group, a decaline group, a norbornyl group, a norbornenyl group, a cedrol group, a group having a plurality of cyclohexyl groups, a group having a plurality of cycloheptyl groups, a group having a plurality of cyclooctyl groups, a group having a plurality of cyclodecanyl groups, a group having a plurality of cyclododecanyl groups and a tricyclodecanyl group, and an adamantyl group is most preferable from the viewpoint of dry etching resistance. The chemical formula of the polycyclic aliphatic hydrocarbon structure in the polycyclic-type aliphatic hydrocarbon group of X₂ includes the same as the chemical formula of the polycyclic aliphatic hydrocarbon structure in the group having the polycyclic aliphatic hydrocarbon structure described before, and also the same as the preferred range. The polycyclic aliphatic hydrocarbon group of X₂ includes a monovalent group in which arbitrary one hydrogen atom is set as a combined hand in the polycyclic aliphatic hydrocarbon structure described before.

Furthermore, the aliphatic hydrocarbon group may have a substituent, and the substituent includes the same as those described above for the substituent which the polycyclic aliphatic hydrocarbon structure may have.

The position of substitution of —O—Y—X$_2$ in the general formula (4) may be the para-position, the meta-position, or the ortho-position with respect to the bonding position of a benzene ring to a polymer main chain, but, and the para-position is preferred.

In the present invention, the repeating unit represented by the general formula (3) described above is most preferably a repeating unit represented by the following general formula (4').

[Chem. 28]

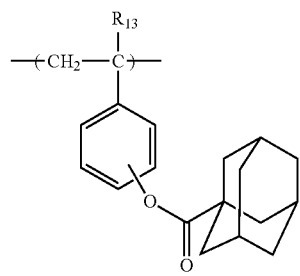

(4')

In the general formula (4'), R$_{13}$ represents a hydrogen atom or a methyl group.

In the general formula (4'), R$_{13}$ represents a hydrogen atom or a methyl group, but a hydrogen atom is particularly preferred.

The position of substitution of an adamantyl ester group in the general formula (4') may be the para-position, the meta-position, or the ortho-position with respect to the bonding position of a benzene ring to a polymer main chain, but, and the para-position is preferred.

Specific examples of the repeating unit shown by the general formula (3) include the following.

[Chem. 29]

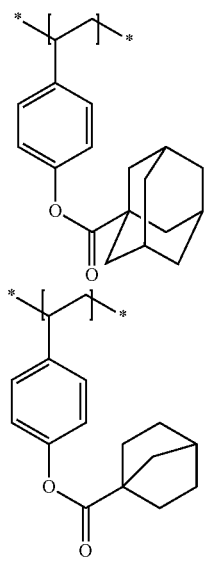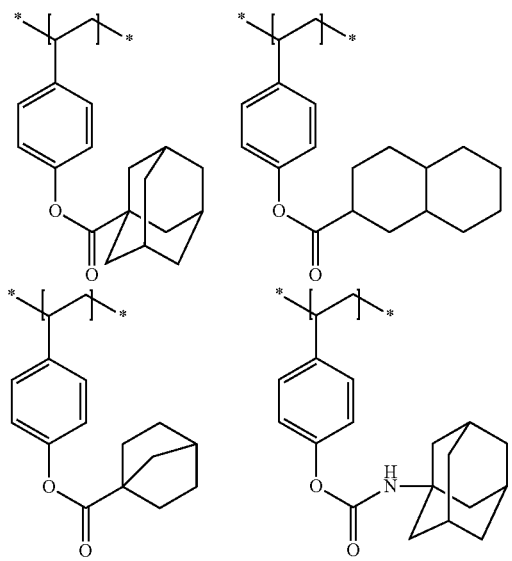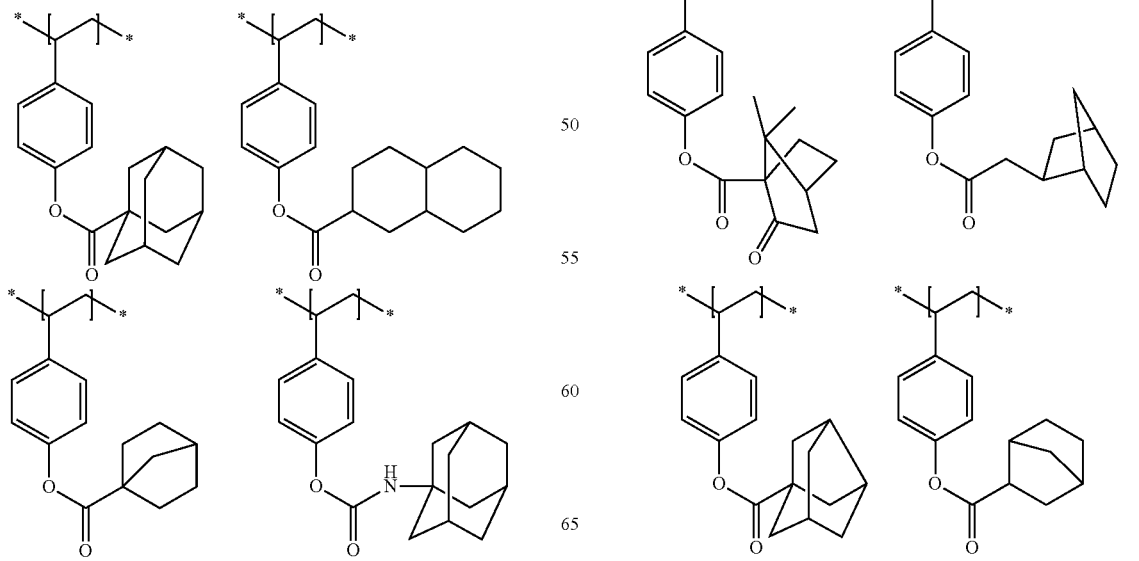

-continued

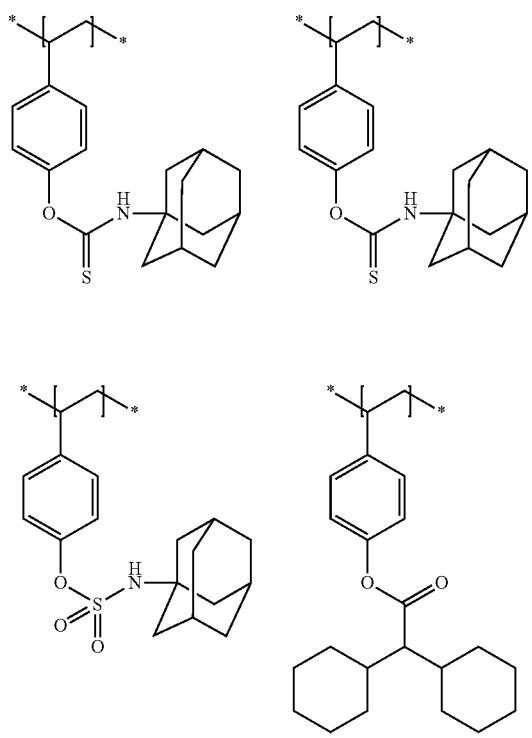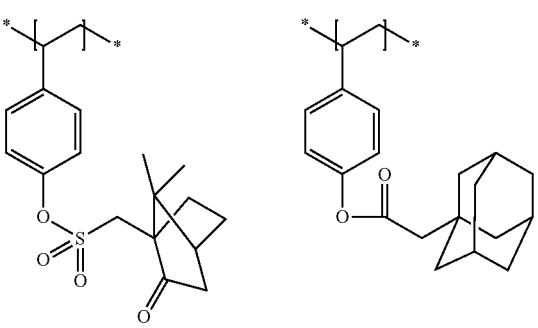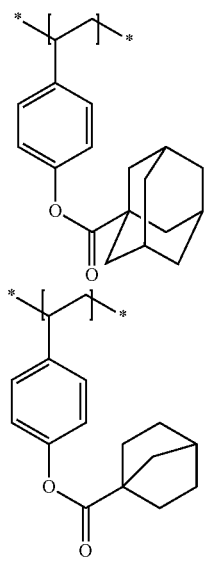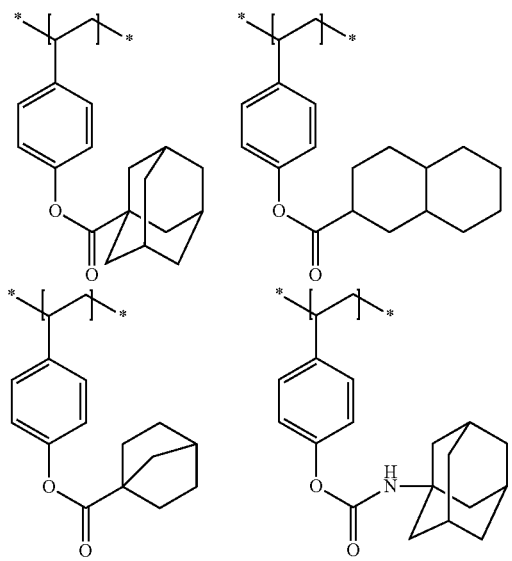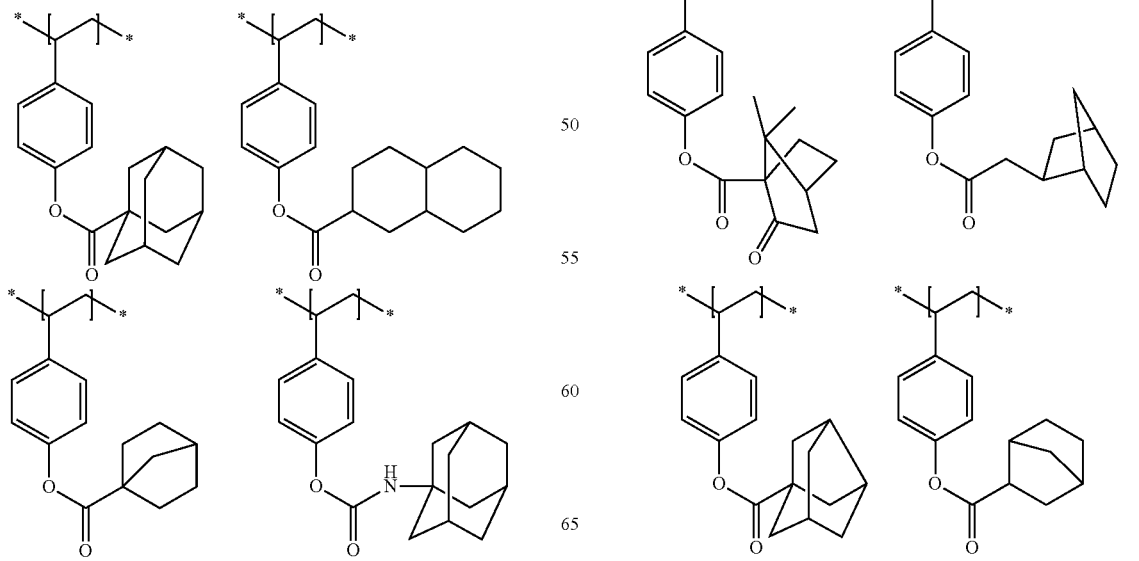

[Chem. 30]
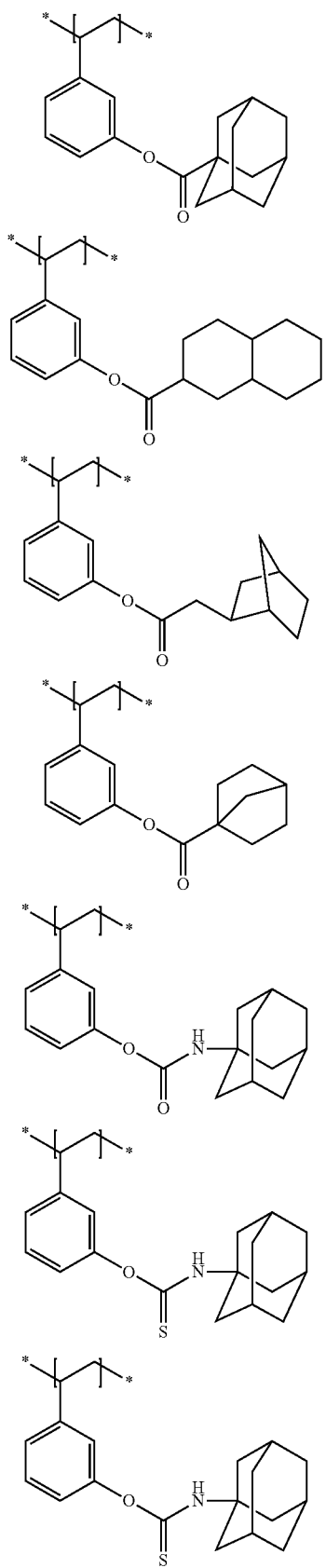
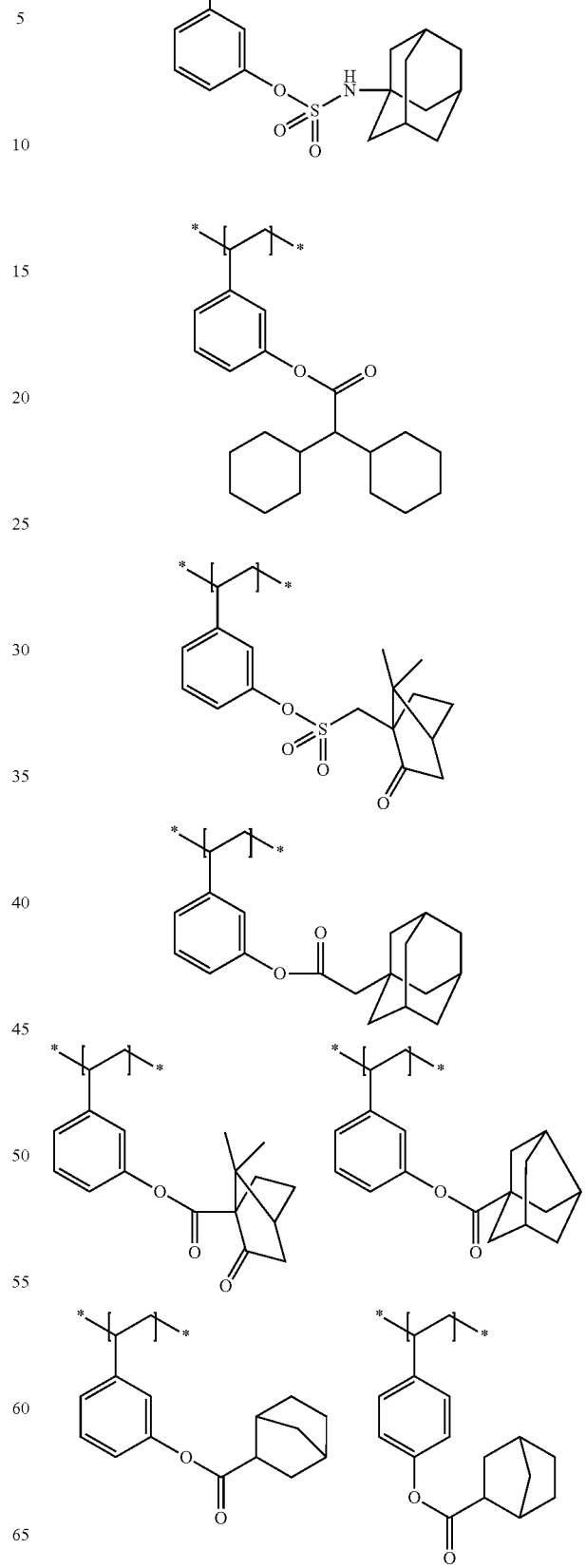

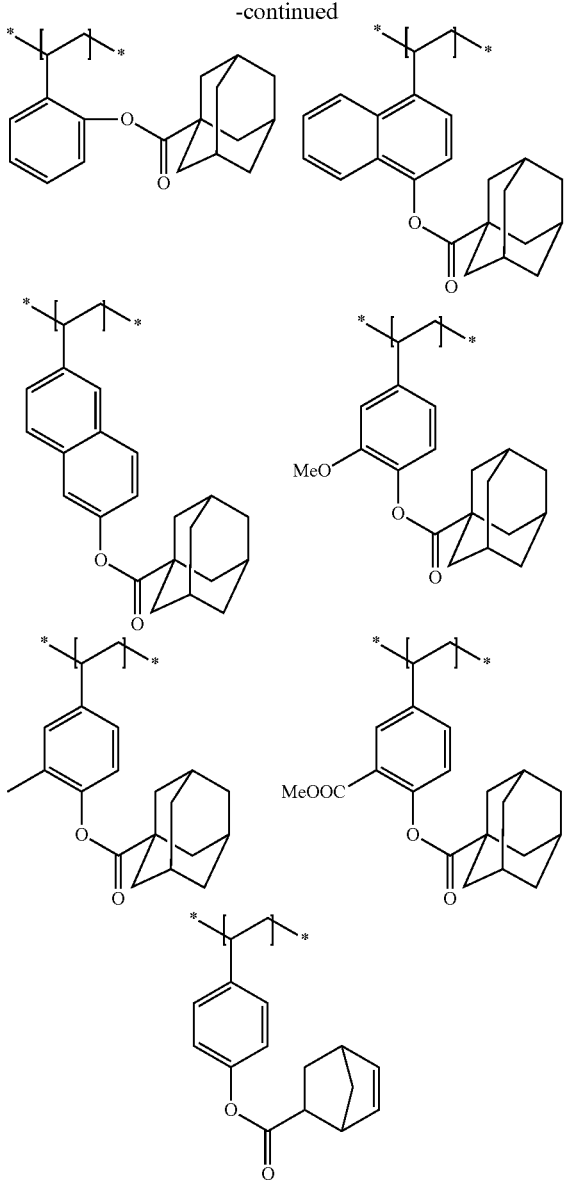

In a case where the compound (B1) is a polymer compound, furthermore, includes a repeating unit having a structure in which a hydrogen atom of a phenolic hydroxyl group is substituted with the group having an acid-non-decomposable polycyclic aliphatic hydrocarbon structure described before, the content rate of the repeating unit is preferably from 1 to 40% by mol and more preferably from 2 to 30% by mol with respect to the total repeating units of the compound (B1) as a polymer compound.

It is also preferable that the composition (B1) as a polymer compound used in the present invention further have a repeating unit as described below (hereinafter, also referred as "the other repeating unit") as a repeating unit other than the repeating unit described above.

Examples of the polymerizable monomer for forming these other repeating units include styrene, alkyl-substituted styrene, alkoxy-substituted styrene, halogen-substituted styrene, O-alkylated styrene, O-acylated styrene, hydrogenated hydroxystyrene, maleic anhydride, an acrylic acid derivative (acrylic acid, acrylic acid ester, and the like), a methacrylic acid derivative (methacrylic acid, methacrylic acid ester, and the like), N-substituted maleimide, acrylonitrile, methacrylonitrile, vinylnaphthalene, vinylanthracene, indene which may have a substituent, and the like.

The compound (B1) as a polymer compound may not have these other repeating units, however in a case of having the other repeating unit, the content of these other repeating units in the compound (B1) as a polymer compound is generally from 1 to 30% by mol, preferably from 1 to 20% by mol and more preferably from 2 to 10% by mol with respect to the total repeating units configuring the compound (B1) as a polymer compound.

The compound (B1) as a polymer compound can be synthesized by a well-known radical polymerization method, a well-known anion polymerization method and a well-known living radical polymerization method (an iniferter method, and the like). For example, in an anion polymerization method, a vinyl monomer is dissolved in proper organic solvent, a metallic compound (butyllithium, and the like) is set as an initiator and a polymer can be obtained by usually reacting under cooling conditions.

As the compound (B1) as a polymer compound, a polyphenol compound manufactured by the condensation reaction of an aromatic ketone or an aromatic aldehyde and a compound having 1 to 3 phenolic hydroxyl groups (for example, JP2008-145539A), a calixarene derivative (for example, JP2004-18421A), a Noria derivative (for example, JP2009-222920A), and a polyphenol derivative (for example, JP2008-94782A) can be also applied, and the compound (B1) may also be modified by a polymer reaction to synthesize.

In addition, the compound (B1) as a polymer compound is preferably synthesized by modifying a polymer synthesized by a radical polymerization method or an anion polymerization method, by a polymer reaction.

The weight average molecular weight of the compound (B1) as a polymer compound is preferably from 1,000 to 200,000, more preferably from 2,000 to 50,000, even more preferably from 2,000 to 15,000.

The dispersity (the molecular weight distribution) (Mw/Mn) of the compound (B1) as a polymer compound is preferably 2.0 or less, and from the viewpoint of improvement of sensitivity and resolution, is preferably from 1.0 to 1.80, more preferably from 1.0 to 1.60 and most preferably from 1.0 to 1.20. It is preferable to use a living polymerization such as a living anionic polymerization since the dispersity (the molecular weight distribution) of the obtained polymer compound becomes uniform. The weight average molecular weight and the dispersity of the compound (B1) as a polymer compound are defined as values that are measured by GPC and expressed in terms of polystyrene. In the specification, the weight average molecular weight (Mw) and the number average molecular weight (Mn) of the compound (B1) may be obtained by using, for example, an HLC-8120 (manufactured by Tosoh Corporation) using a TSK gel Multipore HXL-M column (manufactured by Tosoh Corporation, 7.8 mm ID×30.0 cm) as a column and THF (tetrahydrofuran) as an eluent.

The addition amount of the compound (B1) with respect to the composition in the present invention is preferably from 30 to 95% by mass, more preferably from 40 to 90% by mass and particularly preferably 50 to 85% by mass, with respect to the total solid contents of the composition.

Specific examples of the compound (B1) are shown below, but the present invention is not limited thereto.

[Chem. 31]
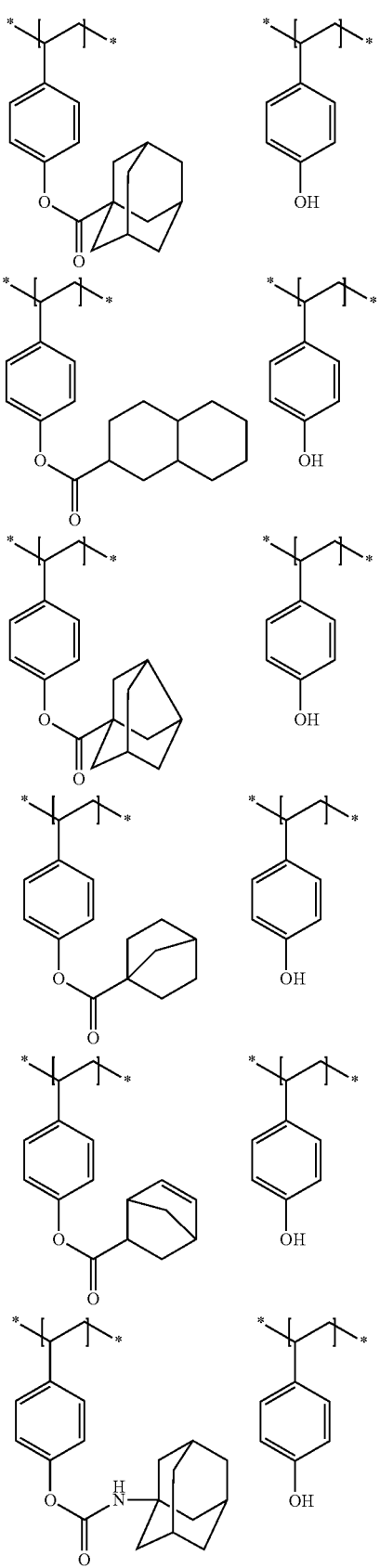
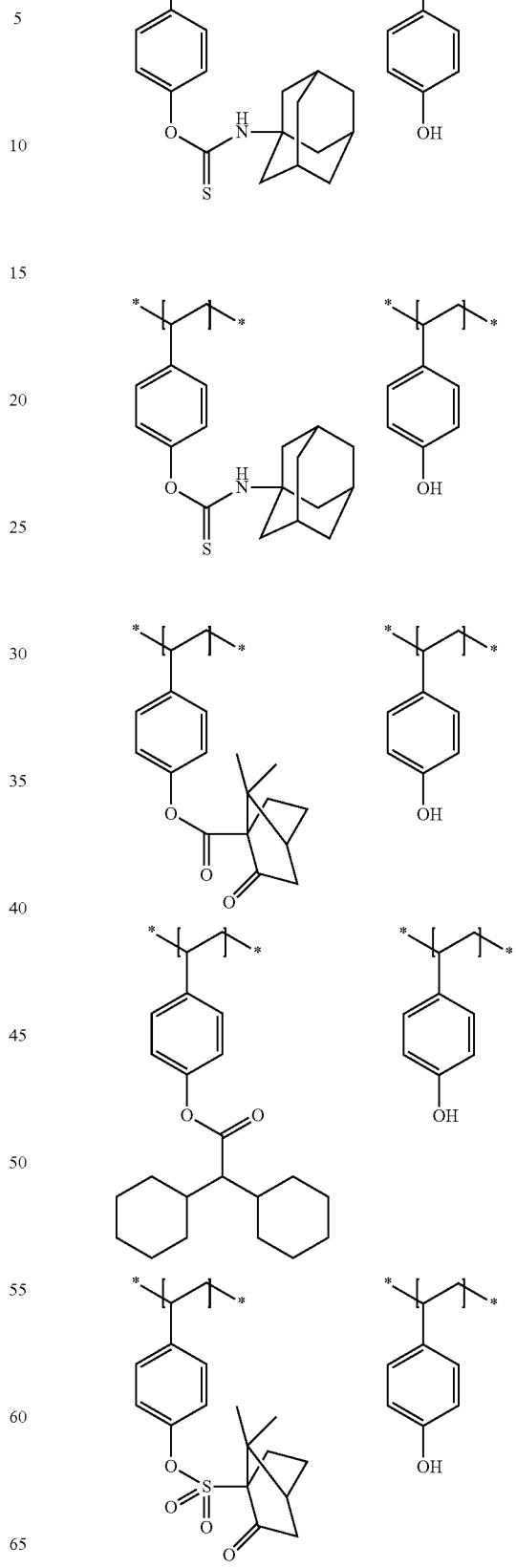

55
-continued
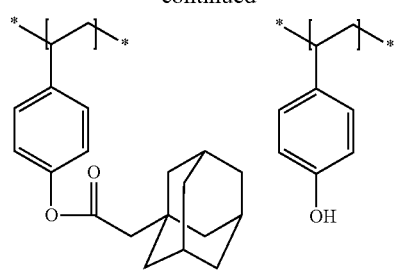
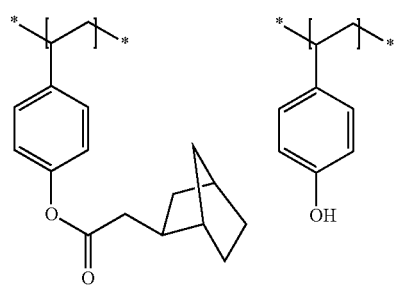
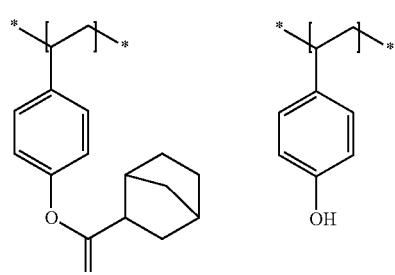
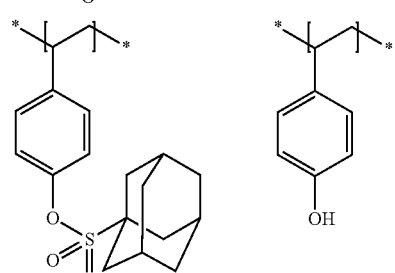
[Chem. 32]
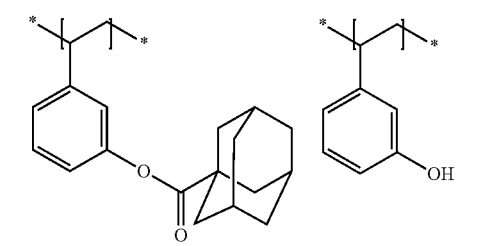
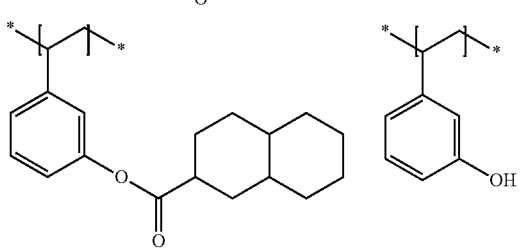
56
-continued
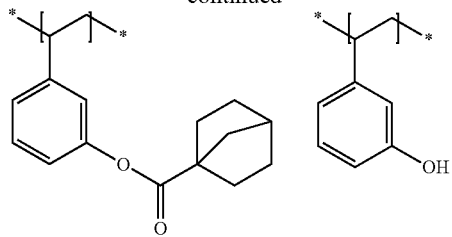
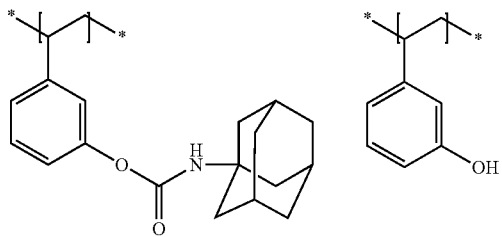
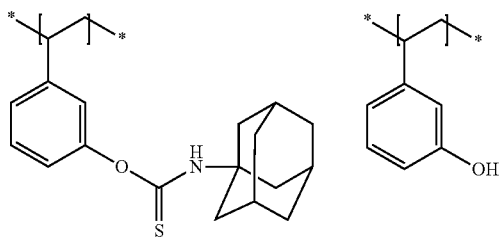
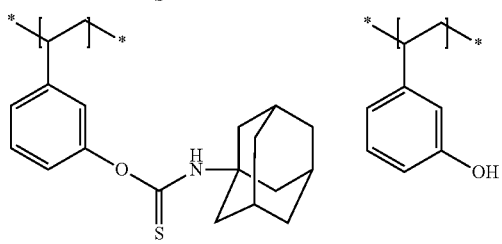
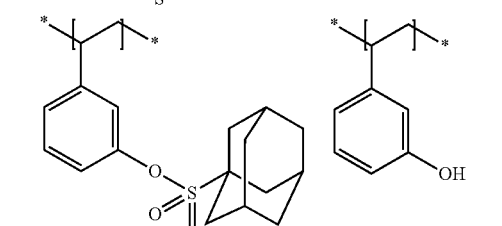

57
-continued
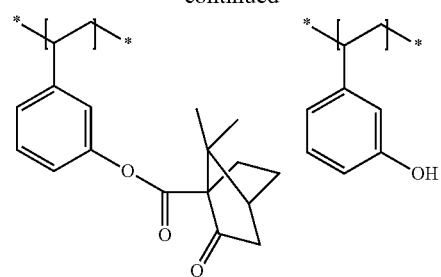
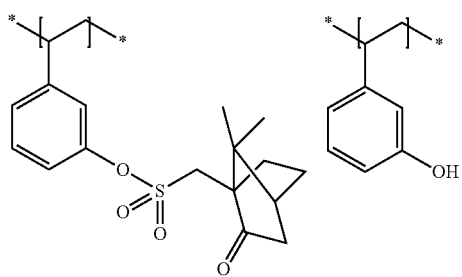
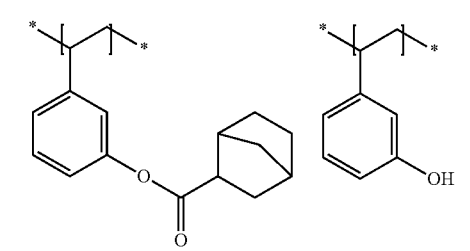
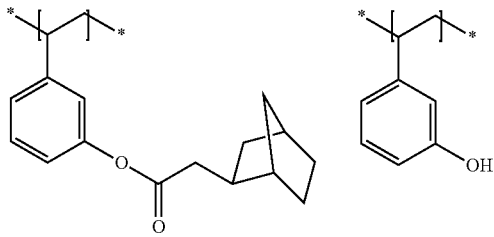
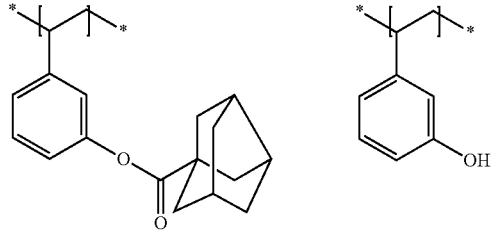
[Chem. 33]
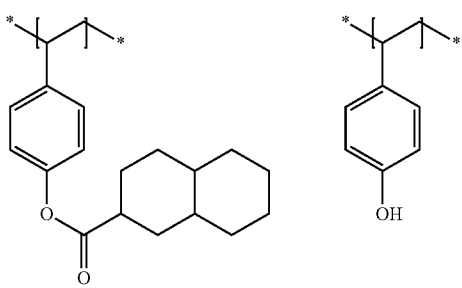
58
-continued
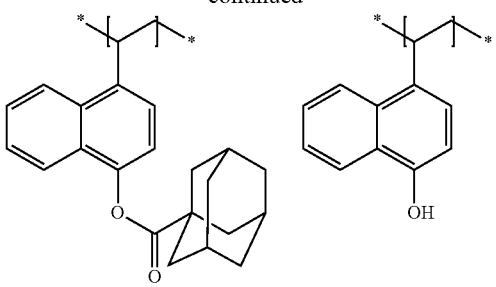
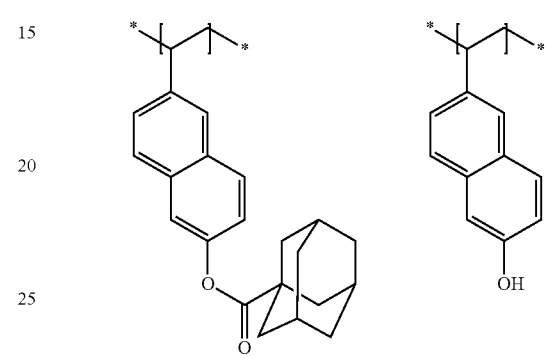
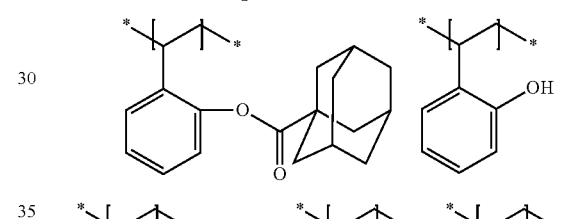
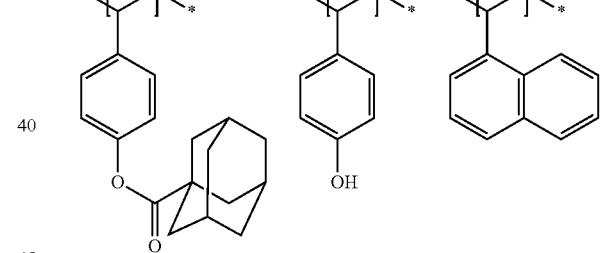
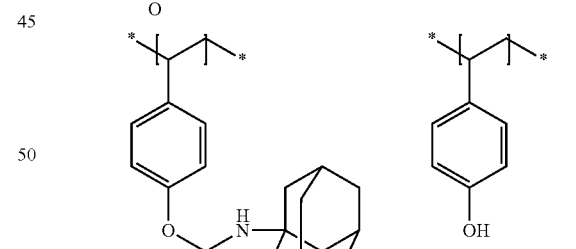
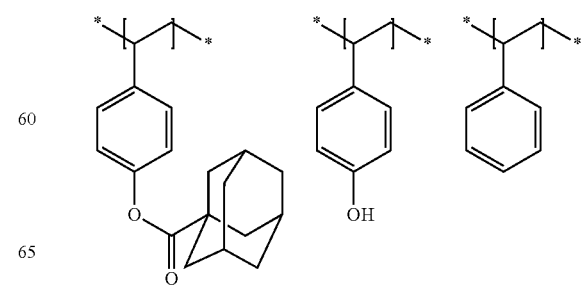

-continued

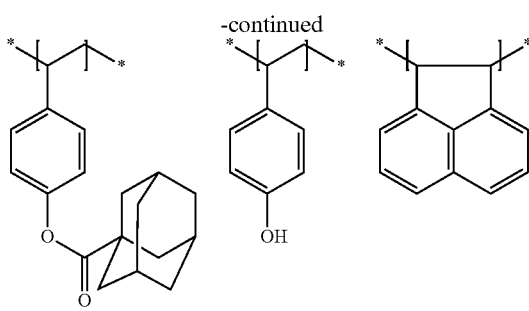
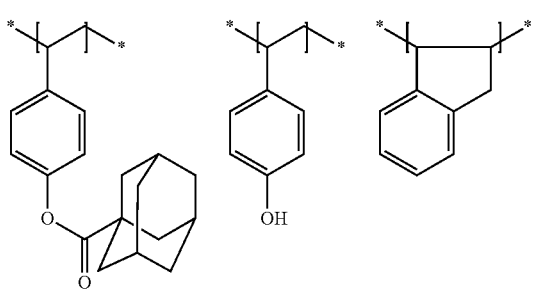
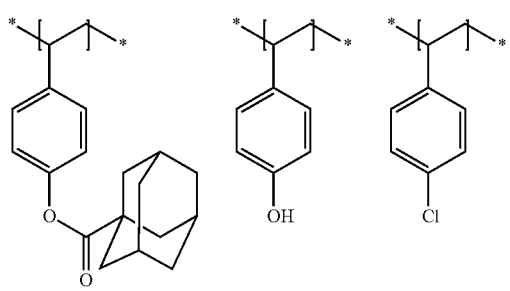
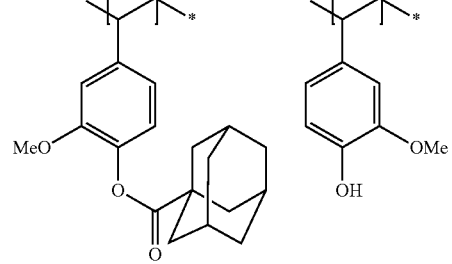
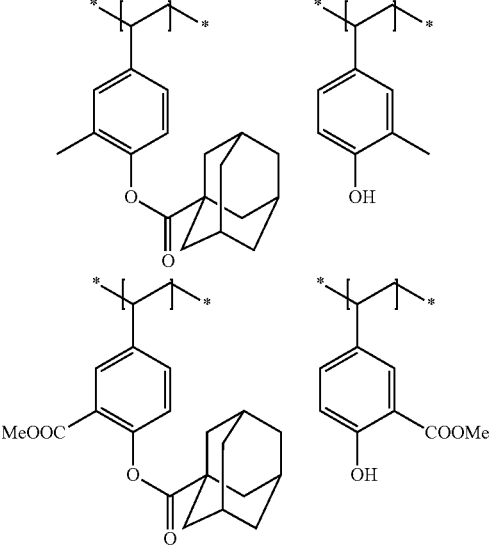

-continued

[Chem. 34]

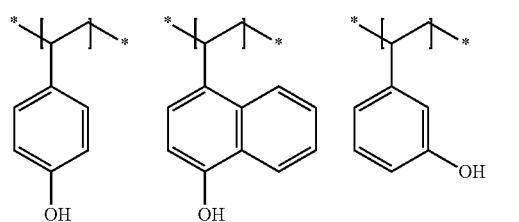

[3] Cross-Linking Agent (C)

In a case where the composition in the present invention is used for a formation of the negative-tone pattern, the composition in the present invention preferably includes a compound having two or more methylol groups in a molecule as a cross-linking agent (hereinafter, also referred as a "compound (C)", a "cross-linking agent", or the like). Here, a methylol group is a group represented by the general formula (M) described before.

As a preferred cross-linking agent, a hydroxymethylated or an alkoxymethylated phenol compound, an alkoxymethylated melamine-based compound, an alkoxymethyl glycoluril-based compound and an alkoxymethylated urea-based compound are included and they may have an arbitrary substituent. A particularly preferred compound (C) as a cross-linking agent includes a phenol derivative and an alkoxymethyl glycoluril derivative which contains 3 to 5 benzene rings in a molecule, further has two or more hydroxymethyl groups or alkoxymethyl groups in total (has more preferably two or more alkoxymethyl groups), and has a molecular weight of 1,200 or less.

The alkoxymethyl group is preferably a methoxymethyl group or an ethoxymethyl group.

Among the cross-linking agents, the phenol derivative having a hydroxymethyl group can be obtained by allowing a corresponding phenol compound which does not have a hydroxymethyl group and formaldehyde to react in the presence of a base catalyst. Furthermore, the phenol derivative having an alkoxymethyl group can be obtained by allowing a corresponding phenol derivative having a hydroxymethyl group and an alcohol to react in the presence of an acid catalyst.

Other preferred examples of the cross-linking agent can further include a compound having a N-hydroxymethyl group or a N-alkoxymethyl group, such as an alkoxymethylated melamine-based compound, alkoxymethyl glycoluril-based compounds, and an alkoxymethylated urea-based compound.

Examples of these compounds include hexamethoxymethyl melamine, hexaethoxymethyl melamine, tetramethoxymethyl glycoluril, 1,3-bismethoxymethyl-4,5-bismethoxyethylene urea, bismethoxymethyl urea, and the like, and these are disclosed in EP 0,133,216 A, German Patent 3,634,671, German Patent 3,711,264, and EP 0, 212, 482 A.

Particularly preferred examples among these cross-linking agents will be shown below.

[Chem. 35]

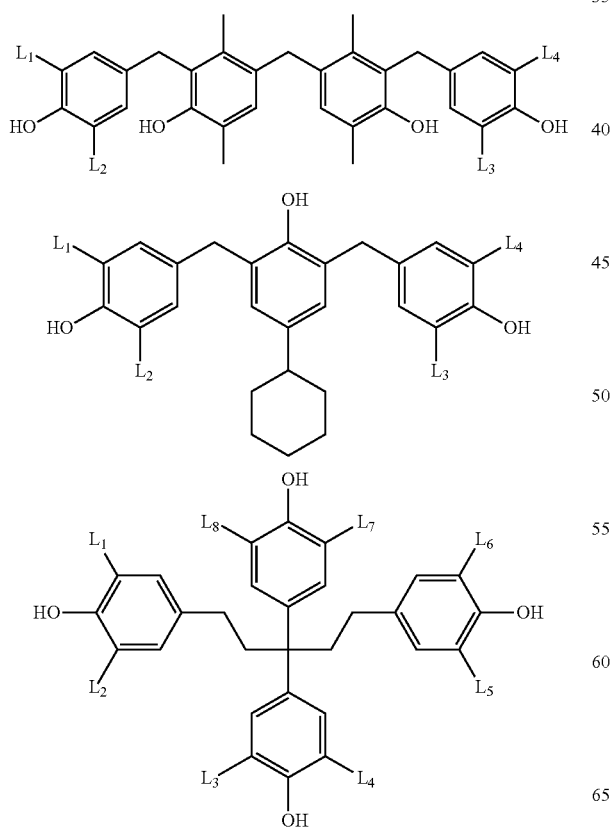

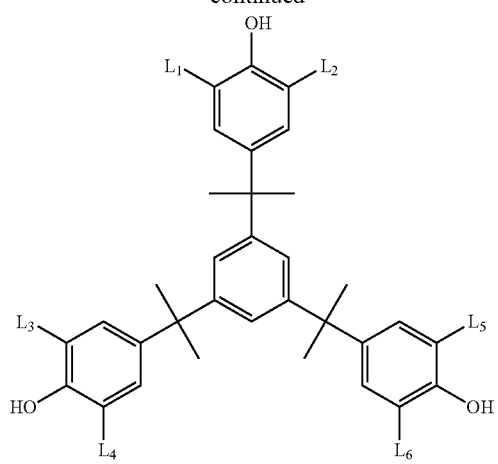

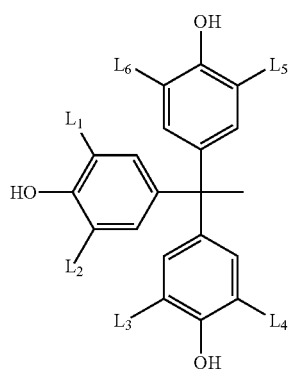

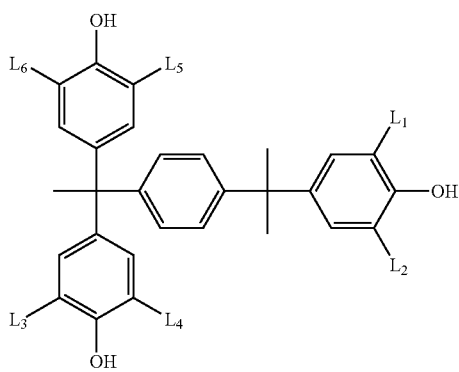

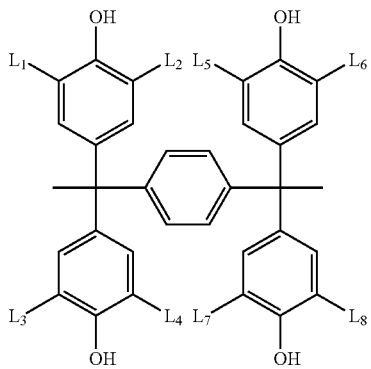

-continued

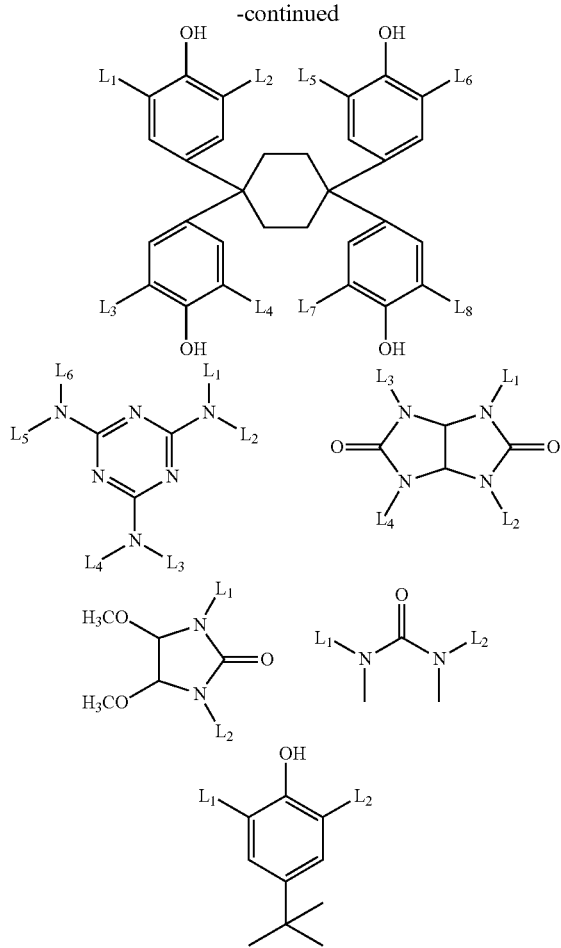

In the formula, $L_1$ to $L_5$ each independently represent a hydrogen atom, a hydroxymethyl group, a methoxymethyl group, an ethoxymethyl group, or an alkyl group having 1 to 6 carbon atoms.

The cross-linking agent in the present invention is preferably from 3 to 65% by mass and more preferably from 5 to 50% by mass in the total solid contents of the composition for negative-tone pattern formation. When the content rate of the cross-linking agent is set to the range of 3 to 65% by mass, decreases in the residual film ratio and resolving power are prevented, and the stability upon storage of the composition in the present invention can be satisfactorily maintained.

In the present invention, the cross-linking agent (C) may be used alone, or two or more kinds may be used in combination. From the viewpoint of an excellent pattern shape, it is preferable to use two or more kinds in combination.

For example, in a case where the other cross-linking agent, for example, the compound having an N-alkoxymethyl group described before, is used in combination with the phenol derivative described above, the proportion of the phenol derivative and the other cross-linking agent is, as a molar ratio, usually from 90/10 to 20/80, preferably from 85/15 to 40/60, and preferably from 80/20 to 50/50.

[4] Compound Having a Group which is Capable of Decomposing by the Action of an Acid (B2)

In one embodiment, the composition according to the present invention includes a compound having a group which is capable of decomposing by the action of an acid (hereinafter, also referred as a "compound (B2)").

The compound (B2) is preferably insoluble or slightly soluble to an alkali developer.

The compound (B2) is preferably a resin having a repeating unit having a group which is capable of decomposing by the action of an acid (hereinafter, also referred as an "acid-decomposable group").

Examples of the acid-decomposable group include a group in which a hydrogen atom of an alkali-soluble group such as a carboxyl group, a phenolic hydroxyl group, a sulfonic acid group, and a thiol group is protected with a group leaving by the action of an acid.

Examples of the group leaving by the action of an acid include —$C(R_{36})(R_{37})(R_{38})$, —$C(R_{36})(R_{37})(OR_{39})$, —$C(=O)$—O—$C(R_{36})(R_{37})(R_{38})$, —$C(R_{01})(R_{02})(OR_{39})$, —$C(R_{01})(R_{02})$—$C(=O)$—O—$C(R_{36})(R_{37})(R_{38})$, and the like.

In the formulae, $R_{36}$ to $R_{39}$ each independently represent an alkyl group, a cycloalkyl group, an aryl group, an aralkyl group, or an alkenyl group. $R_{36}$ and $R_{37}$ may be bonded to each other to form a ring. $R_{01}$ to $R_{02}$ each independently represent a hydrogen atom, an alkyl group, a cycloalkyl group, an aryl group, an aralkyl group, or an alkenyl group.

In one embodiment, the compound (B2) preferably includes a repeating unit represented by the following general formula (AI) as a repeating unit having an acid-decomposable group.

[Chem. 36]

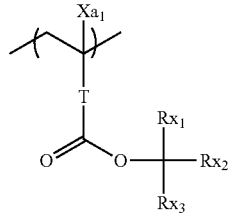

(AI)

In the general formula (AI), $Xa_1$ represents a hydrogen atom, a methyl group or a group represented by —$CH_2$—$R_9$. $R_9$ represents a hydroxyl group or a monovalent organic group, for example, includes an alkyl group having 5 or less carbon atoms or an acyl group, is preferably an alkyl group having 3 or less carbon atoms and more preferably a methyl group. $Xa_1$ is preferably a hydrogen atom, a methyl group, a trifluoromethyl group, or a hydroxymethyl group;

T represents a single bond or a divalent linking group;

$Rx_1$ to $Rx_3$ each independently represent an alkyl group (linear or branched) or a cycloalkyl group (monocyclic or polycyclic); and At least two of $Rx_1$ to $Rx_3$ may be bonded to each other to form a cycloalkyl group (monocyclic or polycyclic).

Examples of the divalent linking group of T include an alkylene group, —COO-Rt-group, —O-Rt-group, and the like. In the formulae, Rt represents an alkylene group or a cycloalkylene group.

T is preferably a single bond or —COO-Rt-group. Rt is preferably an alkylene group having 1 to 5 carbon atoms and more preferably —$CH_2$— group, or —$(CH_2)_3$— group.

The alkyl group of $Rx_1$ to $Rx_3$ is preferably an alkyl group having 1 to 4 carbon atoms such as a methyl group, an ethyl group, an n-propyl group, an isopropyl group, an n-butyl group, an isobutyl group, and a t-butyl group.

The cycloalkyl group of $Rx_1$ to $Rx_3$ is preferably a monocyclic cycloalkyl group such as a cyclopentyl group and a cyclohexyl group, or a polycyclic cycloalkyl group such as a norbornyl group, a tetracyclodecanyl group, a tetracyclododecanyl group, and an adamantyl group.

The cycloalkyl group formed by at least two of $Rx_1$ to $Rx_3$ being bonded is preferably a monocyclic cycloalkyl group such as a cyclopentyl group and a cyclohexyl group, or a polycyclic cycloalkyl group such as a norbornyl group, a tetracyclodecanyl group, a tetracyclododecanyl group, and an adamantyl group.

An embodiment where $Rx_1$ is a methyl group or an ethyl group, and $Rx_2$ and $Rx_3$ are bonded to each other to form the above-described cycloalkyl group is preferable.

The respective groups described above may have a substituent, and examples of the substituent include an alkyl group (having 1 to 4 carbon atoms), a halogen atom, a hydroxyl group, an alkoxy group (having 1 to 4 carbon atoms), a carboxyl group and an alkoxycarbonyl group (having 2 to 6 carbon atoms), and the like, and the number of carbon atoms is preferably 8 or less.

In another embodiment, the compound (B2) preferably includes at least one kind of repeating units represented by the following general formulae (A1) and (A2).

[Chem. 37]

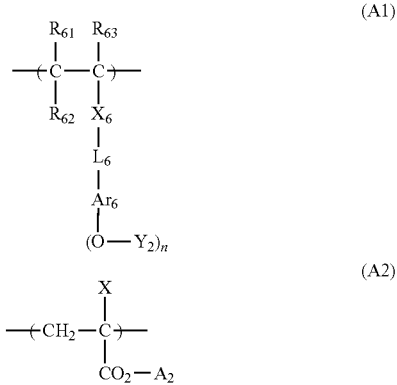

In the general formula (A1), $R_{61}$, $R_{62}$ and $R_{63}$ each independently represent a hydrogen atom, an alkyl group, a cycloalkyl group, a halogen atom, a cyano group or an alkoxycarbonyl group. However, $R_{62}$ may be bonded to $Ar_6$ to form a ring, and in this case, $R_{62}$ represents a single bond or an alkylene group.

$X_6$ represents a single bond, —COO—, or —CONR$_{64}$—.

$R_{64}$ represents a hydrogen atom or an alkyl group.

$L_6$ represents a single bond or an alkylene group.

$Ar_6$ represents a (n+1)-valent aromatic ring group and in a case of being bonded to $R_{62}$ to form a ring, represents a (n+2)-valent aromatic ring group.

In a case of n≥2, $Y_2$ each independently represents a hydrogen atom or a group leaving by the action of an acid. However, at least one of $Y_2$'s represents a group leaving by the action of an acid.

n represents an integer of 1 to 4.

The general formula (A1) will be described in more detail.

Examples of the alkyl group of $R_{61}$ to $R_{63}$ in the general formula (A1) preferably include an alkyl group having 20 or less carbon atoms such as a methyl group, an ethyl group, a propyl group, an isopropyl group, an n-butyl group, a sec-butyl group, a hexyl group, a 2-ethylhexyl group, an octyl group, a dodecyl group, which may have a substituent, and more preferably include an alkyl group having 8 or less carbon atoms.

Examples of the alkyl group included in an alkoxycarbonyl group are preferably the same as an alkyl group of $R_{61}$ to $R_{63}$ described above.

A cycloalkyl group may be a monocyclic type or polycyclic type and preferably includes a monocyclic type cycloalkyl group having 3 to 8 carbon atoms such as a cyclopropyl group, a cyclopentyl group, a cyclohexyl group, which may have a substituent.

Examples of the halogen atom include a fluorine atom, a chlorine atom, a bromine atom and an iodine atom and a fluorine atom is more preferable.

In a case where $R_{62}$ represents an alkylene group, examples of the alkylene group preferably include an alkylene group having 1 to 8 carbon atoms such as a methylene group, an ethylene group, a propylene group, a butylene group, a hexylene group and an octylene group, which may have a substituent.

Examples of the alkyl group in $R_{64}$ in —CONR$_{64}$— ($R_{64}$ represents a hydrogen atom or an alkyl group) represented by $X_6$ include the same as an alkyl group of $R_{61}$ to $R_{63}$.

As $X_6$, a single bond, —COO— and —CONH— are preferable and a single bond and —COO— are more preferable.

Examples of the alkylene group in $L_6$ preferably include a an alkylene group having 1 to 8 carbon atoms such as a methylene group, an ethylene group, a propylene group, a butylene group, a hexylene group and an octylene group, which may have a substituent. A ring to be formed by $R_{62}$ and $L_6$ being bonded is particularly preferably a 5 or 6-membered ring.

$Ar_6$ represents a (n+1)-valent aromatic ring group. A divalent aromatic ring group may have a substituent in a case where n is 1 and, for example, an arylene group having 6 to 18 carbon atoms such as a phenylene group, a tolylene group, a naphthylene group or, for example, a divalent aromatic ring group including a hetero ring such as thiophene, furan, pyrrole, benzothiophene, benzofuran, benzopyrrole, triazine, imidazole, benzoimidazole, triazole, thiadiazole or thiazole is included as a preferred example.

Specific examples of the (n+1)-valent aromatic ring group in a case where n is an integer of 2 or more suitably include a group where arbitrary (n−1) hydrogen atoms are removed from specific examples of divalent aromatic ring groups described above.

The (n+1)-valent aromatic ring group may further have a substituent.

Examples of the substituent which an alkyl group, a cycloalkyl group, an alkoxycarbonyl, an alkylene group and (n+1)-valent aromatic ring group described above can have, include an alkyl group, a cycloalkyl group, an aryl group, an amino group, an amido group, a ureido group, a urethane group, a hydroxyl group, a carboxyl group, a halogen atom, an alkoxy group, a thioether group, an acyl group, an acyloxy group, an alkoxycarbonyl group, a cyano group, a nitro group, and the like and the number of carbon atoms of the substituent is preferably 10 or less.

n is preferably 1 or 2 and more preferably 1.

n $Y_2$'s each independently represent a hydrogen atom or a group leaving by the action of an acid. However, at least one of n represents a group leaving by the action of an acid.

Examples of $Y_2$ of the group leaving by the action of an acid include —C($R_{36}$)($R_{37}$)($R_{38}$), —C(=O)—O—C($R_{36}$)($R_{37}$)($R_{38}$), —C($R_{01}$)($R_{02}$)(O$R_{39}$), —C($R_{01}$)($R_{02}$)—C(=O)—O—C($R_{36}$)($R_{37}$)($R_{38}$), —CH($R_{36}$)(Ar), and the like.

In the formulae, $R_{36}$ to $R_{39}$ each independently represent an alkyl group, a cycloalkyl group, a monovalent aromatic ring group, a group formed by a combination of an alkylene group and a monovalent aromatic ring group, or an alkenyl group. $R_{36}$ and $R_{37}$ may be bonded to each other to form a ring.

$R_{01}$ and $R_{02}$ each independently represent a hydrogen atom, an alkyl group, a cycloalkyl group, a monovalent aromatic ring group, a group formed by a combination of an alkylene group and a monovalent aromatic ring group, or an alkenyl group.

Ar represents a monovalent aromatic ring group.

An alkyl group in $R_{36}$ to $R_{39}$, $R_{01}$ and $R_{02}$ is preferably an alkyl group having 1 to 8 carbon atoms and, for example, a methyl group, an ethyl group, a propyl group, an n-butyl group, a sec-butyl group, a hexyl group, an octyl group, and the like are included.

A cycloalkyl group in $R_{36}$ to $R_{39}$, $R_{01}$ and $R_{02}$ may be a monocyclic type or polycyclic type. As a monocyclic type, a cycloalkyl group having 3 to 8 carbon atoms is preferable and, for example, a cyclopropyl group, a cyclobutyl group, a cyclopentyl group, a cyclohexyl group, a cyclooctyl group, and the like are included. As a polycyclic type, a cycloalkyl group having 6 to 20 carbon atoms is preferable and, for example, an adamantyl group, a norbornyl group, an isobornyl group, a camphanyl group, a dicyclopentyl group, an α-pinanyl group, a tricyclodecanyl group, a tetracyclododecyl group, an androstanyl group, and the like are included. Incidentally, parts of carbon atoms in the cycloalkyl group may be substituted with a heteroatom such as an oxygen atom.

A monovalent aromatic ring group of $R_{36}$ to $R_{39}$, $R_{01}$, $R_{02}$ and Ar is preferably a monovalent aromatic ring group having 6 to 10 carbon atoms and, for example, an aryl group such as a phenyl group, a naphthyl group or anthryl group and a divalent aromatic ring group including a hetero ring such as thiophene, furan, pyrrole, benzothiophene, benzofuran, benzopyrrole, triazine, imidazole, benzoimidazole, triazole, thiadiazole or thiazole is included.

As a group formed by a combination of an alkylene group and a monovalent aromatic ring group of $R_{36}$ to $R_{39}$, $R_{01}$ and $R_{02}$, an aralkyl group having 7 to 12 carbon atoms is preferable and, for example, a benzyl group, a phenethyl group, a naphthylmethyl group, and the like are included.

An alkenyl group in $R_{36}$ to $R_{39}$, $R_{01}$ and $R_{02}$ is preferably an alkenyl group having 2 to 8 carbon atoms and, for example, a vinyl group, an allyl group, a butenyl group, a cyclohexenyl group, and the like are included.

A ring in which $R_{36}$ and $R_{37}$ are bonded to each other to form may be a monocyclic type or polycyclic type. As a monocyclic type, a cycloalkyl structure having 3 to 8 carbon atoms is preferable and, for example, a cyclopropane structure, a cyclobutane structure, a cyclopentane structure, a cyclohexane structure, a cycloheptane structure, a cyclooctane structure, and the like and included. As a polycyclic type, a cycloalkyl structure having 6 to 20 carbon atoms is preferable and, for example, an adamantane structure, a norbornane structure, a dicyclopentane structure, a tricyclodecane structure, a tetracyclododecane structure, and the like are included. Incidentally, parts of carbon atoms in the cycloalkyl structure may be substituted with a heteroatom such as an oxygen atom.

The respective groups described above as $R_{36}$ to $R_{39}$, $R_{01}$, $R_{02}$ and Ar may have a substituent, and examples of the substituent include an alkyl group, a cycloalkyl group, an aryl group, an amino group, an amido group, a ureido group, a urethane group, a hydroxyl group, a carboxyl group, a halogen atom, an alkoxy group, a thioether group, an acyl group, an acyloxy group, an alkoxycarbonyl group, a cyano group, a nitro group, and the like and the number of carbon atoms of the substituent is preferably 8 or less.

As $Y_2$ of the group leaving by the action of an acid, a structure represented by the following general formula (VI-A) is more preferable.

[Chem. 38]

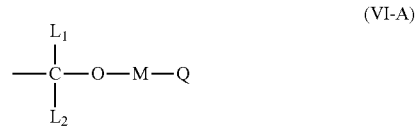

(VI-A)

Here, $L_1$ and $L_2$ each independently represent a hydrogen atom, an alkyl group, a cycloalkyl group, a monovalent aromatic ring group or a group formed by a combination of an alkylene group and a monovalent aromatic ring group;

M represents a single bond or a divalent connecting group; and

Q represents an alkyl group, a cycloalkyl group which may include a heteroatom, a monovalent aromatic ring group which may include a heteroatom, an amino group, an ammonium group, a mercapto group, a cyano group or an aldehyde group.

At least two of Q, M, $L_1$ may be bonded to form a ring (preferably a 5-membered or a 6-membered ring).

An alkyl group as $L_1$ and $L_2$, for example, is an alkyl group having 1 to 8 carbon atoms, and specifically, a methyl group, an ethyl group, a propyl group, an n-butyl group, a sec-butyl group, a hexyl group and an octyl group are preferably included.

A cycloalkyl group as $L_1$ and $L_2$, for example, is a cycloalkyl group having 3 to 15 carbon atoms, and specifically, a cyclopentyl group, a cyclohexyl group, a norbornyl group, an adamantyl group, and the like are included as a preferable example.

A monovalent aromatic ring group as $L_1$ and $L_2$, for example, is an aryl group having 6 to 15 carbon atoms, and specifically, a phenyl group, a tolyl group, a naphthyl group, an anthryl group, and the like are included as a preferable example.

A group formed by a combination of an alkylene group and a monovalent aromatic ring group as $L_1$ and $L_2$, for example, is a group having 6 to 20 carbon atoms, and an aralkyl group such as a benzyl group or a phenethyl group is included.

A divalent linking group as M, for example, is an alkylene group (for example, a methylene group, an ethylene group, a propylene group, a butylene group, a hexylene group, an octylene group, or the like), a cycloalkylene group (for example, a cyclopentylene group, a cyclohexylene group, an adamantylene group, or the like), an alkenylene group (for example, a vinylene group, a propenylene group, a butenylene group, or the like), a divalent aromatic ring group (for example, a phenylene group, a tolylene group, a naphthylene group, or the like), —S—, —O—, —CO—, —SO2-, —N($R_0$)— and a divalent linking group formed by a combination of a plurality of these groups. $R_0$ is a hydrogen atom or an alky group (for example, it is an alkyl group having 1 to 8 carbon atoms, and specifically, a methyl group, an ethyl group, a propyl group, an n-butyl group, a sec-butyl group, a hexyl group, an octyl group, or the like).

An alkyl group as Q is the same as each group as $L_1$ and $L_2$ described above.

As an aliphatic hydrocarbon ring group which does not have a heteroatom and a monovalent aromatic ring group which does not include a heteroatom in a cycloalkyl group which may include a heteroatom and a monovalent aromatic ring group which may include a heteroatom as Q, a cycloalkyl group, a monovalent aromatic ring group and the like as $L_1$ and $L_2$ described above are included, and the number of carbon atoms is preferably 3 to 15.

Examples of the cycloalkyl group including a heteroatom and the monovalent aromatic ring group including a heteroatom include a group having a heterocycle structure such as thiirane, cyclothiolane, thiophene, furan, pyrrole, benzothiophene, benzofuran, benzopyrrole, triazine, imidazole, benzoimidazole, triazole, thiadiazole, thiazole or pyrrolidone, however, as long as a group has a structure which is generally called a heterocycle (a ring formed by a carbon atom and a heteroatom or a ring formed by heteroatoms), but the present invention is not limited thereto.

Examples of the ring in which at least two of Q, M and $L_1$ may be bonded to form include a case where at least two of Q, M and $L_1$ are bonded to form, for example, a propylene group or a butylene group and a 5-membered or a 6-membered ring containing an oxygen atom is formed.

Each group represented by $L_1$, $L_2$, M and Q in the general formula (VI-A) may have a substituent, for example, a substituent which is described as a substituent which $R_{36}$ to $R_{39}$, $R_{01}$, $R_{02}$ and Ar may have described before is included, and the number of carbon atoms of a substituent is preferably 8 or less.

As a group represented by -M-Q, a group which is configured by 1 to 30 carbon atoms is preferable and a group which is configured by 5 to 20 carbon atoms is more preferable.

The repeating unit represented by the general formula (A1) particularly preferably has a structure represented by the following general formula (A1').

[Chem. 39]

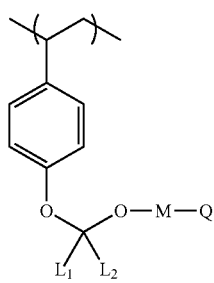

(A1')

$L_1$, $L_2$, M and Q in the general formula (A1') is as defined in the general formula (VI-A) described above.

Hereinafter, specific examples of the repeating unit represented by the general formula (A1) are illustrated, but the present invention is not limited thereto.

[Chem. 40]

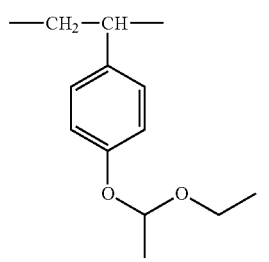 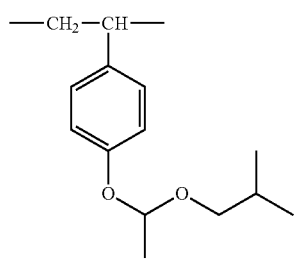

-continued

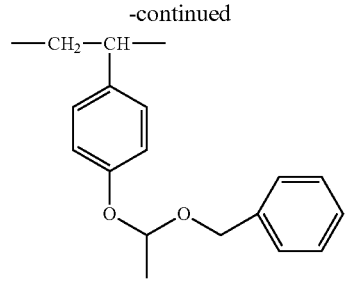

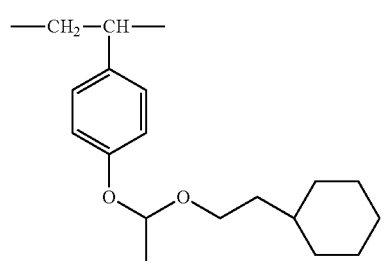

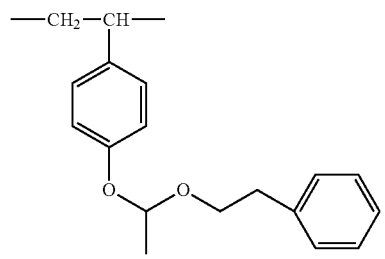

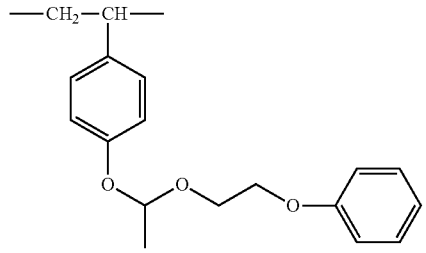

[Chem. 41]

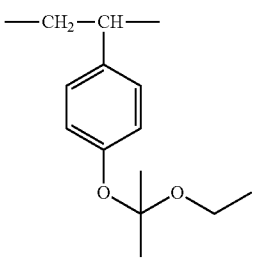 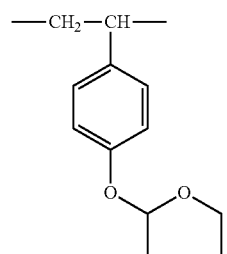

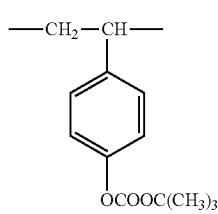 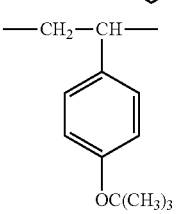

-continued

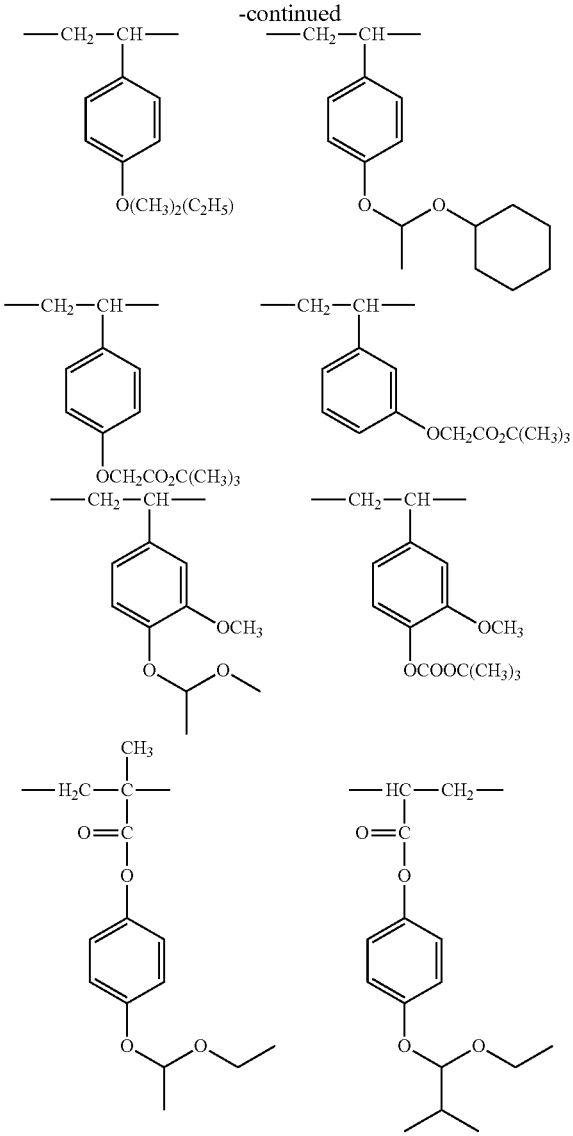

Next, the repeating unit represented by the general formula (A2) will be described.

As described above, X represents a hydrogen atom, an alkyl group, a hydroxyl group, an alkoxy group, a halogen atom, a cyano group, a nitro group, an acyl group, an acyloxy group, a cycloalkyl group, a cycloalkyloxy group, an aryl group, a carboxyl group, an alkyloxycarbonyl group, an alkylcarbonyloxy group, or an aralkyl group.

The alkyl group as X may have a substituent and may be either linear or branched. The linear alkyl group is preferably an alkyl group having 1 to 30 carbon atoms, more preferably 1 to 20, and examples thereof include a methyl group, an ethyl group, an n-propyl group, an n-butyl group, a sec-butyl group, a t-butyl group, a n-pentyl group, a n-hexyl group, a n-heptyl group, a n-octyl group, a n-nonyl group, a n-decanyl group, and the like. The branched alkyl group is preferably an alkyl group having 3 to 30 carbon atoms, more preferably 3 to 20, and examples thereof include an i-propyl group, an i-butyl group, a t-butyl group, an i-pentyl group, a t-pentyl group, an i-hexyl group, a t-hexyl group, an i-heptyl group, a t-heptyl group, an i-octyl group, a t-octyl group, an i-nonyl group, a t-decanoyl group, and the like.

The alkoxy group as X may have a substituent and, for example, is the alkoxy group having 1 to 8 carbon atoms, and examples thereof include a methoxy group, an ethoxy group, a propoxy group, a butoxy group, a pentyloxy group, a hexyloxy group, and a cyclohexyloxy group, and the like.

Examples of the halogen atom as X include a fluorine atom, a chlorine atom, a bromine atom and an iodine atom, and a fluorine atom is preferable.

The acyl group as X may have a substituent, and, for example, is an acyl group having 2 to 8 carbon atoms, specifically, a formyl group, an acetyl group, a propanoyl group, a butanoyl group, a pivaloyl group, a benzoyl group, and the like are preferably included.

The acyloxy group as X may have a substituent and is preferably an acyloxy groups having 2 to 8 carbon atoms, and, examples thereof include an acetoxy group, a propionyloxy group, a butylyloxy group, a valeryloxy group, a pivaloyloxy group, a hexanoyloxy group, an octanoyloxy group, a benzoyloxy group, and the like.

The cycloalkyl group as X may have a substituent and may be a monocyclic type, a polycyclic type, or a bridged type. For example, the cycloalkyl group may have a bridged structure. The monocyclic type is preferably a cycloalkyl group having 3 to 8 carbon atoms, and examples thereof include a cyclopropyl group, a cyclopentyl group, a cyclohexyl group, a cyclobutyl group, a cyclooctyl group, and the like. The polycyclic type includes a group having a bicyclo structure, a tricyclo structure, a tetracyclo structure, and the like and having 5 or more carbon atoms, a cycloalkyl group having 6 to 20 carbon atoms is preferable, and examples thereof include an adamantyl group, a norbornyl group, an isobornyl group, a camphanyl group, a dicyclopentyl group, an α-pinanyl group, a tricyclodecanyl group, a tetracyclododecyl group, an androstanyl group, and the like. Here, the part of carbon atoms in the cycloalkyl group may be substituted with a heteroatom such as an oxygen atom.

The aryl group as X may have a substituent and is preferably an aryl group having 6 to 14 carbon atoms, and examples thereof include a phenyl group, a xylyl group, a tolyl group, a cumenyl group, a naphthyl group, an anthracenyl group, and the like.

The alkyloxycarbonyl group as X may have a substituent, is preferably an alkyloxycarbonyl group having 2 to 8 carbon atoms, and examples thereof include a methoxycarbonyl group, an ethoxycarbonyl group, and a propoxycarbonyl group.

The alkylcarbonyloxy group as X may have a substituent and is preferably an alkylcarbonyloxy group having 2 to 8 carbon atoms, and examples thereof include a methylcarbonyloxy group and an ethylcarbonyloxy group.

The aralkyl group as X may have a substituent and is preferably an aralkyl group having 7 to 16 carbon atoms, and examples thereof include a benzyl group.

Examples of the substituent which an alkyl group, an alkoxy group, an acyl group, a cycloalkyl group, an aryl group, an alkyloxycarbonyl group, an alkylcarbonyloxy group, an aralkyl group as X may further have, include a hydroxyl group, a fluorine atom, a chlorine atom, a bromine atom, an iodine atom, an alkyl group, an alkoxy group, a halogen atom, a cyano group, a nitro group, an acyl group, an acyloxy group, a cycloalkyl group, an aryl group, a carboxyl group, an alkyloxycarbonyl group, an alkylcarbonyloxy group, an aralkyl group, and the like.

$A_2$ represents the group leaving by the action of an acid described before. That is, the repeating unit represented by the general formula (A2) is provided with a group represented by "—COOA$_2$" as an acid-decomposable group.

Examples of $A_2$ include the same as those described before for $Y_2$ in the general formula (A1).

$A_2$ is preferably a hydrocarbon group (preferably having 20 or less carbon atoms, and more preferably having 4 to 12 carbon atoms), and more preferably a t-butyl group, a t-amyl group, or a hydrocarbon group having an alicyclic structure (for example, an alicyclic group itself, and a group in which the alkyl group is substituted with an alicyclic group).

$A_2$ is preferably a tertiary alkyl group or a tertiary cycloalkyl group.

The alicyclic structure may be monocyclic or polycyclic. Specifically, a monocyclo structure, a bicyclo structure, a tricyclo structure, a tetracyclo structure, and the like, each having 5 or more carbon atoms are included. The number of carbon atoms is preferably 6 to 30, and particularly preferably 7 to 25. The hydrocarbon groups having these alicyclic structures may have a substituent.

Examples of the alicyclic structures are shown below.

[Chem. 42]

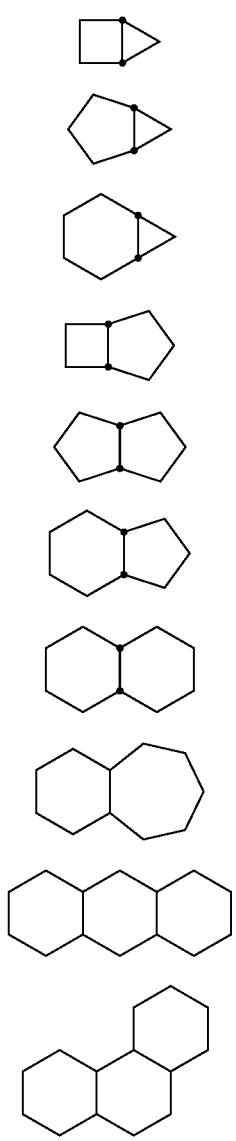

(1)
(2)
(3)
(4)
(5)
(6)
(7)
(8)
(9)
(10)

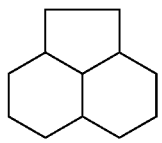

(11)

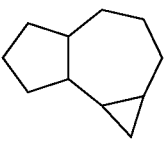

(12)

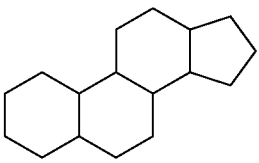

(13)

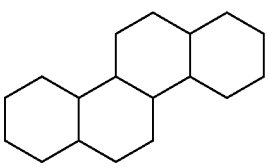

(14)

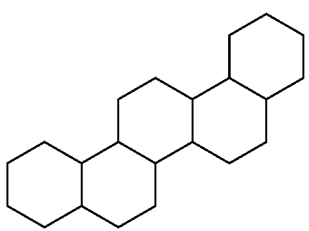

(15)

(16)

(17)

(18)

(19)

(20)

(21)

(22)

[Chem. 43]
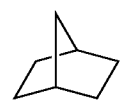 (23)
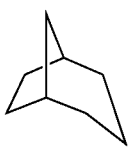 (24)
 (25)
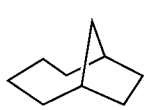 (26)
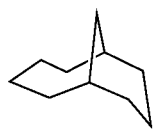 (27)
 (28)
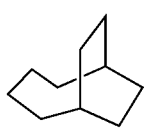 (29)
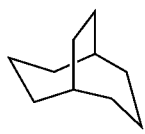 (30)
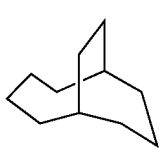 (31)
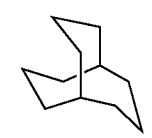 (32)
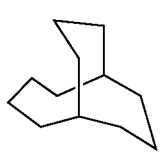 (33)
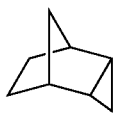 (34)
 (35)
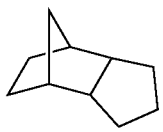 (36)
 (37)
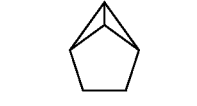 (38)
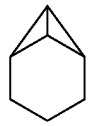 (39)
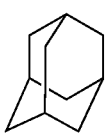 (40)
 (41)
 (42)
 (43)
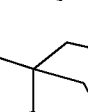 (44)
 (45)

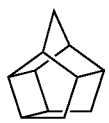 (46)

 (47)

 (48)

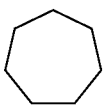 (49)

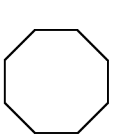 (50)

In the present invention, preferred examples of the alicyclic structure include an adamantyl group, a noradamantyl group, a decalin residue, a tricyclodecanyl group, a tetracyclododecanyl group, a norbornyl group, a cedrol group, a cyclohexyl group, a cycloheptyl group, a cyclooctyl group, a cyclodecanyl group and a cyclododecanyl group as a representation of a monovalent alicyclic group. More preferred examples thereof include an adamantyl group, a decalin residue, a norbornyl group, a cedrol group, a cyclohexyl group, a cycloheptyl group, a cyclooctyl group, a cyclodecanyl group and a cyclododecanyl group.

Examples of the substituents which these alicyclic structures may have include an alkyl group, a halogen atom, a hydroxyl group, an alkoxy group, a carboxyl group and an alkoxycarbonyl group. The alkyl group is preferably a lower alkyl group such as a methyl group, an ethyl group, a propyl group, an isopropyl group and a butyl group, and more preferably a methyl group, an ethyl group, a propyl group or an isopropyl group. The alkoxy group includes an alkoxy group having 1 to 4 carbon atoms, such as a methoxy group, an ethoxy group, a propoxy group and a butoxy group. The alkyl group and the alkoxy group each may further have a substituent. Examples of the substituent which the alkyl group and alkoxy group may further have include a hydroxyl group, a halogen atom and an alkoxy group.

An acid-decomposable group having an alicyclic structure is preferably a group shown in the following general formula (pI) to the general formula (pV).

[Chem. 44]

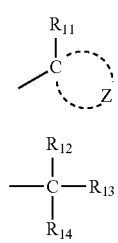

(pI)

(pII)

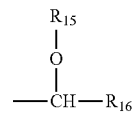 (pIII)

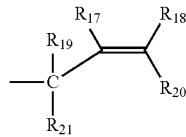 (pIV)

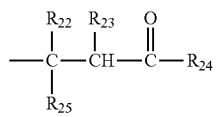 (pV)

In the general formulae (pI) to (pV), $R_{11}$ represents a methyl group, an ethyl group, an n-propyl group, an isopropyl group, an n-butyl group, an isobutyl group or a sec-butyl group, and Z represents an atomic group necessary for forming an alicyclic hydrocarbon group together with the carbon atom;

$R_{12}$ to $R_{16}$ each independently represent a linear or branched alkyl group having 1 to 4 carbon atoms or an alicyclic hydrocarbon group, provided that at least one of $R_{12}$ to $R_{14}$ or either one of $R_{15}$ and $R_{16}$ represents an alicyclic hydrocarbon group;

$R_{17}$ to $R_{21}$ each independently represent a hydrogen atom, a linear or branched alkyl group or an alicyclic hydrocarbon group having 1 to 4 carbon atoms, provided that at least one of $R_{17}$ to $R_{21}$ represents an alicyclic hydrocarbon group. In addition, either one of $R_{19}$ and $R_{21}$ represents a linear or branched alkyl group or an alicyclic hydrocarbon group having 1 to 4 carbon atoms; and $R_{22}$ to $R_{25}$ each independently represent a hydrogen atom, a linear or branched alkyl group or an alicyclic hydrocarbon group having 1 to 4 carbon atoms, provided that at least one of $R_{22}$ to $R_{25}$ represents an alicyclic hydrocarbon group. In addition, $R_{23}$ and $R_{24}$ may be bonded to each other to form a ring.

In the general formulae (pI) to (pV), the alkyl group of $R_{11}$ to $R_{25}$ represents a linear or branched alkyl group having 1 to 4 carbon atoms, which may be substituted or unsubstituted. Examples of the alkyl group include a methyl group, an ethyl group, an n-propyl group, an isopropyl group, an n-butyl group, an isobutyl group, a sec-butyl group, a t-butyl group, and the like.

In addition, examples of the substituent which the alkyl group may further have include an alkoxy group having 1 to 4 carbon atoms, a halogen atom (a fluorine atom, a chlorine atom, a bromine atom, and an iodine atom), an acyl group, an acyloxy group, a cyano group, a hydroxyl group, a carboxyl group, an alkoxycarbonyl group, a nitro group, and the like.

Examples of the alicyclic hydrocarbon group in $R_{11}$ to $R_{25}$ or the alicyclic hydrocarbon group formed by Z together with the carbon atom include the same groups mentioned above as the alicyclic structure.

In one embodiment, the repeating unit represented by the general formula (A2) is preferably a repeating unit represented by the following formula.

[Chem. 45]

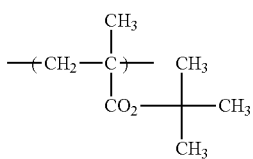

In addition, in another embodiment, the repeating unit represented by the general formula (A2) is also preferably a repeating unit represented by the general formula (A3) shown below.

[Chem. 46]

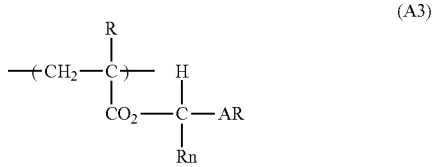

(A3)

In the general formula (A3),

AR represents an aryl group;

Rn represents an alkyl group, a cycloalkyl group, or an aryl group. Rn and AR may be bonded to each other to form a non-aromatic ring; and R represents a hydrogen atom, an alkyl group, a cycloalkyl group, a halogen atom, a cyano group, or an alkyloxycarbonyl group.

The repeating unit represented by the general formula (A3) will be described in detail.

AR represents an aryl group as described above. As the aryl group of AR, those having 6 to 20 carbon atoms, such as a phenyl group, a naphthyl group, an anthryl group, or a fluorene group are preferred, and those having 6 to 15 carbon atoms are more preferred.

In the case where AR is a naphthyl group, an anthryl group, or a fluorene group, the bonding position between the carbon atom to which Rn is bonded and AR is not particularly limited. For example, when AR is a naphthyl group, the carbon atom may be bonded to the α-position or the β-position of the naphthyl group. Or when AR is an anthryl group, the carbon atom may be bonded to the 1-position, the 2-position or the 9-position of the anthryl group.

The aryl group as AR may have one or more substituents. Specific examples of such a substituent include a linear or branched chain alky group having 1 to 20 carbon atoms, such as a methyl group, an ethyl group, a propyl group, an isopropyl group, an n-butyl group, an isobutyl group, a t-butyl group, a pentyl group, a hexyl group, an octyl group, and a dodecyl group, an alkoxy group containing such an alkyl group moiety, a cycloalkyl group such as cyclopentyl group and cyclohexyl group, a cycloalkoxy group containing such a cycloalkyl group moiety, a hydroxyl group, a halogen atom, an aryl group, a cyano group, a nitro group, an acyl group, an acyloxy group, an acylamino group, a sulfonylamino group, an alkylthio group, an arylthio group, an aralkylthio group, a thiophenecarbonyloxy group, a thiophenemethylcarbonyloxy group, and a heterocyclic residue such as a pyrrolidone residue. The substituent is preferably a linear or branched chain alkyl group having 1 to 5 carbon atoms or an alkoxy group containing such an alkyl group moiety, and more preferably a paramethyl group or a paramethoxy group.

In a case where an aryl group as AR has a plurality of substituents, at least two of a plurality of substituents may be bonded to each other to form a ring. The ring is preferably a 5- to 8-membered ring, and more preferably a 5- or 6-membered ring. The ring may be also a heterocycle containing a heteroatom such as an oxygen atom, a nitrogen atom and a sulfur atom in the ring members.

Furthermore, this ring may have a substituent. Examples of the substituent include the same as those described later for the further substituent which Rn may have.

In addition, from the viewpoint of the roughness performance, the repeating unit represented by the general formula (A3) preferably contains two or more aromatic rings. The number of aromatic rings contained in the repeating unit is usually preferably 5 or less, and more preferably 3 or less.

In addition, from the viewpoint of the roughness performance, in the repeating unit represented by the general formula (A3), AR preferably contains two or more aromatic rings, and AR is more preferably a naphthyl group or a biphenyl group. The number of the aromatic rings contained in AR is usually preferably 5 or less, and more preferably 3 or less.

As described above, Rn represents an alkyl group, a cycloalkyl group or an aryl group.

The alkyl group of Rn may be a linear alkyl group or a branched-chain alkyl group. As the alkyl group, an alky group having 1 to 20 carbon atoms, such as a methyl group, an ethyl group, a propyl group, an isopropyl group, an n-butyl group, an isobutyl group, a t-butyl group, a pentyl group, a hexyl group, a cyclohexyl group, an octyl group, and a dodecyl group is preferably included. The alkyl group of Rn is preferably an alkyl group having 1 to 5 carbon atoms, and more preferably an alkyl group having 1 to 3 carbon atoms.

Examples of the cycloalkyl group of Rn include a cycloalkyl group having 3 to 15 carbon atoms, such as a cyclopentyl group and a cyclohexyl group.

As an aryl group of Rn, for example, an aryl group having 6 to 14 carbon atoms, such as a phenyl group, a xylyl group, a tolyl group, a cumenyl group, a naphthyl group and an anthryl group is preferred.

Each of the alkyl group, the cycloalkyl group, and the aryl group as Rn may further have a substituent. Examples of the substituent include an alkoxy group, a hydroxyl group, a halogen atom, a nitro group, an acyl group, an acyloxy group, an acylamino group, a sulfonylamino group, dialkylamino group, an alkylthio group, an arylthio group, an aralkylthio group, a thiophenecarbonyloxy group, a thiophenemethylcarbonyloxy group, and heterocyclic residues such as a pyrrolidone residue. Among these, an alkoxy group, a hydroxyl group, a halogen atom, a nitro group, an acyl group, an acyloxy group, an acylamino group, and a sulfonyl amino group are particularly preferred.

As described above, R represents a hydrogen atom, an alkyl group, a cycloalkyl group, a halogen atom, a cyano group or an alkyloxycarbonyl group.

Examples of the alkyl group and the cycloalkyl group of R include the same as those described above for Rn. Each of these alkyl groups and cycloalkyl groups may have a substituent. Examples of this substituent include the same as those described above for Rn.

In the case where R is an alkyl group or a cycloalkyl group having a substituent, particularly preferred examples of R include a trifluoromethyl group, an alkyloxycarbonyl methyl group, an alkylcarbonyloxymethyl group, a hydroxymethyl group and an alkoxymethyl group.

The halogen atom of R includes a fluorine atom, a chlorine atom, a bromine atom and an iodine atom. Among these, the fluorine atom is particularly preferable.

As the alkyl group moiety contained in the alkyloxycarbonyl group of R, for example, the configuration described above as the alkyl group of R may be employed.

Rn and AR are preferably bonded to each other to form a non-aromatic ring and, in particular, this can further improve the roughness performance.

The non-aromatic ring in which Rn and AR may be bonded to each other to form is preferably a 5- to 8-membered ring, and more preferably a 5- or 6-membered ring.

The non-aromatic ring may be an aliphatic ring or a heterocycle containing a heteroatom such as an oxygen atom, a nitrogen atom and a sulfur atom, as a ring member.

The non-aromatic ring may have a substituent. Examples of the substituent are the same as those described above for the further substituent which Rn may have.

Hereinafter, specific examples of the monomer corresponding to the repeating unit represented by the general formula (A2) are illustrated, but the present invention is not limited thereto.

[Chem. 47]

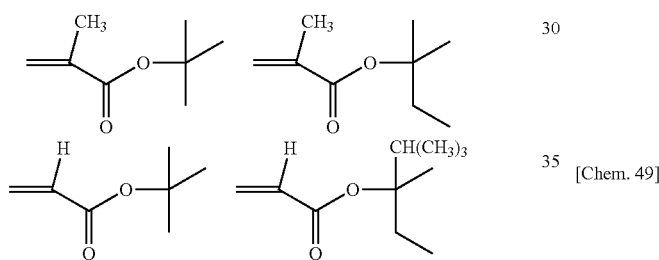

[Chem. 48]

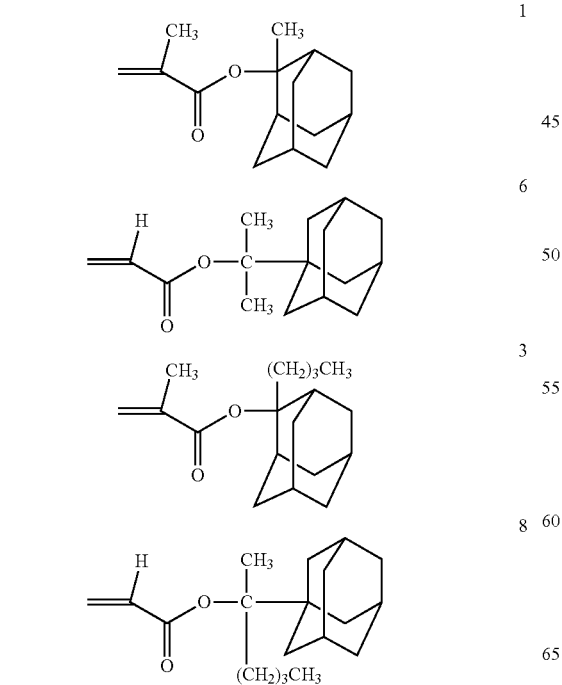

[Chem. 49]

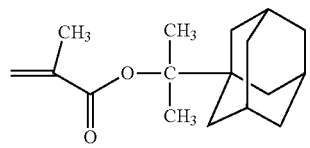

5

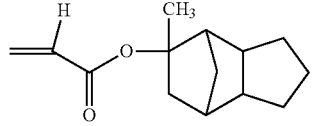

14

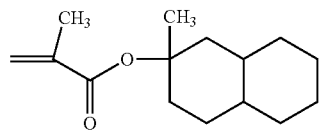

9

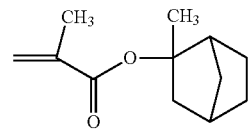

15

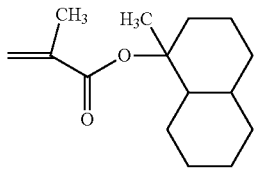

11

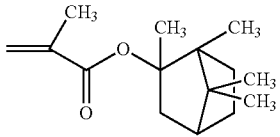

17

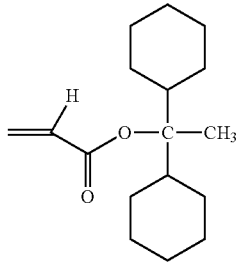

22

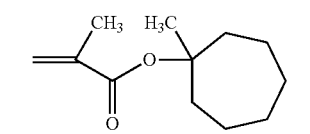

19

25

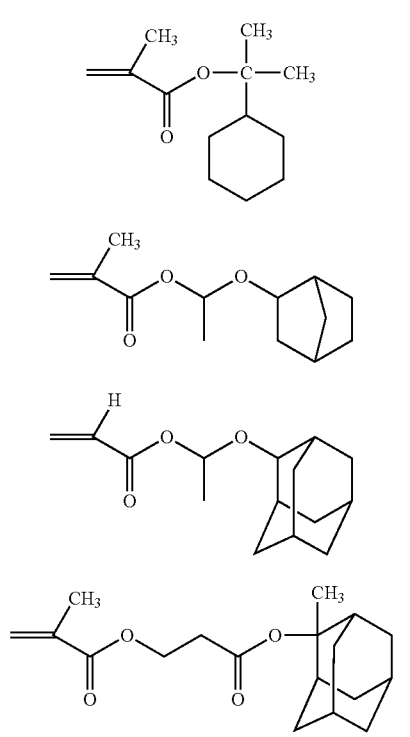
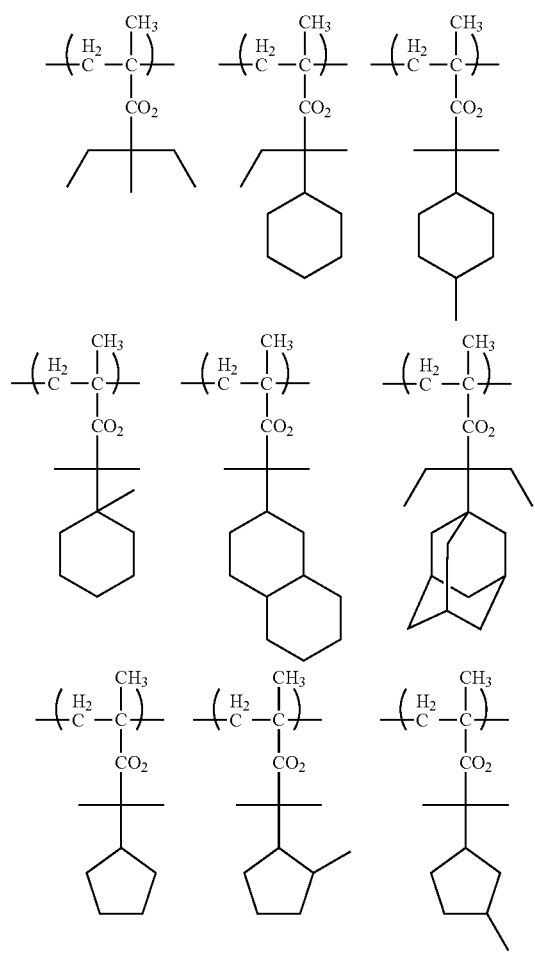
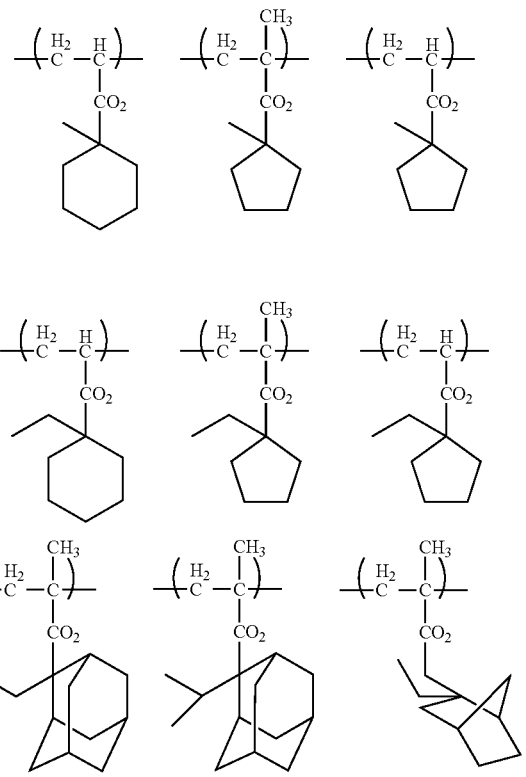
Specific examples of the structure of the repeating unit represented by the general formula (A3) are illustrated below, but the present invention is not limited thereto.
[Chem. 51]
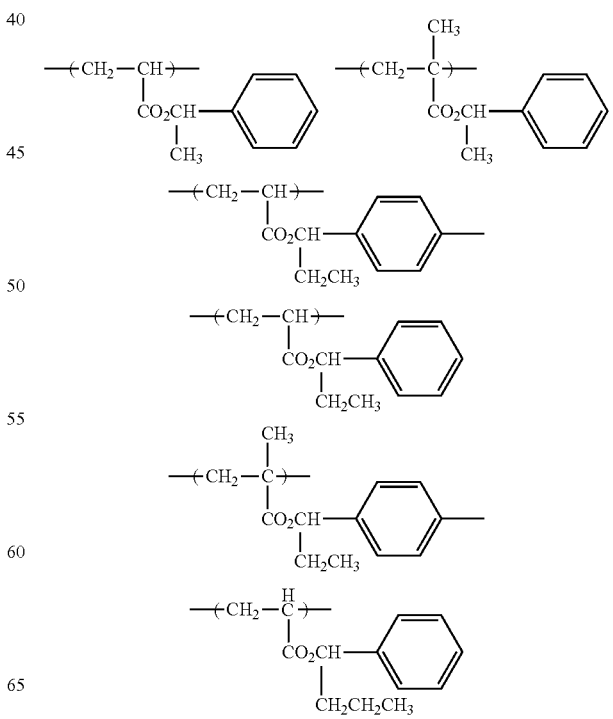

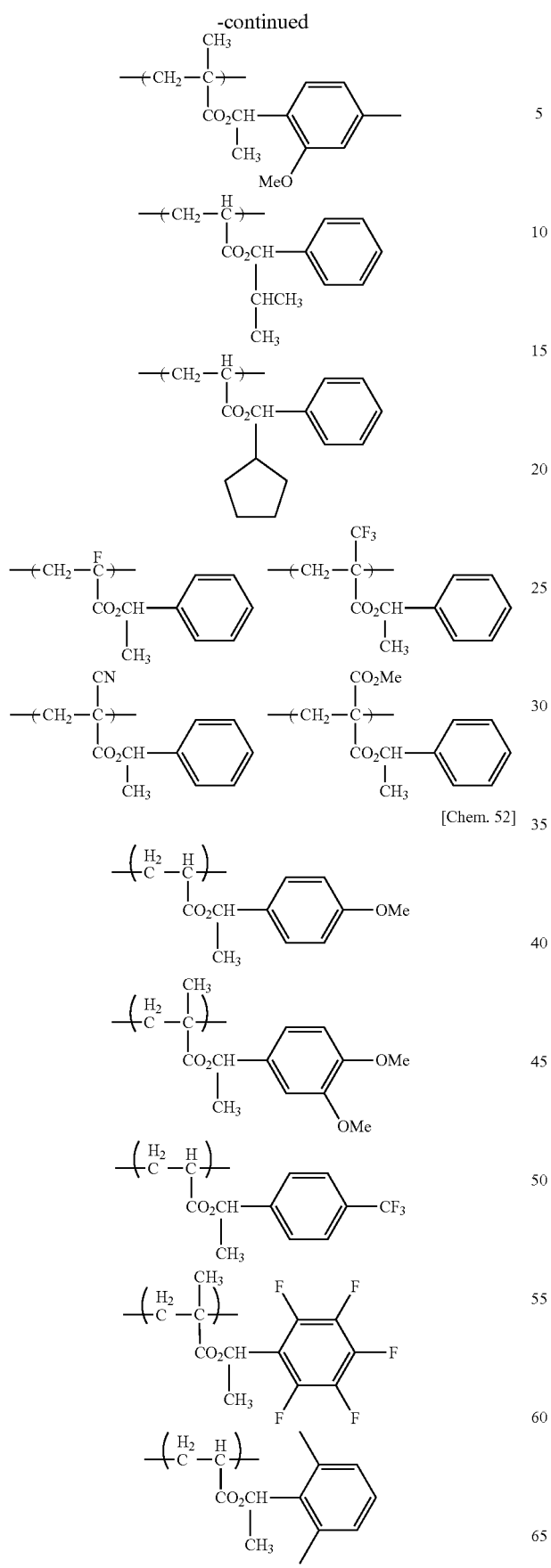
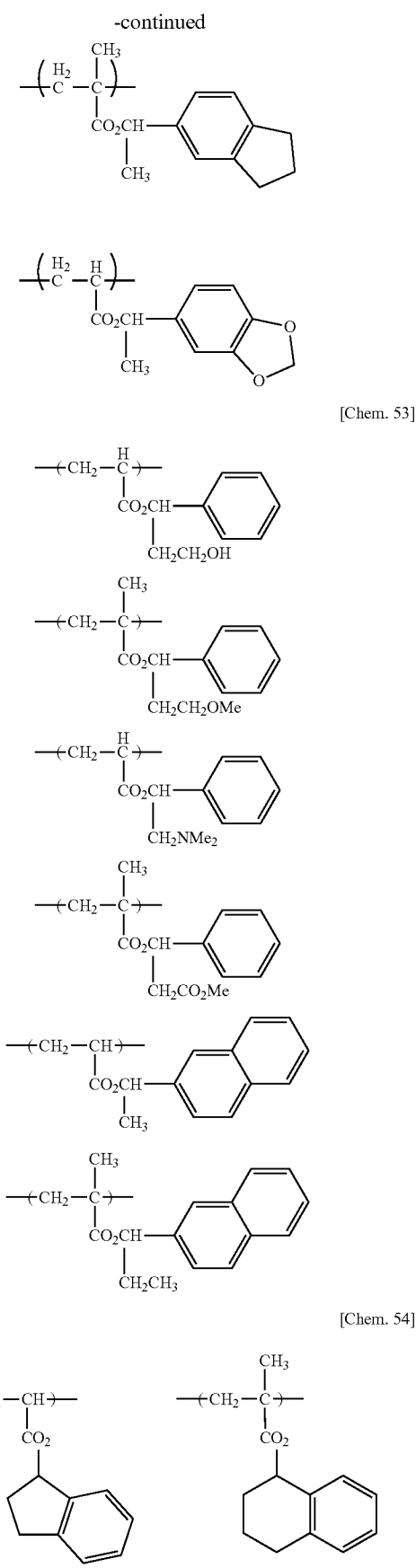
[Chem. 52]
[Chem. 53]
[Chem. 54]

-continued
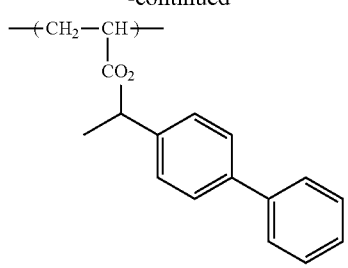
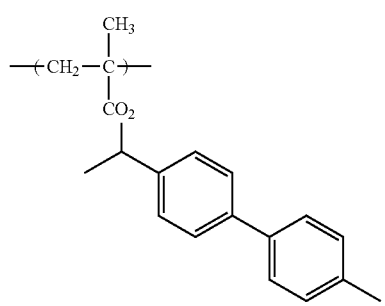
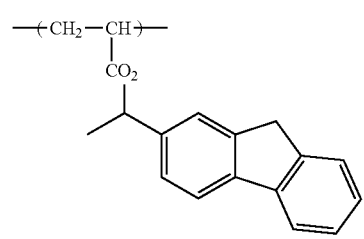
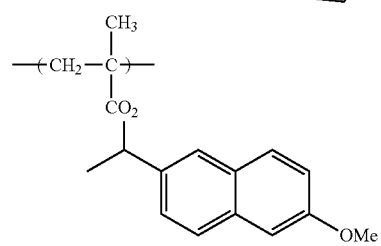
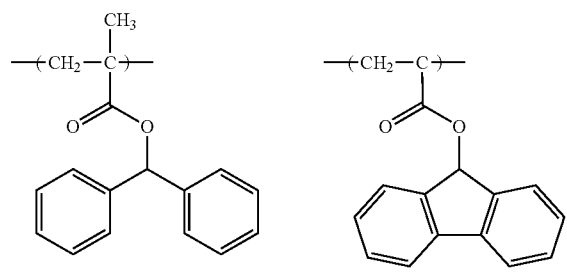
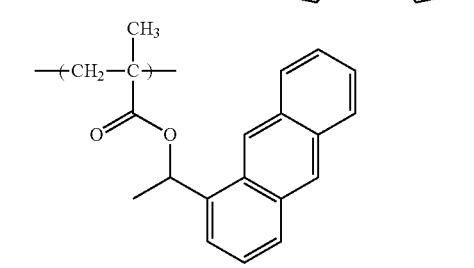
-continued
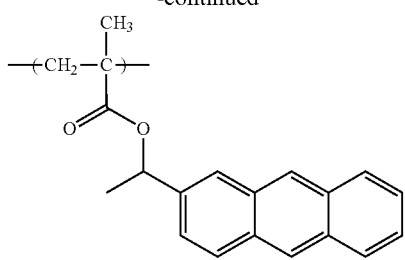
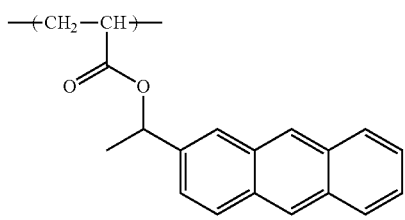
[Chem. 55]
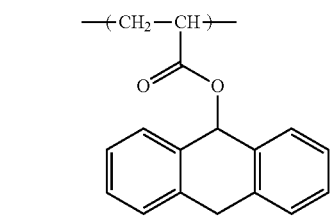
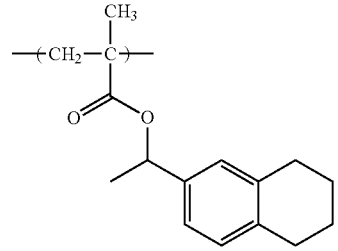
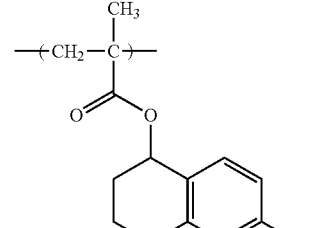
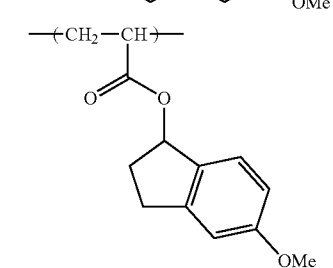
The compound (B2) may further contain a repeating unit represented by the following general formula (A5).

[Chem. 56]

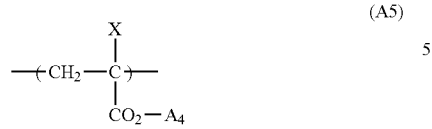
(A5)

In the formula (A5),

X represents a hydrogen atom, an alkyl group, a hydroxyl group, an alkoxy group, a halogen atom, a cyano group, a nitro group, an acyl group, an acyloxy group, a cycloalkyl group, an aryl group, a carboxyl group, an alkyloxycarbonyl group, an alkylcarbonyloxy group, or an aralkyl group; and $A_4$ represents a hydrocarbon group incapable of leaving by the action of an acid.

In the general formula (A5), examples of the hydrocarbon group incapable of leaving by the action of an acid of $A_4$ include a hydrocarbon group other than the above acid-decomposable group and, for example, an alkyl group incapable of leaving by the action of an acid (preferably having 1 to 15 carbon atoms), a cycloalkyl group incapable of leaving by the action of an acid (preferably having 3 to 15 carbon atoms), an aryl group incapable of leaving by the action of an acid (preferably having 6 to 15 carbon atoms), and the like are included.

The hydrocarbon group incapable of leaving by the action of an acid of $A_4$ may be further substituted with a hydroxyl group, an alkyl group, a cycloalkyl group, an aryl group, and the like.

Specific examples of the repeating unit represented by the general formula (A5) are illustrated below, but the present invention is not limited thereto.

[Chem. 57]

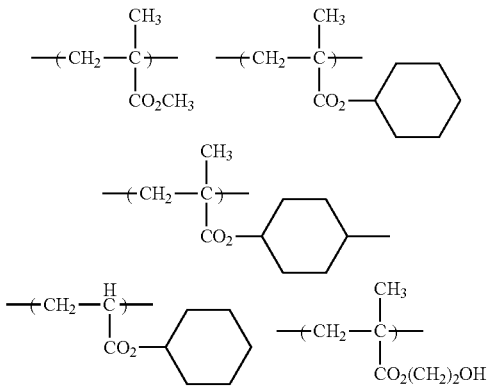

It is also preferable for the compound (B2) to further have a repeating unit represented by the general formula (A6).

[Chem. 58]

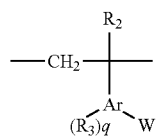
(A6)

In the general formula (A6), $R_2$ represents a hydrogen atom, a methyl group, a cyano group, a halogen atom, or a perfluoro group having 1 to 4 carbon atoms;

$R_3$ represents a hydrogen atom, an alkyl group, a cycloalkyl group, a halogen atom, an aryl group, an alkoxy group, or an acyl group;

q represents an integer of 0 to 4;

Ar represents a (q+2)-valent aromatic ring; and

W represents a group incapable of decomposing by the action of an acid, or a hydrogen atom.

The aromatic ring represented by Ar is preferably a benzene ring, a naphthalene ring, or an anthracene ring, and more preferably a benzene ring.

W represents a group incapable of decomposing by the action of an acid (also referred to as an "acid-stable group"), a group other than the above-described acid-decomposable group is included, and specifically, a halogen atom, an alkyl group, a cycloalkyl group, an alkenyl group, an aryl group, an acyl group, an alkylamide group, an arylamidomethyl group, an arylamide group, and the like are included. The acid-stable group is preferably an acyl group or an alkylamide group, more preferably an acyl group, an alkylcarbonyloxy group, an alkyloxy group, a cycloalkyloxy group, or an aryloxy group.

In the acid-stable group of W, the alkyl group is preferably one having 1 to 4 carbon atoms, such as a methyl group, an ethyl group, a propyl group, an n-butyl group, a sec-butyl group, and a t-butyl group; the cycloalkyl group is preferably one having 3 to 10 carbon atoms, such as a cyclopropyl group, a cyclobutyl group, a cyclohexyl group, and an adamantyl group; the alkenyl group is preferably one having 2 to 4 carbon atoms, such as a vinyl group, a propenyl group, an allyl group, and a butenyl group; the alkenyl group is preferably one having 2 to 4 carbon atoms, such as a vinyl group, a propenyl group, an allyl group, and a butenyl group; and the aryl group is preferably one having 6 to 14 carbon atoms, such as a phenyl group, a xylyl group, a tolyl group, a cumenyl group, a naphthyl group, and an anthracenyl group. W may be at any position of the benzene ring, but is preferably at the meta-position or the para-position of the styrene skeleton, and particularly preferably at the para-position.

Specific examples of the repeating unit represented by the general formula (A6) are shown below, but the present invention is not limited thereto.

[Chem. 59]

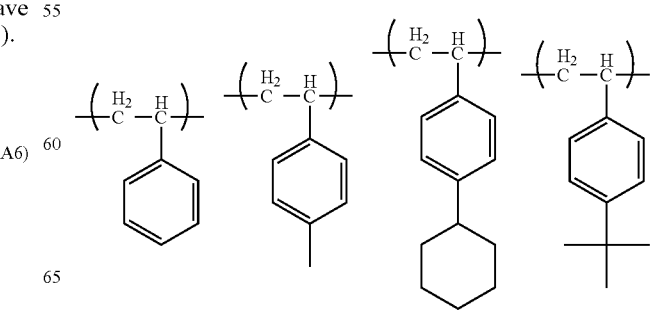

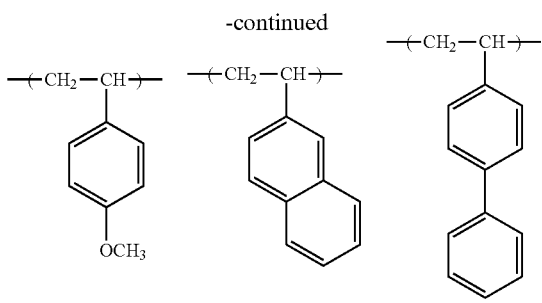

The content rate of the repeating units having the acid-decomposable groups in the compound (B2) is preferably from 5 to 95% by mol, more preferably from 10 to 60% by mol, and particularly preferably 15 to 50% by mol, in the total repeating units.

In addition, the compound (B2) may be copolymerized with other appropriate polymerizable monomers so that an alkali-soluble group, for example, a phenolic hydroxyl group or a carboxyl group can be introduced for the purpose of maintaining good developability with an alkali developer, or may be copolymerized with other hydrophobic polymerizable monomers such as alkyl acrylate and alkyl methacrylate for the purpose of enhancing the film quality.

In one embodiment, the compound (B2) preferably contains a repeating unit represented by the following general formula (A).

[Chem. 60]

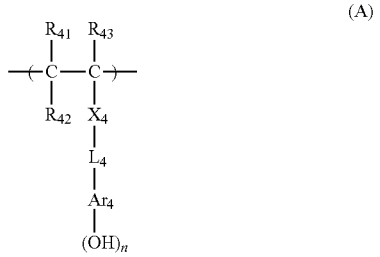

In the formula (A), $R_{41}$, $R_{42}$, and $R_{43}$ each independently represent a hydrogen atom, an alkyl group, a halogen atom, a cyano group, or an alkoxycarbonyl group. However, $R_{42}$ may be bonded to $Ar_4$ to form a ring, in this case, $R_{42}$ represents a single bond or an alkylene group.

$X_4$ represents a single bond, —COO—, or —CONR$_{64}$— and $R_{64}$ represents a hydrogen atom, and an alkyl group.

$L_4$ represents a single bond and an alkylene group.

$Ar_4$ represents a (n+1)-valent aromatic ring group, and in a case of being bonded to $R_{42}$ to form a ring, represents a (n+2)-valent aromatic ring group.

n represents an integer of 1 to 4.

Specific examples of the alkyl group, the cycloalkyl group, the halogen atom and the alkoxycarbonyl group of $R_{41}$, $R_{42}$ and $R_{43}$, and the substituent which these groups can have in the formula (A) include, for example, an alkyl group, a cycloalkyl group, an aryl group, an amino group, an amido group, a ureido group, a urethane group, a hydroxyl group, a carboxyl group, a halogen group, an alkoxy group, a thioether group, an acyl group, an acyloxy group, an alkoxy-carbonyl group, a cyano group, a nitro group, and the like and the number of carbon atoms of the substituent is preferably 10 or less.

$Ar_4$ represents a (n+1)-valent aromatic ring group. A divalent aromatic ring group in a case where n is 1 may have a substituent, and for example, an arylene group having 6 to 18 carbon atoms such as a phenylene group, a tolylene group, a naphthylene group, an anthracenylene group, or for example, an aromatic ring group including a hetero ring such as thiophene, furan, pyrrole, benzothiophene, benzofuran, benzopyrrole, triazine, imidazole, benzoimidazole, triazole, thiadiazole or thiazole is included as a preferred example.

Specific examples of the (n+1)-valent aromatic ring group in a case where n is an integer of 2 or more suitably can include a group where arbitrary (n−1) hydrogen atoms are removed from specific examples of the divalent aromatic ring group described above.

The (n+1)-valent aromatic ring group may further have a substituent.

Examples of the substituent which the alkyl group, the cycloalkyl group, the alkoxycarbonyl, the alkylene group and the (n+1)-valent aromatic ring group can have include an alkyl group, an alkoxy group such as a methoxy group, an ethoxy group, a hydroxyethoxy group, a propoxy group, a hydroxypropoxy group and a butoxy group, and an aryl group such as a phenyl group.

Examples of the alkyl group of $R_{64}$ in —CONR$_{64}$— ($R_{64}$ represents a hydrogen atom or an alkyl group) represented by $X_4$ include the same as an alkyl group of $R_{61}$ to $R_{63}$ in the general formula (A1) described above.

As $X_4$, a single bond, —COO— and —CONH— are preferable and a single bond and —COO— are more preferable.

Examples of the alkylene group in $L_4$ preferably include an alkylene group having 1 to 8 carbon atoms such as a methylene group, an ethylene group, a propylene group, a butylene group, a hexylene group or an octylene group, which may have a substituent.

As $Ar_4$, an aromatic ring group having 6 to 18 carbon atoms which may have a substituent is more preferable and a benzene ring group, a naphthalene ring group and a biphenylene ring group are particularly preferable.

A repeating unit (A) is preferably provided with a hydroxystyrene structure. That is, Ar4 is preferably a benzene ring group.

Hereinafter, specific examples of the repeating unit (A) represented by the general formula (A) are illustrated, but the present invention is not limited thereto.

[Chem. 61]

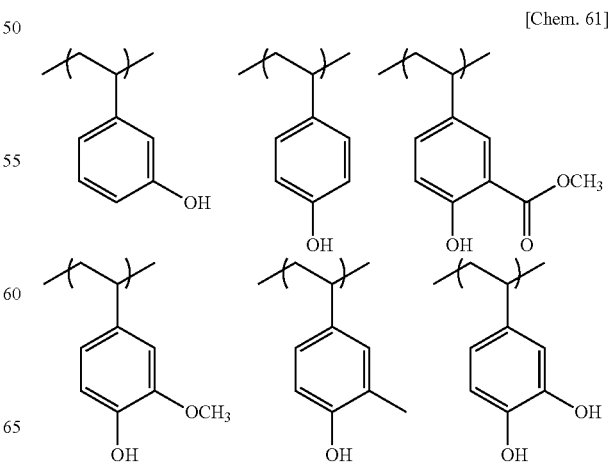

-continued

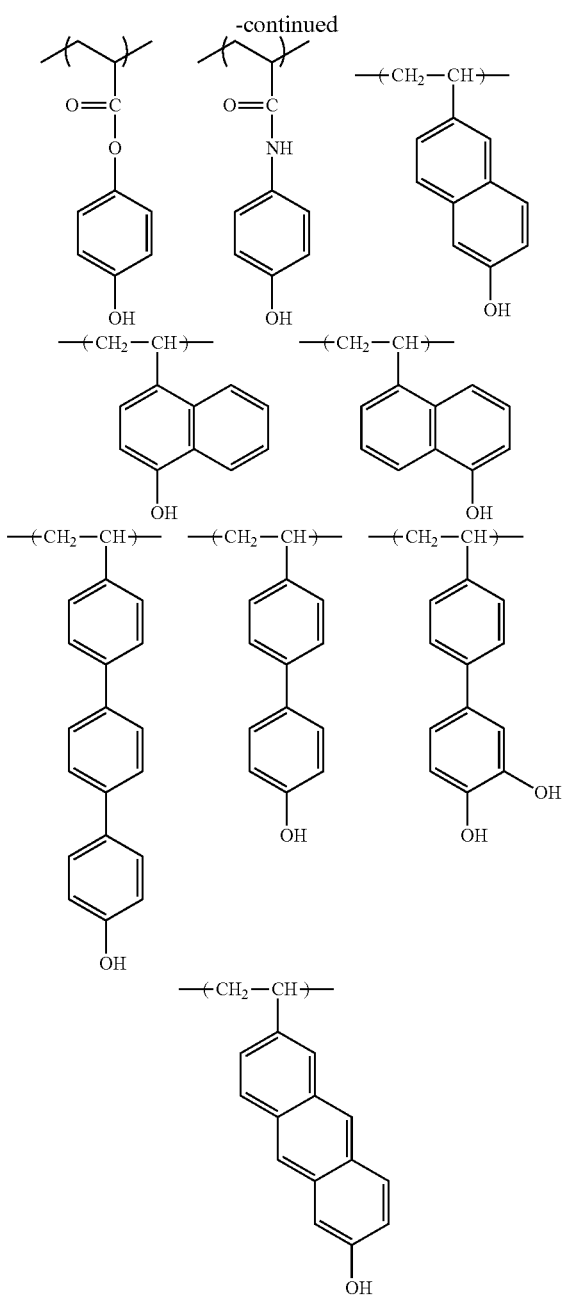

In one embodiment, a compound (B2) preferably includes at least a repeating unit represented by the following formula as a repeating unit represented by the general formula (A).

[Chem. 62]

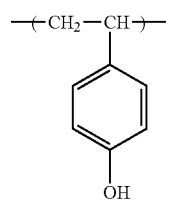

The content rate of repeating unit represented by the general formula (A) in the compound (B2) is preferably from 0 to 90% by mol, more preferably from 5 to 80% by mol, even more preferably from 10 to 70% by mol, and particularly preferably from 20 to 60% by mol, with respect to the total repeating units in the compound (B2).

In one embodiment, a compound (B2) may have a repeating unit (B) having a structural moiety which is capable of decomposing by irradiation with actinic rays or radiation and generates an acid.

In addition, when a composition of the present invention is exposed with ArF excimer laser, from the viewpoint of the transparency with respect to ArF excimer laser, a resin not having an aromatic ring as a compound (B2) is preferably used.

The compound (B2) may be used in combination of two or more kinds thereof.

The content rate of the compound (B2) usually from 10 to 99% by mass, preferably form 20 to 99% by mass and particularly preferably from 30 to 99% by mass, with respect to the total solid contents of the composition in the present invention.

The weight average molecular weight (Mw) of the compound (B2) is each preferably in the range of 1,000 to 200,000. In views of the dissolution rate with respect to an alkali and sensitivity of the resin itself, 200,000 or less is preferable. The dispersity (Mw/Mn) is preferably from 1.0 to 3.0, more preferably from 1.0 to 2.5 and particularly preferably from 1.0 to 2.0.

The weight average molecular weight (Mw) of compound (B2) is more preferably in a range of from 1,000 to 100,000, particularly preferably in a range of from 1,000 to 50,000 and most preferably in a range of from 1,000 to 25,000.

Here, the weight average molecular weight is defined as values that are measured by gel permeation chromatography and expressed in terms of polystyrene.

The compound (B2) having a dispersity of 2.0 or less can be synthesized by carrying out radical polymerization using an azo-based polymerization initiator. More preferably, the compound (B2) having a dispersity of 1.0 to 1.5 can be synthesized by, for example, living radical polymerization.

The compound (B2) is preferably polymerized by a well-known anion polymerization method, a radical polymerization method, and the like. For example, the compound (B2) can be synthesized by using a method described in JP2010-13428A.

Hereinafter, specific examples of the compound (B2) are illustrated, but the present invention is not limited thereto.

[Chem. 63]

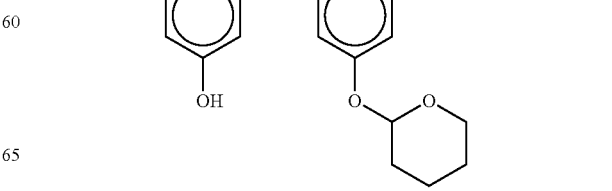

(Ab-1)

(Ab-2)
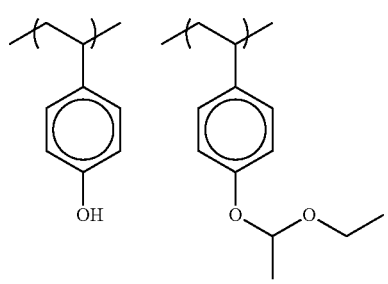
(Ab-7)
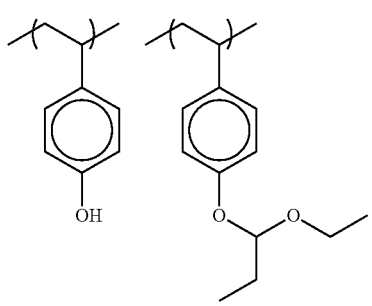
(Ab-3)
(Ab-8)
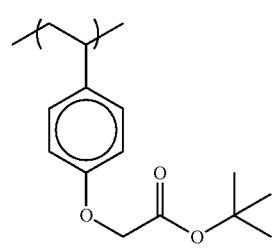
(Ab-4)
(Ab-9)
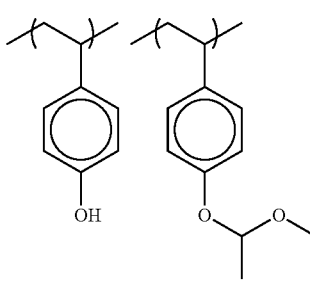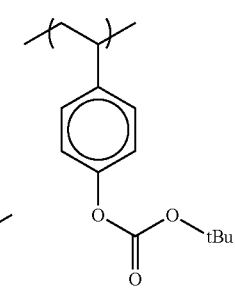
(Ab-5)
(Ab-10)
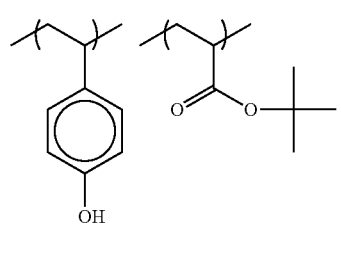
(Ab-6)
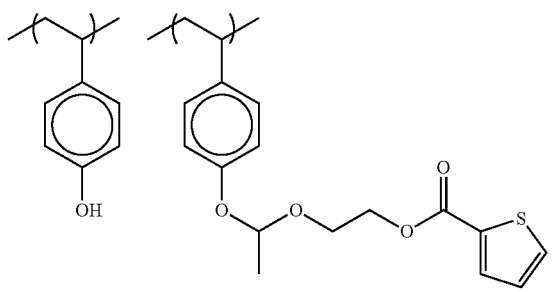

-continued
(Ab-11)
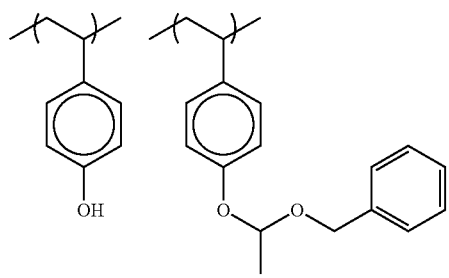
(Ab-12)
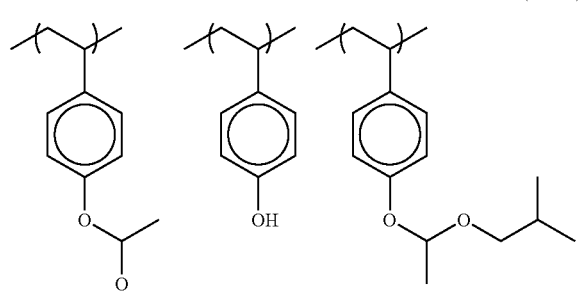
[Chem. 64]
(Ab-13)
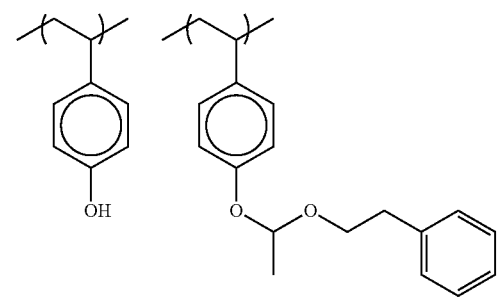
(Ab-14)
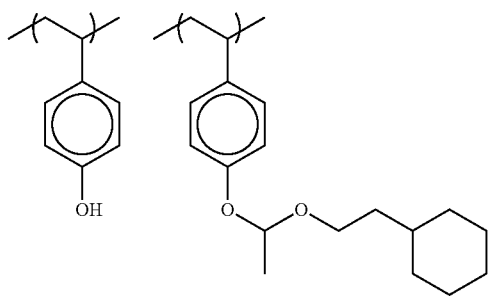
(Ab-16)
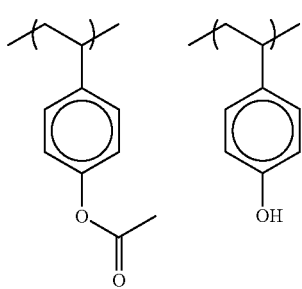
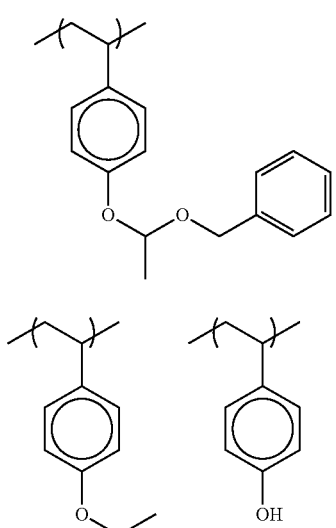
(Ab-17)
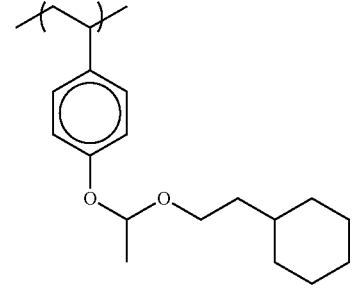

-continued (Ab-19)

(Ab-20)

(Ab-21)

(Ab-22)

-continued (Ab-23)

(Ab-24)

(Ab-25)

(Ab-26)

[Chem. 65]

(Ab-27)

(Ab-28)

(Ab-29)
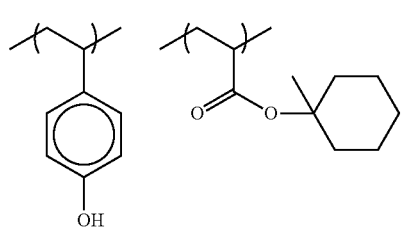
[Chem. 66]
(Ab-30)
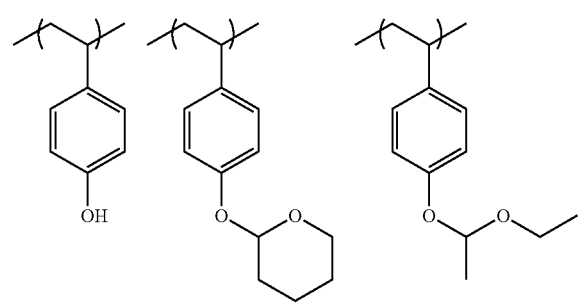
(Ab-31)
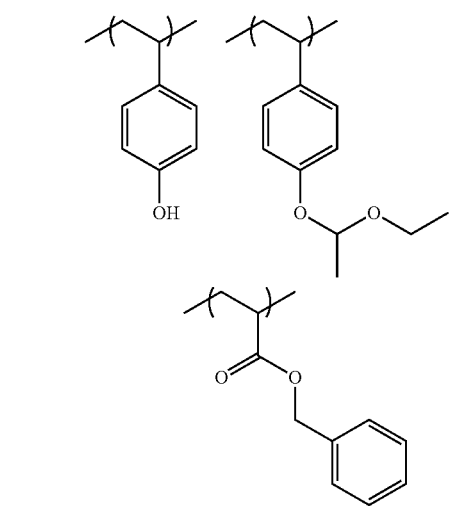
(Ab-32)
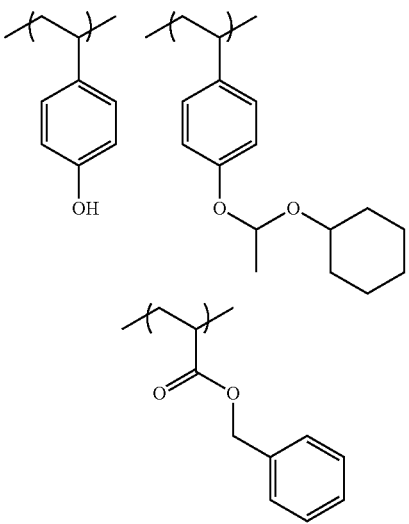
[Chem. 67]
(Ab-33)
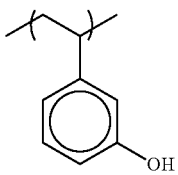
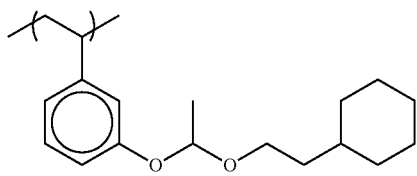
(Ab-34)
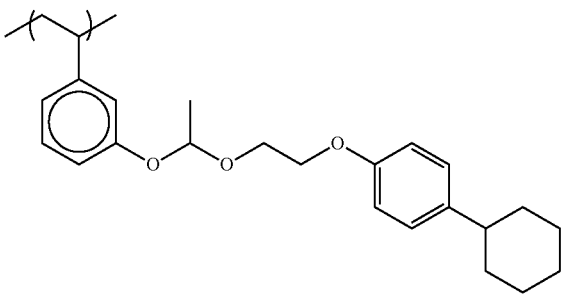
(Ab-35)
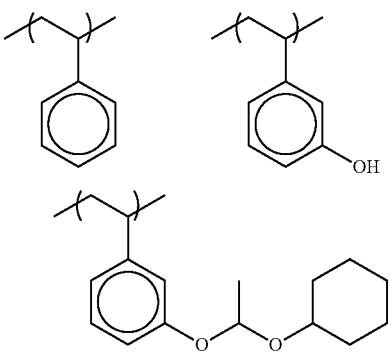
(Ab-36)
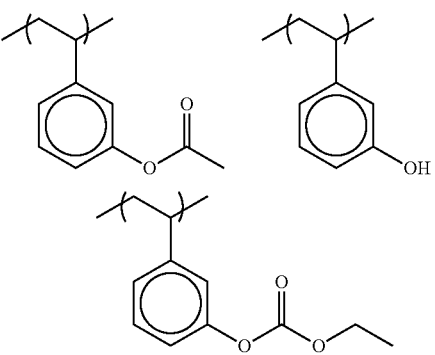

(Ab-37)
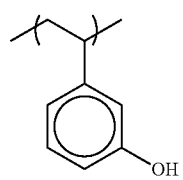 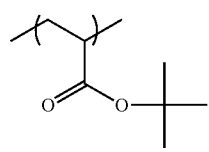
(Ab-42)
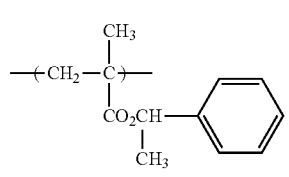
(Ab-38)
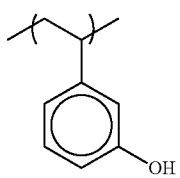 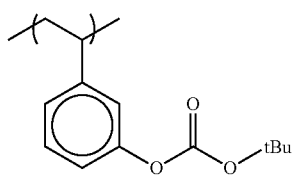
[Chem. 68]
(Ab-43)
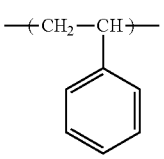
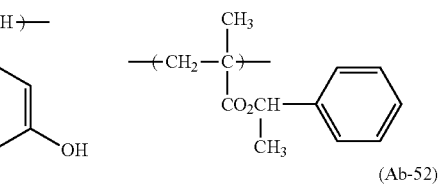
(Ab-39)
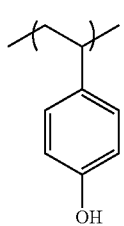 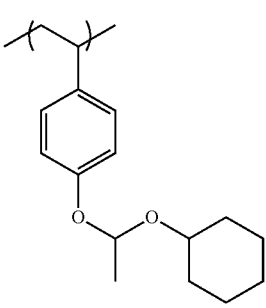
(Ab-52)
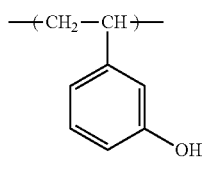
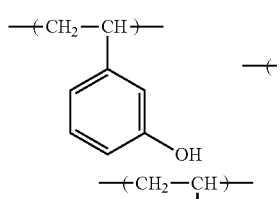
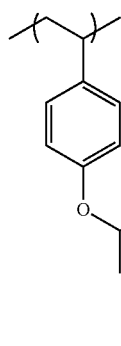
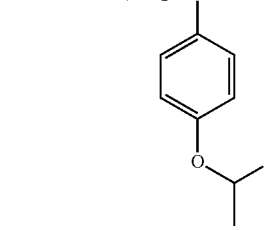
(Ab-40)
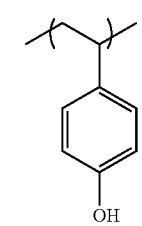 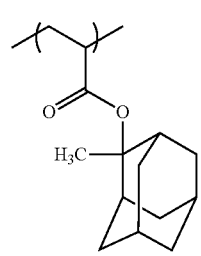
(Ab-53)
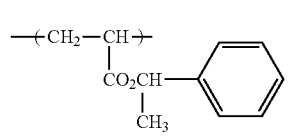
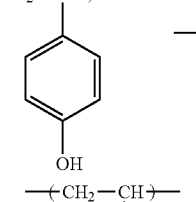
(Ab-41)
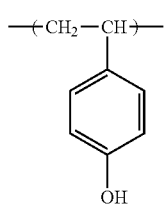 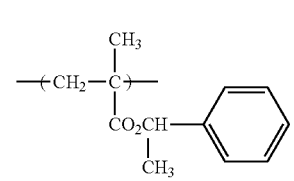
(Ab-56)
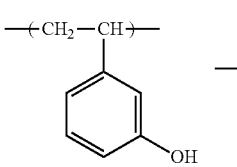 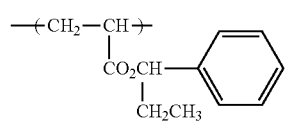

105
-continued
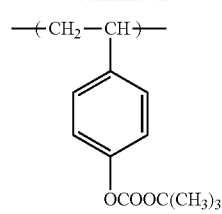
[Chem. 69]
(Ab-57)
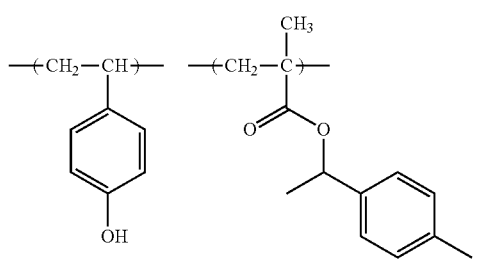
(Ab-58)
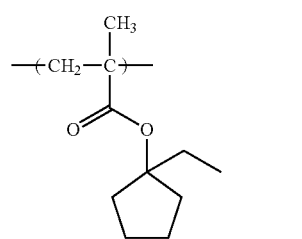
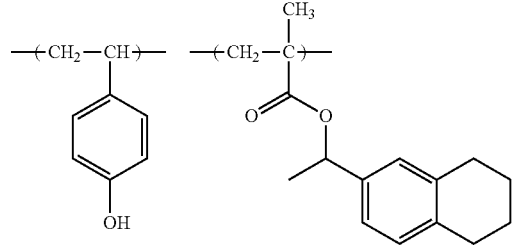
(Ab-59)
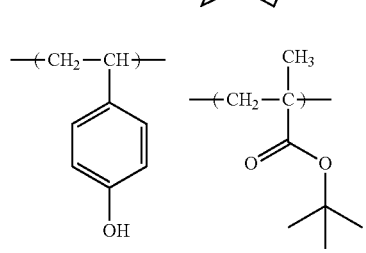
106
-continued
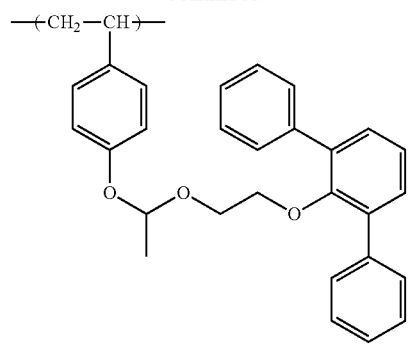
(Ab-60)
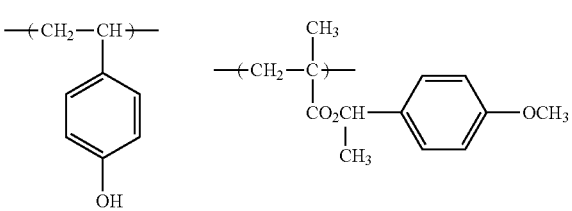
(Ab-61)
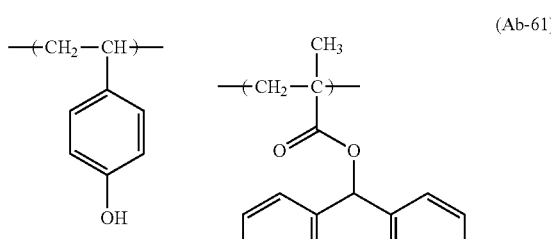
(Ab-62)
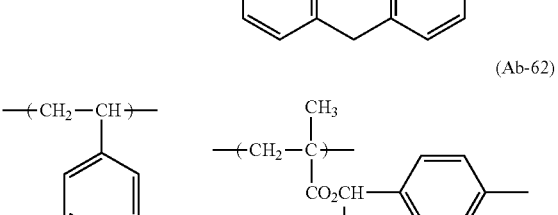
[Chem. 70]
(Ab-68)
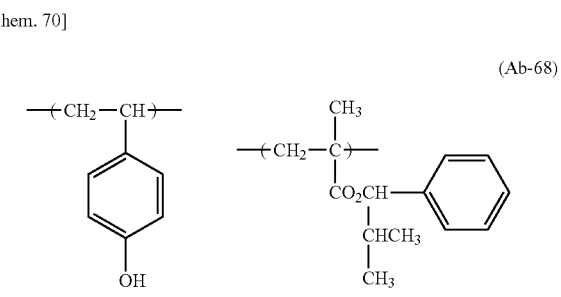
(Ab-71)
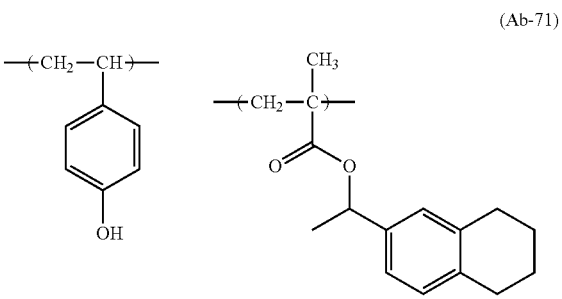

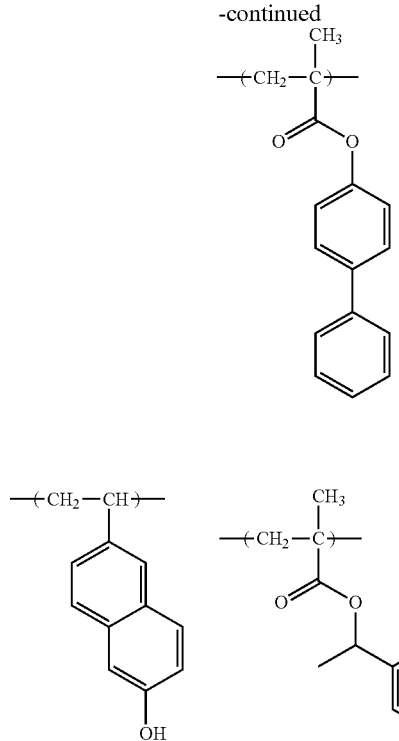
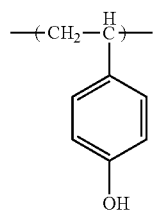 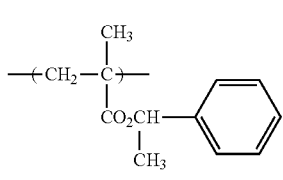
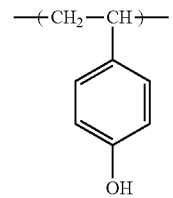
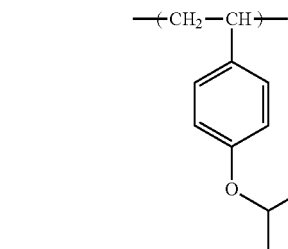
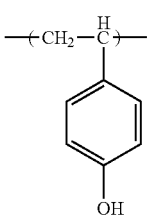 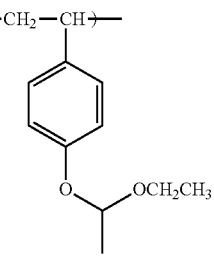
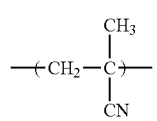
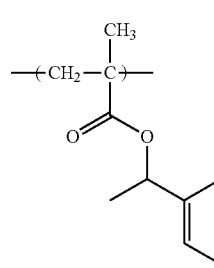
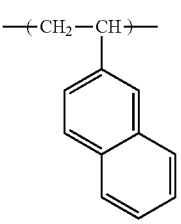
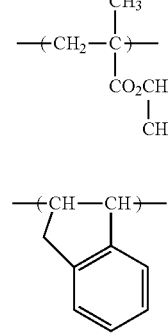

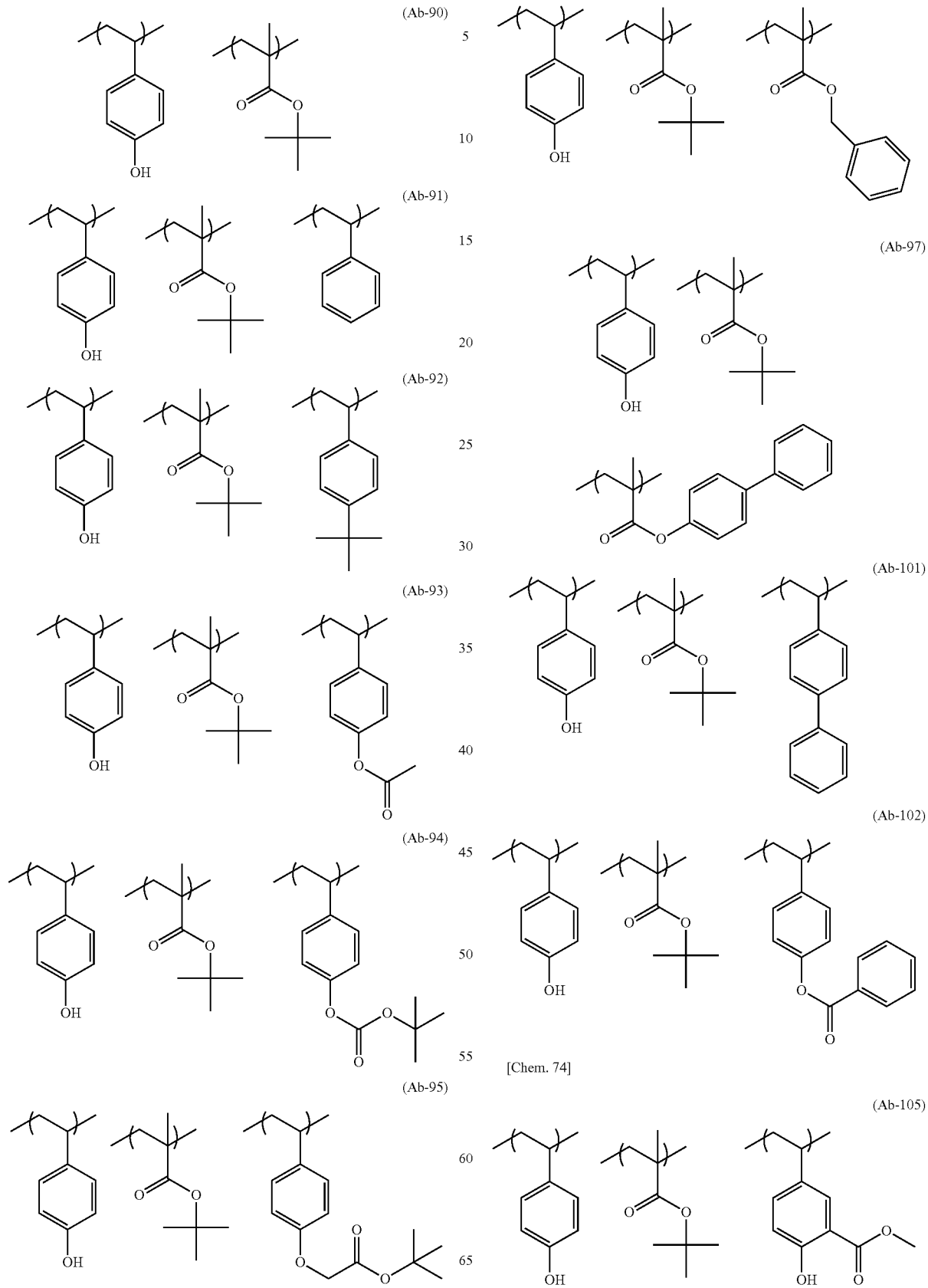

(Ab-106)
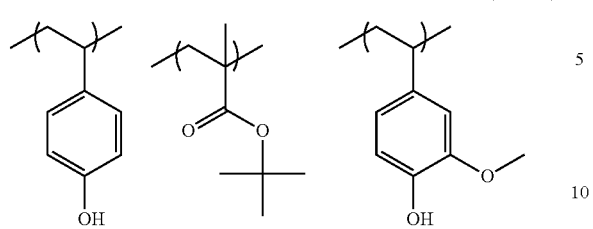
(Ab-120)
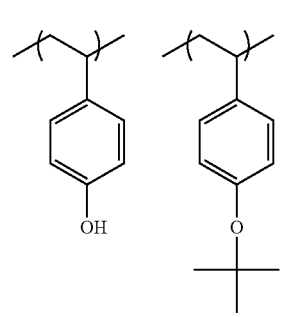
[Chem. 75]
(Ab-121)
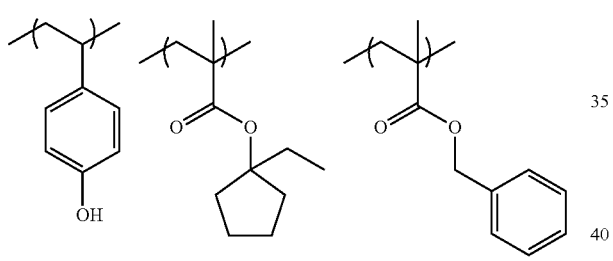
(Ab-125)
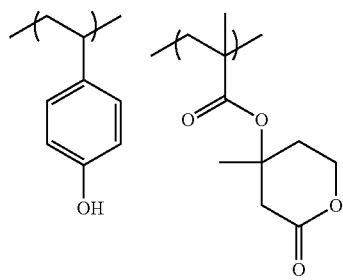
(Ab-126)
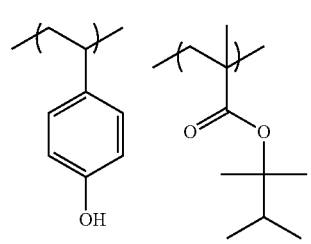
(Ab-127)
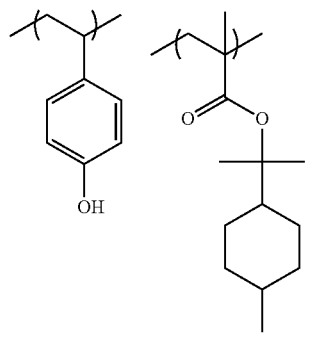
(Ab-128)
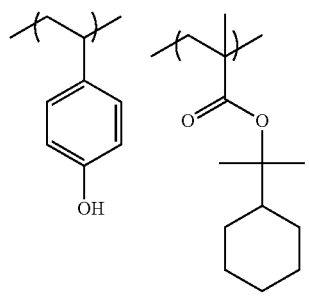
(Ab-129)
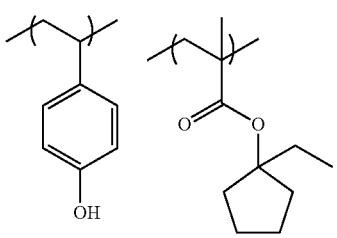
(Ab-130)
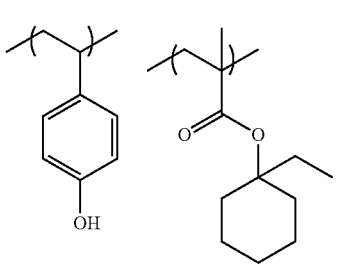
(Ab-133)
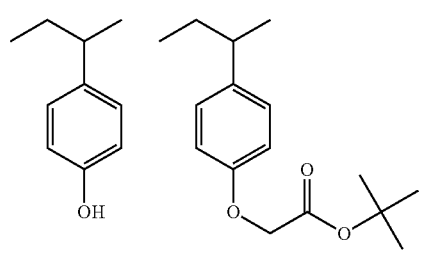
(Ab-134)
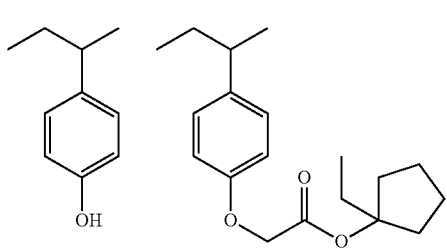

(Ab-135)
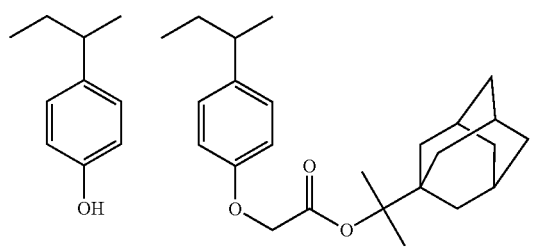
(Ab-136)
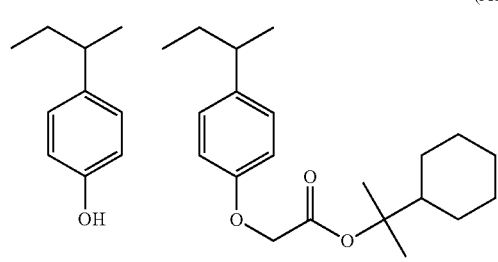
(Ab-137)
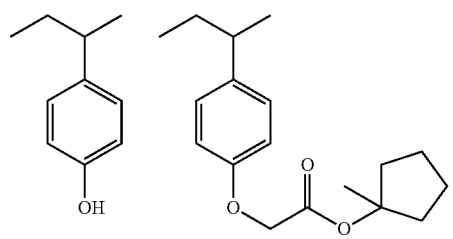
(Ab-138)
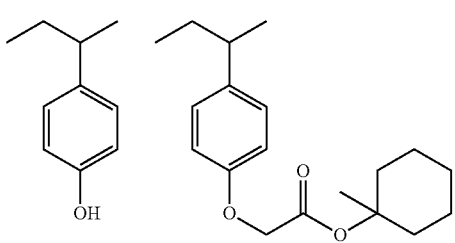
[Chem. 76]
(Ab-139)
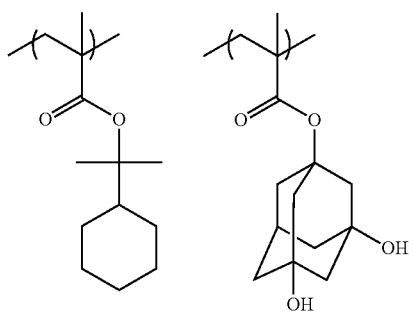
(Ab-140)
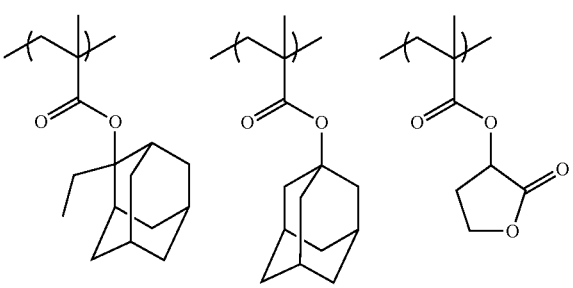
(Ab-141)
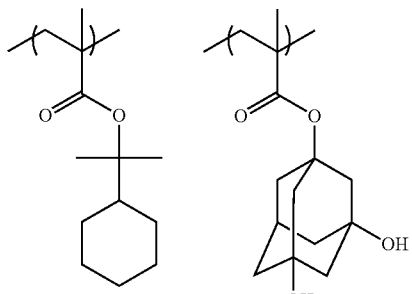
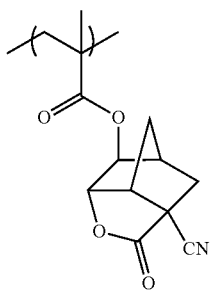
(Ab-142)
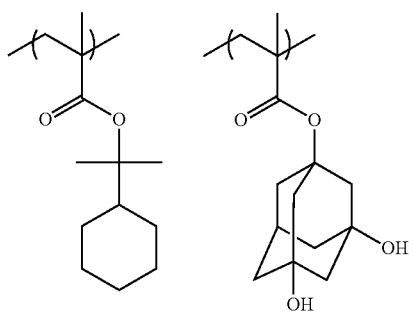

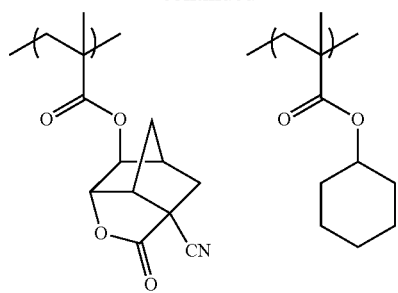
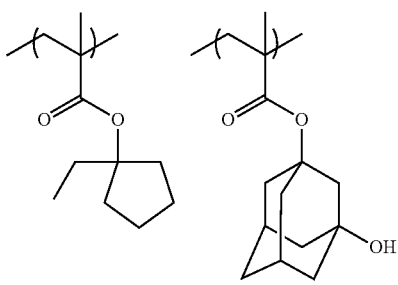
(Ab-145)
(Ab-143)
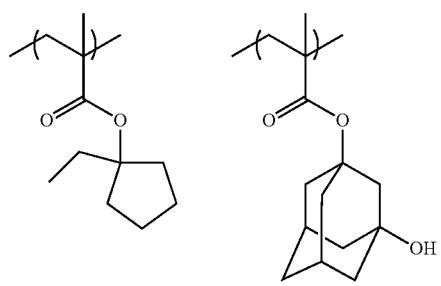
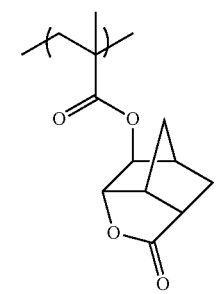
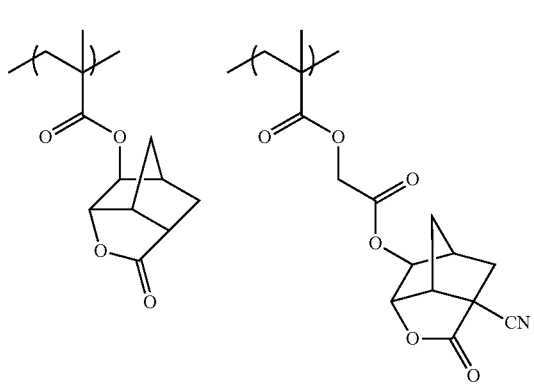
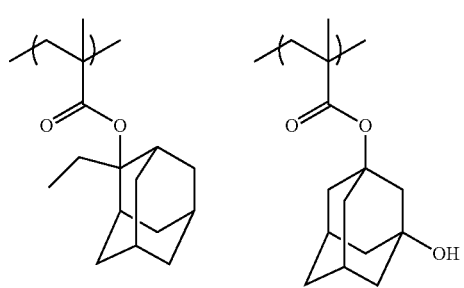
(Ab-146)
(Ab-144)
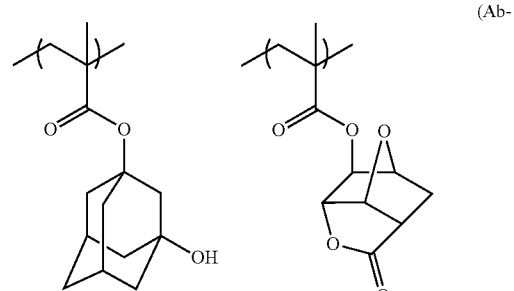
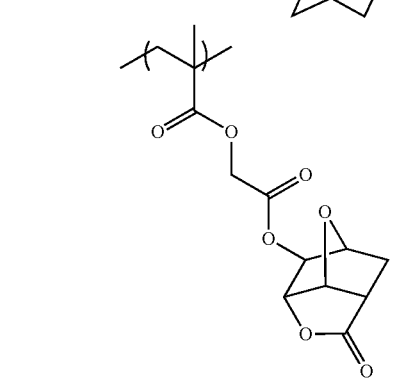
(Ab-147)
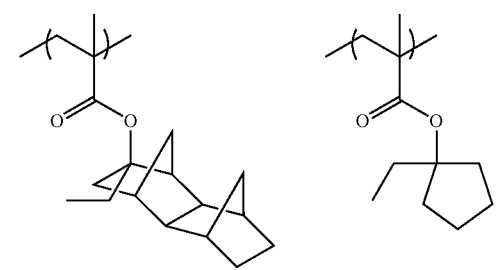
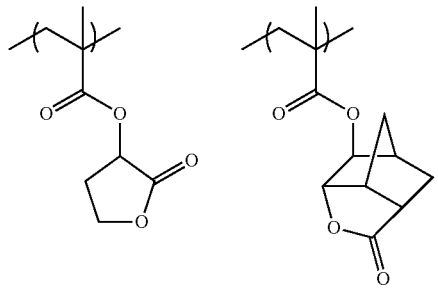

117
-continued
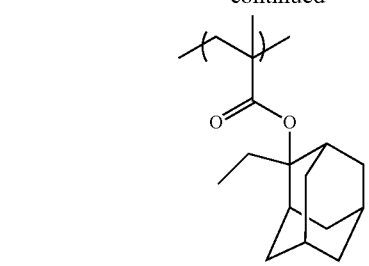
(Ab-148)
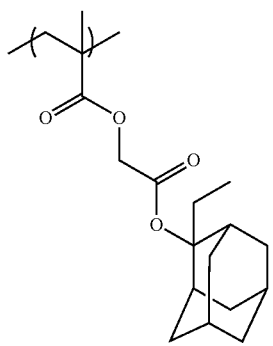
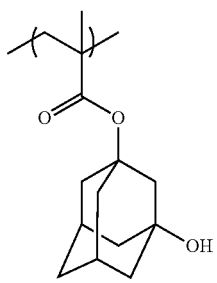
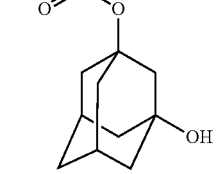
[Chem. 77]
(Ab-157)
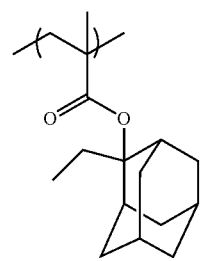
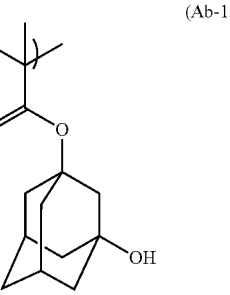
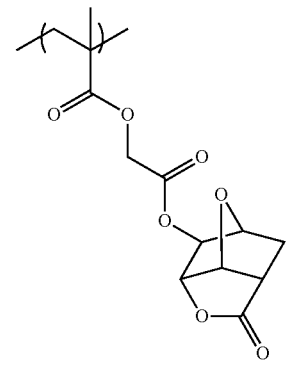
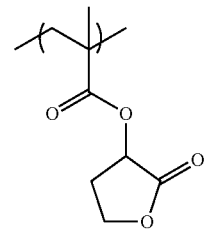
118
-continued
(Ab-158)
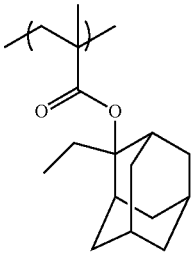
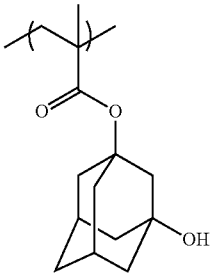
(Ab-159)
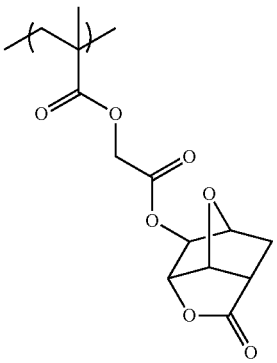
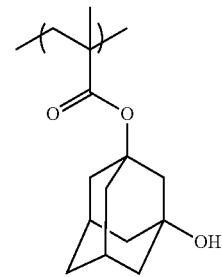
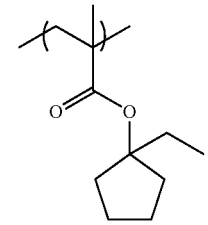
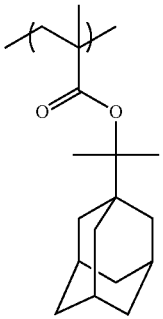
(Ab-160)
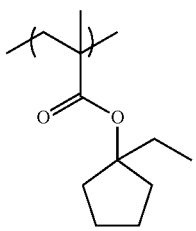
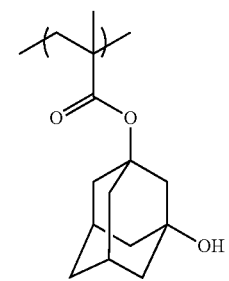

119
-continued
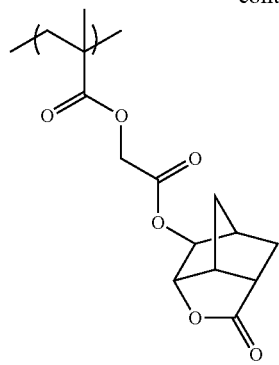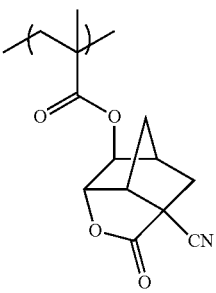
(Ab-161)
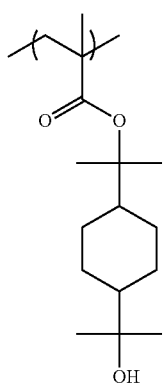
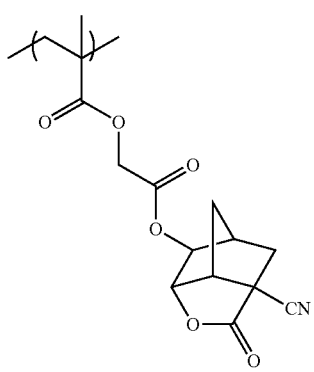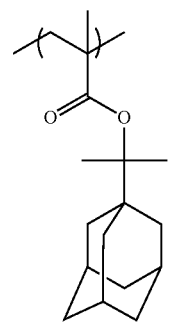
(Ab-162)
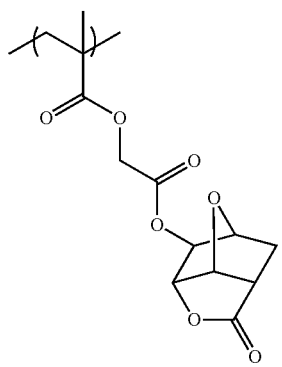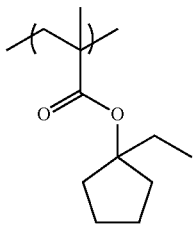
120
-continued
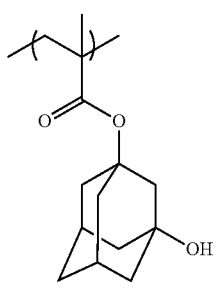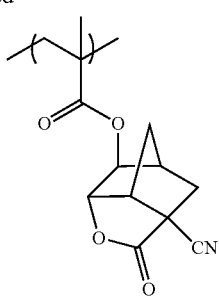
(Ab-163)
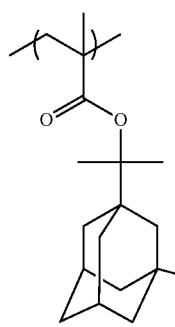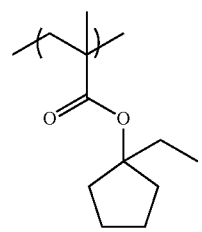
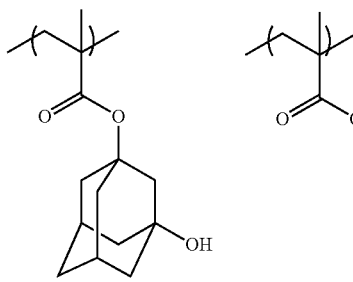
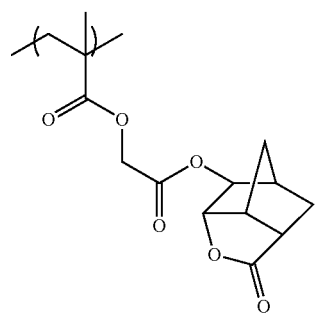
(Ab-164)
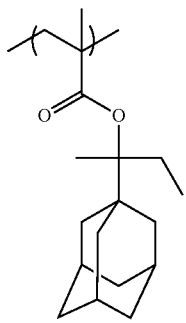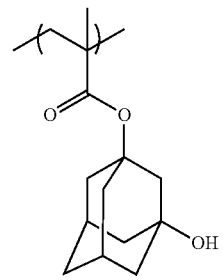

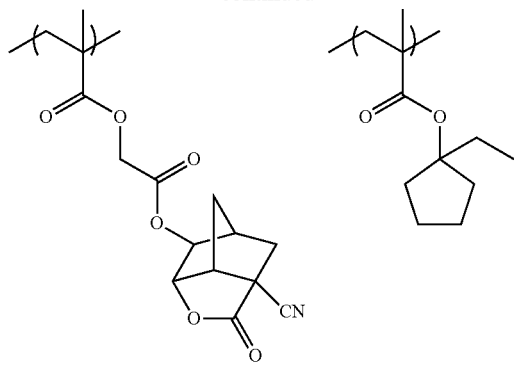
[Chem. 78]
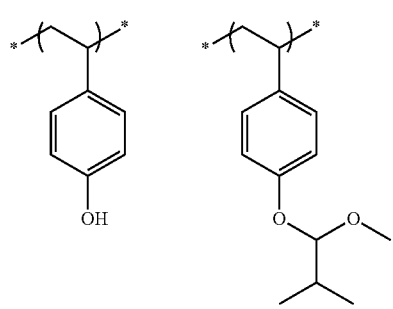
(Ab-165)
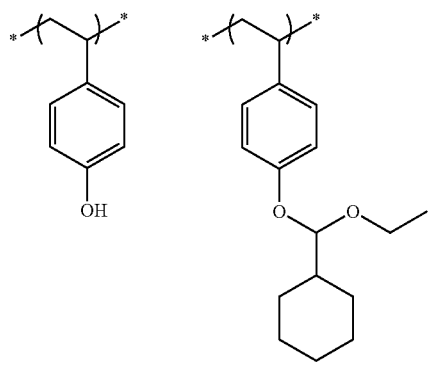
(Ab-166)
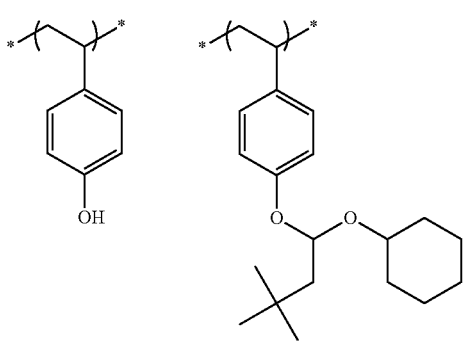
(Ab-167)
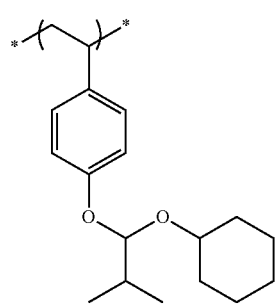
(Ab-168)
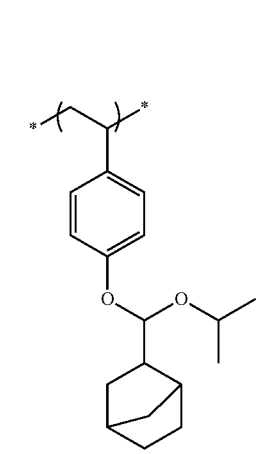
(Ab-169)
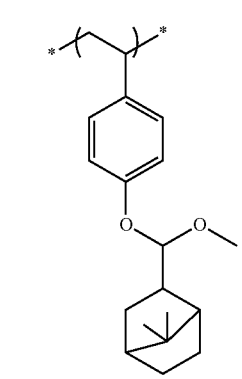
(Ab-170)
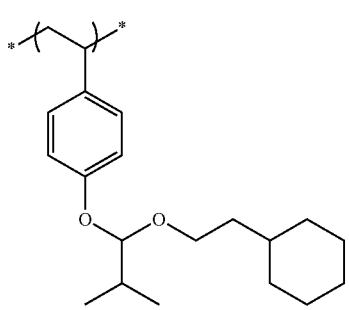
(Ab-171)

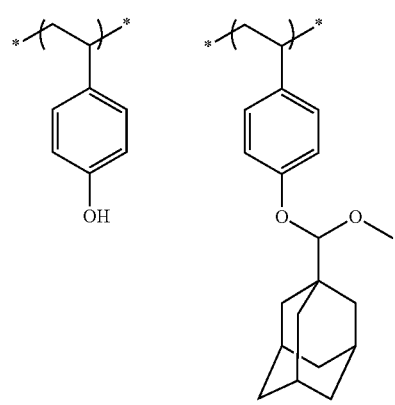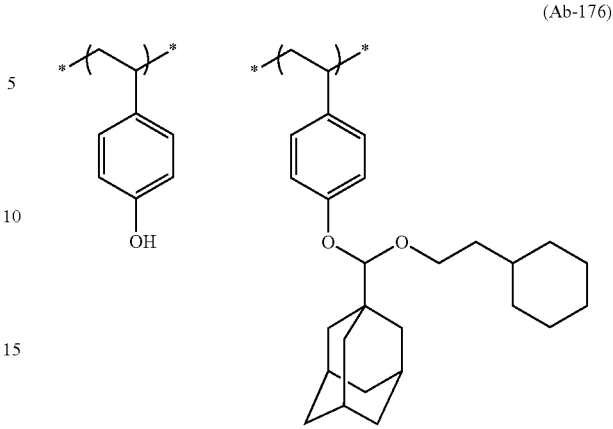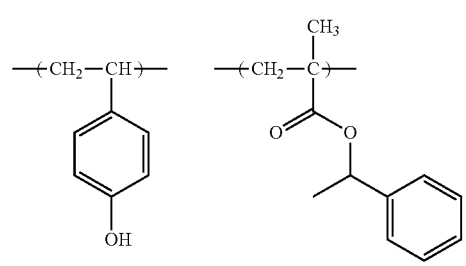

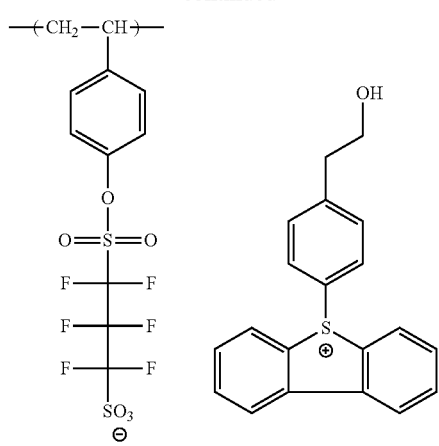
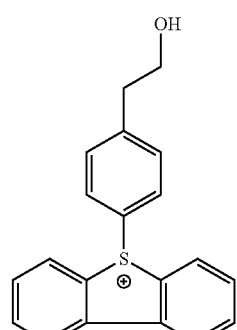
Ab-179
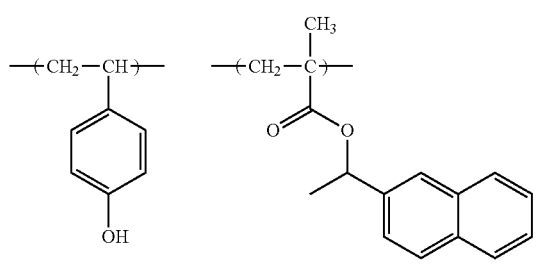
Ab-182
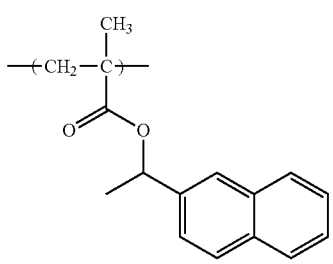
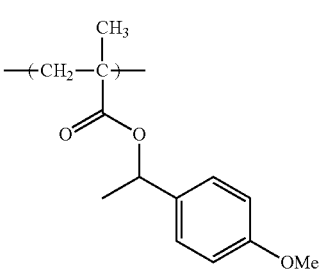
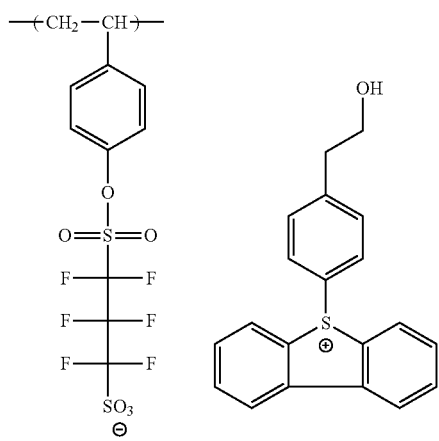
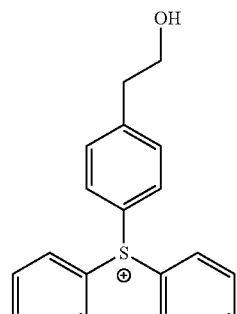
Ab-180
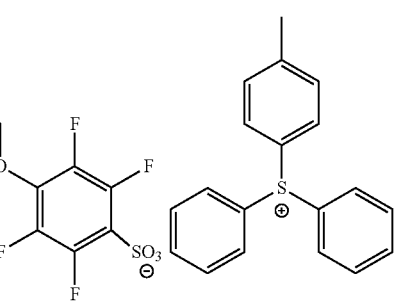
Ab-183
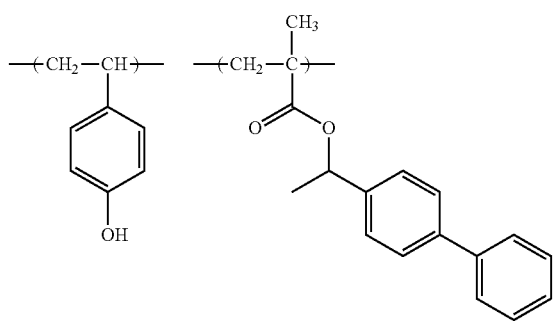
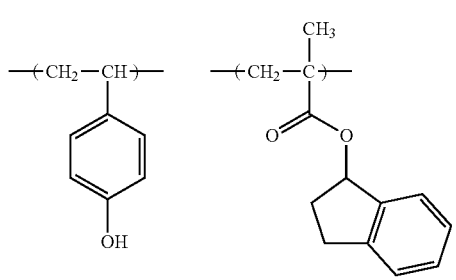

127
-continued
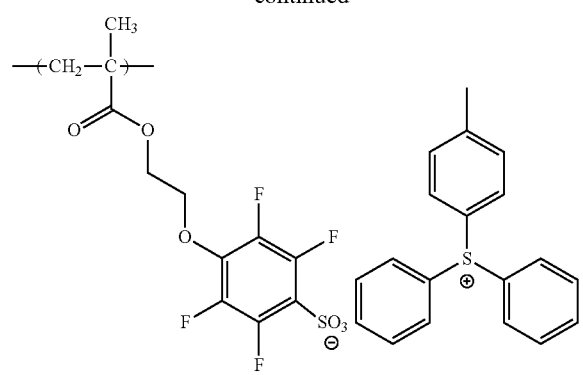
[Chem. 80]
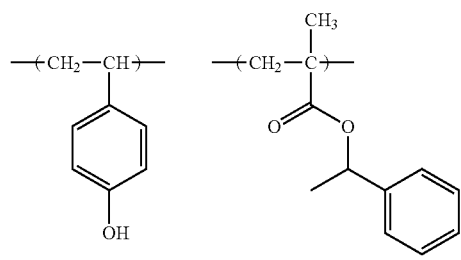
Ab-185
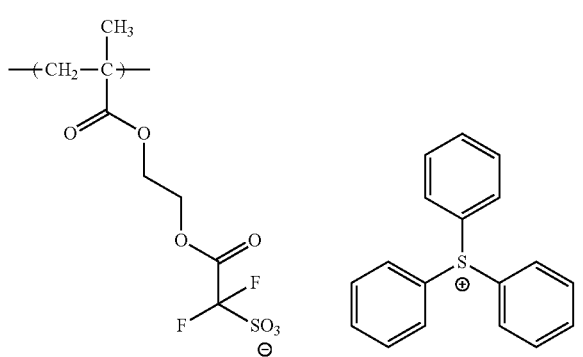
Ab-186
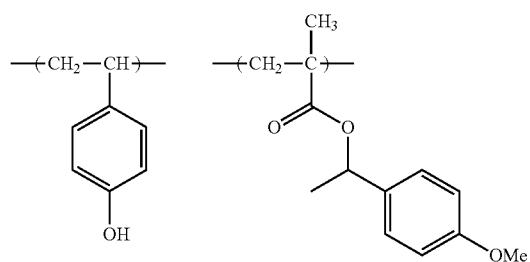
128
-continued
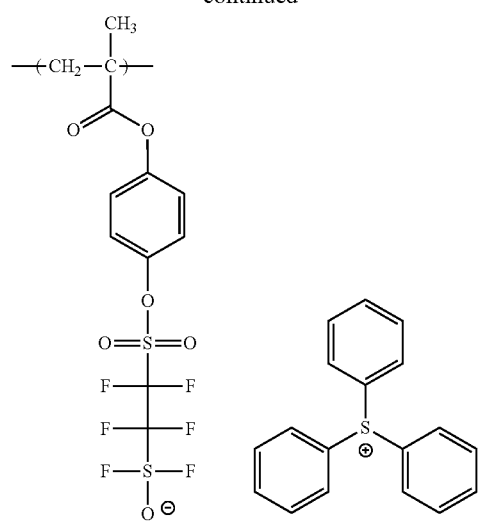
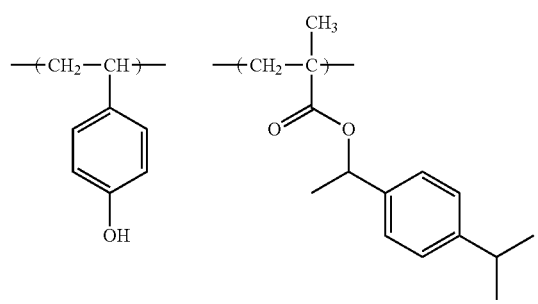
Ab-187
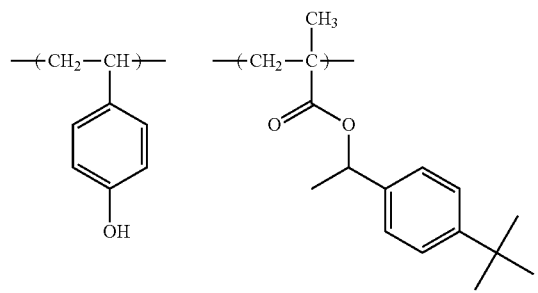
Ab-189

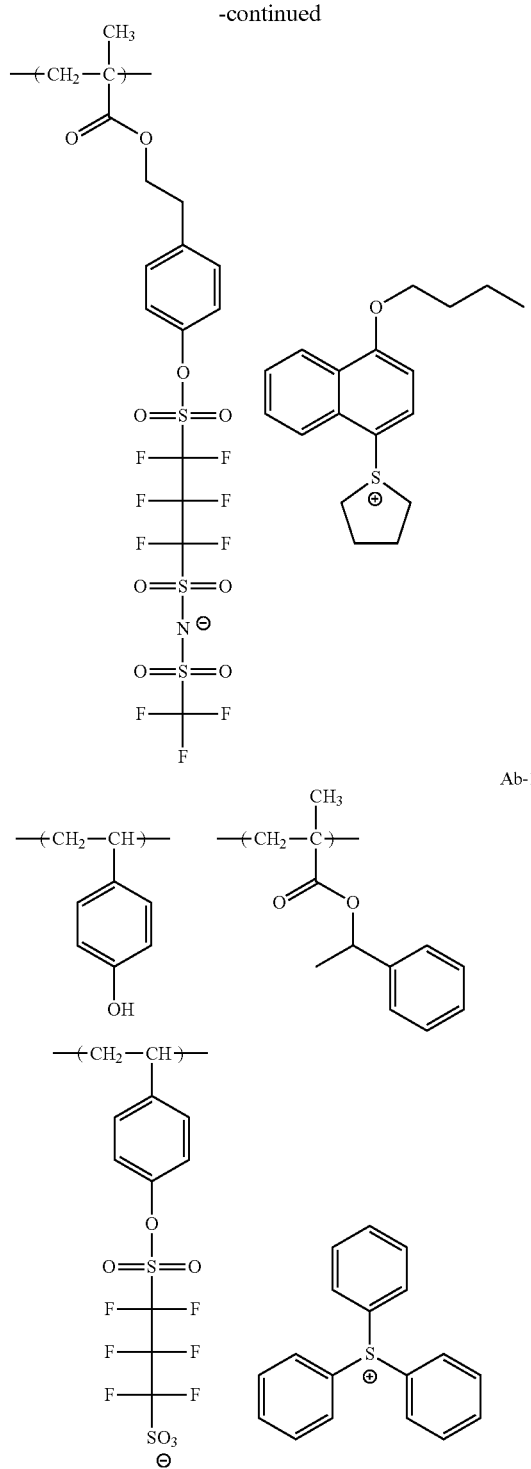
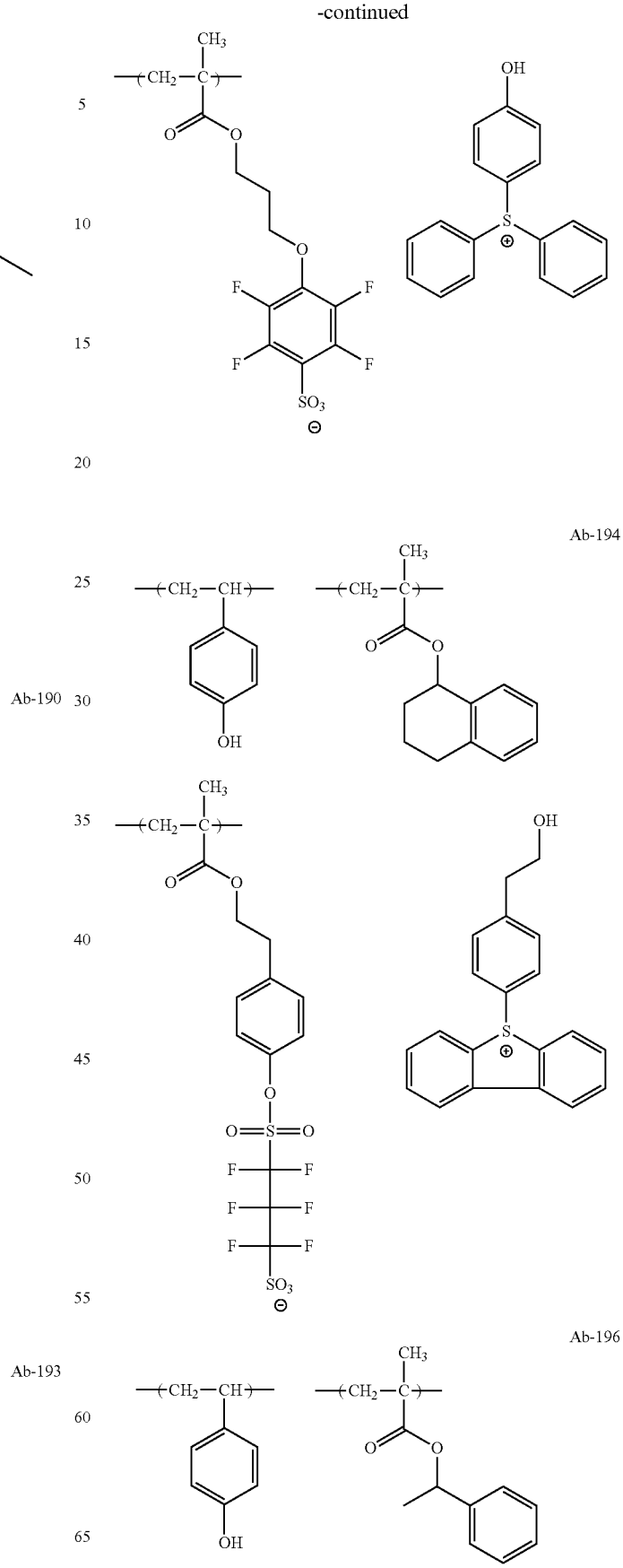
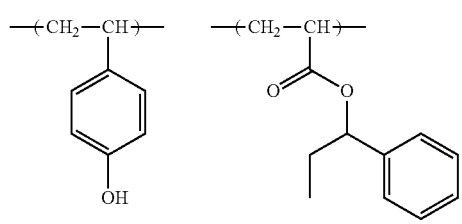

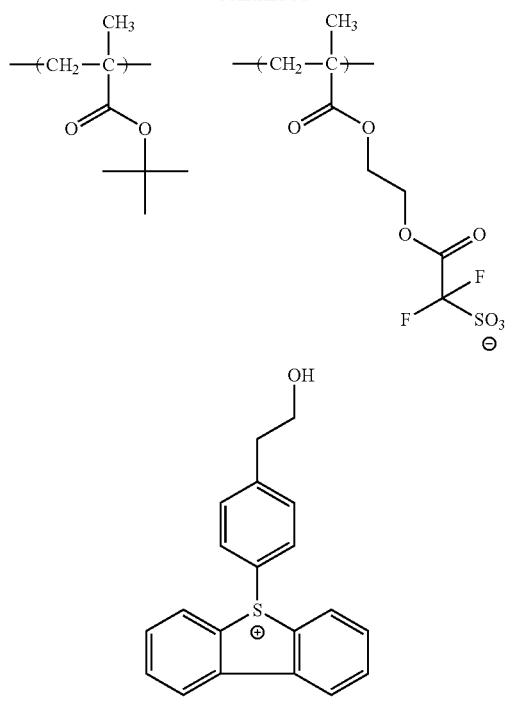
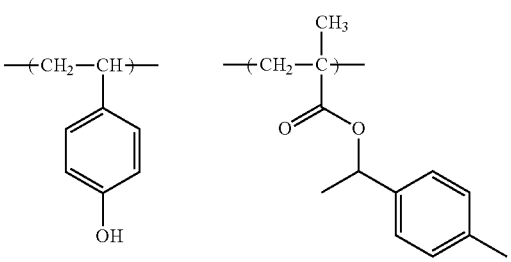
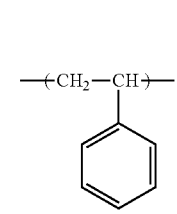
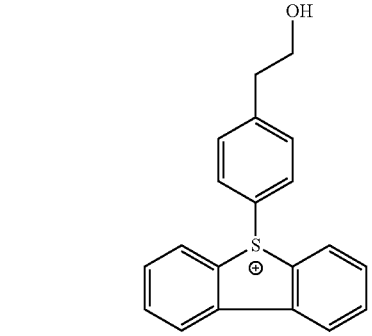
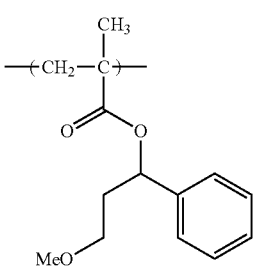
[Chem. 82]

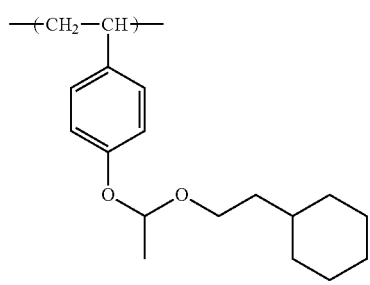
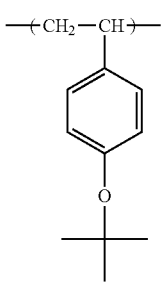
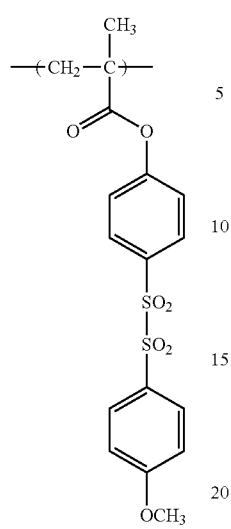
Ab-201
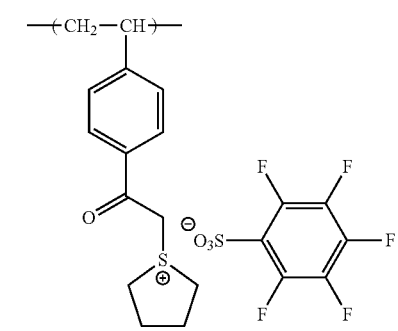
Ab-203
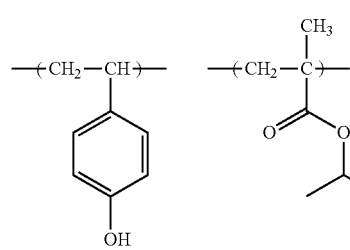
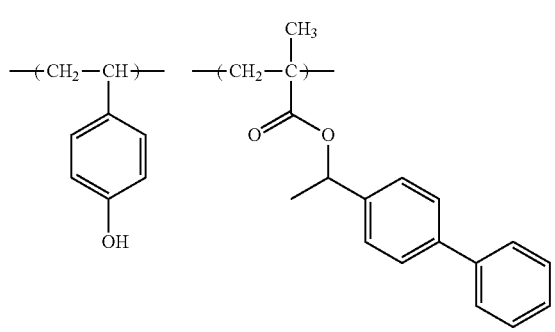
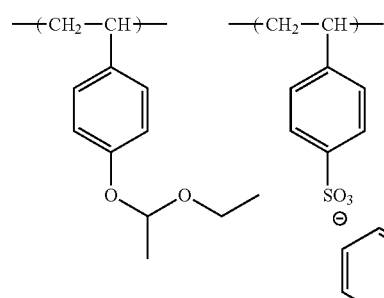
[Chem. 83]
Ab-204
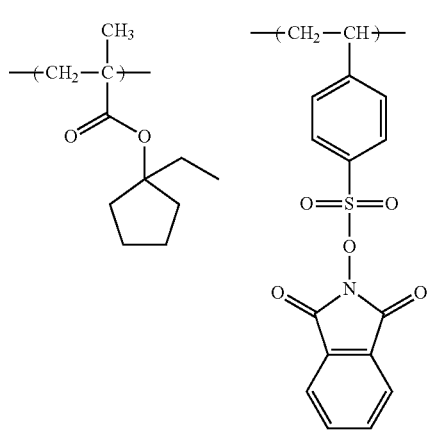
Ab-202
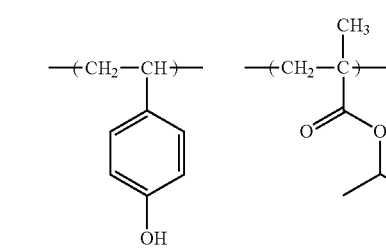
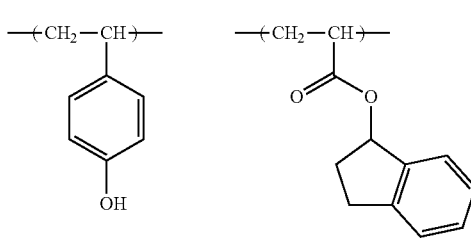
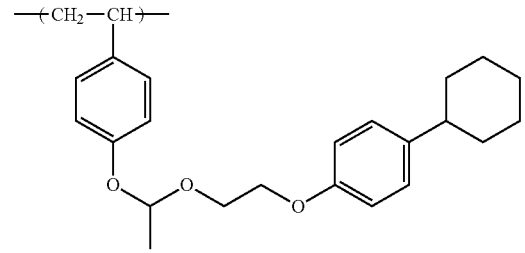

-continued
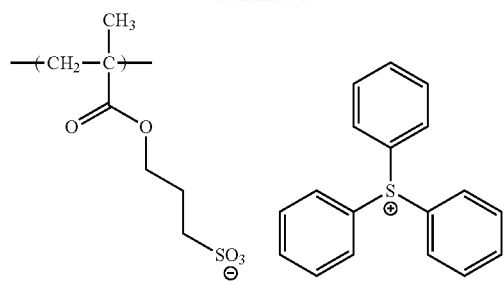
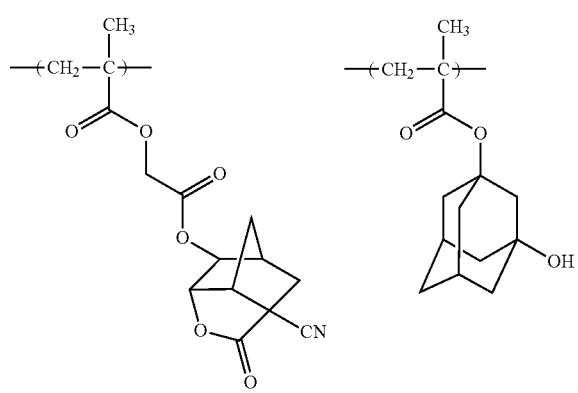
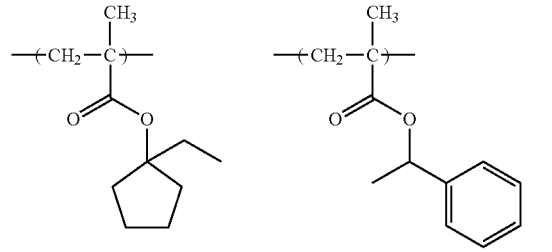
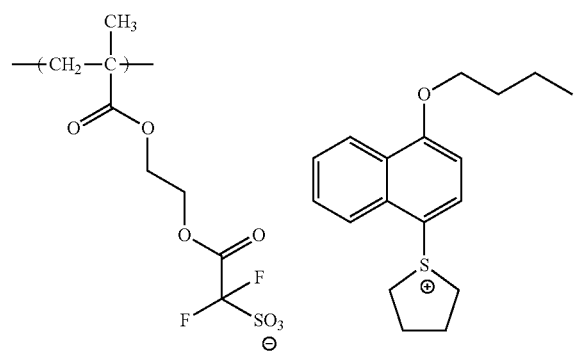
Ab-207
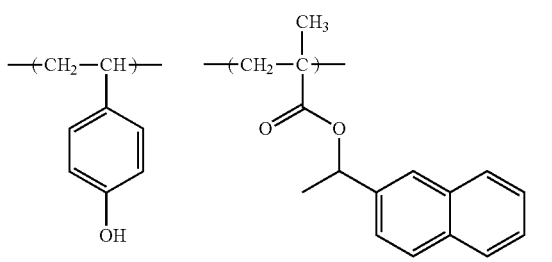
-continued
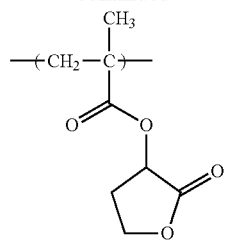
Ab-206
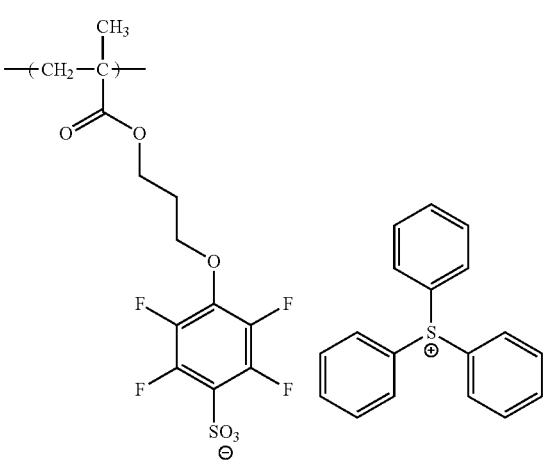
[Chem. 84]
Ab-206
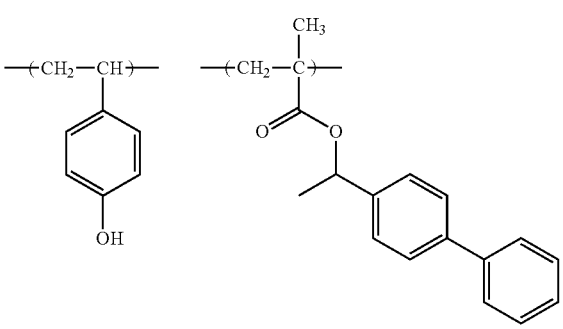
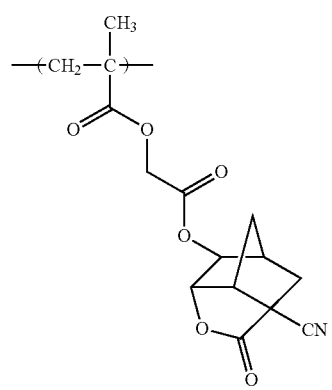

-continued
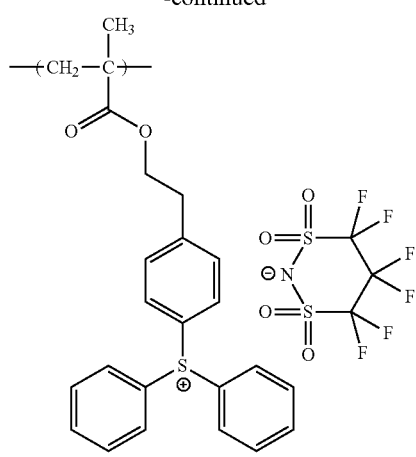
Ab-209
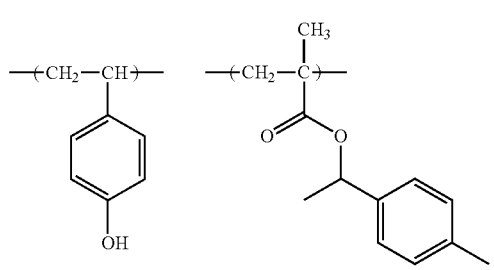
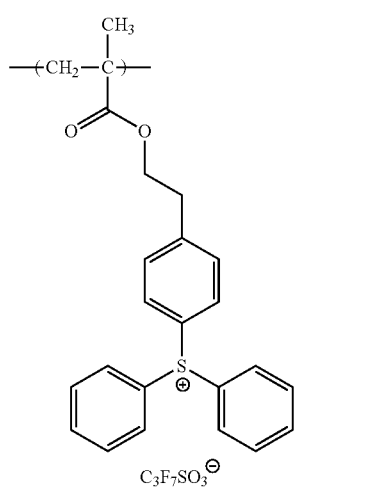
Ab-210
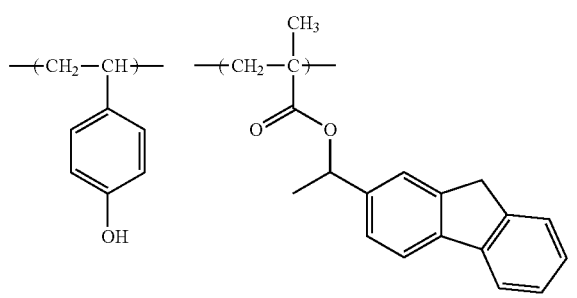
-continued
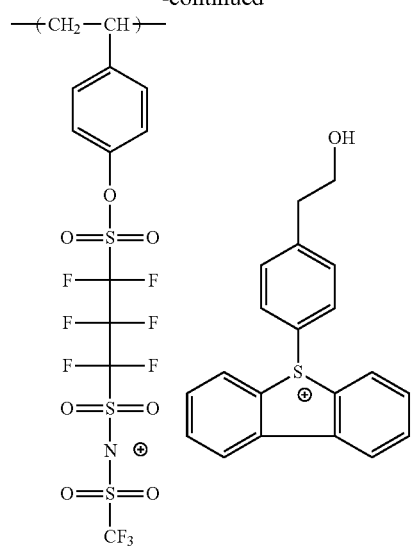
Ab-212
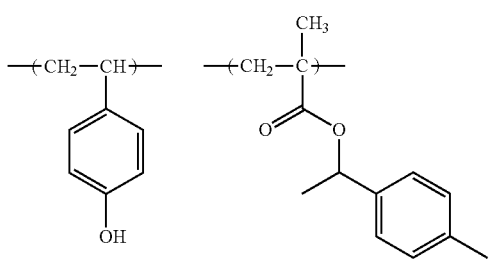
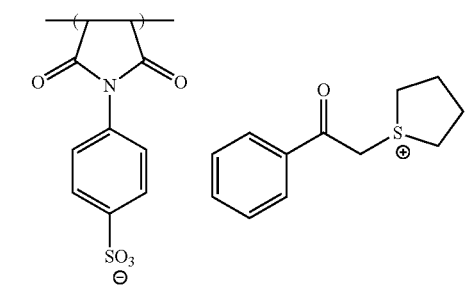
Ab-213
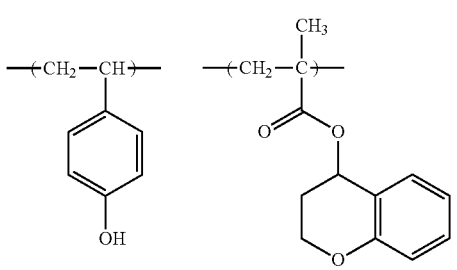

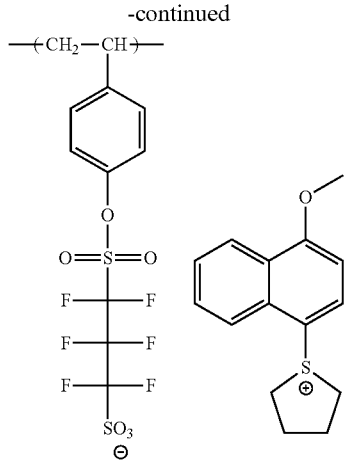
[Chem. 85]
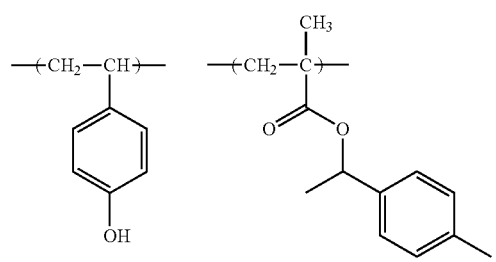
Ab-214
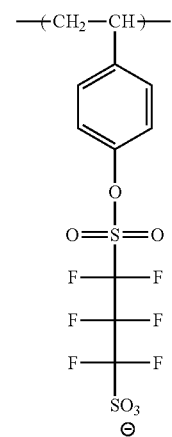
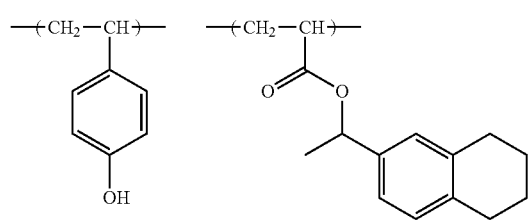
Ab-216
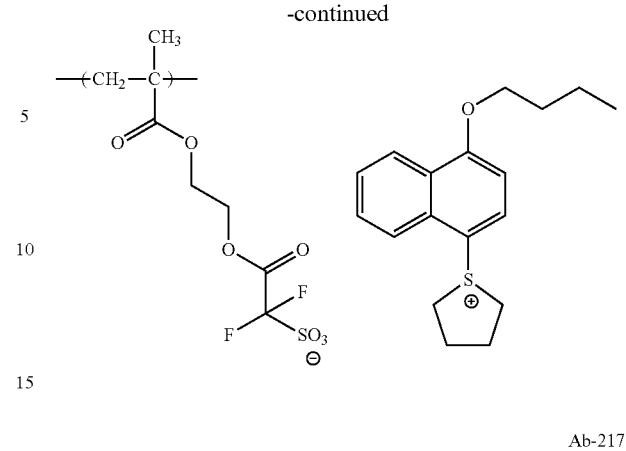
Ab-217
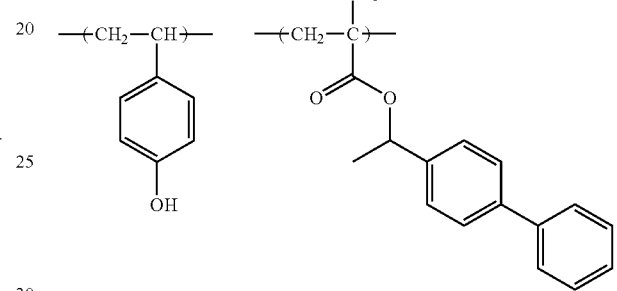
Ab-218
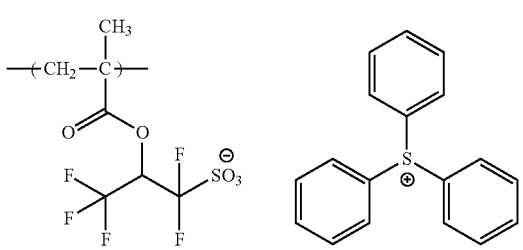
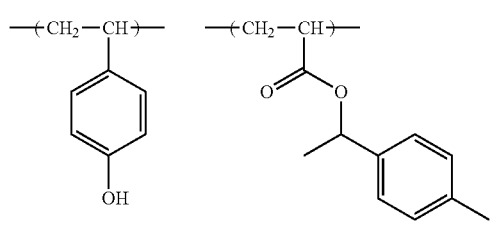
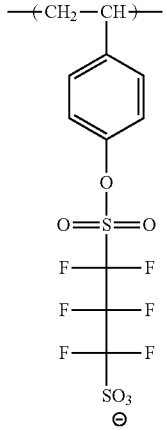

[Chem. 86]
Ab-219
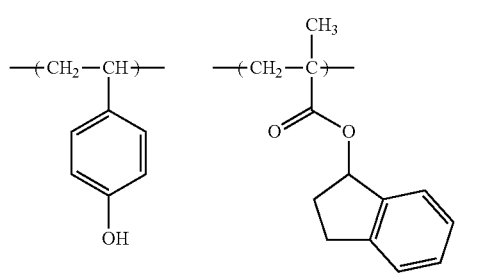
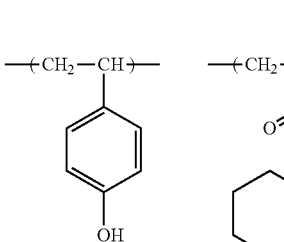
Ab-220
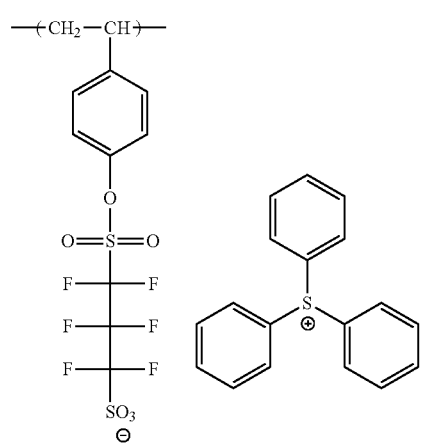
Ab-221
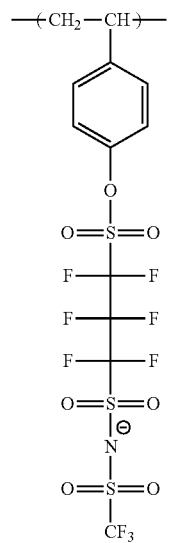
Ab-222
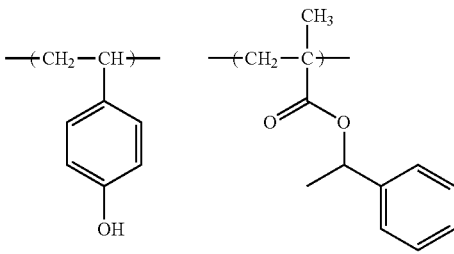
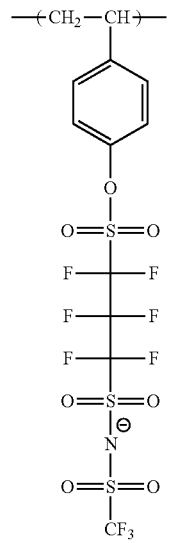

Ab-223
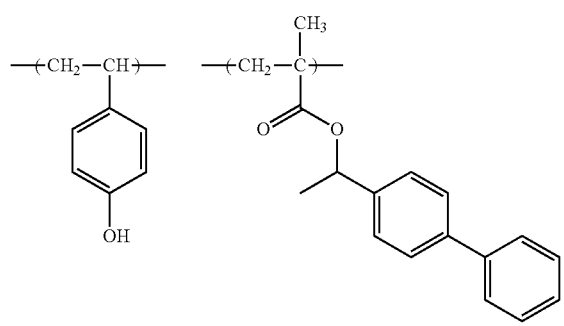
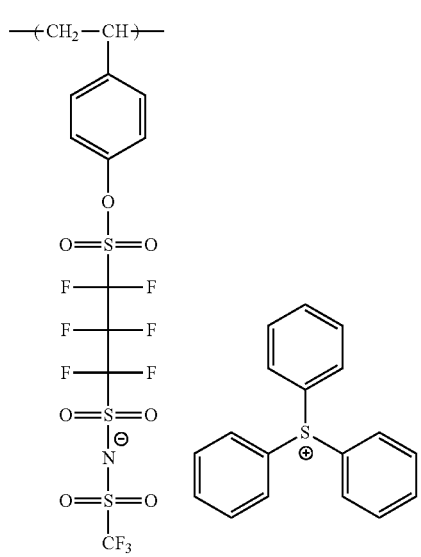
[Chem. 87]
Ab-226
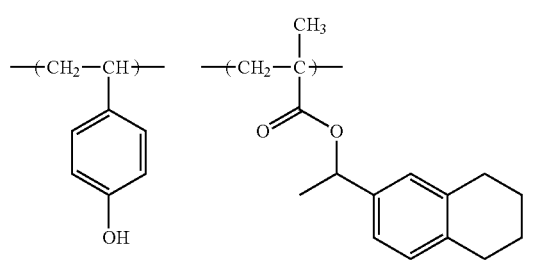
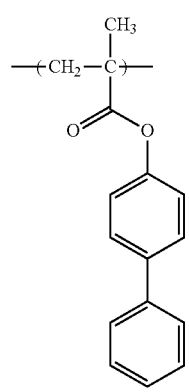
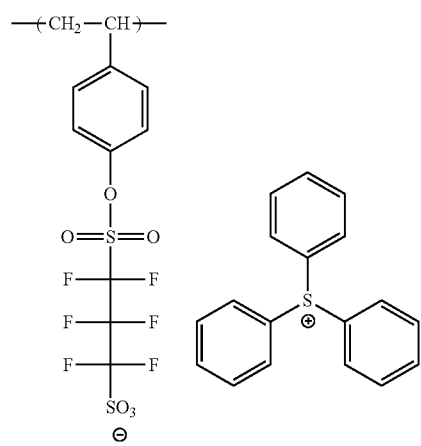
Ab-227
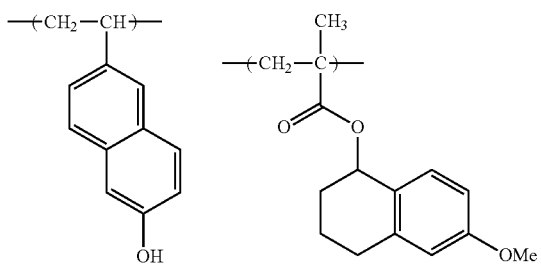
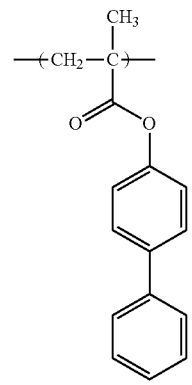
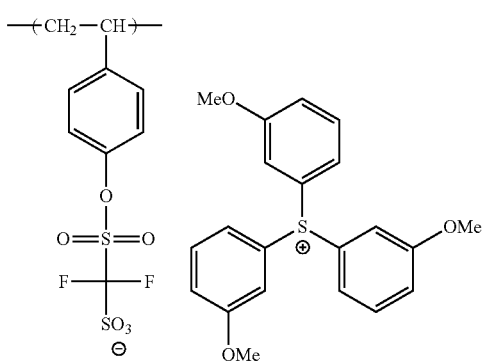

Ab-228
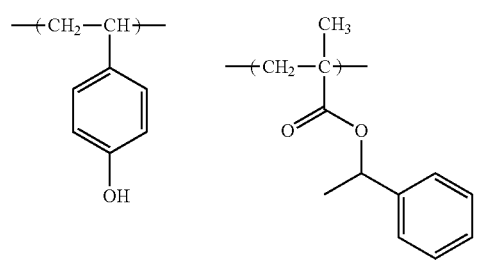
[Chem. 88]
Ab-230
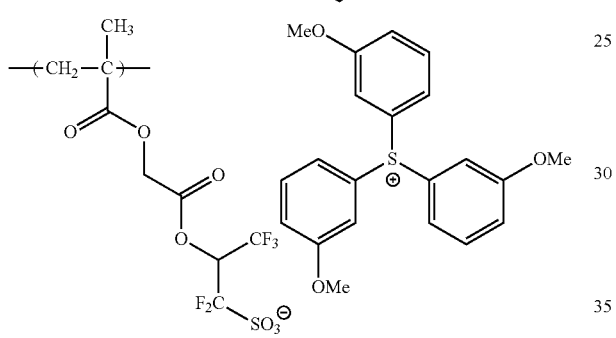
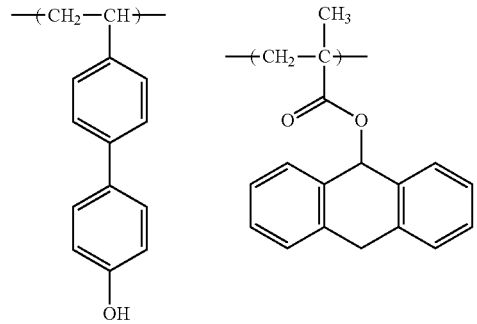
Ab-231
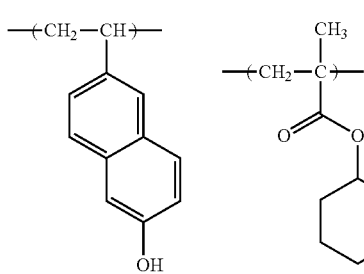
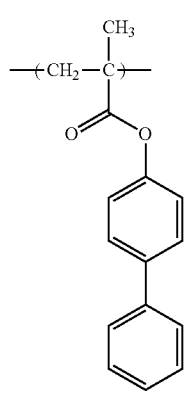
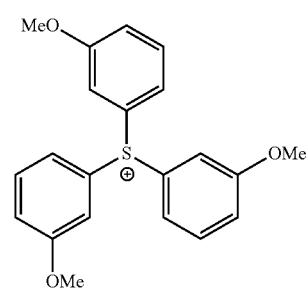
Ab-232
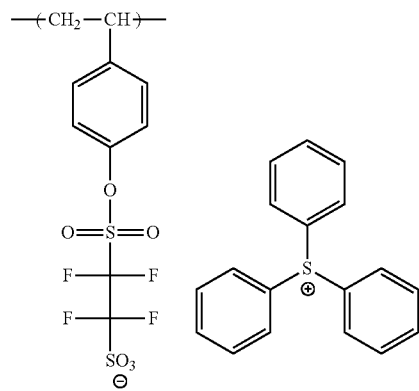 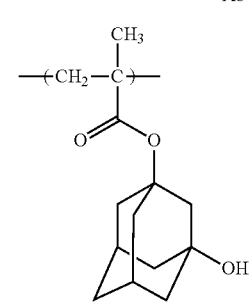

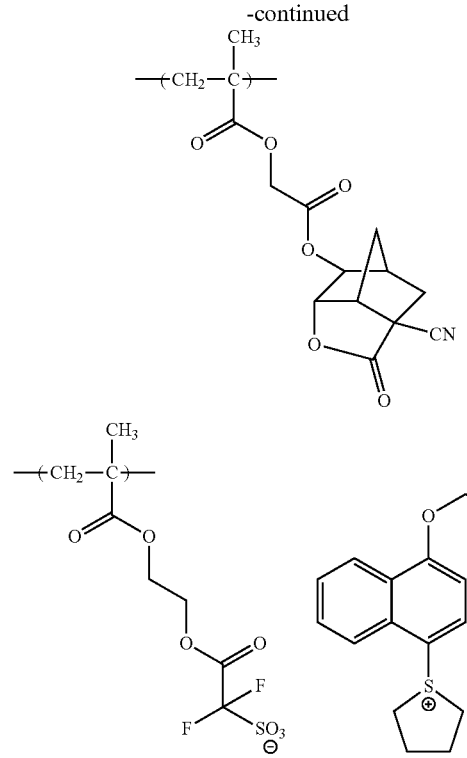
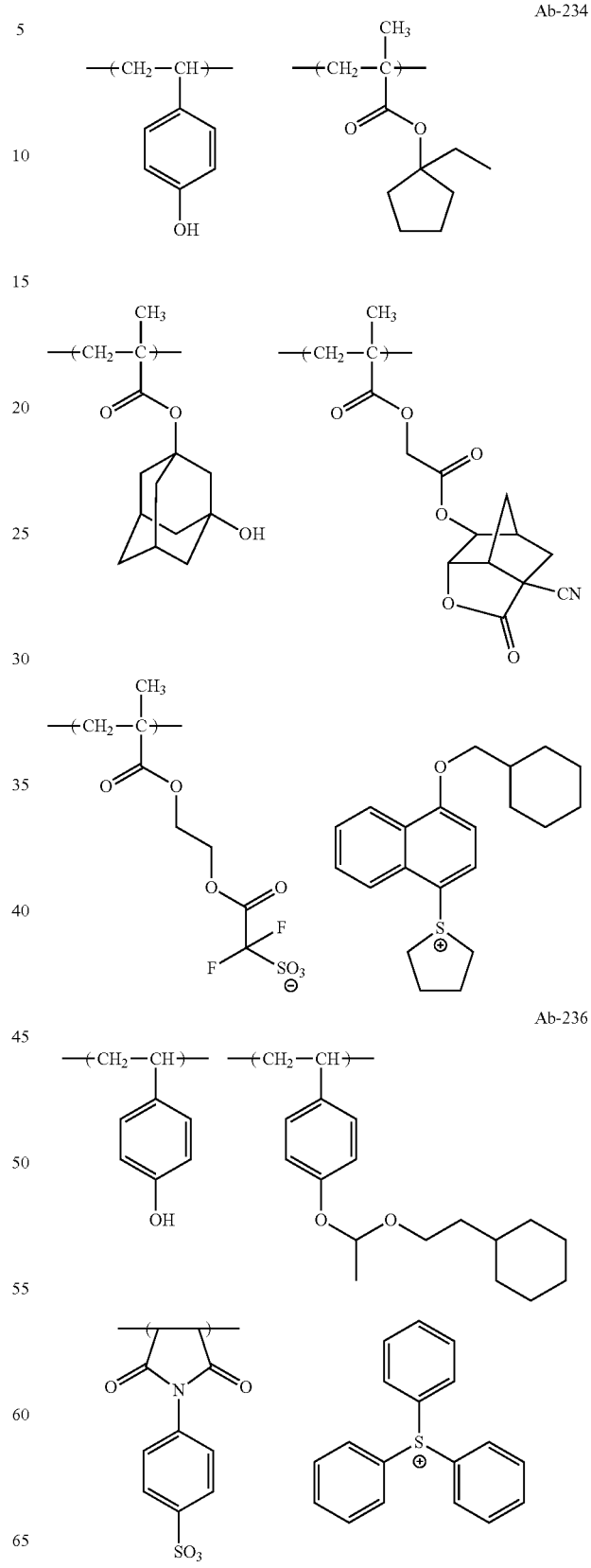

Ab-237
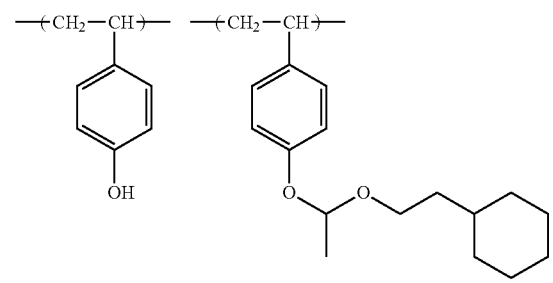
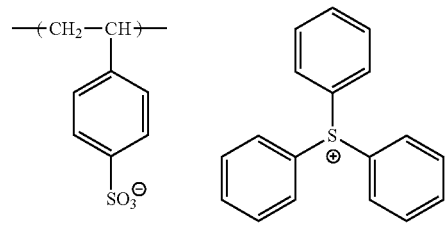
Ab-238
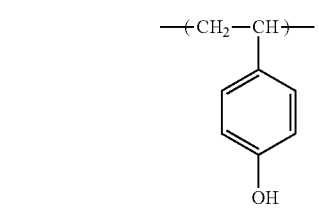
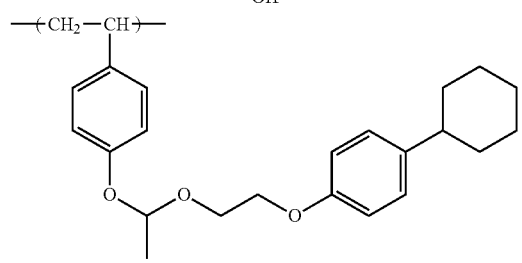
[Chem. 90]
Ab-239
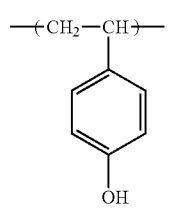
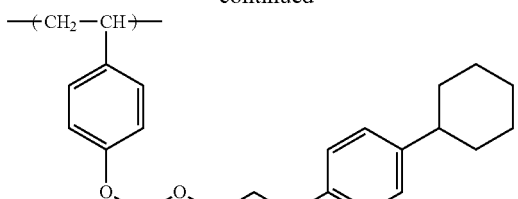
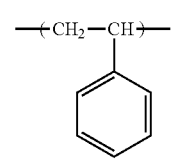
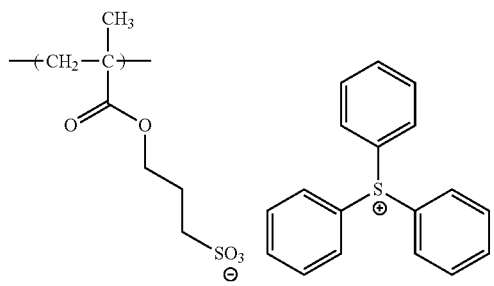
Ab-240
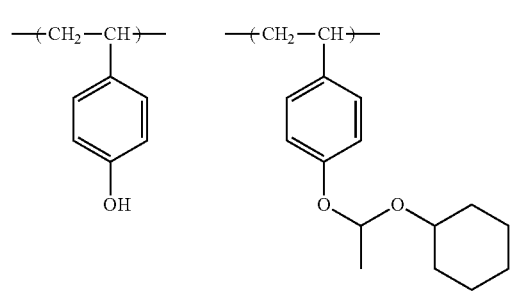
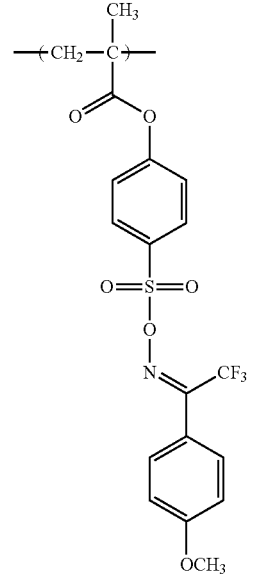

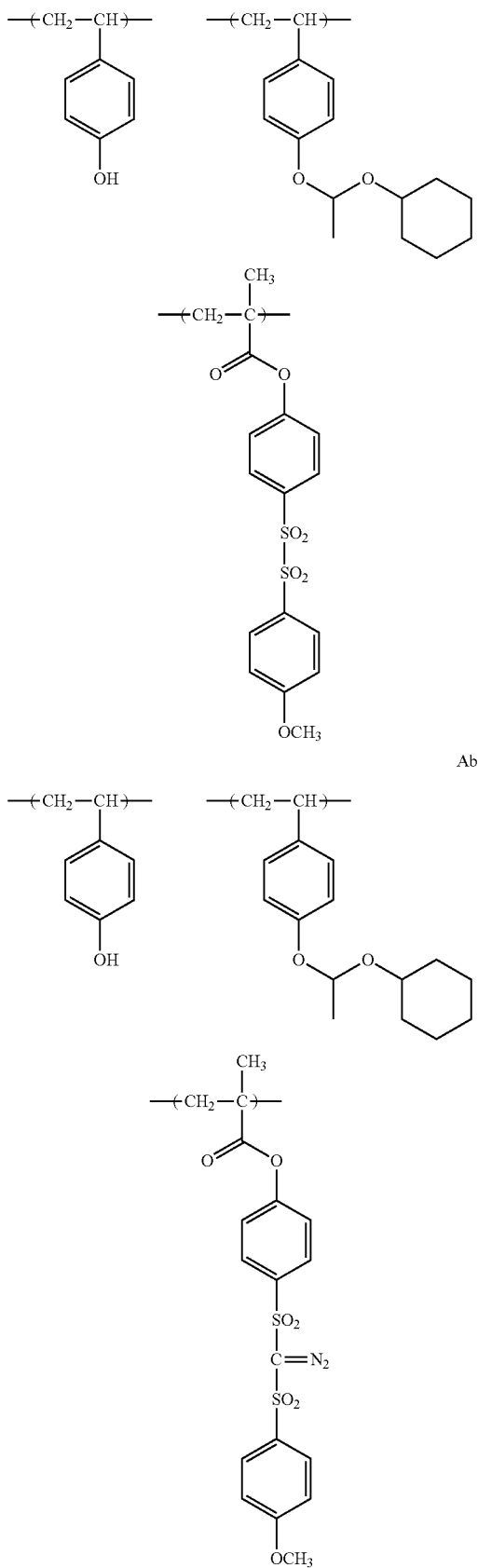
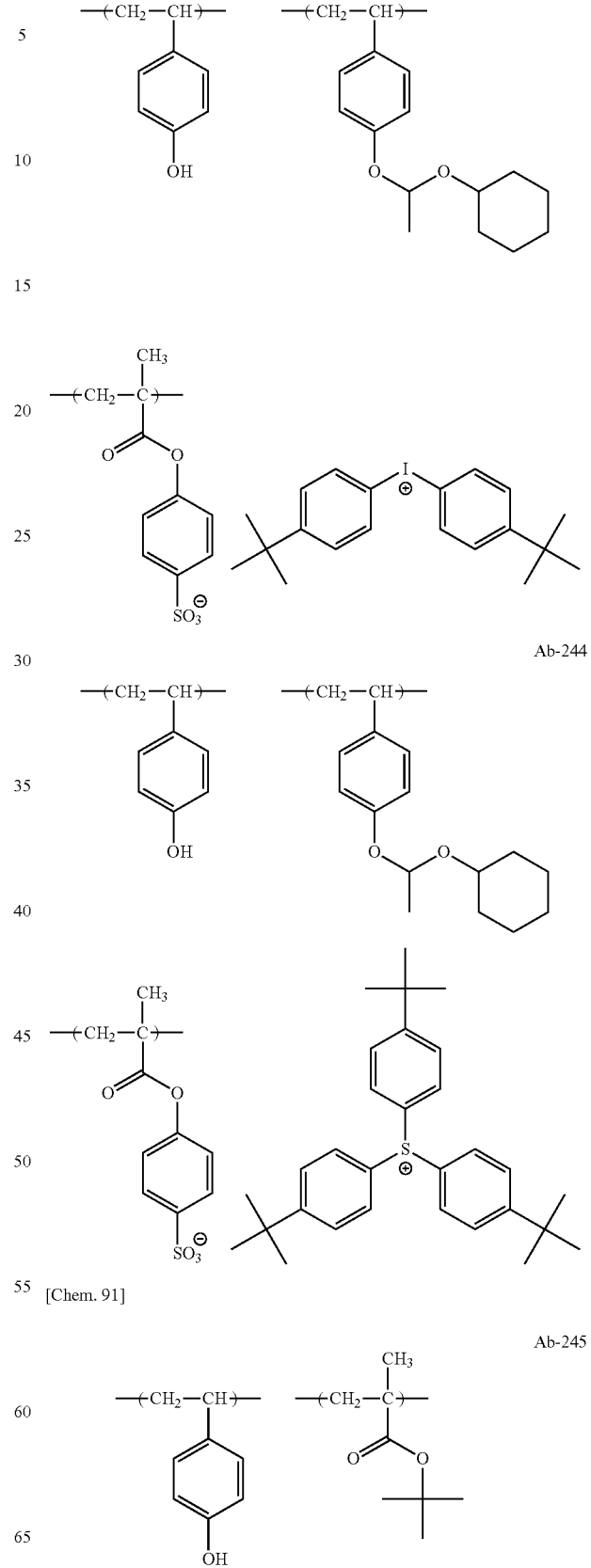

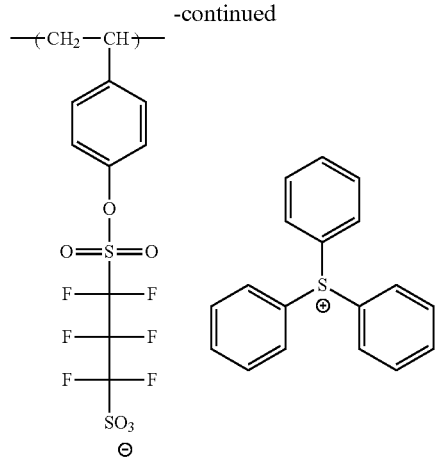
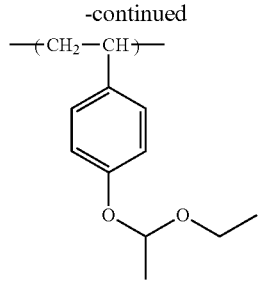
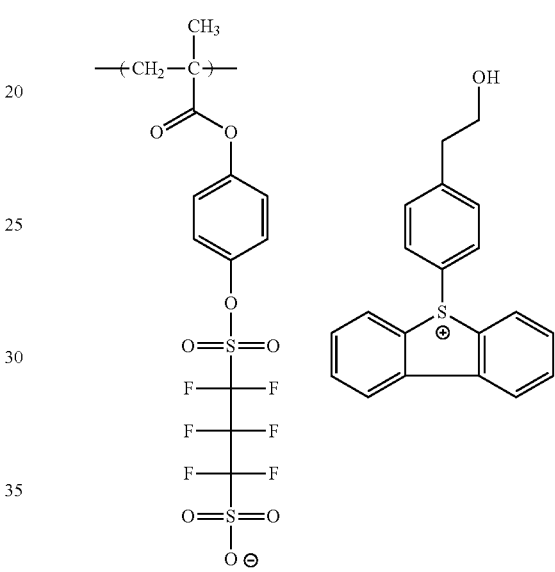
Ab-247
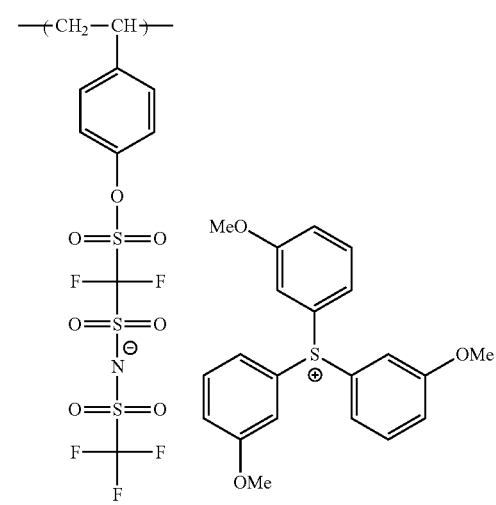
Ab-248
[Chem. 92]
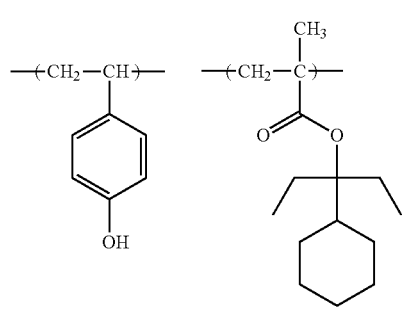
Ab-249
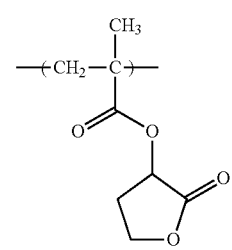

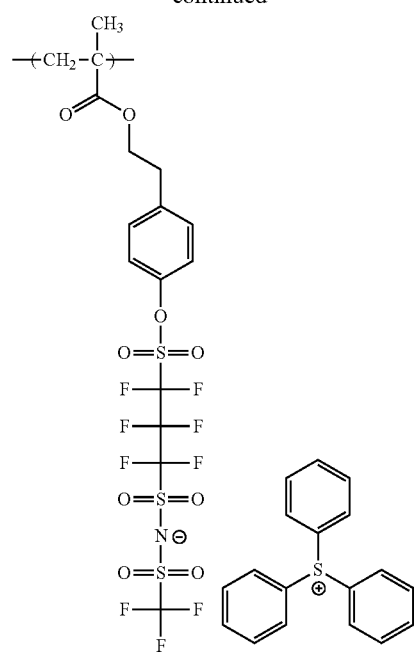
Ab-250
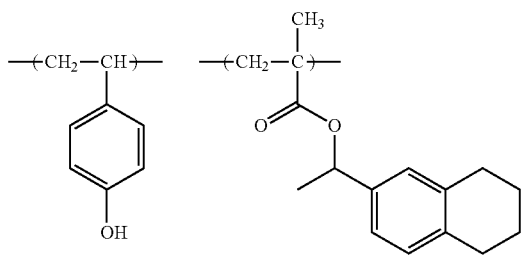
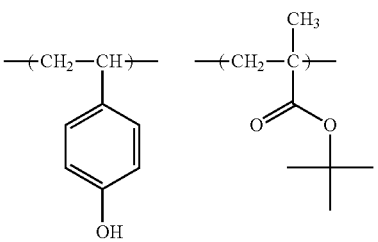
Ab-251
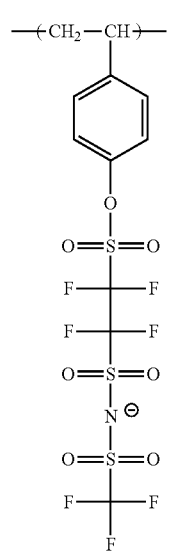
[Chem. 93]
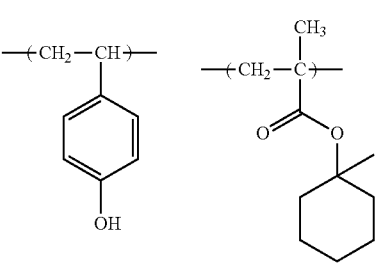
Ab-253
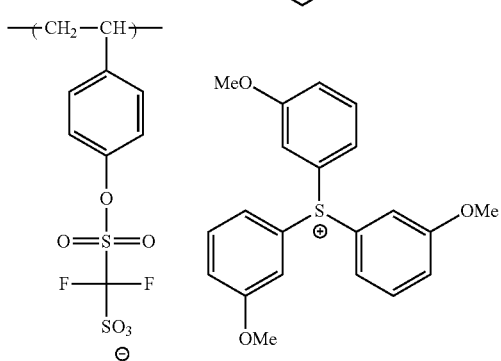
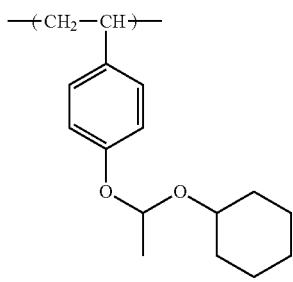

157
-continued
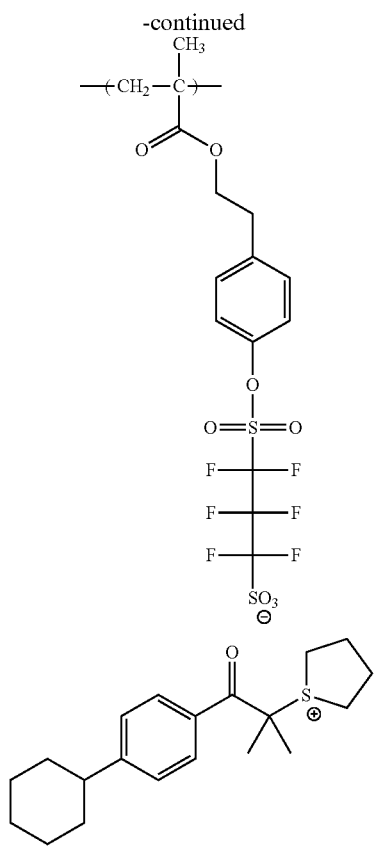
158
-continued
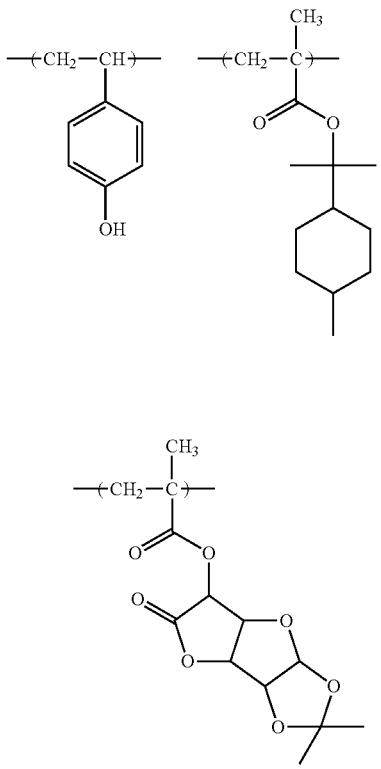
Ab-256
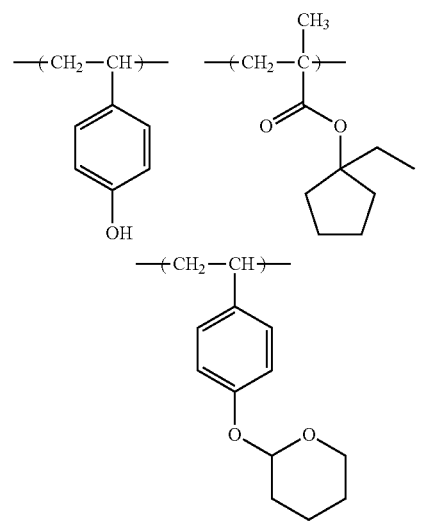
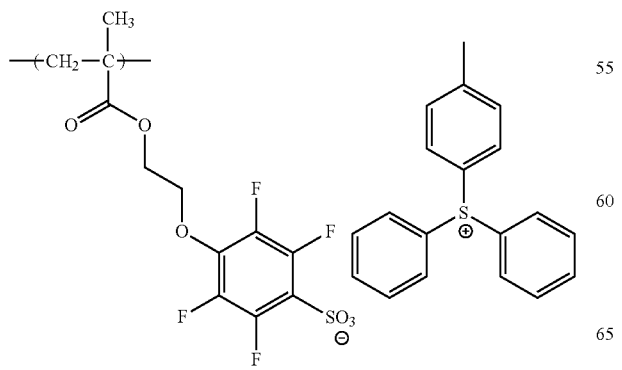
Ab-256
Ab-259
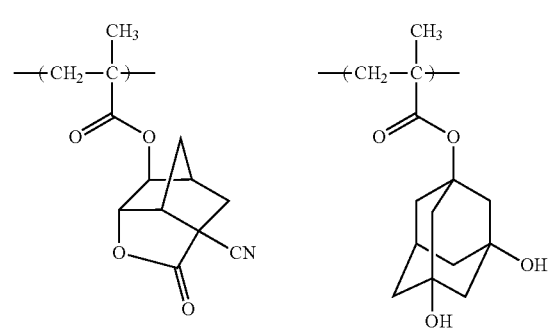

-continued
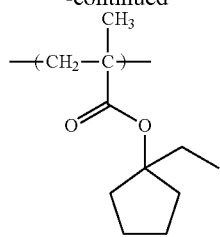
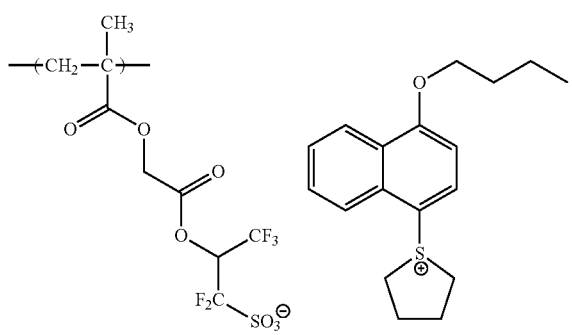
Ab260
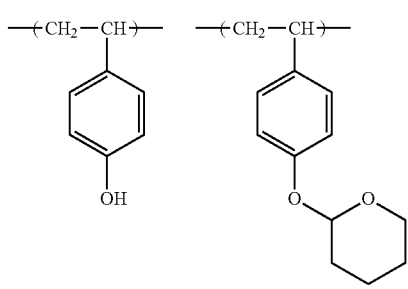
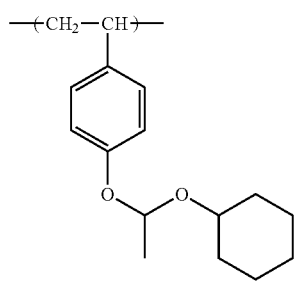
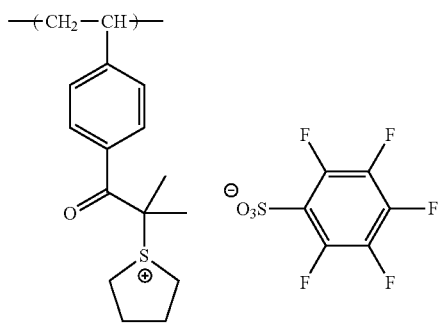
[Chem. 94]
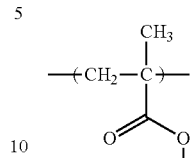
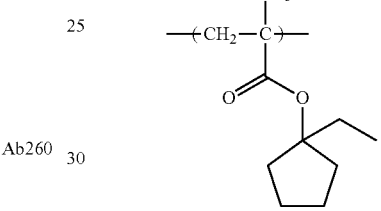
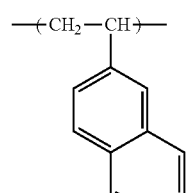
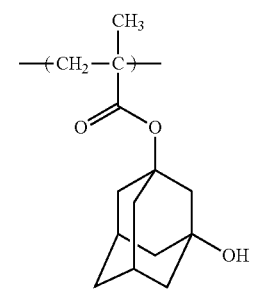
Ab-261
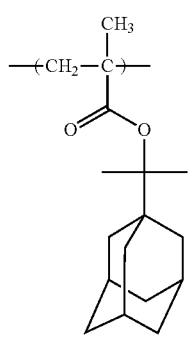
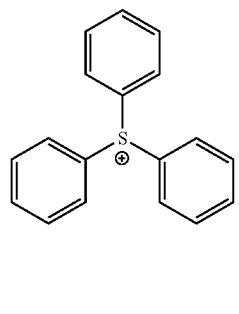
Ab-262
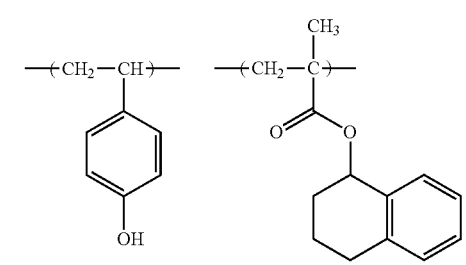

-continued
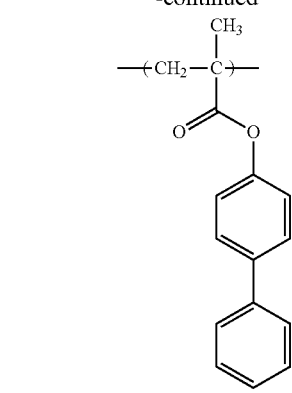
[Chem. 95]
Ab-263
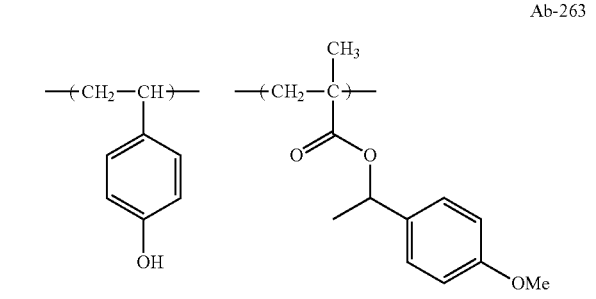
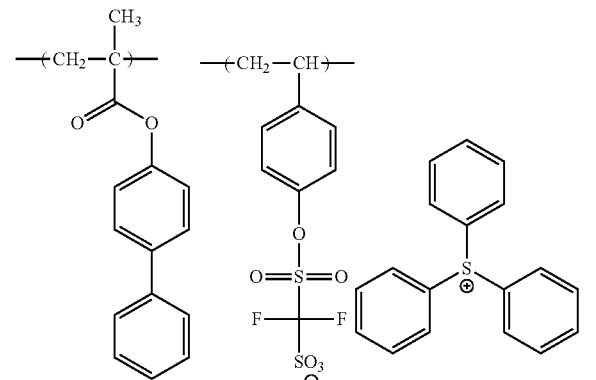
-continued
Ab-264
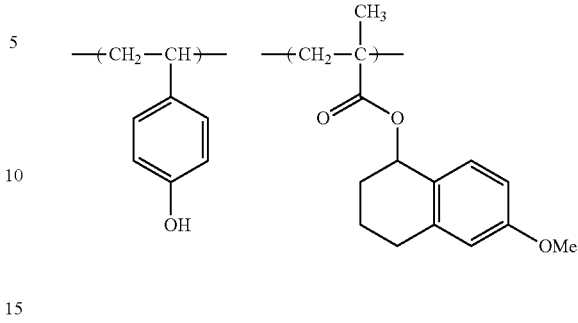
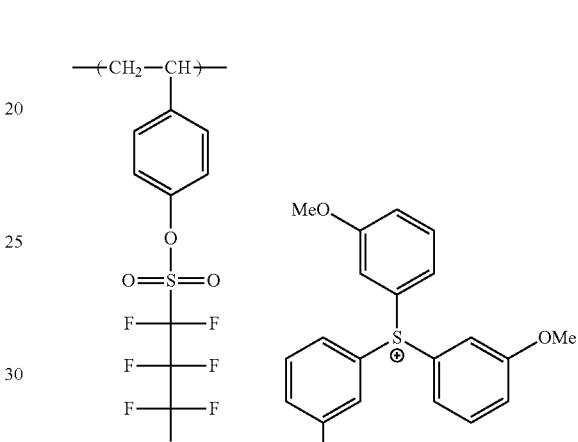
Ab-265
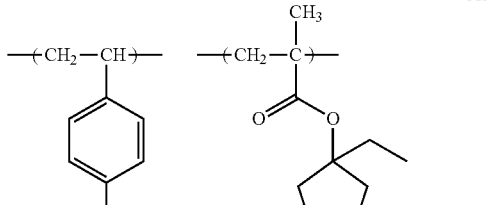
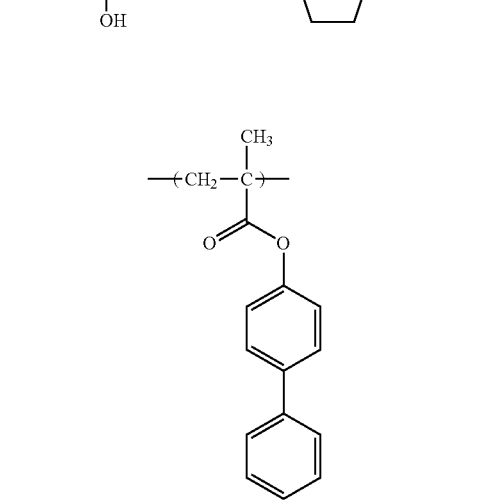

-continued

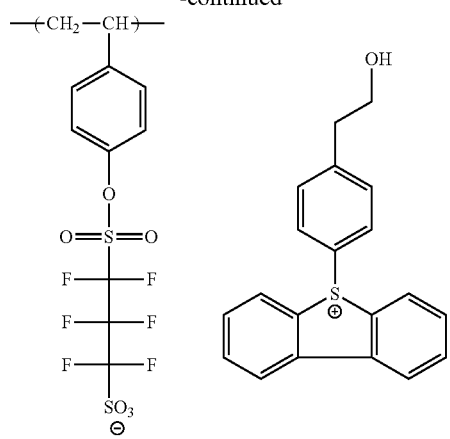

Ab-267

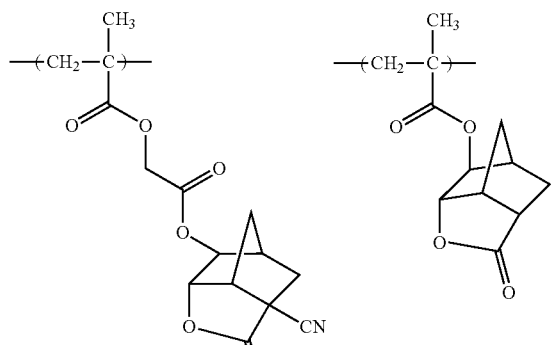

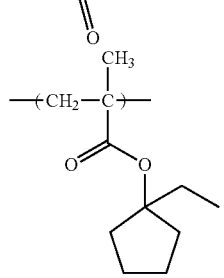

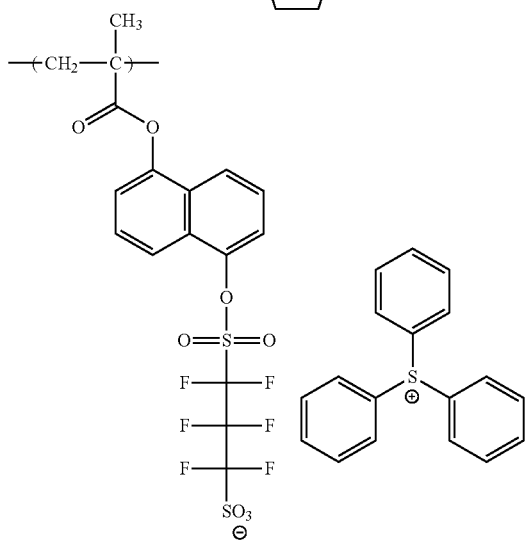

[5] Acid Generator (D)

In one embodiment, the composition in the present invention may further include a acid generator which is different form the compound (A) as an acid generator, in other words, a compound capable of generating an acid which dose not includes a cross-linking group in a molecule by irradiation with actinic rays or radiation (hereinafter, also referred as a "compound (D)" or an "acid generator (D)").

A preferred forms of the acid generator (D) include an onium salt compound. Examples of such an onium salt compound include a sulfonium salt, an iodonium salt, and a phosphonium salt, and the like.

Furthermore, another preferred form of the acid generator (D) include a compound capable of generating sulfonic acid, imide acid or a methide acid by irradiation with actinic rays or radiation. Examples of the acid generator in that form include a sulfonium salt, an iodonium salt, a phosphonium salt, an oxime sulfonate, an imide sulfonate, and the like.

The acid generator (D) is preferably a compound capable of generating an acid by irradiation with an electron beam or extreme ultraviolet rays.

In the present invention, preferred examples of the onium salt compound include a sulfonium compound represented by the following general formula (7) or an iodonium compound represented by the general formula (8).

[Chem. 96]

$$R_{a2}-\overset{R_{a1}}{\underset{R_{a3}}{S^+}} \quad X^- \quad (7)$$

$$R_{a4}-I^+-R_{a5} \quad X^- \quad (8)$$

In the general formulae (7) and the general formula (8), $R_{a1}$, $R_{a2}$, $R_{a3}$, $R_{a4}$ and $R_{a5}$ each independently represent an organic group.

$X^-$ represents an organic anion.

Hereinafter, the sulfonium compound represented by the general formula (7) and the iodonium compound represented by the general formula (8) will be described in more detail.

$R_{a1}$, $R_{a2}$ and $R_{a3}$ in the general formula (7) and $R_{a4}$ and $R_{a5}$ of the general formula (8) each independently represent an organic group as described above, and preferably, at least one of $R_{a1}$, $R_{a2}$ and $R_{a3}$ and at least one of $R_{a4}$ and $R_{a5}$ are respectively an aryl group. The aryl group is preferably a phenyl group and a naphthyl group, and more preferably a phenyl group.

Examples of the organic anion of $X^-$ in the general formulae (7) and (8) include a sulfonate anion, a carboxylate anion, a bis(alkylsulfonyl)amide anion, a tris(alkylsulfonyl) methide anion, and the like, and an organic anion represented by the following general formulae (9), (10) or (11) is preferable, and an organic anion represented by the following general formula (9) is more preferable.

[Chem. 97]

$$R_{c1}-SO_3^{\ominus} \quad (9)$$

$$\underset{R_{c3}SO_2}{\overset{R_{c2}SO_2}{\diagdown}} N^{\ominus} \quad (10)$$

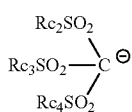
(11)

In the general formulae (9), (10) and (11), $Rc_1$, $Rc_2$, $Rc_3$ and $Rc_4$ each respectively represent an organic group.

The organic anion of $X^-$ corresponds to sulfonic acid, imide acid, methide acid, and the like, which are acids generated by irradiation with actinic rays or a radiation such as an electron beam or extreme ultraviolet rays.

Examples of the organic group of $Rc_1$, $Rc_2$, $Rc_3$ and $Rc_4$ include an alkyl group, an aryl group, and a group in which a plurality of these groups are linked. Among these organic groups, more preferred examples include an alkyl group in which the 1-position is substituted with a fluorine atom or a fluoroalkyl group and a phenyl group in which the 1-position is substituted with a fluorine atom or a fluoroalkyl group. When the organic group has a fluorine atom or a fluoroalkyl group, the acidity generated by light irradiation is increased, and sensitivity is enhanced. However, it is preferable that a terminal group dose not contain a fluorine atom as a substituent.

Hereinafter, a particularly preferred acid generator (D) in the present invention will be illustrated.

[Chem. 98]

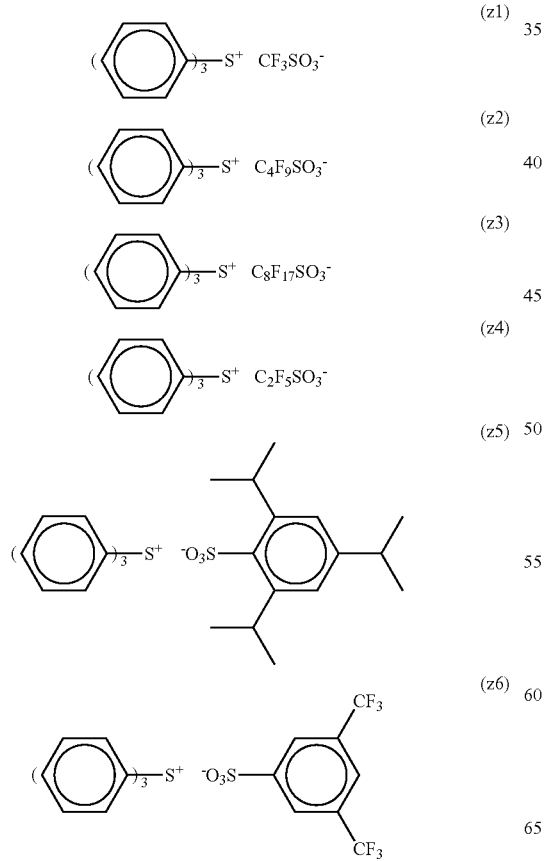

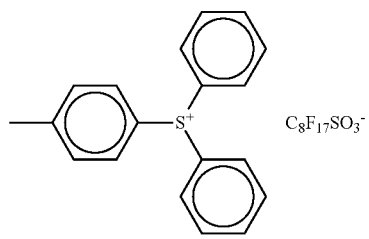

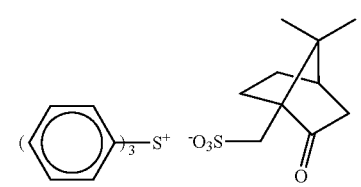

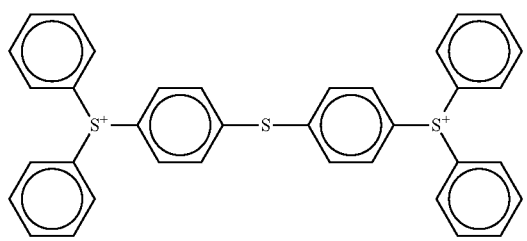

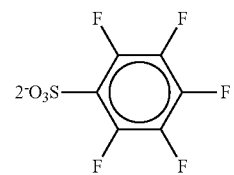

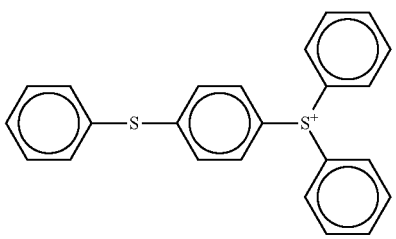

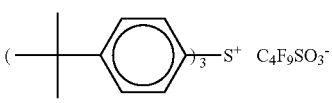

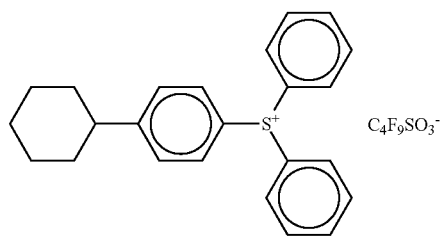

-continued
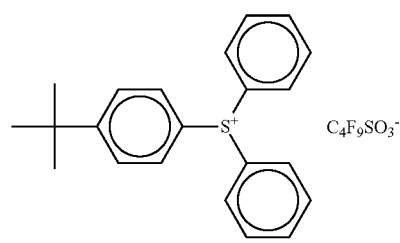 (z13)
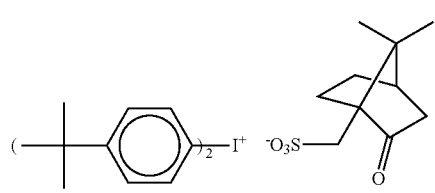 (z14)
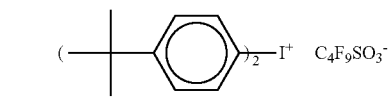 (z15)
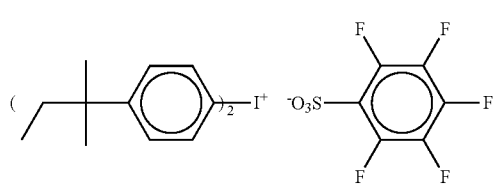 (z16)
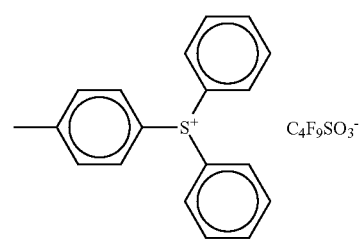 (z17)
[Chem. 99]
 (z18)
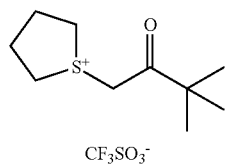 (z19)
 (z20)
-continued
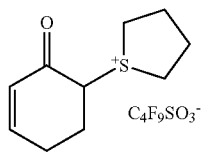 (z21)
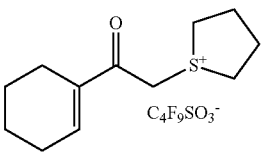 (z22)
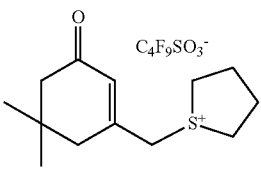 (z23)
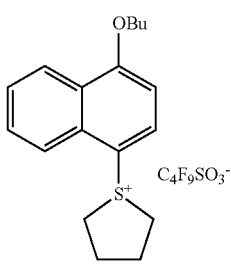 (z24)
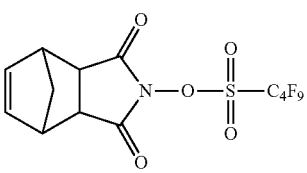 (z25)
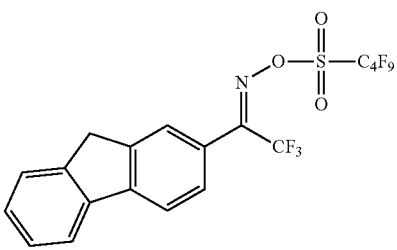 (z26)
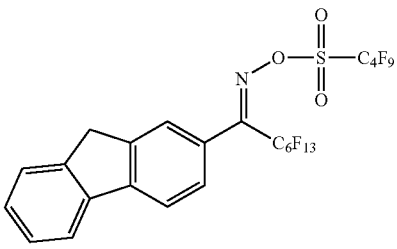 (z27)
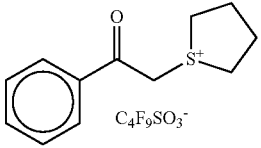 (z28)

-continued
(z29) 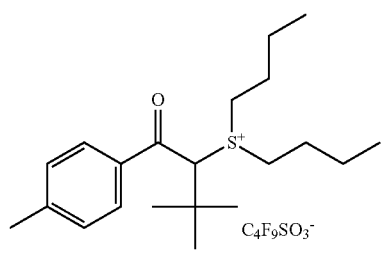
(z30) 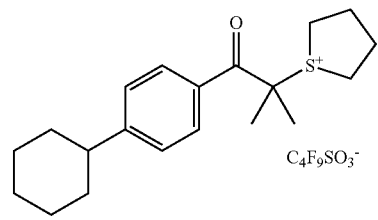
(z31) 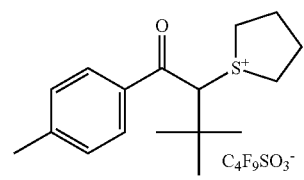
(z32) 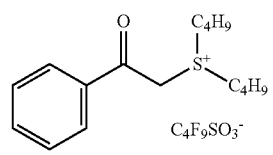
(z33) 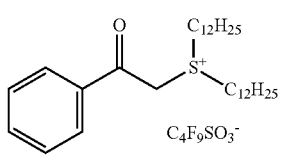
(z34) 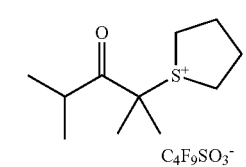
(z35) 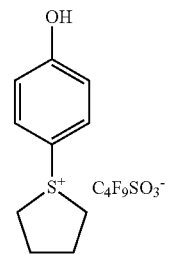
(z36) 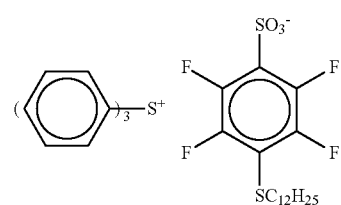
-continued
(z37) 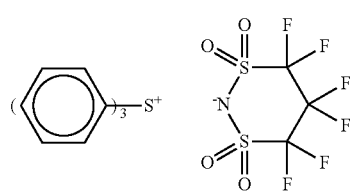
(z38) 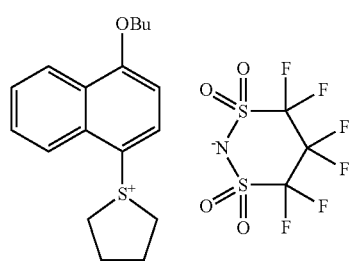
(z39) 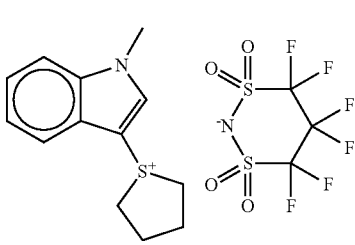
(z40) 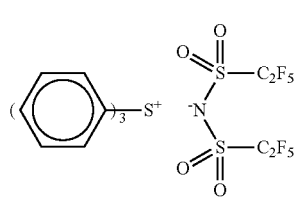
(z41) 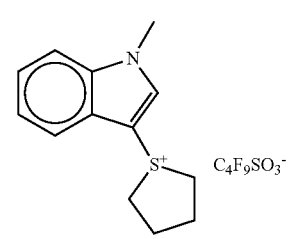
[Chem. 100]
(z42) 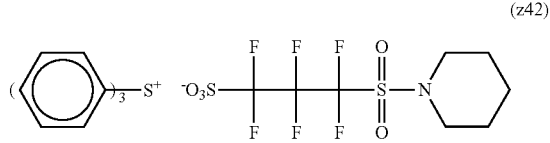
(z43) 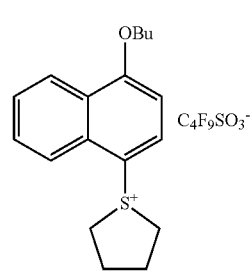

(z44) 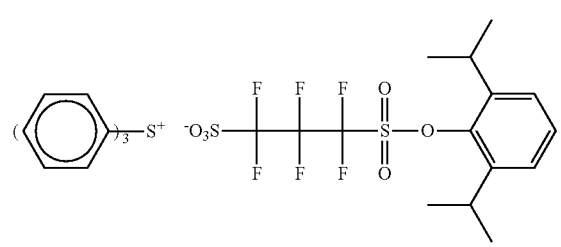
(z49) 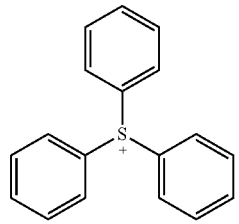
(z45) 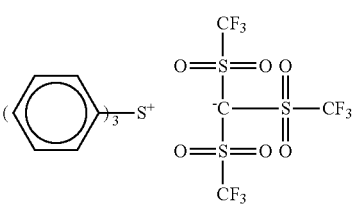
(z50) 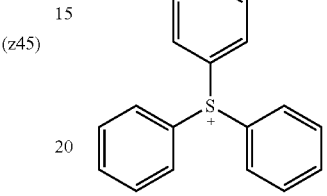
(z46) 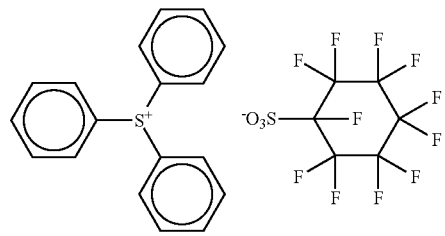
(z51) 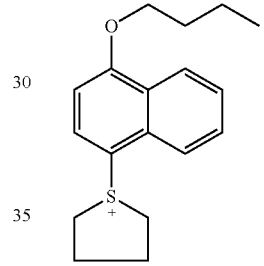
(z47) 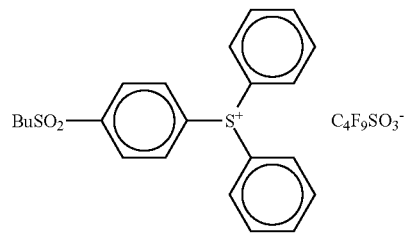
(z52) 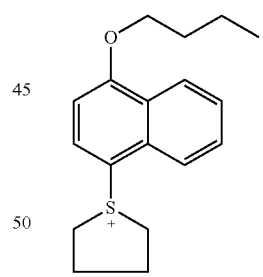
(z48) 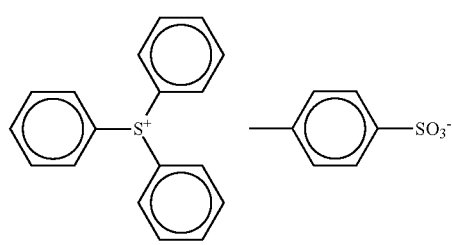
(z53) 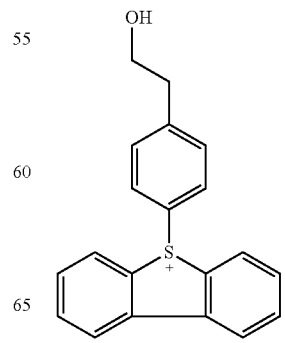 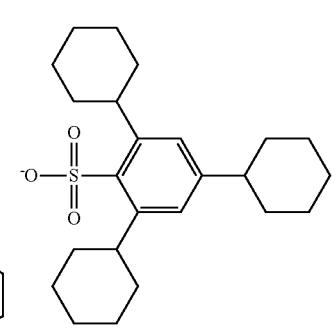
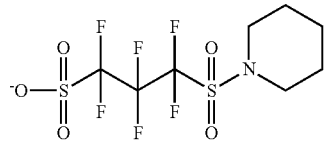

-continued
(z54)
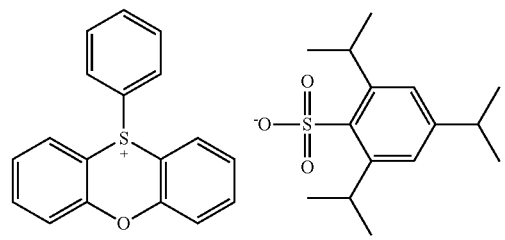
(z58)
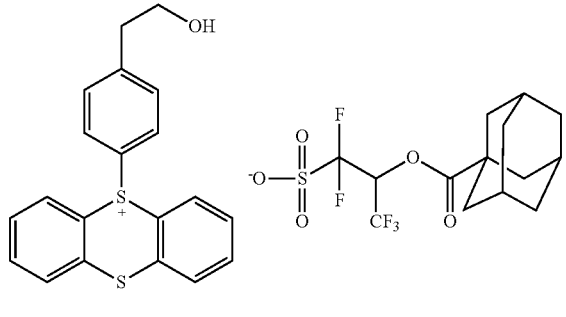
(z55)
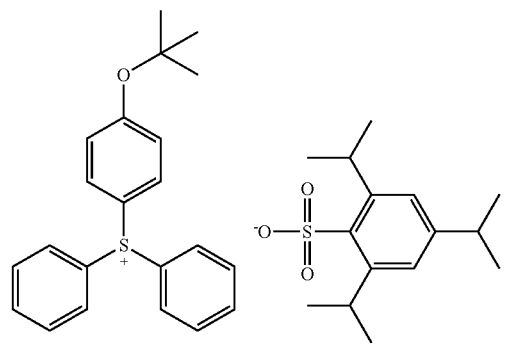
(z59)
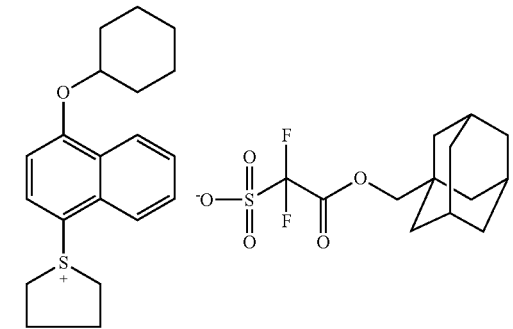
[Chem. 101]
(z56)
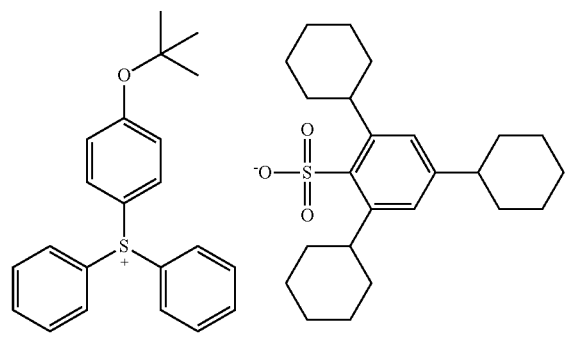
(z60)
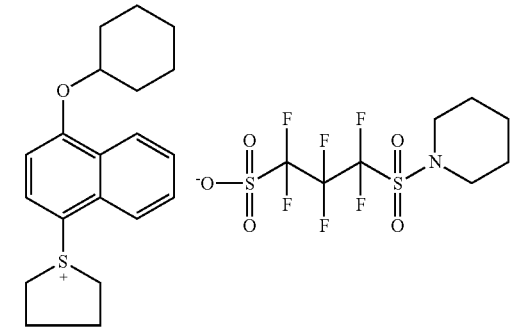
(z57)
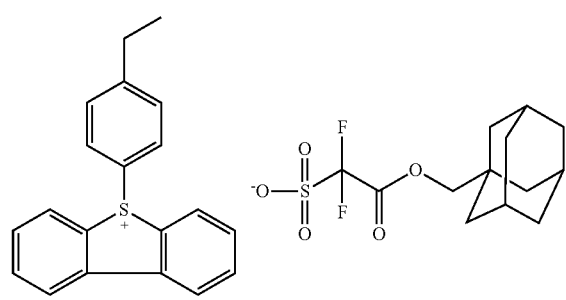
(z61)
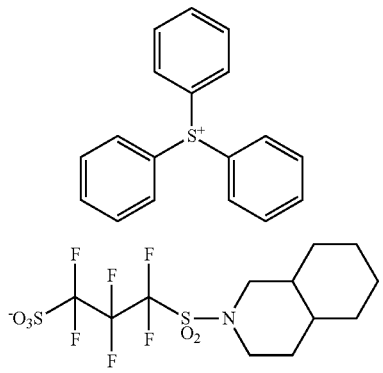

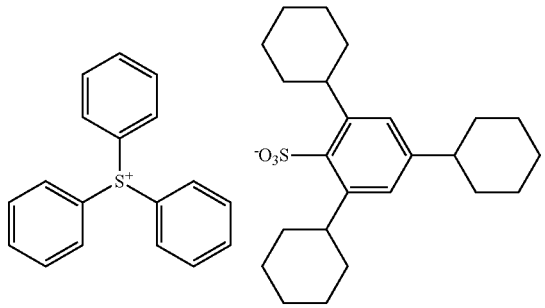
(z62)

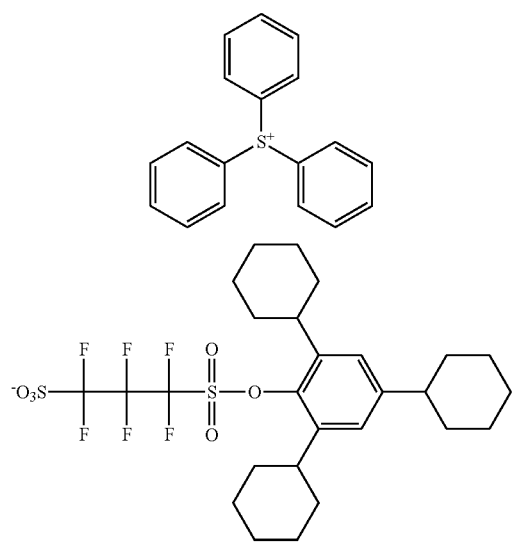
(z63)

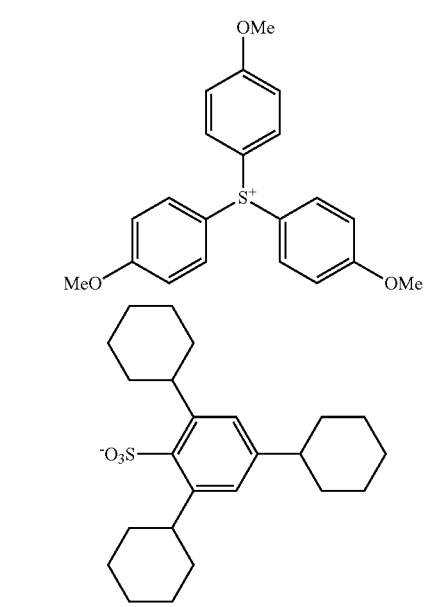
(z64)

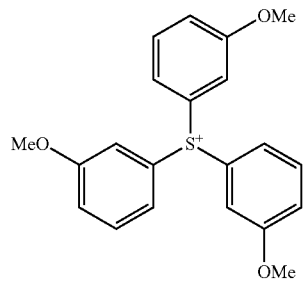
(z65)

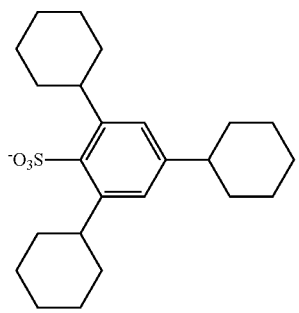

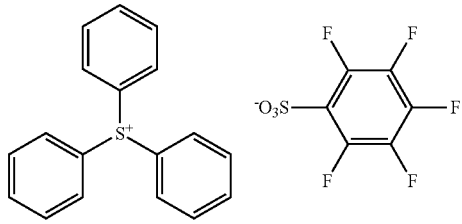
(z66)

The content rate of the acid generator (D) in the composition is preferably from 0 to 25% by mass, more preferably 0 to 20% by mass, and even more preferably 0 to 15% by mass, based on the total solid contents of the composition.

The acid generator (D) may be used alone, or in combination of two or more kinds thereof.

[6] Basic Compound

The composition of the present invention preferably contains a basic compound as an acid complement agent, in addition to the components described above. When a basic compound is used, the performance change due to the passage of time from the exposure to the post-heating can be reduced. Such a basic compound is preferably an organic basic compound, and more specific examples thereof include aliphatic amines, aromatic amines, heterocyclic amines, a nitrogen-containing compound having a carboxyl group, a nitrogen-containing compound having a sulfonyl group, a nitrogen-containing compound having a hydroxy group, a nitrogen-containing compounds having a hydroxyphenyl group, an alcoholic nitrogen-containing compound, an amide derivative, an imide derivative, and the like. An amine oxide compound (described in JP2008-102383A), and an ammonium salt (A hydroxide or a carboxylate is preferred. More specifically, tetraalkyl ammonium hydroxide typified by tetrabutyl ammonium hydroxide is preferred from the viewpoint of LER) are also appropriately used.

Furthermore, a compound which increases basicity by the action of an acid can be also used as one kind of the basic compound.

Specific examples of the amines include tri-n-butylamine, tri-n-pentylamine, tri-n-octylamine, tri-n-decylamine, triisodecylamine, dicyclohexylmethylamine, tetradecylamine, pentadecylamine, hexadecylamine, octadecylamine, didecylamine, methyloctadecylamine, dimethylundecylamine, N,N-dimethyldodecylamine, methyldioctadecylamine, N,N-dibutylaniline, N,N-dihexylaniline, 2,6-diisopropylaniline, 2,4,6-tri(t-butyl)aniline, triethanolamine, N,N-dihydroxyethylaniline, tris(methoxyethoxyethyl)amine, the compounds exemplified in column 3, line 60 of U.S. Pat. No. 6,040,112B; 2-[2-{2-(2,2-dimethoxy-phenoxyethoxy)ethyl}-bis-(2-methoxyethyl)]-amine, compounds (C1-1) to (C3-3) exemplified in paragraph <0066> of US2007/0224539A1, and the like. Examples of the compound having a nitrogen-containing heterocyclic structure include 2-phenylbenzoimidazole, 2,4,5-triphenylimidazole, N-hydroxyethylpiperidine, bis(1,2,2,6,6-pentamethyl-4-piperidyl)sebacate, 4-dimethylaminopyridine, antipyrine, hydroxyantipyrine, 1,5-diazabicyclo[4.0.3]-none-5-ene, 1,8-diazabicyclo[5.0.4.0]-undeca-7-ene, tetrabutylammonium hydroxide, and the like.

In addition, a photo-decomposable basic compound (a compound in which a basic nitrogen atom initially acts as a base and thereby the compound exhibits basicity, but as the compound is decomposed by irradiation with actinic rays or radiation and generates a zwitterionic compound having a basic nitrogen atom and an organic acid moiety, these moieties are neutralized in the molecule, and basicity is decreased or lost. For example, the onium salts described in JP 3577743B, JP2001-215689A, JP2001-166476A, and JP2008-102383A), and a photobase generator (for example, the compounds described in JP 2010-243773 A) are also appropriately used.

Among these basic compounds, an ammonium salt is preferred from the viewpoint of the improvement of resolution.

The content rate of the basic compound in the present invention is preferably from 0.01 to 10% by mass, more preferably from 0.03 to 5% by mass, and particularly preferably from 0.05 to 3% by mass, with respect to the total solid contents of the composition.

[7] Surfactant

The composition of the present invention may further contain a surfactant in order to enhance coatability. Examples of the surfactant include, but are not particularly limited to, a nonionic surfactant such as polyoxyethylene alkyl ethers, polyoxyethylene alkyl allyl ethers, polyoxyethylene polyoxypropylene block copolymers, sorbitan fatty acid esters, and polyoxyethylene sorbitan fatty acid esters; a fluorine-based surfactant such as MEGAFACE F171 (manufactured by Dainippon Ink and Chemicals, Inc.), Fluorad FC430 (manufactured by Sumitomo 3M, Ltd.), Surfinol E1004 (manufactured by Asahi Glass Co., Ltd.), PF656 and PF6320 manufactured by Omnova Solutions, Inc.; and a organosiloxane polymer.

In a case where the composition of the present invention contains a surfactant, the content rate thereof is preferably 0.0001 to 2% by mass, and more preferably 0.0005 to 1% by mass, with respect to the total amount (excluding the solvent) of the composition.

[8] Organic Carboxylic Acid

The composition of the present invention preferably contains an organic carboxylic acid in addition to the components described above. Examples of such an organic carboxylic acid compound include an aliphatic carboxylic acid, an alicyclic carboxylic acid, an unsaturated aliphatic carboxylic acid, an oxycarboxylic acids, an alkoxycarboxylic acid, a ketocarboxylic acid, a benzoic acid derivative, a phthalic acid, a terephthalic acid, an isophthalic acid, a 2-naphthoic acid, a 1-hydroxy-2-naphthoic acid, and a 2-hydroxy-3-naphthoic acid, but, since there is a risk that when exposure of an electron beam is carried out in a vacuum, the organic carboxylic acid compound may evaporate from the resist film surface and contaminate in the drawing chamber, as a preferred compound, aromatic organic carboxylic acids, and among them, for example, benzoic acid, 1-hydroxy-2-naphthoic acid, and 2-hydroxy-3-naphthoic acid are suitable.

The mixing amount of the organic carboxylic acid is preferably in the range of 0.01 to 10 parts by mass, more preferably 0.01 to 5 parts by mass, and even more preferably 0.01 to 3 parts by mass, with respect to 100 parts by mass of the polymer compound (A).

The composition of the present invention may further contain a dye, a plasticizer, an acid proliferating agent (described in WO95/29968, WO98/24000, JP1996-305262A (JP-H08-305262 A), JP1997-34106A (JP-H09-34106A), JP1996-248561A (JP-H08-248561 A), JP1996-503082A (JP-H08-503082A), U.S. Pat. No. 5,445,917B, JP 1996-503081 A (JP-H08-503081 A), U.S. Pat. No. 5,534,393B, U.S. Pat. No. 5,395,736B, U.S. Pat. No. 5,741,630B, U.S. Pat. No. 5,334,489B, U.S. Pat. No. 5,582,956B, U.S. Pat. No. 5,578,424B, U.S. Pat. No. 5,453,345B, U.S. Pat. No. 5,445,917B, EP665,960B, EP757,628B, EP665,961B, U.S. Pat. No. 5,667,943B, JP1998-1508A (JP-H10-1508A), JP1998-282642A (JP-H10-282642A), JP1997-512498A (JP-H09-512498A), JP2000-62337A, JP2005-17730A, JP2008-209889A, and the like), and the like, if necessary. Any of these compounds include the respective compounds described in JP2008-268935A.

[9] Carboxylic Acid Onium Salt

The composition of the present invention may contain a carboxylic acid onium salt. Examples of the carboxylic acid onium salt include a carboxylic acid sulfonium salt, a carboxylic acid iodonium salt, a carboxylic acid ammonium salt, and the like. Particularly, the carboxylic acid onium salt is preferably a carboxylic acid sulfonium salt and a carboxylic acid iodonium salt. Furthermore, in the present invention, the carboxylate residue of the carboxylic acid onium salt preferably does not contain an aromatic group or a carbon-carbon double bond. As a particularly preferred anionic moiety, a linear or branched, monocyclic or polycyclic cyclic alkylcarboxylic acid anion having 1 to 30 carbon atoms is preferred. An anion of a carboxylic acid in which a part or all of these alkyl groups are substituted with fluorine, is more preferred. The carboxylic acid onium salt may also contain an oxygen atom in the alkyl chain. Thereby, transparency to light having a wavelength of 220 nm or less is secured, sensitivity and resolving power are enhanced, and the compactness dependency and exposure margin are improved.

[10] Solvent

The composition of the present invention may contain a solvent, and the solvent is preferably ethylene glycol monoethyl ether acetate, cyclohexanone, 2-heptanone, propylene glycol monomethyl ether (PGME, also known as 1-methoxy-2-propanol), propylene glycol monomethyl ether acetate (PGMEA, also known as 1-methoxy-2-acetoxypropane), propylene glycol monomethyl ether propionate, propylene glycol monoethyl ether acetate, methyl 3-methoxypropionate, ethyl 3-ethoxypropionate, methyl β-methoxyisobutyrate, ethyl butyrate, propyl butyrate, methyl isobutyl ketone, ethyl acetate, isoamyl acetate, ethyl lactate, toluene, xylene, cyclohexyl acetate, diacetone alcohol, N-methylpyrrolidone, N,N-dimethylformamide, γ-butyrolactone, N,N-dimethylacetamide, propylene carbonate, ethylene carbonate, and the like. These solvents are used alone or in combination.

The solid contents of the composition of the present invention is dissolved in the solvents described above, and it is preferable that the solid contents be dissolved as a solids concentration of from 1 to 40% by mass. From 1 to 30% by mass is more preferable and 3 to 20% by mass is even more preferable.

In a case where the composition of the present invention includes the compound (B2) having an acid-decomposable group described above, the composition can suitably be used in the formation process of a negative-tone pattern shown below. That is, after the composition of the present invention containing the compound (B2) having an acid-decomposable group is applied onto a substrate to make a film and is exposed, a developer containing an organic solvent as a main component (hereinafter, referred as an "organic-based developer") is used to develop, and the composition can also suitably be used in a process for obtaining a negative-tone pattern. As such a process, for example, processes described in JP2008-292975A, JP2010-217884A, and the like can be used.

As an organic-based developer, a polar solvent such as an ester-based solvent (butyl acetate, ethyl acetate, or the like), a ketone-based solvent (2-heptanone, cyclohexanone, or the like), an alcohol-based solvent, an amide-based solvent, or an ether-based solvent and a hydrocarbon-based solvent can be used. The moisture content in the whole organic-based developer is preferably less than 10% by mass, and it is more preferable that the developer substantially do not contain moisture.

The present invention also relates to an actinic ray-sensitive or radiation-sensitive film formed by the composition of the present invention, and such a film, for example, is formed by applying the composition of the present invention onto a support such as a substrate. The thickness of the film is preferably from 0.02 to 0.1 μm. As a method for applying onto a substrate, the composition is applied onto a substrate by an appropriate applying method such as a spin coating, a roll coating, a flow coating, a dip coating, a spray coating, or a doctor coating, but a spin coating is preferred, and the speed of rotation thereof is preferably from 1,000 rpm to 3,000 rpm. The applied film is prebaked for 1 to 20 minutes at 60 to 150° C., and preferably for 1 to 10 minutes at 80 to 120° C. to form a thin film.

As the material that constitutes the substrate to be processed and its outermost layer, for example, in the case of a semiconductor wafer, a silicon wafer can be used and examples of the material that forms the outermost layer include Si, $SiO_2$, SiN, SiON, TiN, WSi, BPSG, SOG, an organic antireflection film, and the like.

Furthermore, the present invention also relates to mask blanks applied an actinic ray-sensitive or radiation-sensitive film obtained as described above. In the case of forming a pattern on photomask blanks for photomask production in order to obtain mask blanks provided with such an actinic ray-sensitive or radiation-sensitive film, examples of a transparent substrate to be used include transparent substrates of quartz, calcium fluoride, and the like. Generally, a light-shielding film, an antireflection film, and a phase shift film, with any necessary one of additional functional films such as an etching stopper film and an etching mask film are laminated on the substrate. As the material of the functional films, films containing silicon or a transition metal such as chromium, molybdenum, zirconium, tantalum, tungsten, titanium, or niobium are laminated. Furthermore, as a material to be used in the outermost layer, a material which has, as a main constituent material, a material containing silicon or silicon with oxygen and/or nitrogen; and a silicon compound material which has, as a main constituent material, a material containing transition metals in addition thereto; and a transition metal compound material which has, as a main constituent material, transition metals, in particular, one kind or more selected from chromium, molybdenum, zirconium, tantalum, tungsten, titanium and niobium, and the like, or a material further containing one or more elements selected from oxygen, nitrogen and carbon in addition thereto are exemplified.

The light-shielding film may be a single layer, but a multilayer structure reapplied plural materials is more preferable. In a case of the multilayer structure, the film thickness per layer is not particularly limited, but the thickness is preferably from 5 to 100 nm, and more preferably from 10 to 80 nm. The thickness of the entire light-shielding film is not particularly limited, but the thickness is preferably from 5 to 200 nm, and more preferably from 10 to 150 nm.

Among these materials, generally, in a case where a pattern formation is carried out on photomask blanks provided with a material containing oxygen or nitrogen together with chromium in the outermost layer, by using the composition, a so-called undercut shape by which a constricted shape is formed near the substrate is likely to be produced, however, in the case of using the composition of the present invention, the problem of undercut can be improved as compared with those of the related art.

The actinic ray-sensitive or radiation-sensitive film is irradiated with actinic rays or radiation (an electron beam, and the like) and is developed preferably after baking is performed (normally at 80 to 150° C. and more preferably at 90 to 130° C.). Thereby, a satisfactory pattern can be obtained. Thus, a semiconductor fine circuit and a mold structure for imprint, and the like are produced by using this pattern as a mask, and conducting an appropriate etching treatment, ion implantation and the like.

Meanwhile, the process in the case of producing the mold for imprint by using the composition of the present invention is described in, for example, JP4109085B, JP2008-162101A, and "Fundamentals and Technological Development and Application Deployment of Nanoimprint—Nanoimprint Substrate Technology and Recent Technology Deployment, edited by Hirai, Yoshihiko, published by Frontier Publishing Co., Ltd."

The usage form and a pattern forming method of the actinic ray-sensitive or radiation-sensitive resin composition of the present invention will be described below.

The present invention also relates a pattern forming method, which includes exposing the actinic ray-sensitive or radiation-sensitive film or mask blanks in which the film is formed, and developing the exposed actinic ray-sensitive or radiation-sensitive film or mask blanks provided with the exposed film. In the present invention, it is preferable that the exposure be performed by using an electron beam or extreme ultraviolet rays.

In the production of precision integrated circuit elements and the like, first, it is preferable to conduct the exposure onto the actinic ray-sensitive or radiation-sensitive film (a pattern forming process) by irradiating patternwise the actinic ray-sensitive or radiation-sensitive film of the present invention with an electron beam or extreme ultraviolet rays (EUV). The exposure is conducted so that the exposure amount is, in the case of an electron beam, about 0.1 to 20 μC/cm², and preferably about 3 to 10 μC/cm², and in the case of extreme ultraviolet rays, about 0.1 to 20 mJ/cm², preferably about 3 to 15 mJ/cm². Subsequently, a pattern is formed by performing heating after exposure (Post Exposure Bake) at 60 to 150° C. for 1 to 20 minutes on a hot plate and preferably at 80 to 120° C. for 1 to 10 minutes, and developing, rinsing and drying. The developer is a 0.1 to 5% by mass, and preferably 2 to 3% by mass alkaline aqueous solution of tetramethylammonium hydroxide (TMAH), tetrabutylammonium hydroxide (TBAH), and the like, and development is carried out by a routine method such as a dipping method, a puddle method or a spray method, for 0.1 to 3 minutes, and preferably 0.5 to 2 minutes. An appropriate amount of alcohols and/or a surfactant may also be added to the alkali developer. Thus, in a case where the composition of the present invention is a negative-tone composition which is used for the formation of a negative-tone pattern, a film of the non-exposed portion is dissolved and it is difficult for the exposed portion to be dissolved in a developer since the compound (A) is cross-linked, and in a case where the composition of the present invention is a positive-tone composition which is used for the formation of a positive-tone pattern, the exposed portion is dissolved in a developer and it is difficult for the non-exposed portion to be dissolved in a developer and a objective pattern is formed on a substrate.

EXAMPLES

Below, the present invention will be described in further detail with reference to Examples, but the contents of the present invention are not limited thereto.

[Synthesis of Compound A]

<Synthesis of Compounds (A-1) to (A-29)>

As a cross-linking group-containing photo-acid generator, compounds (A-1) to (A-29) shown in Table 1 described below were synthesized as below.

Synthesis Example 1: Synthesis of Compound (A-1)

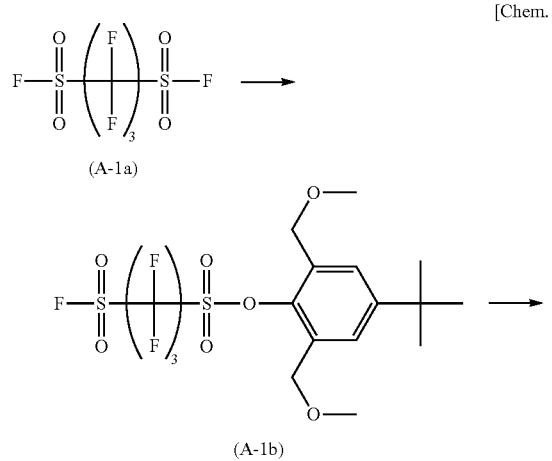

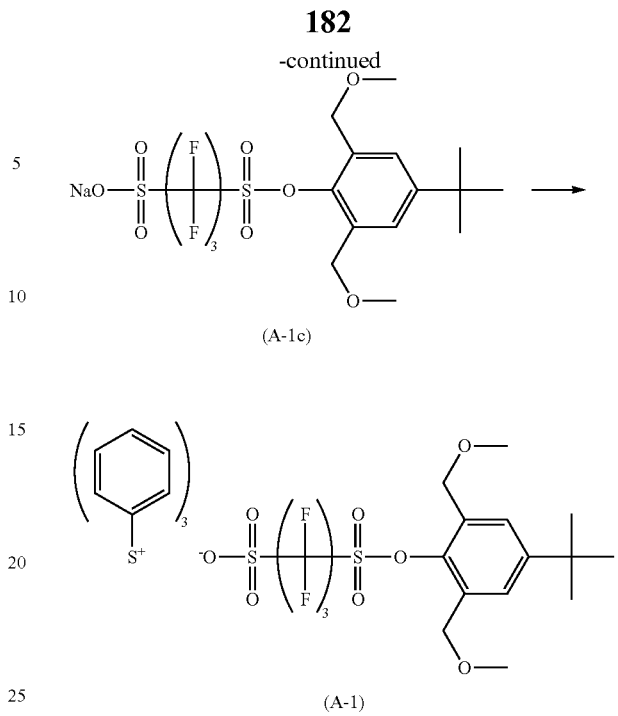

(Synthesis of A-1b)

After 7.5 g of 2,5-di(methoxymethyl)-4-t-butylphenol was dissolved in 20 mL of tetrahydrofuran and 60 mL of triethylamine was added thereto, temperature was cooled with ice to 0° C. to obtain the reaction solution. Next, the solution in which 10 g of 1,1,2,2,3,3-heptafluoropropane-1,3-disulfonyl fluoride was dissolved in 10 mL of tetrahydrofuran, was added dropwise into the reaction solution and was stirred for 8 hours. 100 mL of ethyl acetate and 100 mL of distilled water were added to the obtained reaction solution and the obtained solution was moved to a separating funnel and the aqueous layer was removed. Thereafter, the organic layer was washed with 200 mL of distilled water for three times, and then the organic layer was condensed to obtain 16 g of a compound (A-1b).

$^1$H-NMR (CDCl$_3$: ppm) δ: 1.33 (9H, s), 3.41 (6H, s), 4.58 (4H, s), 7.50 (2H, s)

$^{19}$H-NMR (CDCl$_3$: ppm) δ: −118.457 (2F, t, J=15.2 Hz), −113.874 (2F, t, J=15.2 Hz), −108.212 (2F, t, J=15.2 Hz).

(Synthesis of A-1c)

16 g of A-1b was dissolved in 50 mL of tetrahydrofuran, 50 mL of methanol and 50 mL of 1N of sodium hydroxide was added thereto, and the mixture was stirred at room temperature. After the reaction ends, the obtained reaction solution was condensed under reduced pressure and 100 mL of ethyl acetate and 100 mL of distilled water were added thereto. Next, the obtained solution was moved to a separating funnel and the aqueous layer was removed. Thereafter, the organic layer was washed with 200 mL of distilled water for three times, and then the organic layer was condensed. After the concentrate was purified by using a silica gel column chromatography (eluent: ethyl acetate) and a solvent was distilled off at reduced pressure, 16 g of a compound (A-1c) was obtained by performing vacuum drying.

$^1$H-NMR (CDCl$_3$: ppm) δ: 1.28 (9H, s), 3.28 (6H, s), 4.50 (4H, s), 7.42 (2H, s)

$^{19}$H-NMR (CDCl$_3$: ppm) δ: −118.710 (2F, t, J=15.2 Hz), −113.968 (2F, t, J=15.2 Hz), −108.393 (2F, t, J=15.2 Hz).

(Synthesis of A-1)

10 g of A-1c was dissolved in 100 mL of methanol, 7.7 g of triphenylsulfonium bromide was added thereto, and the mixture was stirred at room temperature. After the reaction ends, the obtained reaction solution was condensed under reduced pressure and 100 mL of ethyl acetate and 100 mL of distilled water were added thereto. Next, the obtained solution was moved to a separating funnel and the aqueous layer was removed. Thereafter, the organic layer was washed with 200 mL of distilled water for three times, and then the organic layer was condensed. After the concentrate was purified by using a silica gel column chromatography (eluent: methanol) and a solvent was distilled off at reduced pressure, 8 g of a compound (A-1) was obtained by performing vacuum drying.

$^1$H-NMR (CDCl$_3$: ppm) δ: 1.33 (9H, s), 3.39 (6H, s), 4.58 (4H, s), 7.49 (2H, s), 7.73 (15H, m)

$^{19}$H-NMR (CDCl$_3$: ppm) δ: −118.314 (2F, t, J=15.2 Hz), −114.020 (2F, t, J=15.2 Hz), −107.933 (2F, t, J=15.2 Hz).

Synthesis Example 2: Synthesis of Compound (A-6)

[Chem. 103]

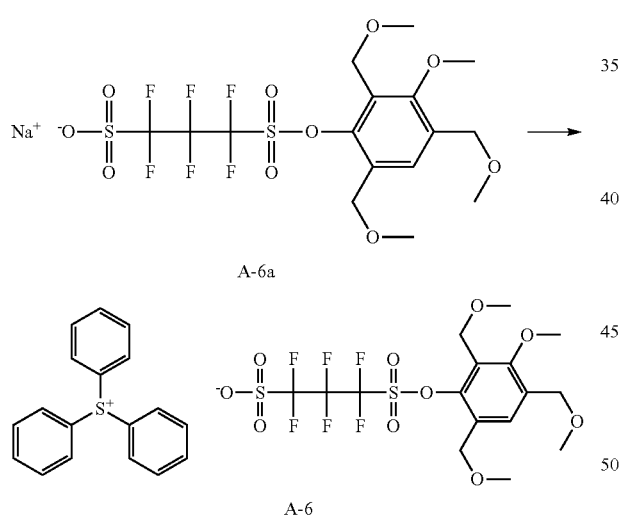

A-6a

A-6

After 10 g of a compound A-6a was dissolved in 200 mL of methanol and 6.1 g of triphenylsulfonium bromide was added thereto, and the mixture was stirred for 4 hours at room temperature. After 200 mL of ethyl acetate and 200 mL of distilled water were added to the obtained reaction solution, the obtained solution was moved to a separating funnel and the aqueous layer was removed. Thereafter, the organic layer was washed with 200 mL of distilled water for three times, and then a solvent of the organic layer was distilled off at reduced pressure to obtain 17.7 g of a compound (A-6). $^1$H-NMR (CDCl$_3$: ppm) δ: 3.36 (3H, s), 3.38 (3H, s), 3.42 (3H, s), 3.86 (3H, s), 4.51 (2H, s), 4.56 (4H, s), 7.63 (1H, s), 7.79-7.66 (15H, m).

Synthesis Example 3: Synthesis of Compound (A-10)

[Chem. 104]

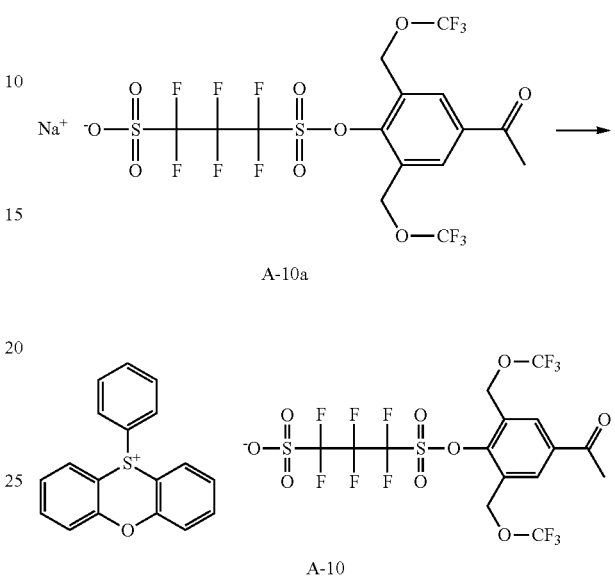

A-10a

A-10

After 10 g of a compound A-10a was dissolved in 200 mL of methanol and 8.5 g of triphenylsulfonium bromide was added thereto, and the mixture was stirred for 4 hours at room temperature. After 200 mL of ethyl acetate and 200 mL of distilled water were added to the obtained reaction solution, the obtained solution was moved to a separating funnel and the aqueous layer was removed. Thereafter, the organic layer was washed with 200 mL of distilled water for three times, and then a solvent of the organic layer was distilled off at reduced pressure to obtain 13.5 g of a compound (A-10).

Synthesis Example 4: Synthesis of Compound (A-13)

[Chem. 105]

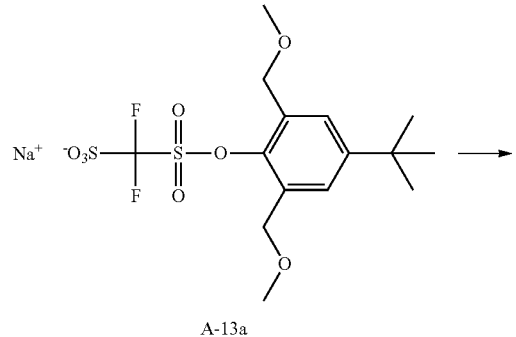

A-13a

-continued

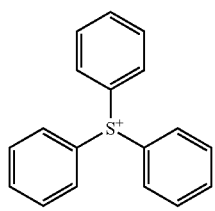 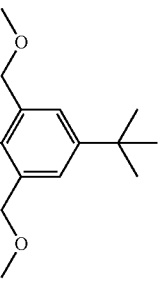

A-13

After 10 g of a compound A-13a was dissolved in 200 mL of methanol and 8.0 g of triphenylsulfonium bromide was added thereto, and the mixture was stirred for 4 hours at room temperature. After 200 mL of ethyl acetate and 200 mL of distilled water were added to the obtained reaction solution, the obtained solution was moved to a separating funnel and the aqueous layer was removed. Thereafter, the organic layer was washed with 200 mL of distilled water for three times, and then a solvent of the organic layer was distilled off at reduced pressure to obtain 14.9 g of a compound (A-13).

$^1$H-NMR (CDCl$_3$: ppm) δ: 1.32 (9H, s), 3.36 (6H, s), 4.64 (4H, s), 7.46 (2H, s), 7.76-7.65 (15H, m).

Synthesis Example 5: Synthesis of Compound (A-17)

[Chem. 106]

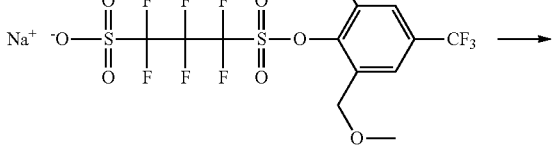

A-17a

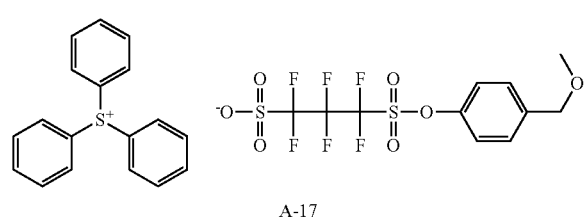

A-17

After 10 g of a compound A-17a was dissolved in 200 mL of methanol and 7.7 g of triphenylsulfonium bromide was added thereto, and the mixture was stirred for 4 hours at room temperature. After 200 mL of ethyl acetate and 200 mL of distilled water were added to the obtained reaction solution, the obtained solution was moved to a separating funnel and the aqueous layer was removed. Thereafter, the organic layer was washed with 200 mL of distilled water for three times, and then a solvent of the organic layer was distilled off at reduced pressure to obtain 14.8 g of a compound (A-17).

Synthesis Example 6: Synthesis of Compound (A-25)

[Chem. 107]

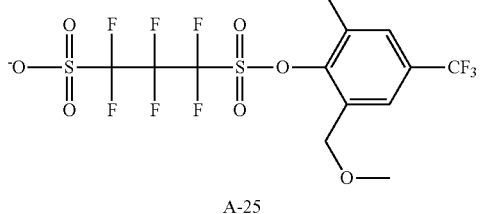

A-25a

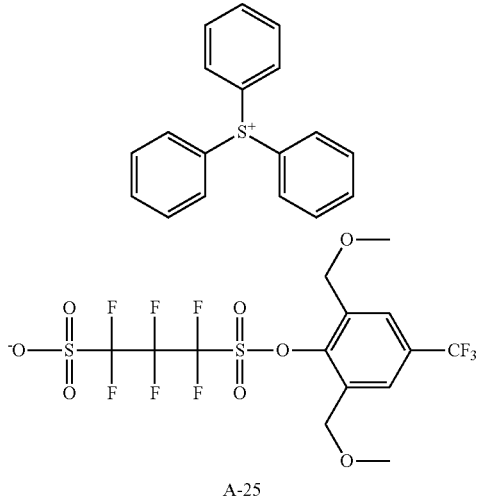

A-25

After 10 g of a compound (A-25a) was dissolved in 200 mL of methanol and 6.1 g of triphenylsulfonium bromide was added thereto, and the mixture was stirred for 4 hours at room temperature. After 200 mL of ethyl acetate and 200 mL of distilled water were added to the obtained reaction solution, the obtained solution was moved to a separating funnel and the aqueous layer was removed. Thereafter, the organic layer was washed with 200 mL of distilled water for three times, and then a solvent of the organic layer was distilled off at reduced pressure to obtain 17.7 g of a compound (A-25).

$^1$H-NMR (CDCl$_3$: ppm) δ: 3.42 (6H, s), 4.61 (4H, s), 7.85-7.68 (15H, m), 8.19 (2H, s).

<Synthesis of Another Compound (A)>

The other compound (A) shown in Table 1 was synthesized using the same method as a synthetic method of the compound (A) described above.

<Reference Compound>

For comparison, compounds (R-1) and (R-2) shown in Table 1 were used.

TABLE 1
| Compound | Chemical formula |
|---|---|
| A-1 | 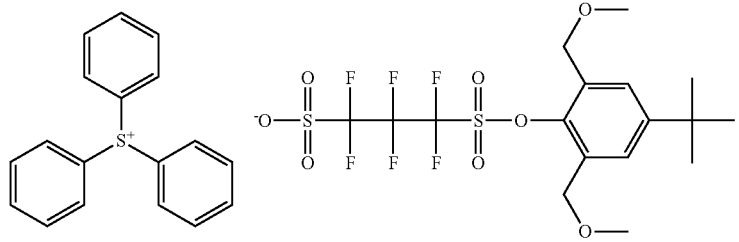 |
| A-2 | 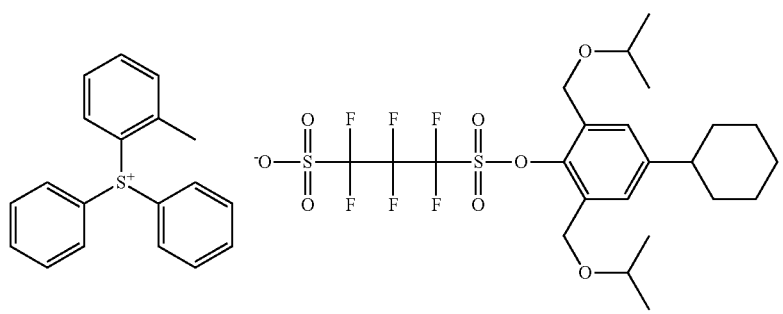 |
| A-3 | 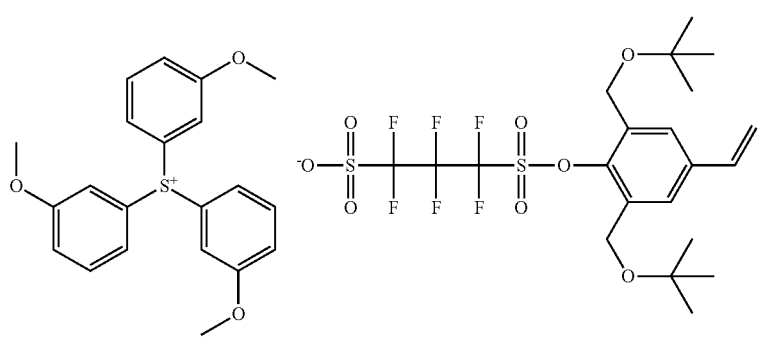 |
| A-4 | 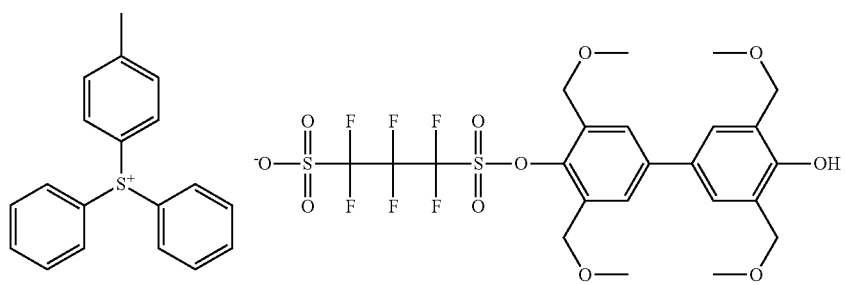 |
| A-5 | 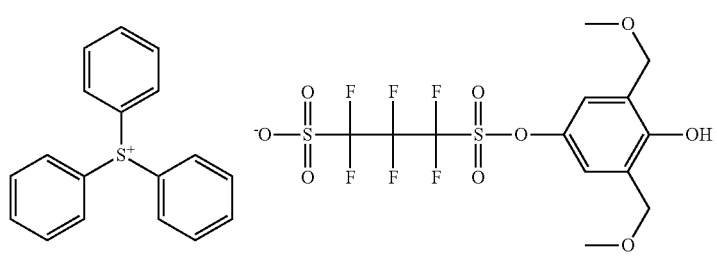 |

TABLE 1-continued

| Compound | Chemical formula |
|---|---|
| A-6 | |
| A-7 | |
| A-8 | |
| A-9 | |
| A-10 | |

TABLE 1-continued

| Compound | Chemical formula |
|---|---|
| A-11 | |
| A-12 | |
| A-13 | |
| A-14 | |
| A-15 | |

TABLE 1-continued
| Compound | Chemical formula |
|---|---|
| A-16 | 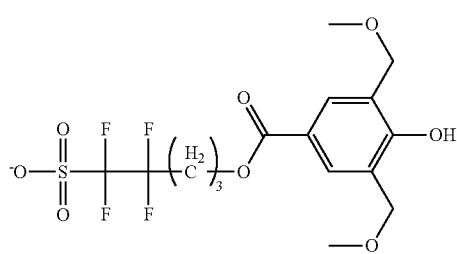 |
| A-17 | 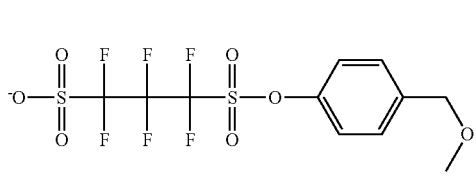 |
| A-18 | 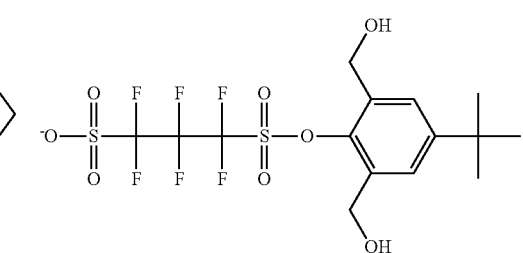 |
| A-19 | 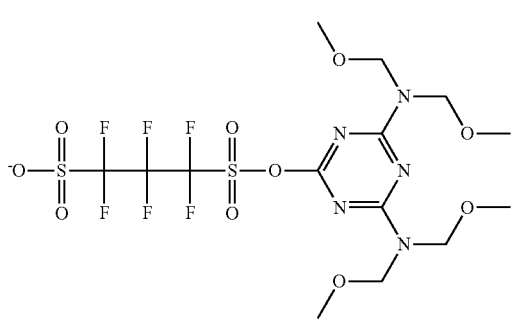 |
| A-20 | 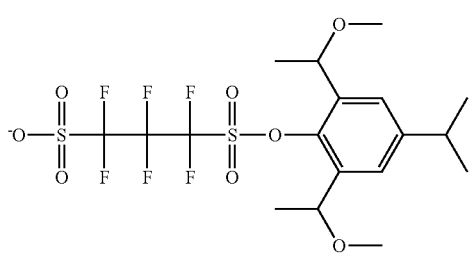 |

TABLE 1-continued
| Compound | Chemical formula |
|---|---|
| A-21 | 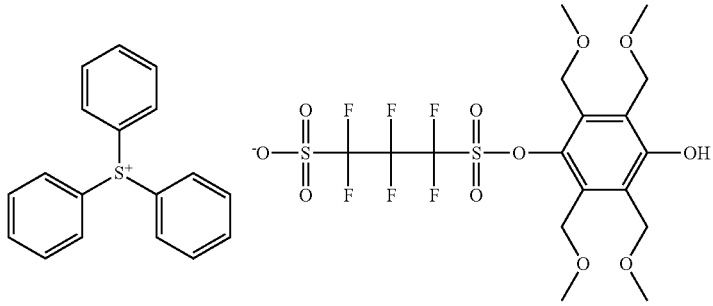 |
| A-22 | 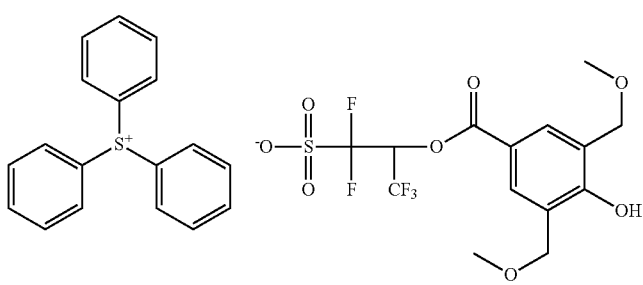 |
| A-23 | 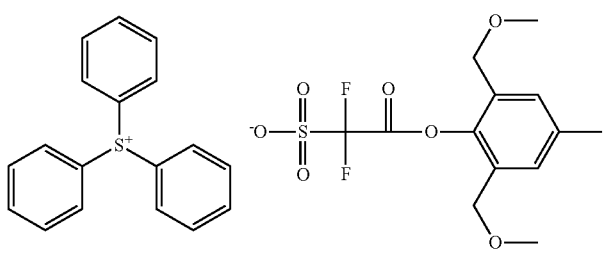 |
| A-24 | 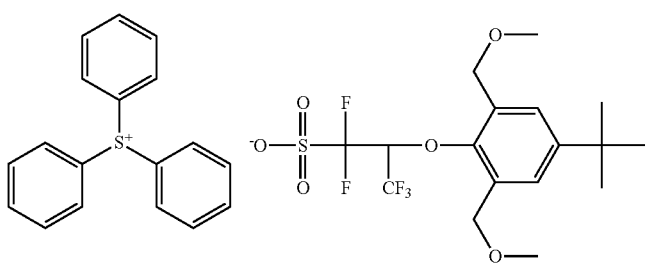 |
| A-25 | 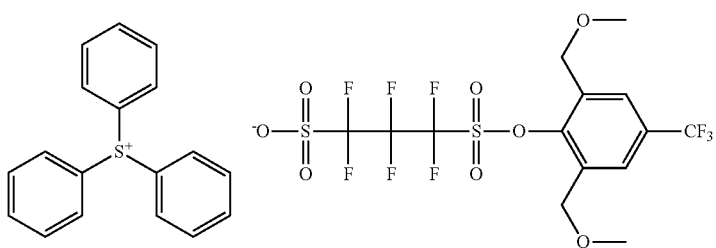 |

TABLE 1-continued
| Compound | Chemical formula |
|---|---|
| A-26 | 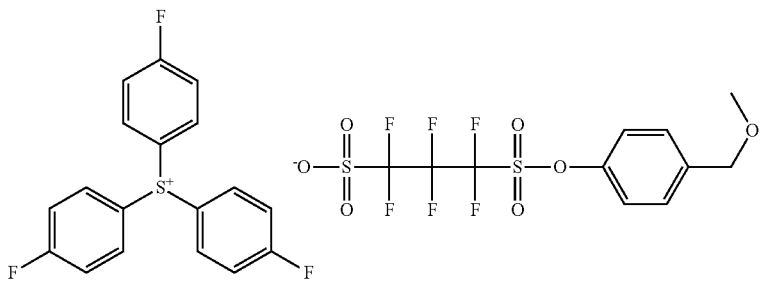 |
| A-27 | 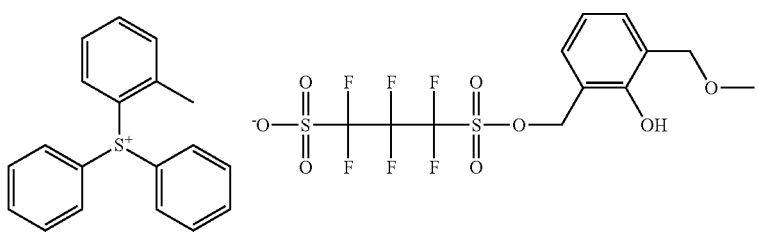 |
| A-28 | 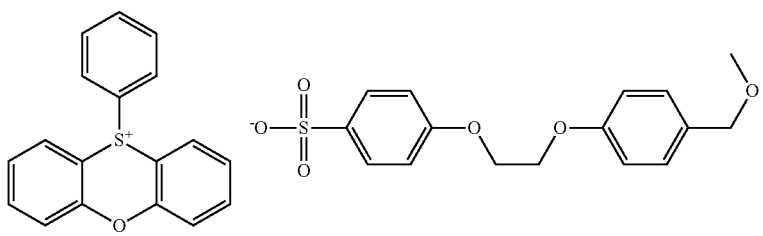 |
| A-29 | 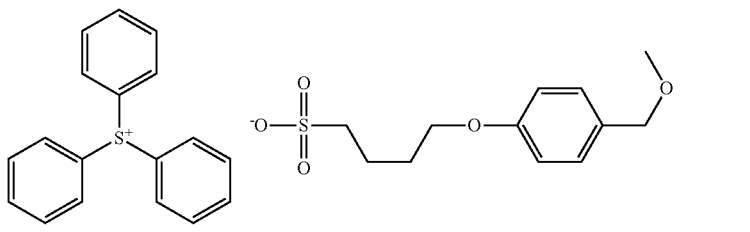 |
| R-1 | 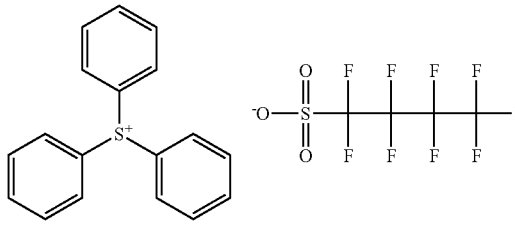 |

TABLE 1-continued

| Compound | Chemical formula |
|---|---|
| R-2 | |

Components other than the compound (A) which were used in Examples described later are shown below.

[Compound (B1) and Compound (B2)]

As a compound (B1), the chemical structures, the compositional ratio (molar ratio) of the repeating units and the weight average molecular weight of polymer compounds P1 to P5 having a phenolic hydroxyl group are shown below. In addition, the chemical structure of a low molecular compound (P6) having a phenolic hydroxyl group is shown below.

As a compound (B2), the chemical structures, the compositional ratio (molar ratio) of the repeating units and the weight average molecular weight of polymer compounds P7 to P10 are shown below.

[Chem. 108]

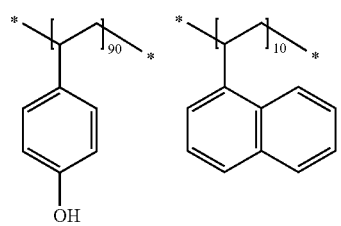

P1

Mw = 12000, Mw/Mn = 2.30

P2

Mw = 4500, Mw/Mn = 1.10

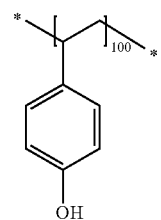

P3

Mw = 3700, Mw/Mn = 1.10

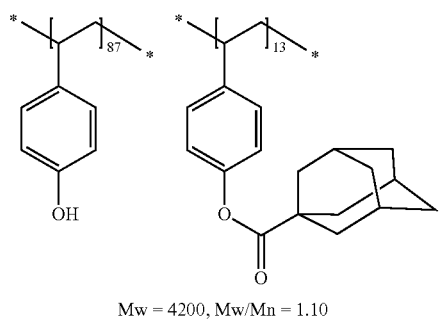

P4

Mw = 4200, Mw/Mn = 1.10

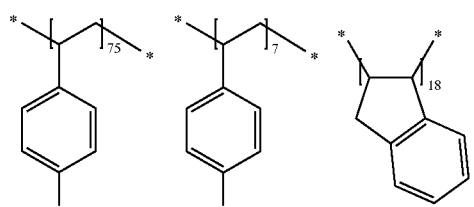

P5

Mw = 4500, Mw/Mn = 1.50

P6
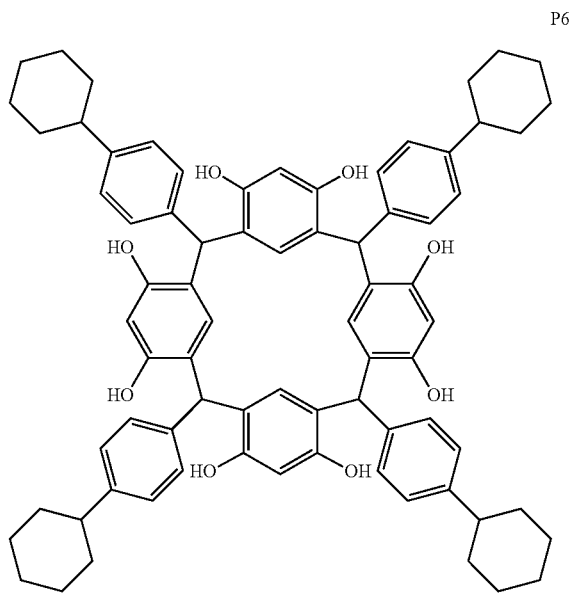
P7
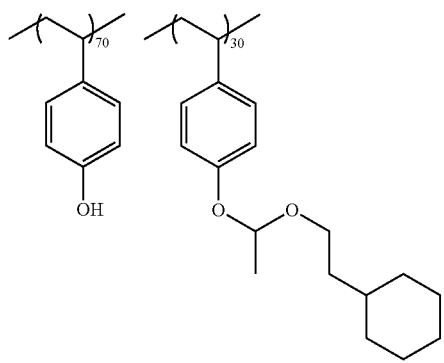
MW = 15100, Mw/Mn = 1.40
P9
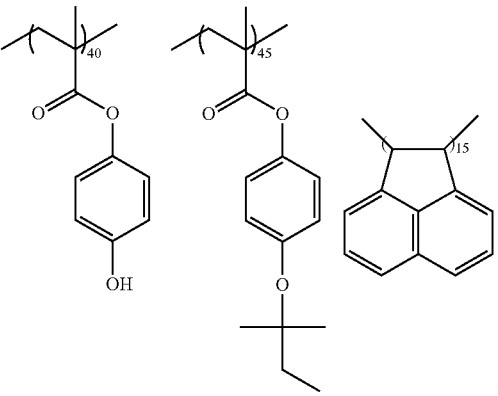
MW = 8000, Mw/Mn = 1.35
P10
MW = 7500, Mw/Mn = 1.50
[Cross-Linking Agent (C)]
As a cross-linking agent (C), compounds represented by the following formulae were used.
[Chem. 109]
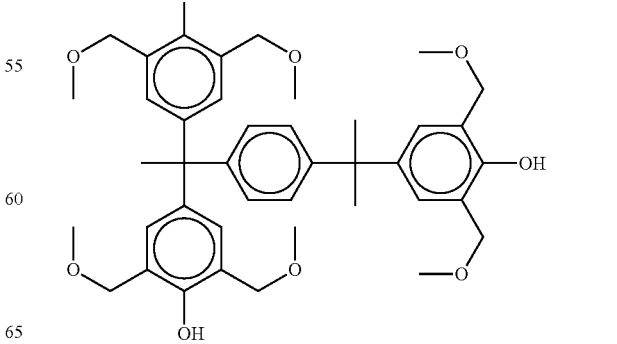
CL-1

CL-2 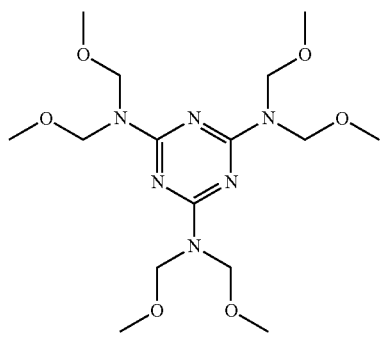
CL-3 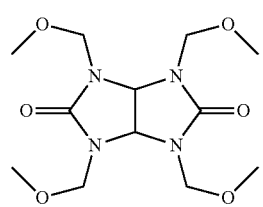
CL-4 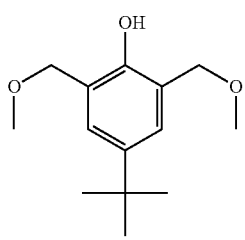
CL-5 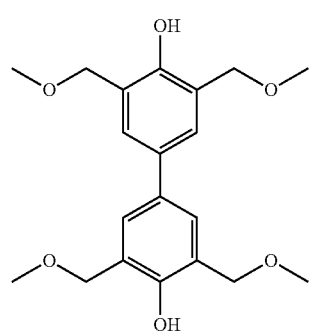
CL-6 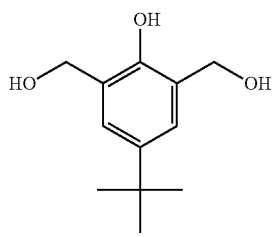
[Basic Compound]
As a basic compound, the following compounds were used.
[Chem. 110]
(BASE-1) 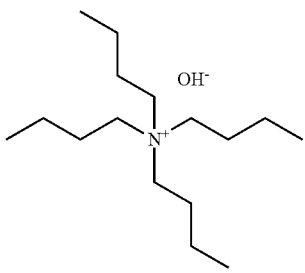
(BASE-2) 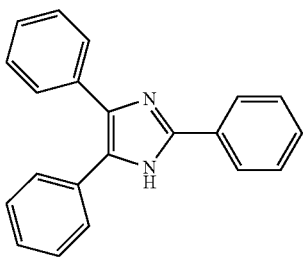
(BASE-3) 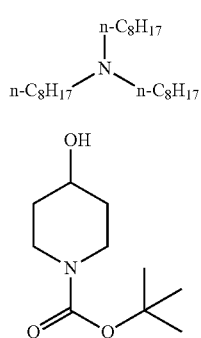
(BASE-4) 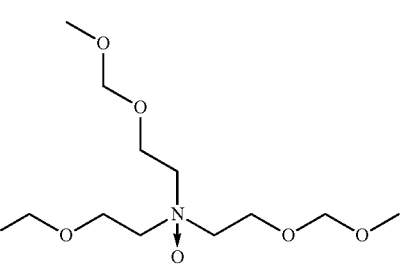
(BASE-5) 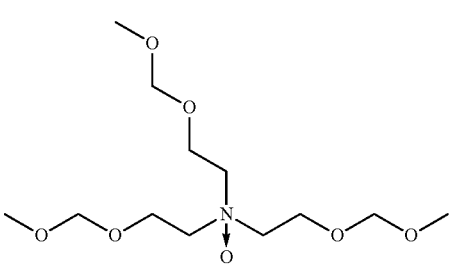
(BASE-6) 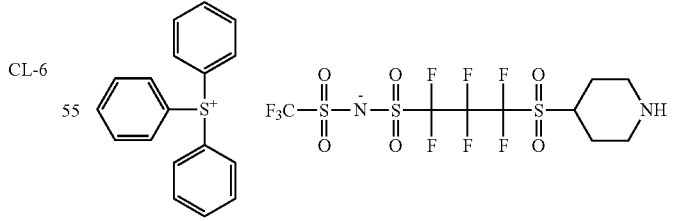
[Organic Carboxylic Acid]
As an organic carboxylic acid, the following were used.
D1: 2-hydroxy-3-naphthoic acid
D2: 2-naphthoic acid
D3: Benzoic acid

[Surfactant]

As s surfactant, the following were used.

W-1: Megaface F176 (manufactured by DIC CORPORATION; a fluorine-based surfactant)

W-2: Megaface R08 (manufactured by DIC CORPORATION; a fluorine and silicon-based surfactant)

W-3: PF6320 (manufactured by OMNOVA solution Inc.; a fluorine-based surfactant)

W-4: polysiloxane polymer (manufactured by Shin-Etsu Chemical Co., Ltd; a silicon-based surfactant)

[Acid Generator (D)]

As an acid generator (D), the following were used.

[Chem. 111]

(PAG-1)
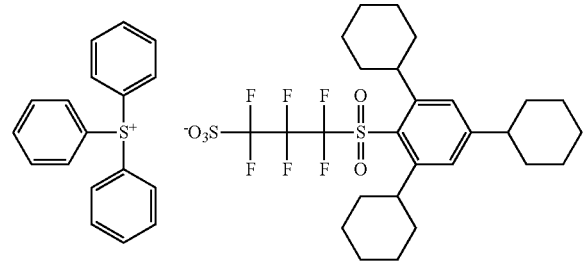

(PAG-2)
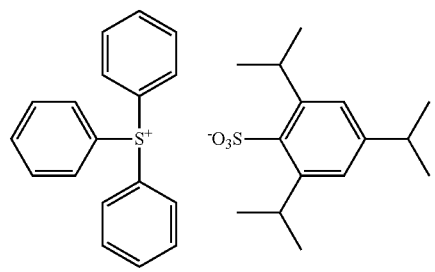

(PAG-3)
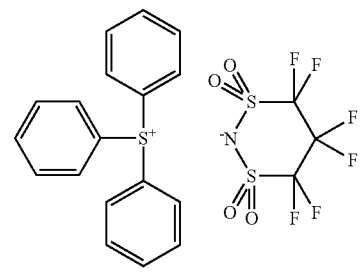

(PAG-4)
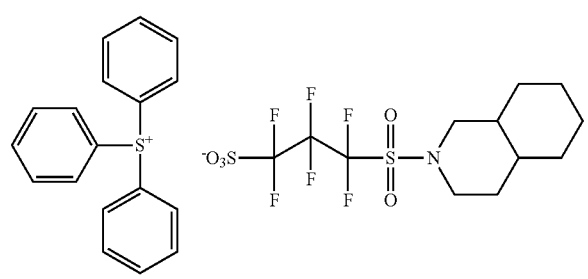

-continued (PAG-5)
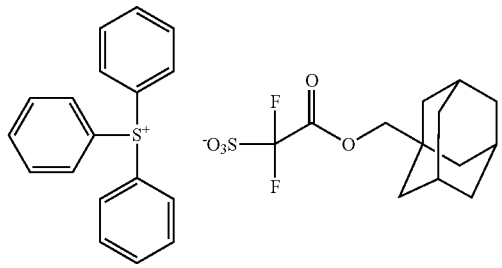

(PAG-6)
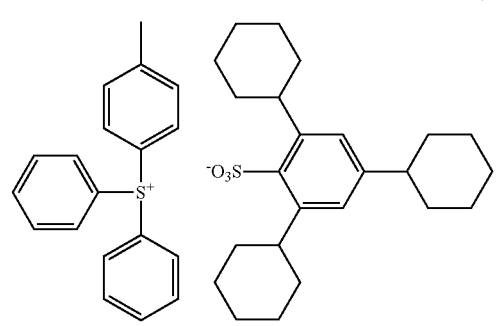

[Solvent]

As a solvent, the following were used.

<Applying Solvent>

S1: propylene glycol monomethyl ether acetate (PGMEA)
S2: propylene glycol monomethyl ether (PGME)
S3: cyclohexanone
S4: ethyl lactate (EL)
S5: 2-heptanone
S6: γ-butyrolactone
S7: propylene carbonate <Developer Rinsing Liquid>

S8: butyl acetate
S9: pentyl acetate
S10: anisole
S11: 1-hexanol
S12: decane

Examples 1A to 43A and Comparative Examples 1A and 2A [Negative-Tone Pattern/EB Exposure, Alkali Development]

(1) Preparation of Support

A 6-inch wafer (a wafer subjected to a shielding film treatment used for conventional photomask blanks), in which chromium oxide was deposited was prepared.

(2) Preparation of Resist Composition

Each component shown in Table 2 described later was dissolved in solvents shown in the same Table. This was finely filtered through a polytetrafluoroethylene filter having a pore size of 0.04 μm to obtain a resist composition having a solid content of 4% by mass.

(3) Production of Resist Film

The resist composition was applied on the 6-inch wafer by using a spin coater Mark 8 manufactured by Tokyo Electron, Ltd., the wafer was dried on a hot plate at 110° C. for 90 seconds, and a resist film having a thickness of 100 nm was obtained. That is, a resist-applied mask blanks was obtained.

(4) Production of Negative-Tone Resist Pattern

This resist film was subjected to pattern irradiation by using an electron beam lithographic apparatus (HL750 manufactured by Hitachi, Ltd., acceleration voltage: 50 keV). After the irradiation, the resist film was heated on a hot plate at 120° C. for 90 seconds and then the heated resist film was immersed in a 2.38% by mass aqueous solution of tetramethylammonium hydroxide (TMAH) for 60 seconds, the immersed resist film was rinsed with water for 30 seconds and dried.

(5) Evaluation of Resist Pattern

The obtained pattern was evaluated for sensitivity, resolution, pattern shape, LER performance, scum, dry etching resistance, and the temporal stability by the methods described below. The results are shown in Table 3.

[Sensitivity]

The cross-sectional shape of the obtained pattern was observed by using a scanning electron microscope (S-4300 manufactured by Hitachi, Ltd.). The amount of exposure (amount of electron beam irradiation) used to resolve a resist pattern of a line and space having a line width of 100 nm (1:1) was designated as sensitivity. The smaller the value is, the higher sensitivity is.

[Resolving Power]

The limit resolving power (minimum line width at which lines and spaces are separated and resolved) at the amount of exposure (amount of electron beam irradiation) exhibiting sensitivity described above was designated as resolving power (nm).

[Pattern Shape]

The cross-sectional shape of a resist pattern of a line and space (1:1) having a line width of 100 nm at the amount of exposure (amount of electron beam irradiation) exhibiting sensitivity described above, was observed by using a scanning electron microscope (S-4300 manufactured by Hitachi, Ltd.). In regard to the cross-sectional shape of the line pattern, a sample in which the ratio represented by [line width at the top part (surface part) of the line pattern/line width in the middle part of the line pattern (height position at a half of the line pattern height)] is 1.5 or more was designated as "inverse taper"; a sample in which the ratio is greater than or equal to 1.2 and less than 1.5 was designated as "slightly inverse taper"; and a sample in which the ratio is less than 1.2 was designated as "rectangular", and an evaluation was performed.

[LER Performance]

A resist pattern of a line and a space (1:1) having a line width of 100 nm was formed by irradiation at the amount of irradiation (amount of electron beam irradiation) exhibiting sensitivity described above. Then, at any arbitrary 30 points included in 50 µm along the length direction, the distance from a reference line at which an edge should exist was measured by using a scanning electron microscope (S-9220 manufactured by Hitachi, Ltd.). Then, the standard deviation of this distance was determined, and $3\sigma$ was calculated. The smaller the value is, the better the performance is.

[Dry Etching Resistance]

A resist film which was formed by conducting the entire surface irradiation at the amount of irradiation (amount of electron beam irradiation) exhibiting sensitivity described above, was subjected to dry etching for 30 seconds with $Ar/C_4F_6/O_2$ gas (gas mixture at a volume ratio of 100/4/2) by using HITACHI U-621. Thereafter, the resist residual film ratio was measured and was used as an indicator for dry etching resistance.

Very satisfactory: a residual film ratio of 95% or greater

Satisfactory: greater than or equal to 90% and less than 95%

Poor: less than 90%

[Scum Evaluation]

A resist pattern of a line and space was formed by the same method as described in section [Pattern Shape]. Thereafter, a cross-section SEM was obtained by using S4800 (manufactured by Hitachi High Technologies Corp.), and the residual of scum in the space portion was observed and evaluated as follows.

A: No scum is observed.

B: Scum is observed, but patterns are not connected to each other.

C: Scum is observed, and patterns are partially connected to each other.

[Temporal Stability]

After each composition was stored over one month at room temperature, the degree of the change of sensitivity (sensitivity measured when exposing described above) before and after storage was evaluated. This evaluation was performed based on the evaluation standard below.

(Evaluation Standard)

A (Good): In a case where the change of sensitivity is less than 0.5 $\mu C/cm^2$ B (Fair): In a case where the change of sensitivity is 0.5 $\mu C/cm^2$ or more and 1 $\mu C/cm^2$ or less C (Insufficient): In a case where the change of sensitivity is more than 1 $\mu C/cm^2$

TABLE 2

| Composition | Compound (% by mass) | Compound B1 (% by mass) | Organic Carboxylic acid (% by mass) | Basic Compound (% by mass) | Surfactant (% by mass) | Cross-Linking Agent C (% by mass) | Acid Generator D (ratio of mass) | Solvent (ratio of mass) |
|---|---|---|---|---|---|---|---|---|
| 1N | A-1 (5.80) | P4 (81.46) | D1 (1.34) | BASE-1 (0.49) | W-3 (0.06) | CL-1/CL-4 (7.19/3.66) | Non | S1/S2 (80/20) |
| 2N | A-2 (6.21) | P4 (81.05) | D1 (1.34) | BASE-1 (0.49) | W-3 (0.06) | CL-1/CL-4 (7.19/3.66) | Non | S1/S2 (80/20) |
| 3N | A-3 (6.41) | P4 (80.05) | D1 (1.34) | BASE-1 (0.49) | W-3 (0.06) | CL-1/CL-4 (7.19/3.66) | Non | S1/S2 (80/20) |
| 4N | A-4 (6.71) | P4 (80.55) | D1 (1.34) | BASE-1 (0.49) | W-3 (0.06) | CL-1/CL-4 (7.19/3.66) | Non | S1/S2 (80/20) |
| 5N | A-5 (5.51) | P4 (81.75) | D1 (1.34) | BASE-1 (0.49) | W-3 (0.06) | CL-1/CL-4 (7.19/3.66) | Non | S1/S2 (80/20) |
| 6N | A-6 (5.71) | P4 (81.55) | D1 (1.34) | BASE-1 (0.49) | W-3 (0.06) | CL-1/CL-4 (7.19/3.66) | Non | S1/S2 (80/20) |
| 7N | A-7 (5.55) | P4 (81.71) | D1 (1.34) | BASE-1 (0.49) | W-3 (0.06) | CL-1/CL-4 (7.19/3.66) | Non | S1/S2 (80/20) |
| 8N | A-8 (5.90) | P4 (81.36) | D1 (1.34) | BASE-1 (0.49) | W-3 (0.06) | CL-1/CL-4 (7.19/3.66) | Non | S1/S2 (80/20) |

TABLE 2-continued

| Composition | Compound (% by mass) | Compound B1 (% by mass) | Organic Carboxylic acid (% by mass) | Basic Compound (% by mass) | Surfactant (% by mass) | Cross-Linking Agent C (% by mass) | Acid Generator D (ratio of mass) | Solvent (ratio of mass) |
|---|---|---|---|---|---|---|---|---|
| 9N | A-9 (6.46) | P4 (80.8) | D1 (1.34) | BASE-1 (0.49) | W-3 (0.06) | CL-1/CL-4 (7.19/3.66) | Non | S1/S5 (80/20) |
| 10N | A-10 (5.90) | P4 (81.36) | D1 (1.34) | BASE-1 (0.49) | W-3 (0.06) | CL-1/CL-4 (7.19/3.66) | Non | S1/S2 (80/20) |
| 11N | A-11 (3.83) | P4 (83.43) | D1 (1.34) | BASE-1 (0.49) | W-3 (0.06) | CL-1/CL-4 (7.19/3.66) | Non | S1/S2 (80/20) |
| 12N | A-12 (5.32) | P4 (81.94) | D1 (1.34) | BASE-1 (0.49) | W-3 (0.06) | CL-1/CL-4 (7.19/3.66) | Non | S1/S2 (80/20) |
| 13N | A-13 (5.07) | P4 (82.19) | D1 (1.34) | BASE-1 (0.49) | W-3 (0.06) | CL-1/CL-4 (7.19/3.66) | Non | S1/S7 (80/20) |
| 14N | A-14 (4.65) | P4 (82.61) | D1 (1.34) | BASE-1 (0.49) | W-3 (0.06) | CL-1/CL-4 (7.19/3.66) | Non | S1/S2 (80/20) |
| 15N | A-15 (4.71) | P4 (82.55) | D1 (1.34) | BASE-1 (0.49) | W-3 (0.06) | CL-1/CL-4 (7.19/3.66) | Non | S1/S2 (80/20) |
| 16N | A-16 (4.98) | P4 (82.28) | D1 (1.34) | BASE-1 (0.49) | W-3 (0.06) | CL-1/CL-4 (7.19/3.66) | Non | S1/S2 (80/20) |
| 17N | A-17 (5.48) | P4 (81.78) | D1 (1.34) | BASE-1 (0.49) | W-3 (0.06) | CL-1/CL-4 (7.19/3.66) | Non | S1/S2 (80/20) |
| 18N | A-18 (5.60) | P4 (81.66) | D1 (1.34) | BASE-1 (0.49) | W-3 (0.06) | CL-1/CL-4 (7.19/3.66) | Non | S1/S2 (80/20) |
| 19N | A-19 (6.28) | P4 (80.98) | D1 (1.34) | BASE-1 (0.49) | W-3 (0.06) | CL-1/CL-4 (7.19/3.66) | Non | S1/S2 (80/20) |
| 20N | A-20 (5.90) | P4 (81.36) | D1 (1.34) | BASE-1 (0.49) | W-3 (0.06) | CL-1/CL-4 (7.19/3.66) | Non | S1/S2 (80/20) |
| 21N | A-21 (6.15) | P4 (81.11) | D1 (1.34) | BASE-1 (0.49) | W-3 (0.06) | CL-1/CL-4 (7.19/3.66) | Non | S1/S2 (80/20) |
| 22N | A-22 (5.11) | P4 (82.15) | D1 (1.34) | BASE-1 (0.49) | W-3 (0.06) | CL-1/CL-4 (7.19/3.66) | Non | S1/S2 (80/20) |
| 23N | A-23 (4.50) | P4 (82.76) | D1 (1.34) | BASE-1 (0.49) | W-3 (0.06) | CL-1/CL-4 (7.19/3.66) | Non | S1/S2 (80/20) |
| 24N | A-24 (5.20) | P4 (82.06) | D1 (1.34) | BASE-1 (0.49) | W-3 (0.06) | CL-1/CL-4 (7.19/3.66) | Non | S1/S2 (80/20) |
| 25N | A-1 (5.80) | P1 (81.46) | D1 (1.34) | BASE-1 (0.49) | W-3 (0.06) | CL-1/CL-4 (7.19/3.66) | Non | S1/S2/S3 (55/25/20) |
| 26N | A-1 (5.80) | P2 (81.46) | D1 (1.34) | BASE-1 (0.49) | W-3 (0.06) | CL-1/CL-4 (7.19/3.66) | Non | S1/S2/S6 (55/25/20) |
| 27N | A-1 (5.80) | P3 (81.46) | D1 (1.34) | BASE-1 (0.49) | W-3 (0.06) | CL-1/CL-4 (7.19/3.66) | Non | S1/S2/S4 (55/25/20) |
| 28N | A-1 (5.80) | P6 (81.46) | D1 (1.34) | BASE-1 (0.49) | W-3 (0.06) | CL-1/CL-4 (7.19/3.66) | Non | S1/S2 (80/20) |
| 29N | A-1 (5.80) | P5 (81.48) | D1 (1.34) | BASE-5 (0.53) | Non | CL-3 (7.19/3.66) | Non | S1/S2 (80/20) |
| 30N | A-1 (5.80) | P4 (81.43) | D1 (1.34) | BASE-1/BASE-6 (0.29/0.29) | Non | CL-1/CL-4 (7.19/3.66) | Non | S1/S2 (80/20) |
| 31N | A-1 (5.80) | P4 (81.63) | D1 (1.34) | BASE-4 (0.38) | Non | CL-3 (10.85) | Non | S1/S2 (80/20) |
| 32N | A-1 (5.80) | P4 (79.67) | D2 (1.22) | BASE-1 (0.49) | W-2 (0.06) | CL-1/CL-5 (7.19/5.57) | Non | S1/S2 (80/20) |
| 33N | A-1 (5.80) | P3 (81.99) | D2 (1.22) | BASE-3 (0.56) | Non | CL-2 (10.43) | Non | S1/S2 (80/20) |
| 34N | A-1 (5.80) | P1/P3 (79.9) | D3 (0.87) | BASE-2 (0.67) | Non | CL-1/CL-5 (7.19/5.57) | Non | S1/S2 (80/20) |
| 35N | A-1 (5.80) | P4 (79.11) | D3 (0.87) | BASE-6 (1.46) | Non | CL-1/CL-5 (7.19/5.57) | Non | S1/S2 (80/20) |
| 36N | A-1 (5.80) | P4 (94.42) | D1 (1.34) | BASE-4 (0.38) | W-1 (0.06) | Non | Non | S1/S2 (80/20) |
| 37N | A-1 (5.80) | P4 (85.25) | D1 (1.34) | BASE-4 (0.38) | W-4 (0.06) | CL-6 (7.17) | Non | S1/S2 (90/10) |
| 38N | A-1 (5.80) | P4 (81.50) | D1 (1.34) | BASE-4 (0.38) | W-4 (0.06) | CL-6 (7.17) | PAG-3/PAG-1 (2.63/1.12) | S1/S2 (90/10) |
| 39N | A-1 (5.80) | P4 (80.81) | D1 (1.34) | BASE-4 (0.38) | Non | CL-6 (7.17) | PAG-2 (4.50) | S1/S2 (90/10) |
| 40N | A-1 (5.80) | P4 (86.69) | D1 (1.34) | BASE-4 (0.38) | W-4 (0.06) | Non | PAG-4 (5.73) | S1/S2 (90/10) |
| 41N | A-1 (5.80) | P4 (87.98) | D1 (1.34) | BASE-4 (0.38) | Non | Non | PAG-5 (4.50) | S1/S2 (90/10) |
| 42N | A-1 (5.80) | P4 (80.98) | Non | BASE-4 (0.38) | W-4 (0.06) | CL-6 (7.17) | PAG-6 (5.61) | S1/S2 (90/10) |
| 43N | A-25 (5.89) | P4 (81.37) | D1 (1.34) | BASE-1 (0.49) | W-3 (0.06) | CL-1/CL-4 (7.19/3.66) | Non | S1/S2 (80/20) |
| Comparative composition 1N | R-1 (3.26) | P2 (84.00) | D1 (1.34) | BASE-1 (0.49) | W-3 (0.06) | CL-3 (10.85) | Non | S1 (100) |
| Comparative composition 2N | R-2 (4.17) | P2 (83.09) | D1 (1.34) | BASE-1 (0.49) | W-3 (0.06) | CL-3 (10.85) | Non | S1 (100) |

TABLE 3

(Negative-Tone pattern/EB Exposure/Alkali Development)

| Example | Composition | Sensitivity ($\mu C/cm^2$) | Resolving Power (nm) | Pattern shape | LER (nm) | Scum | Dry Etching Resistance | Temporal Stability |
|---|---|---|---|---|---|---|---|---|
| 1E | 1N | 10.1 | 50 | rectangular | 3.9 | A | Very satisfactory | A |
| 2E | 2N | 10.5 | 50 | rectangular | 4.1 | A | Very satisfactory | A |
| 3E | 3N | 10.7 | 50 | rectangular | 4.2 | A | Very satisfactory | A |
| 4E | 4N | 9.8 | 37.5 | rectangular | 3.7 | A | Very satisfactory | A |
| 5E | 5N | 9.6 | 37.5 | rectangular | 3.6 | A | Very satisfactory | A |
| 6E | 6N | 10.3 | 37.5 | rectangular | 4.0 | A | Very satisfactory | A |
| 7E | 7N | 10.3 | 50 | rectangular | 4.0 | A | Very satisfactory | A |
| 8E | 8N | 10.5 | 62.5 | rectangular | 4.1 | A | Very satisfactory | A |
| 9E | 9N | 10.3 | 50 | rectangular | 4.1 | A | Very satisfactory | A |
| 10E | 10N | 10.6 | 50 | rectangular | 4.1 | A | Very satisfactory | A |
| 11E | 11N | 10.7 | 37.5 | rectangular | 4.5 | A | Very satisfactory | A |
| 12E | 12N | 9.8 | 50 | rectangular | 4.0 | A | Very satisfactory | A |
| 13E | 13N | 9.9 | 50 | rectangular | 3.8 | A | Very satisfactory | A |
| 14E | 14N | 10.7 | 50 | rectangular | 4.5 | A | Very satisfactory | A |
| 15E | 15N | 10.4 | 50 | rectangular | 4.3 | A | Very satisfactory | A |
| 16E | 16N | 10.4 | 37.5 | rectangular | 4.2 | A | Very satisfactory | A |
| 17E | 17N | 10.5 | 50 | rectangular | 4.1 | A | Very satisfactory | A |
| 18E | 18N | 10.5 | 50 | rectangular | 4.0 | A | Very satisfactory | A |
| 19E | 19N | 10.4 | 50 | rectangular | 4.0 | A | Very satisfactory | A |
| 20E | 20N | 10.2 | 50 | rectangular | 4.0 | A | Very satisfactory | A |
| 21E | 21N | 9.6 | 37.5 | rectangular | 3.6 | A | Very satisfactory | A |
| 22E | 22N | 10.4 | 37.5 | rectangular | 4.0 | A | Very satisfactory | A |
| 23E | 23N | 10.4 | 50 | rectangular | 4.2 | A | Very satisfactory | A |
| 24E | 24N | 10.6 | 50 | rectangular | 4.3 | A | Very satisfactory | A |
| 25E | 25N | 10.3 | 50 | rectangular | 4.1 | A | Very satisfactory | A |
| 26E | 26N | 10.5 | 50 | rectangular | 4.3 | A | Satisfactory | A |
| 27E | 27N | 10.5 | 50 | rectangular | 4.3 | A | Satisfactory | A |
| 28E | 28N | 10.7 | 50 | rectangular | 4.5 | A | Very satisfactory | A |
| 29E | 29N | 10.3 | 50 | rectangular | 4.2 | A | Very satisfactory | A |
| 30E | 30N | 10.2 | 50 | rectangular | 4.0 | A | Very satisfactory | A |
| 31E | 31N | 10.5 | 50 | rectangular | 4.4 | A | Very satisfactory | A |
| 32E | 32N | 10.2 | 50 | rectangular | 4.1 | A | Very satisfactory | A |
| 33E | 33N | 10.3 | 50 | rectangular | 4.4 | A | Satisfactory | A |
| 34E | 34N | 10.2 | 50 | rectangular | 4.3 | A | Satisfactory | A |
| 35E | 35N | 10.2 | 50 | rectangular | 4.4 | A | Very satisfactory | A |
| 36E | 36N | 10.5 | 50 | rectangular | 4.5 | A | Very satisfactory | A |
| 37E | 37N | 10.1 | 50 | rectangular | 4.1 | A | Very satisfactory | A |
| 38E | 38N | 10.0 | 50 | rectangular | 4.5 | A | Very satisfactory | A |
| 39E | 39N | 10.4 | 50 | rectangular | 4.7 | A | Very satisfactory | A |
| 40E | 40N | 10.0 | 50 | rectangular | 4.6 | A | Very satisfactory | A |
| 41E | 41N | 10.3 | 50 | rectangular | 4.7 | A | Very satisfactory | A |
| 42E | 42N | 10.4 | 50 | rectangular | 4.7 | B | Very satisfactory | A |
| 43E | 43N | 10.2 | 50 | rectangular | 4.0 | B | Very satisfactory | A |
| Comparative Example 1E | Comparative Composition 1N | 13.0 | 75 | inverse taper | 6.5 | C | Poor | B |
| Comparative Example 2E | Comparative Composition 2N | 12.8 | 75 | inverse taper | 6.4 | B | Poor | C |

From the results shown in Table 3, it is understood that the negative-tone pattern (EB exposure, alkali development) which is formed using the composition according to the present invention is excellent in sensitivity, resolving power, pattern shape, LER performance, scum, dry etching resistance and the temporal stability.

Examples 1B to 6B and Comparative Examples 1B
[Negative-Tone Pattern/EUV Exposure, Alkali Development]

(Preparation of Resist Composition)

The resist compositions shown in Table 2 described above were filtered through a polytetrafluoroethylene filter having a pore size of 0.04 and the resist compositions having a solid content of 2% by mass were prepared.

(Resist Evaluation)

The prepared resist composition was uniformly applied on a silicon substrate that had been subjected to a hexamethyldisilazane treatment, by using a spin coater, the system was heated and dried on a hot plate at 100° C. for 60 seconds, and thus a resist film having a thickness of 0.05 µm was formed.

The obtained resist film was evaluated for sensitivity, resolving power, pattern shape, LER performance, scum, dry etching resistance and the temporal stability by the methods described below.

[Sensitivity]

After the obtained resist film was exposed through a reflection type mask of a line and space pattern (1:1) having a line width of 100 nm, by using EUV light (wavelength: 13 nm) while changing the amount of exposure by 0.1 mJ/cm² in the range of 0 to 20.0 mJ/cm², and the resist film was baked for 90 seconds at 110° C. Thereafter, the resist film was developed by using a 2.38% by mass aqueous solution of tetramethylammonium hydroxide (TMAH).

The amount of exposure which resolved a pattern with a line width of 100 nm was designated as sensitivity. This smaller this value is, the higher sensitivity is.

[Resolving Power]

The limit resolving power (minimum line width at which lines and spaces are separated and resolved) at the amount of exposure exhibiting sensitivity described above was designated as the resolving power (nm).

[Pattern Shape]

The cross-sectional shape of a resist pattern of a line and space (1:1) having a line width of 100 nm at the amount of exposure exhibiting sensitivity described above, was observed by using a scanning electron microscope (S-4300 manufactured by Hitachi, Ltd.). In regard to the cross-sectional shape of the line pattern, a sample in which the ratio represented by [line width at the bottom part of the line pattern/line width in the middle part of the line pattern (height position at a half of the line pattern height)] is 1.5 or more was designated as "inverse taper"; a sample in which the ratio is greater than or equal to 1.2 and less than 1.5 was designated as "slightly inverse taper"; and a sample in which the ratio is less than 1.2 was designated as "rectangular", and, and an evaluation was performed.

[LER Performance]

A resist pattern of a line and pattern (1:1) having a line width of 100 nm was formed at at the amount of exposure exhibiting sensitivity described above. Then, at any arbitrary 3σ points in 50 μm along the length direction, the distance from a reference line at which an edge should exist was measured by using a scanning electron microscope (S-9220 manufactured by Hitachi, Ltd.). Then, the standard deviation of this distance was determined, and 3σ was calculated. A smaller value indicates satisfactory performance.

[Scum Evaluation]

A resist pattern of a line and space was formed by the same method as described in section [Pattern Shape]. Thereafter, a cross-section SEM was obtained by using S4800 (manufactured by Hitachi High Technologies Corp.), and the residual of scum in the space portion was observed and evaluated as follows.

A: No scum is observed.

B: Scum is observed, but patterns are not connected to each other.

C: Scum is observed, and patterns are partially connected to each other.

[Dry Etching Resistance]

A resist film which was formed by conducting the entire surface irradiation at the amount of irradiation (amount of EUV irradiation) exhibiting sensitivity described above, was subjected to dry etching for 30 seconds with $Ar/C_4F_6/O_2$ gas (gas mixture at a volume ratio of 100/4/2) by using HITACHI U-621. Thereafter, the resist residual film ratio was measured and was used as an indicator for dry etching resistance.

Very satisfactory: a residual film ratio of 95% or greater

Satisfactory: a residual film ratio of greater than or equal to 90% and less than 95%

Poor: a residual film ratio of less than 90%

[Temporal Stability]

After each composition was stored over one month at room temperature, the degree of the change of sensitivity (sensitivity measured when exposing described above) before and after storage was evaluated. This evaluation was conducted based on the Evaluation Standard.

(Evaluation Standard)

A (Good): In a case where the change of sensitivity is less than 1 $mJ/cm^2$

B (Fair): In a case where the change of sensitivity is 1 $mJ/cm^2$ or more and 3 $mJ/cm^2$ or less C (Insufficient): In a case where the change of sensitivity is more than 3 $mJ/cm^2$ The evaluation results described above are shown in Table 4 described above.

TABLE 4

| | (Negative-Tone pattern/EUV Exposure, Alkali Development) | | | | | | | |
|---|---|---|---|---|---|---|---|---|
| Example | Composition | Sensitivity ($mJ/cm^2$) | Resolving Power (nm) | Pattern shape | LER (nm) | Scum | Dry Etching Resistance | Temporal Stability |
| 1B | 1N | 12.5 | 50 | rectangular | 4.0 | A | Very satisfactory | A |
| 2B | 4N | 11.9 | 37.5 | rectangular | 3.8 | A | Very satisfactory | A |
| 3B | 5N | 12.0 | 37.5 | rectangular | 3.9 | A | Very satisfactory | A |
| 4B | 18N | 12.8 | 50 | rectangular | 4.0 | A | Very satisfactory | A |
| 5B | 25N | 13.0 | 50 | rectangular | 4.1 | A | Very satisfactory | A |
| 6B | 27N | 13.5 | 50 | rectangular | 4.0 | A | Very satisfactory | A |
| Comparative Example 1B | Comparative Composition 1N | 15.8 | 75 | inverse taper | 6.5 | C | Poor | C |

From the results shown in Table 4, it is understood that a negative-tone pattern (EUV exposure, alkali development) formed by using the composition according to the present invention is excellent in sensitivity, resolving power, pattern shape, LER performance, scum, dry etching resistance, and the temporal stability.

Examples 1C to 6C and Comparative Examples 1C and 2C [Negative-Tone Pattern/EB Exposure, Organic Solvent Development]

(1) Preparation of Resist Composition and Production of Resist Film

The compositions having components shown in Table 5 described below was finely filtered through a membrane filter having a pore size of 0.1 μm to obtain a resist composition.

The resist composition was applied on the 6-inch Si-wafer in which a hexamethyldisilazane (HMDS) treatment was performed in advance by using a spin coater Mark 8 manufactured by Tokyo Electron, Ltd., the wafer was dried on a hot plate at 100° C. for 60 seconds, and a resist film having a thickness of 50 nm was obtained.

(2) EB Exposure and Development

A wafer applied the resist film obtained in (1) described above was subjected to pattern irradiation by using an electron beam lithographic apparatus (HL750 manufactured by Hitachi, Ltd., acceleration voltage: 50 keV). In this case, drawing was performed so that a line and space (1:1) was formed. After drawing by using an electron beam, the wafer was heated on a hot plate at 110° C. for 60 seconds, then an organic-based developer described in Table 5 was paddled to develop for 30 seconds and was rinsed with a rinsing liquid described in the same Table, next the wafer was rotated at a frequency of rotation of 4,000 rpm for 30 seconds, and subsequently, a resist pattern of a line and space pattern (1:1) having a line width of 50 nm by heating at 90° C. for 60 seconds was obtained.

(3) Evaluation of Resist Pattern

[Sensitivity]

The cross-sectional shape of the obtained pattern was observed by using a scanning electron microscope (S-4300 manufactured by Hitachi, Ltd.). The amount of exposure (amount of electron beam irradiation) used to resolve a resist pattern of a line and space (1:1) having a line width of 100 nm was designated as sensitivity. The smaller this value is, the higher sensitivity is.

[Resolving Power]

The limit resolving power (minimum line width at which a line and space are separated and resolved) at the amount of exposure (amount of electron beam irradiation) exhibiting sensitivity described above was designated as resolving power (nm).

[Pattern Shape]

The cross-sectional shape of a resist pattern of a line and space (1:1) having a line width of 100 nm at the amount of exposure (amount of electron beam irradiation) exhibiting sensitivity described above, was observed by using a scanning electron microscope (S-4300 manufactured by Hitachi, Ltd.). In regard to the cross-sectional shape of the line pattern, a sample in which the ratio represented by [line width at the top (surface part) of the line pattern/line width in the middle part of the line pattern (height position at a half of the line pattern height)] is 1.5 or more was designated as "inverse taper"; a sample in which the ratio is greater than or equal to 1.2 and less than 1.5 was designated as "slightly inverse taper"; and a sample in which the ratio is less than 1.2 was designated as "rectangular", and an evaluation was performed.

[LER Performance]

A resist pattern of a line and space (1:1) having a line width of 100 nm was formed with the amount of irradiation (amount of electron beam irradiation) exhibiting sensitivity described above. Then, at any arbitrary 30 points included in 50 μm along the length direction, the distance from a reference line at which an edge should exist was measured by using a scanning electron microscope (S-9220 manufactured by Hitachi, Ltd.). Then, the standard deviation of this distance was determined, and 3σ was calculated. A smaller value indicates satisfactory performance.

[Temporal Stability]

After each composition was stored over one month at room temperature, the degree of the change of sensitivity (sensitivity measured when exposing described above) before and after storage was evaluated. This evaluation was performed based on the evaluation standard below.

(Evaluation Standard)

A (Good): In a case where the change of sensitivity is less than 0.5 μC/cm$^2$

B (Fair): In a case where the change of sensitivity is 0.5 μC/cm$^2$ or more and 1 μC/cm$^2$ or less C (Insufficient): In a case where the change of sensitivity is more than 1 μC/cm$^2$ The evaluation results described above are shown in Table 6.

TABLE 5

| Composition | Compound A (% by mass) | Compound B2 (% by mass) | Basic Compound (% by mass) | Surfactant (% by mass) | Developer | Rinsing Liquid | Acid generator D (ratio of mass) | Solvent (ratio of mass) |
|---|---|---|---|---|---|---|---|---|
| 101N | A-7 (5.55) | P7 (93.65) | BASE-1 (0.49) | W-1 (0.06) | S8 | S11 | Non | S1/S2 (80/20) |
| 102N | A-1 (5.80) | P8 (93.90) | BASE-1 (0.49) | W-1 (0.06) | S8 | S11 | Non | S1/S2 (80/20) |
| 103N | A-13 (5.07) | P9 (89.62) | BASE-2 (0.67) | W-2 (0.06) | S9 | S12 | Non | S1/S2 (80/20) |
| 104N | A-8 (5.90) | P10 (88.47) | BASE-2 (0.67) | W-2 (0.06) | S10 | S11 | PAG-4 (5.73) | S1/S2 (80/20) |
| 105N | A-15 (4.71) | P8 (97.74) | BASE-1 (0.49) | W-3 (0.06) | S8 | S11 | Non | S1/S2 (80/20) |
| 106N | A-22 (5.11) | P9 (94.16) | BASE-2 (0.67) | W-1 (0.06) | S9 | S10 | PAG-3/PAG-1 (2.63/1.12) | S1/S2 (80/20) |
| Comparative composition 101N | R-1 (5.80) | P9 (93.65) | BASE-1 (0.49) | W-1 (0.06) | S8 | S11 | Non | S1/S2 (80/20) |
| Comparative composition 102N | R-2 (5.8) | P9 (87.74) | BASE-2 (0.67) | W-1 (0.06) | S8 | S11 | PAG-4 (5.73) | S1/S2 (80/20) |

TABLE 6

(Negative-Tone pattern/EB Exposure/Organic Solvent Development)

| Example | Composition | Sensitivity (μC/cm$^2$) | Resolving Power (nm) | Pattern shape | LER (nm) | Temporal Stability |
|---|---|---|---|---|---|---|
| 1C | 101N | 13.0 | 50 | rectangular | 4.3 | A |
| 2C | 102N | 12.0 | 37.5 | rectangular | 3.7 | A |
| 3C | 103N | 12.6 | 37.5 | rectangular | 3.9 | A |
| 4C | 104N | 13.2 | 50 | rectangular | 4.4 | A |
| 5C | 105N | 12.8 | 37.5 | rectangular | 3.8 | A |
| 6C | 106N | 13.2 | 37.5 | rectangular | 4.1 | A |
| Comparative Example 1C | Comparative Composition 101N | 20.2 | 62.5 | inverse taper | 6.0 | B |
| Comparative Example 2C | Comparative Composition 102N | 17.4 | 62.5 | inverse taper | 5.5 | C |

From the results shown in Table 6, it is understood that a negative-tone pattern (EB exposure, Organic solvent development) formed using the composition according to the present invention is excellent in sensitivity, resolving power, pattern shape, LER performance and temporal stability.

Examples 1D to 6D and Comparative Examples 1D and 2D [Negative-Tone Pattern/EUV Exposure, Organic Solvent Development]

(1) Preparation of Resist Composition and Production of Resist Film

The compositions having components shown in Table 5 described above was finely filtered through a membrane filter having a pore size of 0.05 μm to obtain a resist composition.

The resist composition was applied on the 6-inch Si wafer in which a hexamethyldisilazane (HMDS) treatment was performed in advance by using a spin coater Mark 8 manufactured by Tokyo Electron, Ltd., the wafer was dried on a hot plate at 100° C. for 60 seconds, and a resist film having a thickness of 50 nm was obtained.

(2) EUV Exposure and Development

A wafer applied the resist film obtained in (1) described above was subjected to patternwise exposure by using an EUV exposure device (Micro Exposure Tool manufactured by Exitech, NAO. 3, Quadrupole, outer sigma 0.68, inner sigma 0.36) with a exposure mask (line/space=1/1). After irradiation, the wafer was heated on a hot plate at 110° C. for 60 seconds, then an organic-based developer shown in the following Table was paddled to develop for 30 seconds and was rinsed with a rinsing liquid described in the following Table, next the wafer was rotated at a frequency of rotation of 4,000 rpm for 30 seconds, and subsequently, a resist pattern of a line and space pattern (1:1) having a line width of 50 nm by baking at 90° C. for 60 seconds was obtained.

(3) Evaluation of Resist Pattern

Sensitivity, resolving power and LWR of the obtained resist pattern were evaluated by the following method by using a scanning electron microscope (S-9380II manufactured by Hitachi, Ltd.).

[Sensitivity]

The obtained resist film was exposed through a reflection type mask of a line and space pattern (1:1), by using EUV light (wavelength: 13 nm) while changing the amount of exposure by 0.1 mJ/cm² in the range of 0 to 20.0 mJ/cm², and then the resist film was baked for 90 seconds at 110° C. Thereafter, the resist film was developed by using a 2.38% by mass aqueous solution of tetramethylammonium hydroxide (TMAH).

The amount of exposure to resolve a pattern having a line width of 100 nm was designated as sensitivity. The smaller the value is, the higher sensitivity is.

[Resolving Power]

The limit resolving power (minimum line width at which a line and space are separated and resolved) at the amount of exposure exhibiting sensitivity described above was designated as resolving power (nm).

[Pattern Shape]

The cross-sectional shape of a resist pattern of a line and space (1:1) having a line width of 100 nm at the amount of exposure exhibiting sensitivity described above, was observed by using a scanning electron microscope (S-4300 manufactured by Hitachi, Ltd.). In regard to the cross-sectional shape of the line pattern, a sample in which the ratio represented by [line width at the bottom part of the line pattern/line width in the middle part of the line pattern (height position at a half of the line pattern height)] is 1.5 or more was designated as "inverse taper"; a sample in which the ratio is greater than or equal to 1.2 and less than 1.5 was designated as "slightly inverse taper"; and a sample in which the ratio is less than 1.2 was designated as "rectangular", and an evaluation was performed.

[LER Performance]

A resist pattern of a line and space (1:1) having a line width of 100 nm was formed with the amount of exposure exhibiting sensitivity described above. Then, at any arbitrary 30 points in 50 μm along the length direction, the distance from a reference line at which an edge should exist was measured by using a scanning electron microscope (S-9220 manufactured by Hitachi, Ltd.). Then, the standard deviation of this distance was determined, and 3σ was calculated. A smaller value indicates satisfactory performance.

[Temporal Stability]

After each composition was stored over one month at room temperature, the degree of the change of sensitivity (sensitivity measured when exposing described above) before and after storage was evaluated. This evaluation was performed based on the evaluation standard below.

(Evaluation Standard)

A (Good): In a case where the change of sensitivity is less than 1 mJ/cm²

B (Fair): In a case where the change of sensitivity is 1 mJ/cm² or more and 3 mJ/cm² or less C (Insufficient): In a case where the change of sensitivity is more than 3 mJ/cm².

The results are shown in the following Table 7.

TABLE 7

| (Negative-Tone pattern/EUV Exposure/Organic Solvent Development) | | | | | | |
|---|---|---|---|---|---|---|
| Example | Composition | Sensitivity (mJ/cm²) | Resolving Power (nm) | Pattern shape | LER (nm) | Temporal Stability |
| 1D | 101N | 4.4 | 27.0 | rectangular | 5.8 | A |
| 2D | 102N | 3.9 | 24.5 | rectangular | 5.4 | A |
| 3D | 103N | 4.0 | 25.0 | rectangular | 5.5 | A |
| 4D | 104N | 4.5 | 27.5 | rectangular | 6.0 | A |
| 5D | 105N | 4.1 | 26.0 | rectangular | 5.6 | A |
| 6D | 106N | 4.5 | 26.5 | rectangular | 5.7 | A |
| Comparative Example 1D | Comparative Composition 101N | 6.5 | 35.0 | inverse taper | 6.4 | B |
| Comparative Example 2D | Comparative Composition 102N | 6.0 | 32.0 | inverse taper | 6.1 | C |

From the results shown in Table 7, it is understood that a negative-tone pattern (EUV exposure, Organic solvent development) formed using the composition according to the present invention is excellent in sensitivity, resolving power, pattern shape, LER performance and temporal stability.

Examples 1E to 5E and Comparative Examples 1E to 3E [Positive-Tone Pattern/EB Exposure, Alkali Development]

(1) Preparation of Support

A 6-inch wafer (a wafer subjected to a shielding film treatment used for conventional photomask blanks), in which chromium oxide was deposited was prepared.

(2) Preparation of Resist Application Liquid

Each component shown in Table 8 described later was dissolved in solvents shown in the same Table. This was finely filtered through a polytetrafluoroethylene filter having a pore size of 0.04 μm to obtain a resist composition having a solid concentration of 2% by mass.

(3) Production of Resist Film

The resist composition was applied on the 6-inch wafer by using a spin coater Mark 8 manufactured by Tokyo Electron, Ltd., the wafer was dried on a hot plate at 110° C. for 90 seconds and a resist film having a thickness of 40 nm was obtained. That is, resist-applied mask blanks were obtained.

(4) Production of Positive-Tone Resist Pattern

This resist film was subjected to patternwise irradiation by using an electron beam lithographic apparatus (HL750 manufactured by Hitachi, Ltd., acceleration voltage: 50 keV). After the irradiation the resist film was heated on a hot plate at 120° C. for 90 seconds and the heated resist film was immersed in a 2.38% by mass aqueous solution of tetramethylammonium hydroxide (TMAH) for 60 seconds, the immersed resist film was rinsed with water for 30 seconds and dried.

(5) Evaluation of Resist Pattern

The obtained pattern was evaluated for sensitivity, resolving power, pattern shape, line edge roughness (LER), by the methods described below.

[Sensitivity]

The cross-sectional shape of the obtained pattern was observed by using a scanning electron microscope (S-4300 manufactured by Hitachi, Ltd.). The amount of exposure (amount of electron beam irradiation) used to resolve a resist pattern of a line and space (1:1) having a line width of 100 nm was designated as sensitivity. The smaller the value is, the higher sensitivity is.

[Evaluation of Resolving Power]

The limit resolving power (minimum line width at which lines and spaces are separated and resolved) at the amount of exposure (amount of electron beam irradiation) exhibiting sensitivity described above was designated as the resolving power (nm).

[Pattern Shape]

The cross-sectional shape of a line and space pattern (1:1) having a line width of 100 nm at the amount of exposure (amount of electron beam irradiation) exhibiting sensitivity described above, was observed by using a scanning electron microscope (S-4300 manufactured by Hitachi, Ltd.). In regard to the cross-sectional shape of the line pattern, a sample in which the ratio represented by [line width at the bottom part of the line pattern/line width in the middle part of the line pattern (height position at a half of the line pattern height)] is 1.5 or more was designated as "inverse taper"; a sample in which the ratio is greater than or equal to 1.2 and less than 1.5 was designated as "slightly inverse taper"; and a sample in which the ratio is less than 1.2 was designated as "rectangular", and an evaluation was performed.

[Line Edge Roughness (LER)]

A resist pattern of a line and a space (1:1) having a line width of 100 nm was formed at the amount of irradiation exhibiting sensitivity described above (amount of electron beam irradiation). At any arbitrary 30 points included in 50 μm along the length direction, the distance from a reference line at which an edge should exist was measured by using a scanning electron microscope (S-9220 manufactured by Hitachi, Ltd.). Then, the standard deviation of this distance was determined, and 3σ was calculated. A smaller value indicates satisfactory performance.

The results of the above evaluations are shown in Table 9.

TABLE 8

| Composition | Compound A (% by mass) | Compound B2 (% by mass) | Basic Compound (% by mass) | Surfactant (% by mass) | Acid generator D (ratio of mass) | Solvent (ratio of mass) |
| --- | --- | --- | --- | --- | --- | --- |
| 201N | A-17 (5.07) | P7 (89.89) | BASE-1 (0.49) | W-1 (0.05) | PAG-2 (4.50) | S1/S2 (80/20) |
| 202N | A-26 (5.46) | P8 (94.00) | BASE-1 (0.49) | W-1 (0.05) | Non | S1/S2 (80/20) |
| 203N | A-27 (5.39) | P9 (88.47) | BASE-1 (0.49) | W-2 (0.05) | PAG-6 (5.60) | S1/S2/S3 (55/25/20) |
| 204N | A-28 (4.49) | P10 (89.17) | BASE-3 (0.56) | W-2 (0.05) | PAG-4 (5.73) | S1/S2 (80/20) |
| 205N | A-29 (3.92) | P8 (90.54) | BASE-2 (0.67) | W-3 (0.05) | PAG-5 (4.82) | S1/S2/S4 (55/25/20) |
| Comparative composition 201N | R-1 (3.26) | P9 (91.7) | BASE-1 (0.49) | W-1 (0.05) | PAG-2 (4.50) | S1/S2 (80/20) |
| Comparative composition 202N | R-2 (4.17) | P9 (90.79) | BASE-1 (0.49) | W-1 (0.05) | PAG-2 (4.50) | S1/S2 (80/20) |
| Comparative composition 203N | Non | P9 (94.96) | BASE-1 (0.49) | W-1 (0.05) | PAG-2 (4.50) | S1/S2 (80/20) |

TABLE 9

(Positive-Tone pattern/EB Exposure/Alkali Development)

| Example | Composition | Sensitivity (mJ/cm$^2$) | Resolving Power (nm) | Pattern shape | LER (nm) |
| --- | --- | --- | --- | --- | --- |
| 1E | 201N | 18.5 | 37.5 | rectangular | 4.6 |
| 2E | 202N | 18.2 | 25.0 | rectangular | 4.2 |
| 3E | 203N | 18.4 | 25.0 | rectangular | 4.3 |
| 4E | 204N | 18.6 | 37.5 | rectangular | 4.6 |
| 5E | 205N | 18.5 | 37.5 | rectangular | 4.5 |

TABLE 9-continued (Positive-Tone pattern/EB Exposure/Alkali Development)

| Example | Composition | Sensitivity (mJ/cm$^2$) | Resolving Power (nm) | Pattern shape | LER (nm) |
|---|---|---|---|---|---|
| Comparative Example 1E | Comparative Composition 201N | 23.2 | 62.5 | slightly inverse taper | 6.4 |
| Comparative Example 2E | Comparative Composition 202N | 22.8 | 62.5 | slightly inverse taper | 6.0 |
| Comparative Example 3E | Comparative Composition 203N | 23.0 | 62.5 | inverse taper | 6.2 |

From the results shown in Table 9, it is understood that a positive-tone pattern (EB exposure, Alkali development) formed using the composition according to the present invention is excellent in sensitivity, resolving power, pattern shape and LER performance.

Examples 1F to 5F and Comparative Examples 1F to 3F [Positive-Tone Pattern/EUV Exposure, Alkali Development]

(Preparation of Resist Solution)

The composition shown in Table 8 described above was filtered through a polytetrafluoroethylene filter having a pore size of 0.04 μm to prepare a resist composition having a solid concentration of 2% by mass.

(Resist Evaluation)

The prepared resist composition was uniformly applied on a silicon substrate that had been subjected to a hexamethyldisilazane treatment, by using a spin coater, the applied resist composition was heated and dried on a hot plate at 100° C. for 60 seconds, and thus a resist film having a thickness of 0.05 μm was formed.

The obtained resist film was evaluated for sensitivity, resolving power, pattern shape, line edge roughness (LER) by the methods described below.

[Sensitivity]

The obtained resist film was exposed through a reflection type mask of a line and space pattern (1:1), by using EUV light (wavelength: 13 nm) while changing the amount of exposure by 0.1 mJ/cm$^2$ in the range of 0 to 30.0 mJ/cm$^2$, and then the resist film was baked for 90 seconds at 110° C. Thereafter, the resist film was developed by using a 2.38% by mass aqueous solution of tetramethylammonium hydroxide (TMAH).

The amount of exposure which resolved a pattern with a line width of 100 nm was designated as sensitivity. This smaller this value is, the higher sensitivity is.

[Resolving Power]

The limit resolving power (minimum line width at which lines and spaces are separated and resolved) at the amount of exposure exhibiting sensitivity described above was designated as LS resolving power (nm).

[Pattern Shape]

The cross-sectional shape of a line and space pattern (1:1) having a line width of 100 nm at the amount of exposure exhibiting sensitivity described above, was observed by using a scanning electron microscope (S-4300 manufactured by Hitachi, Ltd.). In regard to the cross-sectional shape of the line pattern, a sample in which the ratio represented by [line width at the bottom part of the line pattern/line width in the middle part of the line pattern (height position at a half of the line pattern height)] is 1.5 or more was designated as "inverse taper"; a sample in which the ratio is greater than or equal to 1.2 and less than 1.5 was designated as "slightly inverse taper"; and a sample in which the ratio is less than 1.2 was designated as "rectangular", and an evaluation was performed.

[Line Edge Roughness (LER)]

A line and space pattern (1:1) having a line width of 100 nm was formed at the amount of exposure exhibiting sensitivity described above. Then, at any arbitrary 30 points in 50 μm along the length direction, the distance from a reference line at which an edge should exist was measured by using a scanning electron microscope (S-9220 manufactured by Hitachi, Ltd.). Then, the standard deviation of this distance was determined, and 3σ was calculated. A smaller value indicates satisfactory performance.

The results of the above evaluations shows in the following Table 10.

TABLE 10

(Positive-Tone pattern/EUV Exposure/Alkali Development)

| Example | Composition | Sensitivity (mJ/cm$^2$) | Resolving Power (nm) | Pattern shape | LER (nm) |
|---|---|---|---|---|---|
| 1F | 201N | 19.0 | 25.0 | rectangular | 4.9 |
| 2F | 202N | 18.6 | 20.0 | rectangular | 4.5 |
| 3F | 203N | 18.8 | 20.0 | rectangular | 4.6 |
| 4F | 204N | 19.1 | 25.0 | rectangular | 4.9 |
| 5F | 205N | 19.0 | 25.0 | rectangular | 4.8 |
| Comparative Example 1F | Comparative Composition 201N | 23.2 | 37.5 | slightly inverse taper | 6.7 |
| Comparative Example 2F | Comparative Composition 202N | 22.8 | 37.5 | slightly inverse taper | 6.2 |
| Comparative Example 3F | Comparative Composition 203N | 23.0 | 50.0 | inverse taper | 6.4 |

From the results shown in Table 10, it is understood that a positive-tone pattern (EUV exposure, alkali development) formed by using the composition according to the present invention is excellent in sensitivity, resolving power, pattern shape, and LER performance.

What is claimed is:

1. An actinic ray-sensitive or radiation-sensitive resin composition comprising:
    a compound (A) which generates an acid by irradiation with actinic rays or radiation,
    wherein the acid includes a structure represented by the following general formula (9),

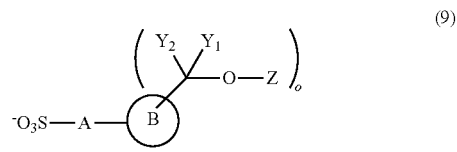

wherein, in the formula (9),
A represents a divalent linking group;
B represents an aromatic ring;
Y$_1$ and Y$_2$ each independently represents a hydrogen atom, an alkyl group, a cycloalkyl group, an alkenyl group, an alkynyl group, an aryl group, or an acyl group;

Z represents a hydrogen atom or a substituent; and
o represents an integer of 1 to 5.

2. The actinic ray-sensitive or radiation-sensitive resin composition according to claim 1, further comprising: a compound (B1) having a phenolic hydroxyl group,
wherein the composition is used for the formation of a negative tone pattern.

3. The actinic ray-sensitive or radiation-sensitive resin composition according to claim 2, wherein the compound (B1) having a phenolic hydroxyl group is a polymer compound having a repeating unit represented by the following general formula (1),

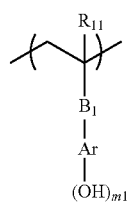

wherein, in the formula (1),
$R_{11}$ represents a hydrogen atom, a methyl group which may have a substituent, or a halogen atom;
$B_1$ represents a single bond or a divalent linking group;
Ar represents an aromatic ring; and
m1 represents an integer of 1 or more.

4. The actinic ray-sensitive or radiation-sensitive resin composition according to claim 1, further comprising: a cross-linking agent (C).

5. The actinic ray-sensitive or radiation-sensitive resin composition according to claim 1, further comprising: a compound (D) that generates an acid which does not include a cross-linking group in a molecule by irradiation with actinic rays or radiation.

6. The actinic ray-sensitive or radiation-sensitive resin composition according to claim 1, further comprising: a compound (B2) having a group which is capable of decomposing by the action of an acid.

7. A negative-tone pattern forming method comprising:
forming a film using the actinic ray-sensitive or radiation-sensitive resin composition according to claim 6;
exposing the film;
and developing the exposed film with a developer containing an organic solvent.

8. An actinic ray-sensitive or radiation-sensitive film which is formed from the actinic ray-sensitive or radiation-sensitive resin composition according to claim 1.

9. Mask blanks comprising: the actinic ray-sensitive or radiation-sensitive film according to claim 8.

10. A pattern forming method comprising:
exposing the actinic ray-sensitive or radiation-sensitive film of the mask blanks according to claim 9; and
developing the exposed actinic ray-sensitive or radiation-sensitive film.

11. A pattern forming method comprising:
exposing the actinic ray-sensitive or radiation-sensitive film according to claim 8; and
developing the exposed film.

12. The pattern forming method according to claim 11, wherein the exposure is performed using an electron beam or extreme ultraviolet rays.

13. An actinic ray-sensitive or radiation-sensitive resin composition comprising:
a compound (A) which generates an acid by irradiation with actinic rays or radiation;
wherein the acid includes an aromatic ring, and the aromatic ring is substituted with two or more groups represented by the following general formula (M),

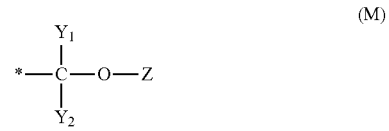

wherein, in the formula (M),
$Y_1$ and $Y_2$ each independently represents a hydrogen atom, an alkyl group, a cycloalkyl group, an alkenyl group, an alkynyl group, an aryl group, or an acyl group;
Z represents a hydrogen atom or a substituent; and
* represents a linking site with the aromatic ring.

14. The actinic ray-sensitive or radiation-sensitive resin composition according to claim 13, wherein the group represented by the general formula (M) is a hydroxymethyl group or an alkoxymethyl group.

15. An actinic ray-sensitive or radiation-sensitive resin composition comprising:
a compound (A) which generates an acid by irradiation with actinic rays or radiation, and a cross-linking agent (C) being a compound having two or more groups represented by the following general formula (M) in a molecule,
wherein the acid includes an aromatic ring, and the aromatic ring is substituted with at least one group represented by the following general formula (M),

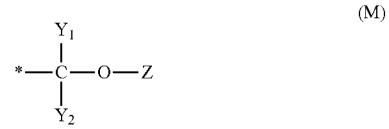

wherein, in the formula (M),
$Y_1$ and $Y_2$ each independently represents a hydrogen atom, an alkyl group, a cycloalkyl group, an alkenyl group, an alkynyl group, an aryl group, or an acyl group;
Z represents a hydrogen atom or a substituent; and
* represents a linking site with the aromatic ring.

16. An actinic ray-sensitive or radiation-sensitive resin composition comprising:
a compound (A) which generates an acid by irradiation with actinic rays or radiation, and a cross-linking agent (C) being a compound having two or more alkoxymethyl groups in a molecule,
wherein the acid includes an aromatic ring, and the aromatic ring is substituted with at least one group represented by the following general formula (M),

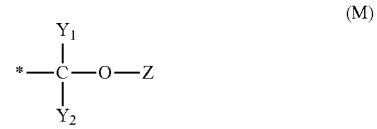

wherein, in the formula (M),

Y₁ and Y₂ each independently represents a hydrogen atom, an alkyl group, a cycloalkyl group, an alkenyl group, an alkynyl group, an aryl group, or an acyl group;

Z represents a hydrogen atom or a substituent; and

* represents a linking site with the aromatic ring.

17. A compound represented by the following general formula (I):

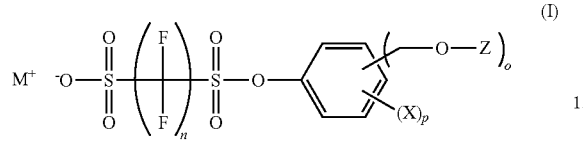

wherein, in the formula (I),

M+ represents a sulfonium cation;

X represents an alkyl group, a cycloalkyl group, an aryl group, a halogen atom, a hydroxyl group, an alkoxy group, or an acyl group;

Z represents a hydrogen atom, an alkyl group, a cycloalkyl group, an aryl group or an acyl group;

n represents an integer of 1 to 3;

o represents an integer of 1 to 5;

p represents an integer of 0 to 4; and o+p≤5 is satisfied.

18. An actinic ray-sensitive or radiation-sensitive resin composition comprising:

a compound (A) which generates an acid by irradiation with actinic rays or radiation, wherein the acid includes an aromatic heterocyclic structure, and the aromatic heterocyclic structure is linked with at least one group represented by the following general formula (M),

wherein, in the formula (M),

Y₁ and Y₂ each independently represents a hydrogen atom, an alkyl group, a cycloalkyl group, an alkenyl group, an alkynyl group, an aryl group, or an acyl group;

Z represents a hydrogen atom or a substituent; and

* represents a linking site with a residue of the aromatic heterocyclic structure.

19. A negative-tone pattern forming method comprising:

forming a film using an actinic ray-sensitive or radiation-sensitive resin composition comprising a compound (A) which generates an acid by irradiation with actinic rays or radiation, wherein the acid includes a structure represented by the following general formula (9); exposing the film;

and developing the exposed film with a developer containing an organic solvent, wherein the actinic ray-sensitive or radiation-sensitive resin composition further comprises a compound (B1) having a phenolic hydroxyl group and a compound (B2) having a group which is capable of decomposing by the action of an acid, the compound (B1) having a phenolic hydroxyl group includes a polymer compound having at least one kind of repeating unit represented by the following general formula (1),

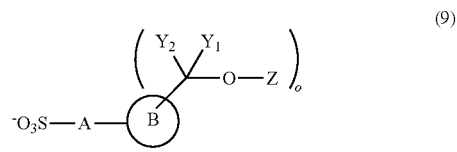

wherein, in the formula (9),

A represents a divalent linking group;

B represents an aromatic ring;

Y₁ and Y₂ each independently represents a hydrogen atom, an alkyl group, a cycloalkyl group, an alkenyl group, an alkynyl group, an aryl group, or an acyl group;

Z represents a hydrogen atom or a substituent; and o represents an integer of 1 to 5, and

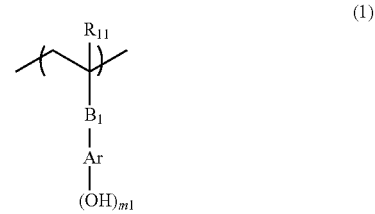

wherein, in the general formula (1),

R₁₁ represents a hydrogen atom, a methyl group which may have a substituent, or a halogen atom;

B₁ represents a single bond or a divalent linking group;

Ar represents an aromatic ring; and m1 represents an integer of 1 or more.

20. The negative-tone pattern forming method according to claim 19, wherein the following group in the general formula (9) is a hydroxymethyl group or an alkoxymethyl group

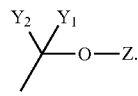

* * * * *